US006380197B1

(12) United States Patent
Bouchard et al.

(10) Patent No.: US 6,380,197 B1
(45) Date of Patent: Apr. 30, 2002

(54) POLYHYDROXYALKYLPYRAZINE DERIVATIVES, THEIR PREPARATION AND MEDICAMENTS CONTAINING THEM

(75) Inventors: Hervé Bouchard, Thiais; Alain Commercon, Vitry sur Seine; Jean-François Peyronel, Palaiseau; Corinne Terrier, Livry Gargan, all of (FR)

(73) Assignee: Aventis Pharma S. A., Antony (FR)

( * ) Notice: Subject to any disclaimer, the term of this patent is extended or adjusted under 35 U.S.C. 154(b) by 0 days.

(21) Appl. No.: 09/484,343

(22) Filed: Jan. 18, 2000

Related U.S. Application Data

(63) Continuation of application No. PCT/FR98/01545, filed on Jul. 15, 1998.

(30) Foreign Application Priority Data

Jul. 18, 1997 (FR) .............................................. 97 09186

(51) Int. Cl.$^7$ ...................... A61K 31/495; C07D 241/02
(52) U.S. Cl. ...................... 514/252.1; 544/336; 544/358
(58) Field of Search ................................ 544/336, 358; 514/252.1

(56) References Cited

U.S. PATENT DOCUMENTS 5,972,342 A 10/1999 Rakoto Ratsimamanga et al. 424/195.1

FOREIGN PATENT DOCUMENTS

WO  9728813  8/1997

OTHER PUBLICATIONS

Abstract CA 55:27094bCALOAD,Kuhn et al."Amino Suygars Synth.", Oct. 2000.*
CAPLUS 1989:455721"Detection of Products.."Wittmann et al.,Z.Leb.Fors. 212–20, 188/3, Oct. 2000.*
Stephen J. Ettelman and Milton S. Feather; "The Alkaline Degradation of 2–amino–2–deoxy–D–glucose"; Carbohydrate Research; 77; 1979; pp. 213–217.
Mahmoud I. Taha; "The Reaction of 2–Amino–2–deoxy–D–glucose Hydrochloride with Aqueous Ammonia"; J. Chem, Soc.; 1961; pp. 2468–2472.
M. S. Feather; "Amine–Assisted Sugar Dehydration Reactions"; Prog. Food Nutr. Sci.; 5; 1981; pp. 37–45.
Martin Avalos, et al; "The Reaction of 2–Amino–2–Deoxyhexopyranoses with Isocyanates, Synthesis of Ureas and Their Transformation into Heterocyclic Derivatives"; Tetrahedron; 49; 1993; pp. 2655–2675.
Eduardo A. Forlano, et al; "The Reaction of Penta–O–Nicotinoyl–x–D–Glucopyranose with Aqueous Ammonia"; Carboyh. Res., 23(11); 1972; pp. 111–119.
Agr. Biol. Chem. 37(11); 1973; pp. 2571–2578.
Carbohydr. Res.; 26(2); 1973; pp. 377–384.
Tsuchida et al., Chemical Abstracts, vol. 81, No. 6 (1974), Abstract No. 1162725.
Hiroshi Kataoka, , Chemical Abstracts, vol. 74, No. 23 (1971), Abstract No. 126009f.
Tsuchida et al., , Chemical Abstracts, vol. 8, No. 6 (1974), Abstract No. 226272.
Forland, , Chemical Abstracts, vol. 77, No. 5 (1972), Abstract No. 34798w.
International Search Report for Priority Application PCT/FR98/01545.

* cited by examiner

*Primary Examiner*—Richard L. Raymond
*Assistant Examiner*—Sudhaker B. Patel
(74) *Attorney, Agent, or Firm*—Irving Newman

(57) ABSTRACT

Provided herein are novel polyhydroxyalkylpyrazine derivatives useful in treating and preventing a plethora of diseases including diabetes, having a general formula of

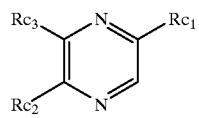

wherein $Rc_1$ represents the chain (II) —$CH(OR_4)CH(OR_3)CH(OR_2)CH_2OR_1$ and either $Rc_2$ represents a hydrogen atom and either $Rc_3$ represents the chain (III)—$CH_2CH(OR_6)CH(OR_7)CH_2OR_8$ or $Rc_2$ represents the chain (IV)—$CH(OR_5)CH(OR_6)CH(OR_7)CH_2OR_8$ or chain (III) —$CH_2CH(OR_6)CH(OR_7)CH_2OR_8$ and $Rc_3$ represents a hydrogen atom, and 1 to 8 substituents $R_1$, $R_2$, $R_3$, $R_4$, $R_5$, $R_6$, $R_7$, $R_8$, identical or different, represent a radical independently selected among the radicals a) —$COR_9$, b) —$COOR_{10}$, c) —$CR_{11}R_{12}OCOR_{13}$, d) —$CR_{11}R_{12}OR_{13}$, e) —$CONR_{14}R_{15}$, and f) one or more pairs of the substituents $R_1$, $R_2$, $R_3$, $R_4$, $R_6$, $R_7$, $R_8$, consecutive or separated by one of the other substituents $R_2$, $R_3$, $R_6$, $R_7$ can also form a group: —C(O)—; the other substituents $R_1$, $R_2$, $R_3$, $R_4$, $R_6$, $R_7$, $R_8$ are hydrogen atoms.

21 Claims, No Drawings

POLYHYDROXYALKYLPYRAZINE DERIVATIVES, THEIR PREPARATION AND MEDICAMENTS CONTAINING THEM

This application is a continuation of PCT/FR98/01545 filed Jul. 15, 1998.

Medicaments containing, as active ingredient, at least one compound of general formula:

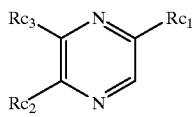
(I)

or one of its stereoisomers or its salts with an inorganic or organic acid, the new derivatives of formula (I), their stereoisomers, their salts with an inorganic or organic acid and their preparation. In general formula (I)

$Rc_1$ represents the chain

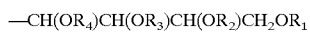
(II)

and either $Rc_2$ represents a hydrogen atom and $Rc_3$ represents the chain

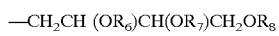
(III)

or $Rc_2$ represents the chain

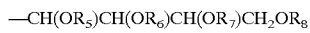
(IV)

or

(III)

and $Rc_3$ represents a hydrogen atom, and 1 to 8 of the substituents $R_1$, $R_2$, $R_3$, $R_4$, $R_5$, $R_6$, $R_7$, $R_8$, which are identical or different, represents a radical independently chosen from the radicals
a) —$COR_9$,
b) —$COOR_{10}$,
c) —$CR_{11}R_{12}OCOR_{13}$,
d) —$CR_{11}R_{12}OR_{13}$,
e) —$CONR_{14}R_{15}$, or
f) one or more pairs of the substituents $R_1$, $R_2$, $R_3$, $R_4$, $R_5$, $R_6$, $R_7$, $R_8$, consecutive or separated by one of the other substituents $R_2$, $R_3$, $R_6$, $R_7$, may also form a group: —C(O)—;

the other substituents $R_1$, $R_2$, $R_3$, $R_4$, $R_5$, $R_6$, $R_7$, $R_8$, representing hydrogen atoms.

$R_9$ represents a hydrogen atom, or an alkenyl radical optionally substituted with one or more identical or different substituents chosen from the following radicals: alkyloxy, carboxyl, alkylcarbonyl, alkyloxycarbonyl, carbamoyl, amino, alkylamino, dialkylamino or a halogen atom; or an alkyl radical, optionally substituted with one or more identical or different substituents chosen from the following radicals: hydroxyl, alkyloxy, carboxyl, alkylcarbonyl, alkyloxycarbonyl, aralkyloxycarbonyl, aryl, aryloxy, carbamoyl, amino, alkylamino, dialkylamino, carboxycarbonyl, heterocyclyl, or a halogen atom; or an amino radical, a heterocyclyl radical, a heteroaryl radical, or an aryl radical optionally substituted with one or more identical or different substituents chosen from the following radicals: aryl, alkyl, alkyloxy, aralkyloxy, alkylcarbonyl, alkyloxyalkyl, alkyloxycarbonyl, alkylcarbonyloxy, nitro, hydroxyl, a halogen atom, an amino, alkylamino, dialkylamino, aminoalkyl, alkylaminoalkyl, dialkylaminoalkyl, carbamoylalkylaminoalkyl, hydroxyalkylaminoalkyl, (hydroxyalkyl)(alkyl)aminoalkyl, dihydroxyalkylaminoalkyl radical, or a heterocyclylalkyl radical, for which the heterocyclyl radical of 5 or 6 atoms, optionally substituted with an alkyl radical on any one of its constituent atoms, contains at least one nitrogen atom and optionally another heteroatom suchas oxygen or nitrogen or sulphur, the said heterocyclyl radical being linked to the alkyl radical by thenitrogen atom, such as piperidinyl, piperazinyl, morpholinyl;

advantageously, in general formula (I), $R_9$ represents a hydrogen atom, or an alkyl, aralkyl, alkyloxyalkyl, aryloxyalkyl, alkyloxycarbonylalkyl, alkyloxycarbonylalkenyl, carboxyalkyl, aralkyloxycarbonylalkyl, heteroaryl radical, or an aryl radical, the said aryl radical being optionally substituted with one or more identical or different substituents chosen from the following radicals: aryl, alkyl, alkyloxy, aralkyloxy, alkylcarbonyl, alkyloxyalkyl, alkyloxycarbonyl, alkylcarbonyloxy, nitro, hydroxyl, a halogen atom, an amino, alkylamino, dialkylamino, aminoalkyl, alkylaminoalkyl, dialkylaminoalkyl, carbamoylalkylaminoalkyl, hydroxyalkylaminoalkyl, (hydroxyalkyl)(alkyl)aminoalkyl, dihydroxyalkylaminoalkyl radical; or a heterocyclylalkyl radical, for which the heterocyclyl radical of 5 or 6 atoms, optionally substituted with an alkyl radical on any one of its constituent atoms, contains at least one nitrogen atom and optionally another heteroatom such as oxygen or nitrogen or sulphur, the said heterocyclyl radical beinglinked to the alkyl radical by the nitrogen atom, such as piperidinyl, piperazinyl, morpholinyl;

and still more advantageously, $R_9$ represents a hydrogen atom, or an alkyl, aralkyl, alkyloxyalkyl, alkyloxycarbonylalkyl, alkyloxycarbonylalkenyl, carboxyalkyl, aralkyloxycarbonylalkyl, heteroaryl radical, such as thienyl, or an aryl radical, the said aryl radical being optionally substituted with one or more identical or different substituents chosen from the following radicals: alkyl, alkyloxy, aralkyloxy, hydroxyl, alkylcarbonyl, alkylcarbonyloxy, nitro, a halogen atom, a dialkylamino radical, dialkylaminoalkyl radical, or a heterocyclylalkyl radical for which the heterocyclyl radical of 6 atoms contains at least one nitrogen atom and optionally another heteroatom such as oxygen or nitrogen, the said heterocyclyl radical being linked to the alkyl radical by the nitrogen atom, such as piperidinyl or morpholinyl;

$R_{10}$ represents an alkyl radical, an aralkyl radical or an aryl radical such as phenyl optionally substituted with one or more identical or different substituents chosen from the following radicals: alkyl, alkyloxy, alkyloxyalkyl, dialkylaminoalkyl, alkylcarbonyloxy, nitro or a halogen atom;

advantageously, in general formula (I), $R_{10}$ represents an alkyl radical;

$R_{11}$, $R_{12}$, $R_{13}$ independently represent a hydrogen atom or an alkyl, aryl or aralkyl radical;

$R_{14}$, $R_{15}$ independently represent a hydrogen atom, an alkyl radical, an aryl radical, an aralkyl radical, a heterocyclyl radical or alternatively $R_{14}$, $R_{15}$ together form with the nitrogen atom to which they are attached a 4- to 7-membered heterocycle which may be substituted with 1 to 3 alkyl radicals or with an aryl radical;

advantageously, in general formula (I), $R_{14}$, $R_{15}$ independently represent a hydrogen atom, or an aryl radical or an aralkyl radical.

In the preceding definitions and in those which follow:

the term alkenyl radical represents the hydrocarbon portions containing from 1 to 6 straight- or branched-chain carbon atoms and possessing one or more double bonds, optionally substituted with one or more identical or different substituents chosen from the following radicals: alkyloxy, carboxyl, alkylcarbonyl, alkyloxycarbonyl, carbamoyl, amino, alkylamino, dialkylamino or a halogen atom;

the term alkyl defines saturated straight- or branched-chain hydrocarbon portions containing 1 to 6 carbon atoms such as methyl, ethyl, propyl, isopropyl, butyl, sec-butyl, tert-butyl, pentyl or hexyl, optionally substituted with one or more identical or different substituents chosen from the following radicals: hydroxyl, alkyloxy, carboxyl, alkylcarbonyl, alkyloxycarbonyl, aralkyloxycarbonyl, aryl, aryloxy, carbamoyl, amino, alkylamino, dialkylamino, carboxycarbonyl, heterocyclyl, or a halogen atom;

the alkyloxy radicals represent an alkyl group containing 1 to 6 straight- or branched-chain carbon atoms which is attached by an oxygen atom such as, for example, methoxy, ethoxy, propoxy, isopropoxy or tert-butoxy;

the aryl radicals refer to mono- or bi-cyclic hydrocarbons optionally substituted with one or more identical or different substituents chosen from the following radicals: alkyl, alkyloxy, a halogen atom, in which at least one ring is aromatic, it being possible for each ring to contain up to 7 carbon atoms. This term aryl includes in particular phenyl, naphthyl, indanyl or biphenyl;

the term heterocycle represents a mono- or polycyclic carbon system optionally substituted with one or more identical or different substituents chosen from the following radicals: alkyl, alkyloxy, a halogen atom, in which each ring may contain up to 7 carbon atoms, saturated or otherwise, and containing from 1 to 4 heteroatoms chosen from N, O and S, capable of being optionally condensed with an aromatic nucleus. This heterocyclic structure may be attached to any atom or heteroatom. The heterocyclic radicals include in particular and without limitation the radicals azepinyl, azetidinyl, benzimidazolyl, benzisoxazolyl, benzofurazannyl, benzopyranyl, benzothiopyrannyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranylsulphone, furyl, imidazolidinyl, imidazolyl, indazolyl, indolinyl, indolyl, isoindolinyl, isoquinolinyl, isothiazolidinyl, isothiazolyl, morpholinyl, naphthyridinyl, oxazolyl, oxadiazolyl, 2-oxoazepinyl, 2-oxopiperazinyl, 2-oxopiperidinyl, 2-oxopyrrolidinyl, piperidinyl, piperidyl, piperazinyl, pyridyl, pyranyl, pyrazinyl, pyrazolidinyl, pyrazolyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, tetrahydropyrranyl, thiamorpholinyl, thiamorpholinosulphoxide, thiazolyl, thiazolinyl, thienofuryl, thienothienyl, thienyl or thiomorpholinyl. The preferred heterocyclic radicals according to the invention are in particular the azepinyl, azetidinyl, benzothiazolyl; furyl, imidazolidinyl, imidazolyl, indolinyl, indolyl, isoindolinyl, isoquinolinyl, oxazolyl, piperazinyl, piperidinyl, piperidyl, pyridyl, pyrazinyl, pyrazolyl, pyrrimidinyl, pyrrolidinyl, pyrrolyl, tetrahydroisoquinolinyl, thiazolyl, thiazolinyl and thiomorpholinyl radicals.

Preferably, when $R_{14}$ and $R_{15}$ represent a heterocyclyl radical, they represent more particularly a radical such as pyrrolidinyl, azetidinyl or piperidinyl or may also form together with the nitrogen atom to which they are attached a ring such as pyrrolidine, azetidine, piperidine, azepine, morpholine, thiomorpholine, piperazine and isoindoline.

Heteroaryl is understood to mean the aromatic heterocyclic radicals, as defined above;

the term aralkyl denotes an aliphatic hydrocarbon of 1 to 4 carbon atoms in a straight or branched chain, linked to a mono- or bi-cyclic system optionally substituted with one or more identical or different substituents chosen from the following radicals: alkyl, alkyloxy, alkylcarbonyl, alkylcarbonyloxy and aryl, each ring containing up to 7 members and in which at least one of the rings is aromatic. An aralkyl radical which is particularly used according to the invention is for example the phenylalkyl radical and more particularly the benzyl radical.

The medicaments according to the invention contain the compounds of general formula (I) which are the following derivatives:

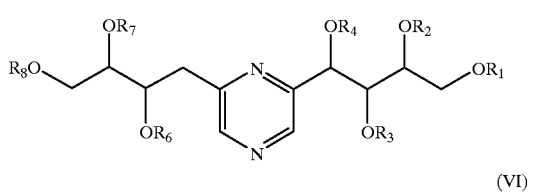

(V)

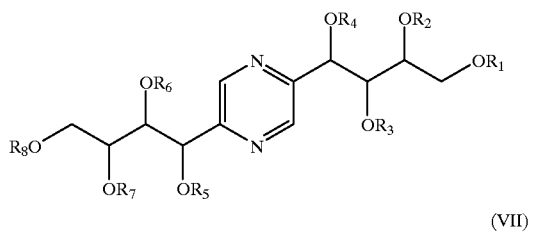

(VI)

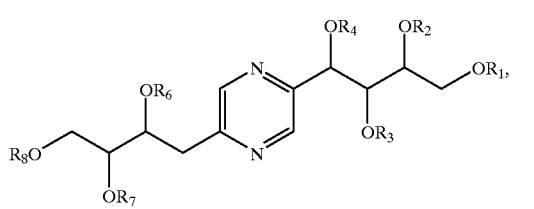

(VII)

it being understood that the substituents $R_1$, $R_2$, $R_3$, $R_4$, $R_5$, $R_6$, $R_7$, $R_8$, which are identical or different, are chosen from a), b), c), d), e) or f) for 1 to 7 of the radicals of the compounds of general formula (V) and (VII) and for 1 to 8 of the radicals of the compounds of general formula (VI), the other substituents $R_1$, $R_2$, $R_3$, $R_4$, $R_5$, $R_6$, $R_7$, $R_8$ representing hydrogen atoms.

The compounds of formula (I) comprise asymmetric carbon atoms and have stereoisomeric forms. These stereoisomers also form part of the invention. The medicaments according to the invention contain the stereoisomers of the compounds of general formula (I); the stereoisomeric forms of the compounds of formula (V), (VI), (VII) which are particularly representative of the invention are respectively the following compounds of general formula (VIII), (IX), (X):

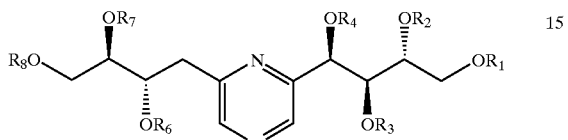

(VIII)

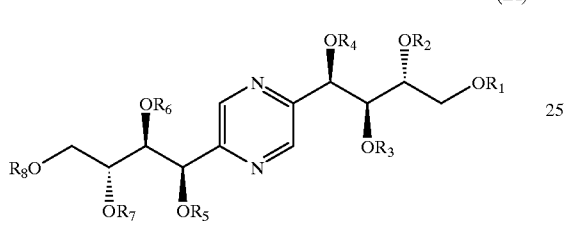

(IX)

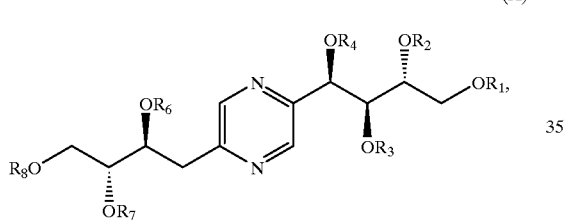

(X)

for which $R_1$, $R_2$, $R_3$, $R_4$, $R_5$, $R_6$, $R_7$, $R_8$ are as defined above.

The preferred medicaments according to the invention are those containing, as active ingredient, at least one of the following compounds:
A—compounds of general formula:

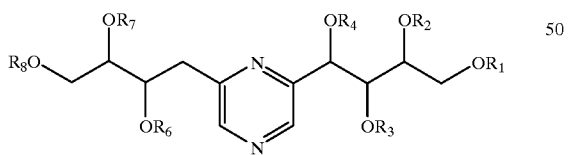

(V)

for which
(1) at least one of the substituents $R_1$, $R_2$, $R_3$, $R_4$, $R_6$, $R_7$, $R_8$ represents a radical chosen from the following list (L), the other substituents $R_1$, $R_2$, $R_3$, $R_4$, $R_6$, $R_7$, $R_8$ representing a hydrogen atom:
(L): a formyl, alkylcarbonyl, aralkylcarbonyl, alkyloxyalkylcarbonyl, alkyloxycarbonylalkylcarbonyl, alkyloxycarbonylalkenylcarbonyl, carboxyalkylcarbonyl, aralkyloxycarbonylalkylcarbonyl, heteroarylcarbonyl, alkyloxycarbonyl, aryloxyalkylcarbonyl, N-arylcarbamoyl or N-aralkylcarbamoyl radical, or an arylcarbonyl radical, the said aryl radical being optionally substituted with one or more identical or different substituents chosen from the following radicals: aryl, alkyl, alkyloxy, alkylcarbonyl, alkyloxyalkyl, alkyloxycarbonyl, aralkyloxy, alkylcarbonyloxy, nitro, hydroxyl, a halogen atom, an amino, alkylamino, dialkylamino, aminoalkyl, alkylaminoalkyl or dialkylaminoalkyl radical, or a heterocyclylalkyl radical for which the heterocyclyl radical of 5 or 6 atoms, optionally substituted with an alkyl radical on any one of its constituent atoms, contains at least one nitrogen atom and optionally another heteroatom such as oxygen or nitrogen, the said heterocyclyl radical being linked to the alkyl radical by the nitrogen atom, advantageously, the radicals of the list (L) may be chosen from the substituents of the following list (L');

(L'): radicals formyl, acetyl, propanoyl, 2-methylpropanoyl, 2,2-dimethylpropanoyl, butanoyl, 2-methylbutanoyl, 3-methylbutanoyl, 2,2-dimethylbutanoyl, 2,3-dimethylbutanoyl, 3,3-dimethylbutanoyl, 2-ethylbutanoyl, 2-ethyl-3-methylbutanoyl, 2-propylbutanoyl, pentanoyl, 2-methylpentanoyl, 3-methyl-pentanoyl, 4-methylpentanoyl, 2,2-dimethylpentanoyl, 2,3-dimethylpentanoyl, 2,4-dimethylpentanoyl, 3,4-dimethylpentanoyl, 3,3-dimethylpentanoyl, 4,4-dimethylpentanoyl, 2-ethylpentanoyl, 3-ethylpentanoyl, hexanoyl, 2-methylhexanoyl, 3-methylhexanoyl, 4-methylhexanoyl, 5-methylhexanoyl, heptanoyl, phenylacetyl, biphenylacetyl, 1-naphthylacetyl, 2-naphthylacetyl, 2-phenylpropanoyl, 3-phenylpropanoyl, 2-biphenylpropanoyl, 3-biphenylpropanoyl, 2-(1-naphthyl)propanoyl, 3-(1-naphthyl)propanoyl, 2-(2-naphthyl)propanoyl, 3-(2-naphthyl)propanoyl, 2-phenylbutanoyl, 3-phenylbutanoyl, 4-phenylbutanoyl, 2-biphenylbutanoyl, 3-biphenylbutanoyl, 4-biphenylbutanoyl, 2-(1-naphthyl)butanoyl, 3-(1-naphthyl)butanoyl, 4-(1-naphthyl)butanoyl, 2-(2-naphthyl)butanoyl, 3-(2-naphthyl)butanoyl, 4-(2-naphthyl)butanoyl, methoxyacetyl, ethoxyacetyl, n-propyloxyacetyl, isopropyloxyacetyl, n-butyloxyacetyl, isobutyloxyacetyl, tert-butyloxyacetyl, 2-methoxypropanoyl, 2-ethoxypropanoyl, 2-n-propyloxypropanoyl, 2-isopropyloxypropanoyl, 2-n-butyloxypropanoyl, 2-isobutyloxypropanoyl, 2-tert-butyloxypropanoyl, 2-methoxybutanoyl, 2-ethoxybutanoyl, 2-n-propyloxybutanoyl, 2-isopropyloxybutanoyl, 2-n-butyloxybutanoyl, 2-isobutyloxybutanoyl, 2-tert-butyloxybutanoyl, aminoacetyl, 2-aminopropanoyl, 3-aminopropanoyl, 2-aminobutanoyl, 3-aminobutanoyl, 4-aminobutanoyl, 2-aminopentanoyl, 3-aminopentanoyl, 4-aminopentanoyl, 5-aminopentanoyl, methylaminoacetyl, ethylaminoacetyl, n-propylaminoacetyl, isopropylaminoacetyl, n-butylaminoacetyl, isobutylaminoacetyl, tert-butylaminoacetyl, 2-methylaminopropanoyl, 2-ethylaminoprbpanoyl, 2-n-propylaminopropanoyl, 2-isopropylaminopropanoyl, 2-n-butylaminopropanoyl, 2-isobutylaminopropanoyl, 2-tert-butylaminopropanoyl, 3-methylaminopropanoyl, 3-ethylaminopropanoyl, 3-n-propylaminopropanoyl, 3-isopropylaminopropanoyl, 3-n- butylaminopropanoyl, 3-isobutylaminopropanoyl, 3-tert-butylaminopropanoyl, 2-mnethylaminobutanoyl, 2-ethylaminobutanoyl, 2-n-propylaminobutanoyl, 2-isopropylaminobutanoyl, 2-n-butylaminobutanoyl, 2-isobutylaminobutanoyl, 2-tert-butylaminobutanoyl, 3-mrethylaminobutanoyl, 3-ethylaminobutanoyl,. 3-n-propylaminobutanoyl, 3-isopropylaminobutanoyl, 3-n-butylaminobutanoyl, 3-isobutylaminobutanoyl, 3-tert-butylaminobutanoyl, 4-methylaminobutanoyl, 4-ethylaminobutanoyl, 4-n-propylaminobutanoyl, 4-isopropylaminobutanoyl, 4-n-butylaminobutanoyl, 4-isobutylaminobutanoyl, 4-tert-butylaminobutanoyl, 2-methylaminopentanoyl, 2-ethylaminopentanoyl, 2-n-propylaminopentanoyl, 2-isopropylaminopentanoyl, 2-n-butylaminopentanoyl, 2-isobutylaminopentanoyl, 2-tert-butylaminopentatoyl, 3-methylaminopentanoyl, 3-ethylaminopentanoyl, 3-n-propylaminopentanoyl, 3-isopropylaminopentanoyl, 3-n-butylaminopentanoyl, 3-isobutylaminopentanoyl, 3-tert-butylaminopentanoyl, 4-methylaminopentanoyl, 4-ethylaminopentanoyl, 4-n-propylaminopentanoyl, 4-isopropylaminopentanoyl, 4-n-butylaminopentanoyl, 4-isobutylaminopentanoyl, 4-tert-butylaminopentanoyl, 5-methylaminopentanoyl, 5-ethylaminopentanoyl, 5-n-propylaminopentanoyl, 5-isopropylaminopentanoyl, 5-n-butylaminopentanoyl, 5-isobutylaminopentanoyl, 5-tert-butylaminopentanoyl, dimethylaminoacetyl, diethylaminoacetyl, di-n-propylaminoacetyl, diisopropylaminoacetyl, di-n-butylaminoacetyl, diisobutylaminoacetyl, di-tert-butylaminoacetyl, 2-dimethylaminopropanoyl, 2-diethylaminopropanoyl, 2-di-n-propylaminopropanoyl, 2-diisopropylaminopropanoyl, 2-di-n-butylaminopropanoyl, 2-diisobutylaminopropanoyl, 2-di-tert-butylaminopropanoyl, 3-dimethylaminopropanoyl, 3-diethylaminopropanoyl, 3-di-n-propylaminopropanoyl, 3-diisopropylaminopropanoyl, 3-di-n-butylaminopropanoyl, 3-diisobutylaminopropanoyl, 3-di-tert-butylaminopropanoyl, 2-dimethylaminobutanoyl, 2-diethylaminobutanoyl, 2-di-n-propylaminobutanoyl, 2-diisopropylaminobutanoyl, 2-di-n-butylaminobutanoyl, 2-diisobutylaminobutanoyl, 2-di-tert-butylaminobutanoyl, 3-dimethylaminobutanoyl, 3-diethylaminobutanoyl, 3-di-n-propylaminobutanoyl, 3-diisopropylaminobutanoyl, 3-di-n-butylaminobutanoyl, 3-diisobutylaminobutanoyl, 3-di-tert-butylaminobutanoyl, 4-dimethylaminobutanoyl, 4-diethylaminobutanoyl, 4-di-n-propylaminobutanoyl, 4-diisopropylaminobutanoyl, 4-di-n-butylaminobutanoyl, 4-diisobutylaminobutanoyl, 4-di-tert-butylaminobutanoyl, 2-dimethylaminopentanoyl, 2-diethylaminopentanoyl, 2-di-n-propylaminopentanoyl, 2-diisopropylaminopentanoyl, 2-di-n-butylaminopentanoyl, 2-diisobutylaminopentanoyl, 2-di-tert-butylaminopentanoyl, 3-dimethylaminopentanoyl, 3-diethylaminopentanoyl, 3-di-n-propylaminopentanoyl, 3-diisopropylaminopentanoyl, 3-di-n-butylaminopentanoyl, 3-diisobutylaminopentanoyl, 3-di-tert-butylaminopentanoyl, 4-dimethylaminopentanoyl, 4-diethylaminopentanoyl, 4-di-n-propylaminopentanoyl, 4-diisopropylaminopentanoyl, 4-di-n-butylaminopentanoyl, 4-diisobutylaminopentanoyl, 4-di-tert-butylaminopentanoyl, 5-dimethylaminopentanoyl, 5-diethylaminopentanoyl, 5-di-n-propylaminopentanoyl, 5-diisopropylaminopentanoyl, 5-di-n-butylaminopentanoyl, 5-diisobutylaminopentanoyl, 5-di-tert-butylaminopentanoyl, benzoyl, 1-naphthoyl, 2-naphthoyl, 1-indanoyl, 2-indanoyl, 2-fluorobenzoyl, 2-chlorobenzoyl, 2-bromobenzoyl, 2-nitrobenzoyl, 2-aminobenzoyl, 2-methylaminobenzoyl, 2-ethylaminobenzoyl, 2-dimethylaminobenzoyl, 2-diethylaminobenzoyl, 2-dimethylaminomethylbenzoyl, 2-hydroxybenzoyl, 2-methoxybenzoyl, 2-ethoxybenzoyl, 2-methoxymethylbenzoyl, 2-ethoxymethylbenzoyl, 2-methylbenzoyl, 2-ethylbenzoyl, 2-isopropylbenzoyl, (2-acetyl)benzoyl, (2-propanoyl)benzoyl, (2-acetyloxy)benzoyl, (2-propanoyloxy)benzoyl, 3-fluorobenzoyl, 3-chlorobenzoyl, 3-bromobenzoyl, 3-nitrobenzoyl, 3-aminobenzoyl, 3-methylaminobenzoyl, 3-ethylaminobenzoyl, 3-dimethylaminobenzoyl, 3-diethylaminobenzoyl, 3-dimethylaminomethylbenzoyl, 3-hydroxybenzoyl, 3-methoxybenzoyl, 3-ethoxybenzoyl, 3-methoxymethylbenzoyl, 3-ethoxymethylbenzoyl, 3-methylbenzoyl, 3-ethylbenzoyl, 3-isopropylbenzoyl, (3-acetyl)benzoyl, (3-propanoyl)benzoyl, (3-acetyloxy)benzoyl, (3-propanoyloxy)benzoyl, 4-fluorobenzoyl, 4-chlorobenzoyl, 4-bromobenzoyl, 4-nitrobenzoyl, 4-aminobenzoyl, 4-methylaminobenzoyl, 4-ethylaminobenzoyl, 4-dimethylaminobenzoyl, 4-diethylaminobenzoyl, 4-dimethylaminomethylbenzoyl, 4-hydroxybenzoyl, 4-methoxybenzoyl, 4-ethoxybenzoyl, 4-methoxymethylbenzoyl, 4-ethoxymethylbenzoyl, 4-methylbenzoyl, 4-ethylbenzoyl, 4-isopropylbenzoyl, (4-acetyl)benzoyl, (4-propanoyl)benzoyl, (4-acetyloxy)benzoyl, (4-propanoyloxy)benzoyl, 2,4-difluorobenzoyl, 2,4-dichlorobenzoyl, 2,4-dibromobenzoyl, 2,4-dinitrobenzoyl, 2,4-diaminobenzoyl, 2,4-dimethylaminobenzoyl, 2,4-diethylaminobenzoyl, 2,4-didimethylaminobenzoyl, 2,4-didiethylaminobenzoyl, 2,4-di(dimethylaminomethyl)benzoyl, 2,4-dihydroxybenzoyl, 2,4-dimethoxybenzoyl, 2,4-diethoxybenzoyl, 2,4-dimethoxymethylbenzoyl, 2,4-diethoxymethylbenzoyl, 2,4-dimethylbenzoyl, 2,4-diethylbenzoyl, 2,4-diisopropylbenzoyl, (2,4-diacetyl)benzoyl, (2,4-dipropanoyl)benzoyl, (2,4-diacetyloxy)benzoyl, (2,4-dipropanoyloxy)benzoyl, 4-benzyloxybenzoyl, 3-benzyloxybenzoyl, 3,5-dichlorobenzoyl, 4-methoxycarbonylbenzoyl, 3-methoxycarbonylbenzoyl, 1-piperidinylmethylenebenzoyl, N-4-methylpiperazinylmethylenebenzoyl, N-morpholinylmethylenebenzoyl, N-(2-hydroxyethyl)aminomethylenebenzoyl, N,N-diisopropylaminomethylenebenzoyl, N-carbamoylmethylaminomethylenebenzoyl, N,N-dimethylaminomethylenebenzoyl, N,N-diethylaminomethylenebenzoyl, N-ethylaminomethylenebenzoyl, aminomethylenebenzoyl, N-(2-hydroxyethyl)-N-(methyl)aminomethylenebenzoyl, methoxycarbonyl, ethoxycarbonyl, n-propoxycarbonyl, isopropoxycarbonyl, n-butoxycarbonyl, isobutoxycarbonyl, tert-butoxycarbonyl, phenoxycarbonyl, 4-nitrophenoxycarbonyl, 4-fluorophenoxycarbonyl, 4-chlorophenoxycarbonyl, 4-bromophenoxycarbonyl, 4-methylphenoxycarbonyl, 4-methoxyphenoxycarbonyl, 4-methoxycarbonylphenoxycarbonyl, 1-naphthoxycarbonyl, 2-naphthoxycarbonyl, 1-indanoxycarbonyl, 2-indanoxycarbonyl, benzyloxycarbonyl, 4-nitrobenzyloxycarbonyl, formyloxymethylene, acetyloxymethylene, propanoyloxymethylene, 2-methylpropanoyloxymethylene, 2,2-dimethylpropanoyloxymethylene, butanoyloxymethylene, 2-methylbutanoyloxymethylene, 3-methylbutanoyloxymethylene, 2,2-dimethylbutanoyloxymethylene, 2,3-dimethylbutanoyloxymethylene, 3,3-dimethylbutanoyloxymethylene, 2-ethylbutanoyloxymethylene, 2-ethyl-3-methylbutanoylmethylbutanoyloxymethylene, 2-propylbutanoyloxymethylene, pentanoyloxymethylene, 2-methylpentanoyloxymethylene, 3-methylpentanoyloxymethylene, 4-methylpentanoyloxymethylene, 2,2-dimethylpentanoyloxymethylene, 2,3-dimethylpentanoyloxymethylene, 2,4-dimethylpentanoyloxymethylene, 3,4-dimethylpentanoyloxymethylene, 3,3-dimethylpentanoyloxymethylene, 4,4-dimethylpentanoyloxymethylene, 2-ethylpentanoyloxymethylene, 3-ethylpentanoyloxymethylene, hexanoyloxymethylene, 2-methylhexanoyloxymethylene, 3-methylhexanoyloxymethylene, 4-methylhexanoyloxymethylene, 5-methylhexanoyloxymethylene, heptanoyloxymethylene, methoxymethylene, ethoxymethylene, propanoxymethylene, 2-methylpropanoxymethylene, 2,2-dimethylpropanoxymethylene, butanoxymethylene, 2-methylbutanoxymethylene, 3-methylbutanoxymethylene, 2,2-dimethylbutanoxymethylene, 2,3-dimethylbutanoxymethylene, 3,3-dimethylbutanoxymethylene, 2-ethylbutanoxymethylene, pentanoxymethylene, 2-methylpentanoxymethylene, 3-methylpentanoxymethylene, 4-methylpentanoxymethylene, hexanoxymethylene, aminocarbonyl, methylaminocarbonyl, dimethylaminocarbonyl, ethylaminocarbonyl, diethylaminocarbonyl, n-propylaminocarbonyl, di-n-propylaminocarbonyl, isopropylaminocarbonyl, diisopropyl-aminocarbonyl, n-butylaminocarbonyl, di-n-butylaminocarbonyl, isobutylaminocarbonyl, diisobutylaminocarbonyl, tert-butylaminocarbonyl, di-tert-butylaminocarbonyl, phenylaminocarbonyl, diphenylaminocarbonyl, 4-nitrophenylaminocarbonyl, 4-fluorophenylaminocarbonyl, 4-chlorophenylaminocarbonyl, 4-bromophenylaminocarbonyl, 4-methylphenylaminocarbonyl, 4-methoxyphenylaminocarbonyl, (4-methylaminocarbonyl)phenylaminocarbonyl, 1-naphthylaminocarbonyl, 2-naphthylaminocarbonyl, 1-indanylaminocarbonyl, 2-indanylaminocarbonyl, benzylylaminocarbonyl, dibenzylylaminocarbonyl, (4-nitrobenzylyl)aminocarbonyl, methoxycarbonylpropanoyl, carboxypropanoyl, carboxybutanoyl, ethoxycarbonylpropenoyl, ethoxycarbonylbutanoyl, benzyloxycarbonylpropanoyl, carboxybutanoyl, benzyloxycarbonylbutanoyl, 2-furanylcarbonyl, 2-thienylcarbonyl, phenoxyacetyl, ethoxycarbonyl, N-phenylcarbamoyl, N-benzylcarbamoyl. Among the substituents of the list (L'), the radicals chosen among the following list (L") are preferred in particular:

(L"): acetyl, 2,2-dimethylpropanoyl, benzoyl, 4-dimethylaminobenzoyl, 4-aminobenzoyl, 4-benzyloxyloxybenzoyl, 4-hydroxybenzoyl, 4-methoxybenzoyl, 4-methylbenzoyl, 3-methylbenzoyl, 4-fluorobenzoyl, 3-hydroxybenzoyl, 4-chlorobenzoyl, 4-methoxycarbonylbepzoyl, (4-acetyl)benzoyl, 4-nitrobenzoyl, 3,5-dichlorobenzoyl, N,N-diisopropylaminomethylenebenzoyl, N,N-diethylaminomethylenebenzoyl, pentanoyl, (2-acetyloxy)benzoyl, phenylacetyl, formyl, butanoyl, methoxyacetyl, methoxycarbonylpropanoyl, carboxypropanoyl, carboxybutanoyl, ethoxycarbonylpropenoyl, ethoxycarbonylbutanoyl, benzyloxycarbonylpropanoyl, benzyloxycarbonylbutanoyl, N-(phenyl)aminocarbonyl, N-(benzyl)aminocarbonyl, 2-thienylcarbonyl, 1-piperidinylmethylenebenzoyl, N-morpholinylmethylenebenzoyl, N,N-dimethylaminomethylenebenzoyl, N-4-methylpiperazinylmethylenebenzoyl, N-(2-hydroxyethyl)aminomethylenebenzoyl, N-carbamoylmethylaminomethylenebenzoyl, N-ethylaminomethylenebenzoyl, aminomethylenebenzoyl, N-(2-hydroxyethyl)-N-(methyl)aminomethylenebenzoyl, 2-furanylcarbonyl, phenoxyacetyl, ethoxycarbonyl, N-phenylcarbamoyl, N-benzylcarbamoyl, 4-dimethylaminobutanoyl; and more particularly (L'"): acetyl, 2,2-dimethylpropanoyl, benzoyl, 4-dimethylaminobenzoyl, 4-benzyloxyloxybenzoyl, 4-hydroxybenzoyl, 4-methoxybenzoyl, 4-methylbenzoyl, 3-methylbenzoyl, 4-fluorobenzoyl, 4-chlorobenzoyl, 4-nitrobenzoyl, 3,5-dichlorobenzoyl, 4-(N,N-diisopropylaminomethylene)benzoyl, 4-(N,N-diethylaminomethylene)benzoyl, 4-(1-piperidinylmethylene)benzoyl, 4-(N-morpholinylmethylene)benzoyl, 4-(N,N-dimethylaminomethylene)benzoyl, pentanoyl, (2-acetyloxy)benzoyl, phenylacetyl, formyl, butanoyl, methoxyacetyl, methoxycarbonylpropanoyl, carboxypropanoyl, carboxybutanoyl, ethoxycarbonylpropenoyl, ethoxycarbonylbutanoyl, benzyloxycarbonylpropanoyl, benzyloxycarbonylbutanoyl, N-(phenyl)aminocarbonyl, N-(benzyl)aminocarbonyl, 2-thienylcarbonyl; preferably:

(1i): either one of the substituents $R_1$ or $R_8$ represents a radical chosen from the list (L), preferably (L'), and still more preferably (L"), more particularly (L'"), and the other substituents $R_1$, $R_2$, $R_3$, $R_4$, $R_6$, $R_7$, $R_8$ represent a hydrogen atom;

(1ii): or the 2 substituents $R_1$ and $R_8$ each represent an identical radical chosen from the list (L), preferably (L'), and still more preferably (L"), more particularly (L'''), and the other substituents $R_2$, $R_3$, $R_4$, $R_6$, $R_7$ represent a hydrogen atom;

(1iii): or $R_1$, $R_2$, $R_3$, $R_4$, $R_6$, $R_7$, $R_8$ each represent an identical radical chosen from the list (L), preferably (L'), and still more preferably (L''), more particularly (L''');

(2) or $R_1$ and $R_2$ together form the group —CO—, and $R_3$, $R_4$, $R_6$, $R_7$, $R_8$ represent a hydrogen atom;

(3) or $R_7$ and $R_8$ together form the group —CO—, and $R_1$, $R_2$, $R_3$, $R_4$, $R_6$ represent a hydrogen atom;

(4) or $R_1$ and $R_2$, on the one hand, and $R_7$ and $R_8$, on the other hand, form in pairs the group —CO— and $R_3$, $R_4$, $R_6$ represent hydrogen atoms;

(5) or $R_1$ and $R_2$, $R_3$ and $R_4$, $R_7$ and $R_8$ form in pairs the group —CO— and $R_6$ represents a hydrogen atom.

By way of advantageous active ingredient according to the invention there may be mentioned in particular the compounds for which $R_1$, $R_2$, $R_3$, $R_4$, $R_6$, $R_7$, $R_8$ each represent an acetyl radical, or $R_1$, $R_2$, $R_3$, $R_4$, $R_6$, $R_7$, $R_8$ each represent a benzoyl radical, or $R_1$ and $R_8$ each represent a benzoyl radical, and the other substituents $R_2$, $R_3$, $R_4$, $R_6$, $R_7$ each represent a hydrogen atom.

B—compounds of general formula:

(VI)

for which:

(1) at least one of the substituents $R_1$, $R_2$, $R_3$, $R_4$, $R_5$, $R_6$, $R_7$, $R_8$ represents a radical chosen from the abovementioned list (L), and the other substituents $R_1$, $R_2$, $R_3$, $R_4$, $R_5$, $R_6$, $R_7$, $R_8$ represent a hydrogen atom; advantageously, the radicals of the list (L) may be chosen from the substituents of the abovementioned list (L');

among the substituents of the list (L'), the radicals chosen from the abovementioned list (L''), more particularly (L'''), are preferred in particular; preferably:

(1i): either one of the substituents $R_1$ or $R_8$ represents a radical chosen from the list (L), preferably (L'), and still more preferably (L''), more particularly (L'''), and the other substituents $R_1$, $R_2$, $R_3$, $R_4$, $R_5$, $R_6$, $R_7$, $R_8$ represent a hydrogen atom;

(1ii): or the 2 substituents $R_1$ and $R_8$ each represent an identical radical chosen from the list (L), preferably (L'), and still more preferably (L''), more particularly (L'''), and the other substituents $R_2$, $R_3$, $R_4$, $R_5$, $R_6$, $R_7$ represent a hydrogen atom;

(1iii) or $R_1$, $R_2$, $R_3$, $R_4$, $R_5$, $R_6$, $R_7$, $R_8$ each represent an identical radical chosen from the list (L), preferably (L'), and still more preferably (L''), more particularly (L''');

(2) or $R_1$ and $R_2$ together form the group —CO—, and $R_3$, $R_4$, $R_5$, $R_6$, $R_7$, $R_8$ represent a hydrogen atom;

(3) or $R_7$ and $R_8$ together form the group —CO—, and $R_1$, $R_2$, $R_3$, $R_4$, $R_5$, $R_6$ represent a hydrogen atom;

(4) or $R_1$ and $R_2$, on the one hand, and $R_7$ and $R_8$, on the other hand, form in pairs the group —CO— and $R_3$, $R_4$, $R_5$, $R_6$ represent hydrogen atoms;

(5) or $R_1$ and $R_2$, $R_3$ and $R_4$, $R_7$ and $R_8$ form in pairs the group —CO— and $R_5$, $R_6$ represents a hydrogen atom;

(6) or $R_1$ and $R_2$, $R_3$ and $R_4$, $R_5$ and $R_6$, $R_7$ and $R_8$ form in pairs the group —CO—.

By way of advantageous active ingredient according to the invention, there may be mentioned in particular the compounds for which $R_1$, $R_2$, $R_3$, $R_4$, $R_5$, $R_6$, $R_7$, $R_8$ each represent an acetyl radical, or $R_1$, $R_2$, $R_3$, $R_4$, $R_5$, $R_6$, $R_7$, $R_8$ each represent a benzoyl radical.

C—compounds of general formula (VII)

for which (1) at least one of the substituents $R_1$, $R_2$, $R_3$, $R_4$, $R_6$, $R_7$, $R_8$ represents a radical chosen from the abovementioned list (L), and the other substituents $R_1$, $R_2$, $R_3$, $R_4$, $R_6$, $R_7$, $R_8$ represent a hydrogen atom; advantageously, the radicals of the list (L) may be chosen from the substituents of the abovementioned list (L');

among the substitutents of the list (L'), the radicals chosen from the abovementioned list (L''), more particularly (L'''), are preferred in particular; preferably:

(1i): either one of the substituents $R_1$ or $R_8$ represents a radical chosen from the list (L), preferably (L') and still more preferably (L''), more particularly (L'''), and the other substituents $R_1$, $R_2$, $R_3$, $R_4$, $R_6$, $R_7$, $R_8$ represent a hydrogen atom;

(1ii): or the 2 substituents $R_1$ and $R_8$ each represent an identical radical chosen from the list (L), preferably (L'), and still more preferably (L''), more particularly (L'''), and the other substituents $R_2$, $R_3$, $R_4$, $R_6$, $R_7$ represent a hydrogen atom;

(1iii): or $R_1$, $R_2$, $R_3$, $R_4$, $R_6$, $R_7$, $R_8$ each represent an identical radical chosen from the list (L), preferably (L'), and still more preferably (L''), more particularly (L''');

(2) or $R_1$ and $R_2$ together form the group —CO—, and $R_3$, $R_4$, $R_6$, $R_7$, $R_8$ represent a hydrogen atom;

(3) or $R_7$ and $R_8$ together form the group —CO—, and $R_1$, $R_2$, $R_3$, $R_4$, $R_6$ represent a hydrogen atom;

(4) or $R_1$ and $R_2$, on the one hand, and $R_7$ and $R_8$, on the other hand, form in pairs the group —CO— and $R_3$, $R_4$, $R_6$ represent hydrogen atoms;

(5) or $R_1$ and $R_2$, $R_3$ and $R_4$, $R_7$ and $R_8$ form in pairs the group —CO— and $R_6$ represents a hydrogen atom;

advantageously, $R_1$ and $R_2$, $R_3$ and $R_4$, $R_7$ and $R_8$ form in pairs the group —CO— and $R_6$ represents a hydrogen atom; also advantageously, $R_1$ and $R_2$, $R_7$ and $R_8$ form in pairs the group —CO— and $R_3$, $R_4$, $R_6$ represent a hydrogen atom;

also advantageously, either $R_1$, $R_2$, $R_6$ or $R_4$, $R_6$ or $R_1$, $R_3$, $R_4$, $R_6$, $R_8$ or $R_2$, $R_3$, $R_4$, $R_6$ or $R_1$, $R_3$, $R_4$, $R_6$, $R_7$ or $R_2$, or $R_1$, $R_2$, $R_8$, or $R_1$, $R_2$, $R_6$, $R_7$, $R_8$ or $R_6$ represent a benzoyl radical and the other substituents $R_1$, $R_2$, $R_3$, $R_4$, $R_6$, $R_7$, $R_8$ represent a hydrogen atom;

also advantageously, $R_2$, $R_6$, $R_7$ represent a benzoyl radical and $R_3$, $R_4$ together form the radical —CO— and $R_1$, $R_8$ represent a hydrogen atom;

also advantageously, $R_8$ represents a pentanoyl or acetyl radical and the other substituents $R_1$, $R_2$, $R_3$, $R_4$, $R_6$, $R_7$ represent a hydrogen atom;

also advantageously, the 2 substituents $R_1$ and $R_8$ each represent an identical radical chosen from the radicals acetyl, 2,2-dimethylpropanoyl, benzoyl, 4-dimethylaminobenzoyl, 4-benzyloxyloxybenzoyl, 4-hydroxybenzoyl, 4-methoxybenzoyl, 4-methylbenzoyl, 3-methylbenzoyl, 4-fluorobenzoyl, 4-chlorobenzoyl, 4-nitrobenzoyl, 3,5-dichlorobenzoyl, 4-(N,N-diisopropylaminomethylene)benzoyl, 4-(N,N-diethylaminomethylene)benzoyl, 4-(1-piperidinylmethylene)benzoyl, 4-(N-morpholinylmethylene)benzoyl, 4-(N,N-dimethylaminomethylene)benzoyl, pentanoyl, (2-acetyloxy)-benzoyl, phenylacetyl, formyl, butanoyl, methoxyacetyl, methoxycarbonylpropanoyl, carboxypropanoyl, carboxybutanoyl, ethoxycarbonylpropenoyl, ethoxycarbonylbutanoyl, benzyloxycarbonylpropanoyl, benzyloxycarbonylbutanoyl, N-(phenyl) aminocarbonyl, N-(benzyl)aminocarbonyl, 2-thienylcarbonyl;

and the other substitutents $R_2$, $R_3$, $R_4$, $R_6$, $R_7$ represent a hydrogen atom;

also advantageously, $R_1$, $R_2$, $R_3$, $R_4$, $R_6$, $R_7$, $R_8$ each represent an identical radical chosen from the radicals benzoyl, acetyl, 2,2-dimethylpropanoyl, (2-acetyloxy) benzoyl, methoxyacetyl, pentanoyl, formyl, methoxycarbonylpropanoyl, carboxypropanoyl, ethoxycarbonylbutanoyl, carboxybutanoyl, ethoxycarbonylpropenoyl, benzyloxycarbonylpropanoyl, benzyloxybutanoyl;

still more preferably, the 2 substituents $R_1$ and $R_8$ each represent a benzoyl radical, and the other substituents $R_2$, $R_3$, $R_4$, $R_6$, $R_7$ each represent a hydrogen atom;

also preferably, $R_1$, $R_2$, $R_3$, $R_4$, $R_6$, $R_7$, $R_8$ each represent a benzoyl radical.

According to the invention, medicaments containing, as active ingredient, at least one compound of general formula (X) in which $R_1$, $R_2$, $R_3$, $R_4$, $R_6$, $R_7$, $R_8$ are as defined in general formula (X) are more particularly preferred.

The following compounds are known:
the derivative 1,2,2',3,3',4,4'-O,O,O,O,O,O,O-heptaacetyl-2-[(1R,2S,3R)(1,2,3,4-tetrahydroxybutyl)]-5-[(2'S,3'R) (2',3',4'-trihydroxybutyl)]pyrazine has been described in particular in Carbohydr. Res. 77, 213–217 (1979), Prog. Food Nutr. Sci. (1981), 5(1–6, Maillard React. Food), 37–45 and Agr. Biol. Chem. 37(11), 2571–2578, 1973:

the compound 1,1',2,2',3,3',4,4'-O,O,O,O,O,O,O,O-octaacetyl-2-[(1R,2S,3R)(1,2,3,4-tetrahydroxybutyl)]-5-[(1'R,2'S,3'R) (1',2',3',4'-tetrahydroxybutyl)]pyrazine has been described by AVALOS et al., Tetrahedron, 49, 2655–2675 (1993)

the compound 1,1',2,2',3,3',4,4'-O,O,O,O,O,O,O,O-octabenzoyl-2-[(1R,2S,3R)(1,2,3,4-tetrahydroxybutyl)]-5-[(1'R,2'S,3'R)(1',2',3',4'-tetrahydroxybutyl)]pyrazine is also known (M.I. TAHA J. Chem. Soc. 2468–2472, 1961)

the compound 1,2,2',3,3',4,4'-O,O,O,O,O,O,O-heptaacetyl-2-[(1R,2S,3R)(1,2,3,4-tetrahydroxybutyl)]-6-[(2'S,3'R)(2',3',4'-trihydroxybutyl)]pyrazine is described in Agr. Biol. Chem. 37(11), 2571–2578, 1973 and Carbohyd. Res. 23(11), 111–119, 1972;

the compound 1,2,2',3,3',4,4'-O,O,O,O,O,O,O-heptaacetyl-2-[(1R,2S,3S)(1,2,3,4-tetrahydroxybutyl)]-6-[(2'S,3'S)(2',3',4'-trihydroxybutyl)]pyrazine has been described in Carbohydr. Res. 26(2), 377–384, 1973.

However, no biological activity relating to these derivatives has so far been discovered.

Another subject of the present invention therefore also relates to the compounds of general formula (I), with the exception of 1,2,2',3,3',4,4'-O,O,O,O,O,O,O-heptaacetyl-2-[(1R,2S,3R)(1,2,3,4-tetrahydroxybutyl)]-5-[(2'S,3'R)(2',3', 4'-trihydroxybutyl)]pyrazine, 1,1,2,2',3,3',4,4'-O,O,O,O,O, O,O,O-octaacetyl- 2-[(1R,2S,3R)(1,2,3,4-tetrahydroxybutyl)]-5-[(1'R,2'S,3'R)(1',2',3',4'-tetrahydroxybutyl)]pyrazine, 1,1',2,2',3,3',4,4'-O,O,O,O,O, O,O-octabenzoyl-2-[(1R,2S,3R)(1,2,3,4-tetrahydroxybutyl)]-5-[(1'R,2'S,3'R)(1',2',3',4'-tetrahydroxybutyl)]pyrazine 1,2,2',3,3',4,4'-O,O,O,O,O,O,O-heptaacetyl-2-[(1R,2S,3R)(1,2,3,4-tetrahydroxybutyl)]-6-[(2'S,3'R)(2',3',4'-trihydroxybutyl)]pyrazine 1,2,2',3,3',4, 4'-O,O,O,O,O,O,O-heptaacetyl-2-[(1R,2S,3S)(1,2,3,4-tetrahydroxybutyl)]-6-[(2'S,3'S)(2',3',4'-trihydroxybutyl)] pyrazine The compounds of general formula (I) which are particularly representative according to the invention are in particular:

A—compounds of general formula:

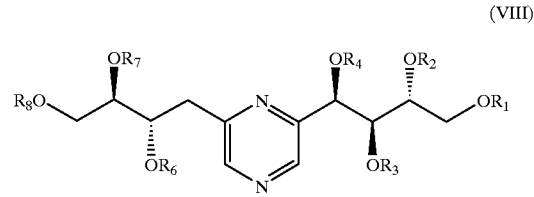

(VIII)

for which
(1) at least one of the substituents $R_1$, $R_2$, $R_3$, $R_4$, $R_6$, $R_7$, $R_8$ represents a radical chosen from the abovementioned list (L), and the other substituents $R_1$, $R_2$, $R_3$, $R_4$, $R_6$, $R_7$, $R_8$ represent a hydrogen atom; advantageously, the radicals of the list (L) may be chosen from the substituents of the abovementioned list (L);

among the substituents of the list (L'), the radicals chosen from the abovementioned list (L"), more particularly (L'''), are preferred in particular; preferably:
(1i) either one of the substituents $R_1$ or $R_8$ represents a radical chosen from the list (L), preferably (L'), and still more preferably (L"), more particularly (L'''), and the other substituents $R_1$, $R_2$, $R_3$, $R_4$, $R_6$, $R_7$, $R_8$ represent a hydrogen atom
(1ii) or the 2 substituents $R_1$ and $R_8$ each represent an identical radical chosen from the list (L), preferably (L'), and still more preferably (L"), more particularly (L'''), and the other substituents $R_2$, $R_3$, $R_4$, $R_6$, $R_7$ represent a hydrogen atom
(1iii) or $R_1$, $R_2$, $R_3$, $R_4$, $R_6$, $R_7$, $R_8$ each represent an identical radical chosen from the list (L), preferably (L'), and still more preferably (L"), more particularly (L''');
(2) or $R_1$ and $R_2$ together form the —CO—, cyclohexyl or cyclopentyl group and $R_3$, $R_4$, $R_6$, $R_7$, $R_8$ represent a hydrogen atom;

(3) or $R_7$ and $R_8$ together form the —CO—, cyclohexyl or cyclopentyl group and $R_1$, $R_2$, $R_3$, $R_4$, $R_6$ represent a hydrogen atom;

(4) $R_1$ and $R_2$, on the one hand, and $R_7$ and $R_8$, on the otter hand, form in pairs the group —CO— and $R_3$, $R_4$, $R_6$ represent hydrogen atoms;

(5) or $R_1$ and $R_2$, $R_3$ and $R_4$, $R_7$ and $R_8$ form in pairs the group —CO— and $R_6$ represents a hydrogen atom; with the exception of:

1,2, 2'3,3',4,4'-O,O,O,O,O,O,O-heptaacetyl-2-[(1R,2S,3R)(1,2,3,4-tetrahydroxybutyl)]-6-[(2'S,3'R)(2',3',4'-trihydroxybutyl)]pyrazine 1,2,2',3,3',4,4'-O,O,O,O,O,O,O-heptaacetyl-2-[(1R,2S,3S)(1,2,3,4-tetrahydroxybutyl)]-6-[(2'S,3'S)(2',3',4'-trihydroxybutyl)]pyrazine.

The advantageous compounds according to the invention are in particular those for which $R_1$, $R_2$, $R_3$, $R_4$, $R_6$, $R_7$, $R_8$ each represent a benzoyl radical, or $R_1$ and $R_8$ each represent a benzoyl radical, and the other substituents $R_2$, $R_3$, $R_4$, $R_6$, $R_7$ each represent a hydrogen atom.

B—compounds of the general formula:

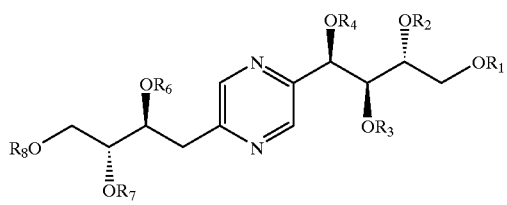

(IX)

for which:

(1) at least one of the substituents $R_1$, $R_2$, $R_3$, $R_4$, $R_5$, $R_6$, $R_7$, $R_8$ represents a radical chosen from the abovementioned list (L), and the other substituents $R_1$, $R_2$, $R_3$, $R_4$, $R_5$, $R_6$, $R_7$, $R_8$ represent a hydrogen atom;

advantageously, the radicals of the list (L) may be chosen from the substituents of the abovementioned list (L');

among the substituents of the list (L'), the radicals chosen from the abovementioned list (L"), more particularly (L'"), are preferred in particular; preferably:

(1i): either one of the substituents $R_1$ or $R_8$ represents a radical chosen from the list (L), preferably (L'), and still more preferably (L"), more particularly (L'"), and the other substituents $R_1$, $R_2$, $R_3$, $R_4$, $R_5$, $R_6$, $R_7$, $R_8$ respresent a hydrogen atom;

(1ii): or the 2 substituents $R_1$ and $R_8$ each represent an identical radical chosen from the list (L), preferably (L'), and still more preferably (L"), more particularly (L'"), and the other substituents $R_2$, $R_3$, $R_4$, $R_5$, $R_6$, $R_7$ represent a hydrogen atom;

(1iii): or $R_1$, $R_2$, $R_3$, $R_4$, $R_5$, $R_6$, $R_7$, $R_8$ each represent an identical radical chosen from the list (L), preferably (L'), and still more preferably (L"), more particularly (L'");

(2) or $R_1$ and $R_2$ together form the group —CO—, and $R_3$, $R_4$, $R_5$, $R_6$, $R_7$, $R_8$ represent a hydrogen atem;

(3) or $R_7$ and $R_8$ together form the group —CO—, and $R_1$, $R_2$, $R_3$, $R_4$, $R_5$, $R_6$ represent a hydrogen atom;

(4) or $R_1$ and $R_2$, on the one hand, and $R_7$ and $R_8$, on the other hand, form in pairs the group —CO— and $R_3$, $R_4$, $R_5$, $R_6$ represent hydrogen atoms;

(5) or $R_1$ and $R_2$, $R_3$ and $R_4$, $R_7$ and $R_8$ form in pairs the group —CO— and $R_5$, $R_6$ represents a hydrogen atom;

(6) or $R_1$ and $R_2$, $R_3$ and $R_4$, $R_5$ and $R_6$, $R_7$ and $R_8$ form in pairs the group —CO— with the exception of 1,1',2,2',3,3',4,4'-O,O,O,O,O,O,O,O-octaacetyl-2-[(1R,2S,3R)(1,2,3,4-tetrahydroxybutyl)]-5-[(1'R,2'S,3'R)(1',2',3',4'-tetrahydroxybutyl)]pyrazine, 1,1',2,2',3,3',4,4'-O,O,O,O,O,O,O,O,-octabenzoyl-2-[(1R,2S,3R)(1,2,3,4-tetrahydroxybutyl)]-5-[(1'R,2'S,3'R)(1',2',3',4'-tetrahydroxybutyl)]pyrazine C—compounds of general formula

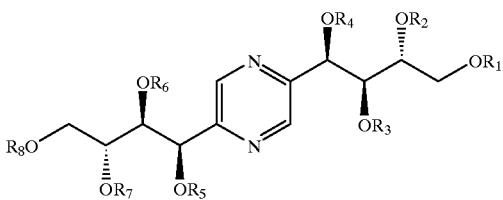

(X)

for which (1) at least one of the substituents $R_1$, $R_2$, $R_3$, $R_4$, $R_6$, $R_7$, $R_8$ represents a radical chosen from the abovementioned list (L), and the other substituents $R_1$, $R_2$, $R_3$, $R_4$, $R_6$, $R_7$, $R_8$ represent a hydrogen atom;

advantageously, the radicals of the list (L) may be chosen from the substituents of the abovementioned list among the substituents of the list (L'), the radicals chosen from the abovementioned list (L"), more particularly (L'"), are preferred in particular; preferably:

(1i): either one of the substituents $R_1$ or $R_8$ represents a radical chosen from the list (L), preferably (L'), and still more preferably (L"), more particularly (L'"), and the other substituents $R_1$, $R_2$, $R_3$, $R_4$, $R_6$, $R_7$, $R_8$ respresent a hydrogen atom;

(1ii): or the 2 substituents $R_1$ and $R_8$ each represent an identical radical chosen from the list (L), preferably (L'), and still more preferably (L"), more particularly (L'"), and the other substituents $R_2$, $R_3$, $R_4$, $R_6$, $R_7$ represent a hydrogen atom;

(1iii): or $R_1$, $R_2$, $R_3$, $R_4$, $R_6$, $R_7$, $R_8$ each represent an identical radical chosen from the list (L), preferably (L') and still more preferably (L"), more particularly (L'");

(2) or $R_1$ and $R_2$ together form the group —CO—, and $R_3$, $R_4$, $R_6$, $R_7$, $R_8$ represent a hydrogen atom;

(3) or $R_7$ and $R_8$ together form the group —CO—, and $R_1$, $R_2$, $R_3$, $R_4$, $R_6$ represent a hydrogen atom;

(4) or $R_1$ and $R_2$, on the one hand, and $R_7$ and $R_8$, on the other hand, form in pairs the group —CO— and $R_3$, $R_4$, $R_6$ represent hydrogen atoms;

(5) or $R_1$ and $R_2$, $R_3$ and $R_4$, $R_7$ and $R_8$ form in pairs the group —CO— and $R_6$ represents a hydrogen atom;

with the exception of 1,2,2',3,3',4,4'-O,O,O,O,O,O,O,-heptaacetyl-2-[(1R,2S,3R)(1,2,3,4-tetrahydroxybutyl)]-5-[(2'S,3'R)(2',3',4'-trihydroxybutyl)]pyrazine, advantageously, $R_1$ and $R_2$, $R_3$ and $R_4$, $R_7$ and $R_8$ form in pairs the group —CO— and $R_6$ represents a hydrogen atom;

also advantageously, $R_1$ and $R_2$, $R_7$ and $R_8$ form in pairs the group —CO— and $R_3$, $R_4$, $R_6$ represent a hydrogen atom;

also advantageously, either $R_1$, $R_2$, $R_6$ or $R_4$, $R_6$ or $R_1$, $R_3$, $R_4$, $R_6$, $R_8$ or $R_2$, $R_3$, $R_4$, $R_6$, or $R_1$, $R_3$, $R_4$, $R_6$, $R_7$ or $R_2$, or $R_1$, $R_2$, $R_8$, or $R_1$, $R_2$, $R_6$, $R_7$, $R_8$ or $R_6$ represent a benzoyl radical and the other substituents $R_1$, $R_2$, $R_3$, $R_4$, $R_6$, $R_7$, $R_8$ represent a hydrogen atom;

also advantageously, $R_2$, $R_6$, $R_7$ represent a benzoyl radical and $R_3$, $R_4$ together form the radical —CO— and $R_1$, $R_8$ represent a hydrogen atom;

also advantageously, $R_8$ represents a pentanoyl or acetyl radical and the other substituents $R_1$, $R_2$, $R_3$, $R_4$, $R_6$, $R_7$ represent a hydrogen atom;

also advantageously, the 2 substituents $R_1$ and $R_8$ each represent an identical radical chosen from the radicals acetyl, 2,2-dimethylpropanoyl, benzoyl, 4-dimethylaminobenzoyl, 4-benzyloxyloxybenzoyl, 4-hydroxybenzoyl, 4-methoxybenzoyl, 4-methylbenzoyl, 3-methylbenzoyl, 4-fluorobenzoyl, 4-chlorobenzoyl, 4-nitrobenzoyl, 3,5-dichlorobenzoyl, 4-(N,N-diisopropylaminomethylene)benzoyl, 4-(N,N-diethylaminomethylene)benzoyl, 4-(1-piperidinylmethylene)benzoyl, 4-(N-morpholinylmethylene)benzoyl, 4-(N,N-dimethylaminomethylene)benzoyl, pentanoyl, (2-acetyloxy))-benzoyl, phenylacetyl, formyl, butanoyl, methoxyacetyl, methoxycarbonylpropanoyl, carboxypropanoyl, carboxybutanoyl, ethoxycarbonylpropenoyl, ethoxycarbonylbutanoyl, benzyloxycarbonylpropanoyl, benzyloxycarbonylbutanoyl, N-(phenyl)aminocarbonyl, N-(benzyl)aminocarbonyl, 2-thienylcarbonyl;

and the other substituents $R_2$, $R_3$, $R_4$, $R_6$, $R_7$ represent a hydrogen atom;

also advantageously, $R_1$, $R_2$, $R_3$, $R_4$, $R_6$, $R_7$, $R_8$ each represent an identical radical chosen from the radicals benzoyl, 2,2-dimethylpropanoyl, (2-acetyloxy)benzoyl, methoxyacetyl, pentanoyl, formyl, methoxycarbonylpropanoyl, carboxypropanoyl, ethoxycarbonylbutanoyl, carboxybutanoyl, ethoxycarbonylpropenoyl, benzyloxycarbonylpropanoyl, benzyloxybutanoyl;

still more preferably, the 2 substituents $R_1$ and $R_8$ each represent a benzoyl radical, and the other substituents $R_2$, $R_3$, $R_4$, $R_6$, $R_7$ each represent a hydrogen atom;

also preferably, $R_1$, $R_2$, $R_3$, $R_4$, $R_6$, $R_7$, $R_8$ each represent a benzoyl radical.

According to the invention, the compounds of formula (X) in which $R_1$, $R_2$, $R_3$, $R_4$, $R_6$, $R_7$, $R_8$ are as defined in general formula (X) are preferred as compounds.

According to the invention, the process of preparation may be carried out in the following manner: The compounds of general formula (V), (VI), (VII), may be obtained respectively by reacting the compounds of formula (XI), resp. (XII), (XIII):

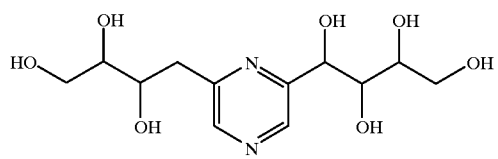
(XI)

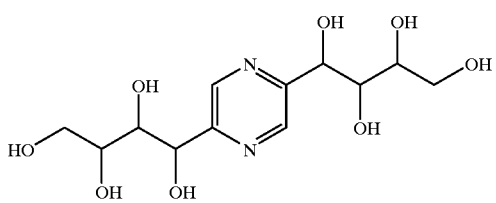
(XII)

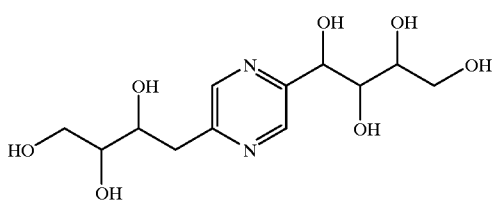
(XIII)

for which the hydroxyl functional groups —OH are optionally protected with protecting groups, either with a compound of formula R—X (XIV) in which R preferably represents the groups —$COR_9$, —$COOR_{10}$, —$CR_{11}R_{12}OCOR_{13}$, —$CR_{11}R_{12}OR_{13}$, —$CONR_{14}R_{15}$ and X represents a halogen atom, preferably chlorine or bromine or with a compound of formula $(R_9CO)_2O$ (XV)

or with a compound of formula $R_{14}N=C=O$ (XVI)

or with a compound of formula $CR_{11}R_{12}(OR_{13})_2$ (XVII), optionally followed by complete deprotection, or optionally followed by selective deprotection and by one or more other functionalizations with the aid of one of the reagents of formula (XIV), (XV), (XVI), (XVII) which are identical to or different from the first, it being possible to repeat the functionalization and deprotection steps several times, it being understood that the reagents of formula (XIV), (XV), (XVI) and (XVII) may be identical or different on each functionalization.

The functionalization reactions are carried out on one or more unprotected hydroxyl groups of the compounds of formula (XI), (XII), (XIII) and consist in the introduction of one or more identical or different substituents $R_1$, $R_2$, $R_3$, $R_4$, $R_5$, $R_6$, $R_7$, $R_8$ which represent one or more of the functional groups of the —$COR_9$, —$COOR_{10}$, —$CR_{11}R_{12}OCOR_{13}$, —$CR_{11}R_{12}OR_{13}$, or —(CO)—$NR_{14}R_{15}$ type. These reactions may be carried out according to any known methods of functionalization of hydroxyl functional groups and more particularly and without limitation, the procedure will be preferably carried out, unless otherwise stated, under the following conditions:

in aprotic polar solvents, aliphatic or aromatic ethers, nitrites, halogenated solvents or two-phase media; the preferred solvents are in particular pyridine, tetrahydrofuran (THF), diethyl ether, dioxane, glyme, dimethylformamide (DMF), dimethyl sulphoxide (DMSO);

in basic medium, in the presence of an organic or inorganic base of the aliphatic or aromatic amine type and preferably triethylamine or pyridine, an amide, alkyllithium compounds, alkali metal carbonates, for example potassium carbonate ($K_2CO_3$), alkali metal hydroxides, alkali metal alkoxides, alkali metal hydrides and more particularly sodium hydride (NaH), or alternatively 1,8-diazabicyclo[5.4.0]undec-7-ene (DBU);

at a temperature of between −78° C. and +100° C.

It is possible in particular to introduce the functional groups ester of the —COR$_9$ type (a),
by the action of a reagent R$_9$COX,
by the action of an anhydride of formula (R$_9$CO)$_2$O According to the invention, the procedure will be preferably carried out more particularly by the action of acyl chloride in pyridine.

carbonate of the —COOR$_{10}$ type (b),
by the action of a compound of formula R$_{10}$OCOX, optionally followed by cyclization in a basic medium to obtain the corresponding carbonate of the cyclic type (f) for which the group —C(O)— links two adjacent oxygen atoms.

The alkyl carbonates obtained with the corresponding alkyl chloroformate in the presence of pyridine are of a most special advantage.

ether
of the —CR$_{11}$R$_{12}$OCOR$_{13}$ type (c),
by the action of a reagent of formula R$_{13}$OCOR$_{11}$R$_{12}$X or
of the —CR$_{11}$R$_{12}$OR$_{13}$ type (d),
by reacting R$_{13}$OCR$_{11}$R$_{12}$X or by the action of CR$_{11}$R$_{12}$(OR$_{13}$)$_2$ in acidic medium. A reagent which is particularly used is of the chloromethylalkyl ether type and the acid used may be any organic or inorganic acid such as methanesulphonic acid, para-toluenesulphonic acid (PTSA), camphorsulphonic acid (CSA), pyridinium p-toluenesulphonate (PPTS), sulphuric acid (H$_2$SO$_4$) or hydrochloric acid (HCl).

carbamate of the —CONR$_{14}$R$_{15}$ type (e),
by the action of R$_{14}$R$_{15}$NCOX or R$_{14}$-N=C=O when R$_{15}$ represents a hydrogen atom;
it being understood that the quantities of reagent used depend on the nature and the number of functionalizations desired.

It is also possible, depending on the operating conditions used, that the functional groups of secondary alcohols migrate to the deprotected primary alcohols (transesterification).

The reagents of formula (XIV), (XV), (XVI) and (XVII) are either commercially available or may be synthesized by application or adaptation of known methods of preparation, such as for example the methods described by J. March, Advanced Organic Chemistry, 4th edition, 1992, J. Wiley (p. 365, 400–401, 405, 437, 1053, 1290, 1294).

The expression "the groups for protecting hydroxyl functional groups" relates to any groups which, depending on the reaction for which they are used, may be removed without affecting the rest of the molecule. In particular, the protecting groups and their use in the process according to the invention are, without limitation, those described by T. W. Greene, Protective Groups in Organic Synthesis, J. Wiley, Interscience publications (1991) and P. J. Kocienski, Protecting groups, Georg Thieme Verlag, 1994.

Preferably, the following protecting groups and procedures will be used:

the alkylene, aralkylene or diarylmethylene groups which form with the carbon atoms and the oxygen atoms to which they are attached a heterocycle preferably containing 5 to 7 members, including 2 oxygen atoms. The cyclic protections of the cyclic acetal or ketal type of formula

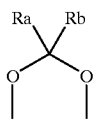

are most particularly preferred according to the invention and may be introduced in the following manner:

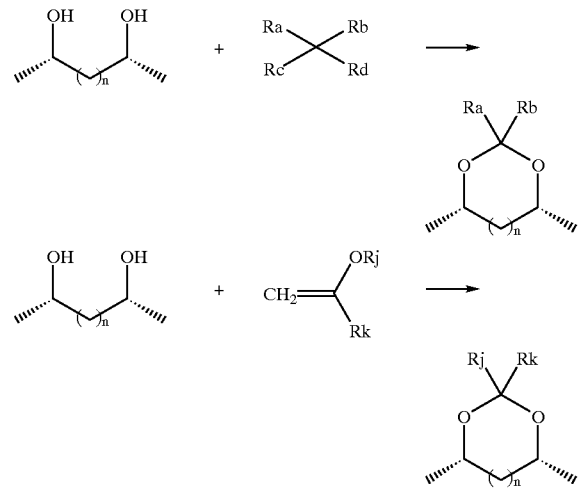

where Ra, Rb are identical or different and independently represent either a hydrogen atom, an optionally substituted alkyl radical such as methyl or ethyl, or an alkyloxy radical, or Ra and Rb form with the carbon to which they are attached a ring of 4 to 7 carbon atoms;

Rc, Rd, which are identical or different, represent an alkyloxy radical or together form with the carbon to which they are attached a carbonyl group —CO—; the reagents such as acetone, 3-pentanone or alternatively cyclopentanone and cyclohexanone are of a most special advantage; an activating agent such as trialkyl orthoformate, and in particular triethyl orthoformate, may be optionally used;

Rj represents an alkyl radical, preferably methyl;

Rk represents a hydrogen atom or an alkyl radical, and in particular methyl; the index n is equal to 0 or 1. This reaction is carried out by acid catalysis, for example in the presence of PPTS, in a suitably chosen solvent, such as ketones, and acetone in particular, THF, dichloromethane, toluene, chloroform, at a temperature between −20° C. and the reflux temperature of the medium used.

This type of acetonide protection may be particularly used to form a simultaneous protection of the hydroxyl groups at the 1-2, 1-3, 2-3, 2-4, 3-4, 1'-2', 1'-3', 2'-3', 2'-4', 3'-4'— which are silylic according to the reaction:

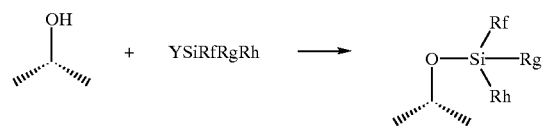

where Rf, Rg, Rh, which are identical or different, are alkyl or aryl and Y represents a halogen atom, in particular the chlorine atom, or a sulphonate group such as trifluoromethanesulphonate. The silylation reaction is carried out at a temperature of between −78° C. and 100° C. in a basic medium.

The silylated protecting groups —SiRfRgRh preferably used are trialkylsilyl, alkyldiphenylsilyl or dialkylphenylsilyl radicals, and preferably trimethylsilyl, tert-butyl (diphenyl)silyl (TBDPS), t-butyl (dimethyl) silyl (TBDMS) and dimethylphenylsilyl radicals.

ethers made with a reagent of formula ReZ, where Re represents 2-trimethylsilylethyl, alkyloxymethyl or aralkyl radicals, preferably the benzyl radical, and Z represents a halogen atom, and in particular a chlorine or bromine atom. Preferably, NaH or NaI will be used as base, in DMF. Optionally, the procedure may be carried out in the presence of an activating agent such as an alkali metal iodide, preferably NaI or an ammonium iodide.

Also, another protection of the ether type may be made with heterocyclic groups, of which a particularly representative example is tetrahydropyran (THP), according to the reaction:

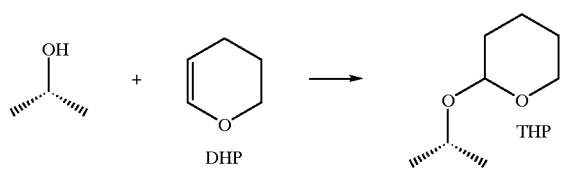

This reaction is preferably carried out in dichloromethane in the presence of PPTS.

carbonates either of the —OCORi type, where Ri represents an alkyl radical, an aryl radical, for example phenyl, or an aralkyl radical such as preferably benzyl, optionally substituted, or of the cyclic type such as

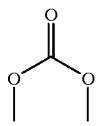

it being possible for these protections to be obtained in particular according to the sequence

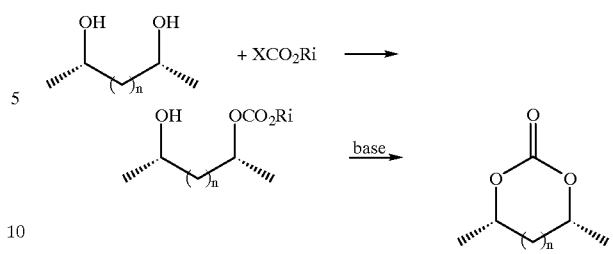

where n is as defined above;

by grafting onto a polymer terminal alcohol radicals according to the method described by J. Y. Wong and C. C. Leznoff, Can. J. Chem., 51, 2452 (1973).

The deprotection steps are carried out on the optionally protected hydroxyl groups of the compounds of formula (XI), (XII), (XIII), that is to say the OH groups for which one or more substituents $R_1$, $R_2$, $R_3$, $R_4$, $R_5$, $R_6$, $R_7$, $R_8$, which are identical or different, represent identical or different groups for protecting hydroxyl radicals. These reactions may be carried out according to the customary methods known to persons skilled in the art. In particular, it will be possible to use the methods cited by T. W. Greene, Protective Groups in Organic Synthesis, J. Wiley, Interscience publications (1991) and P. J. Kocienski, Protecting groups, Georg Thieme Verlag, 1994. Depending on the protecting groups used in the intermediates of formula (XI), (XII), (XIII), it will be possible to use preferably either organic or inorganic bases, or organic or inorganic acids or derivatives thereof, such as acetic acid, trifluoroacetic acid, hydroflu-oric acid or alternatively hydrochloric acid in aqueous or organic solution in catalytic or stoichiometric quantities or in excess, either in the presence of fluoride ions $F^-$, in the form of tetrabutylammonium fluoride, or catalytic hydrogenation on Pd/C for example, or alternatively reduction, preferably with $NaBH_4$.

The following reaction schemes illustrate the methods of preparing the intermediates used according to the invention preferentially and without limitation; they do not give an exhaustive view thereof and are, given only as examples.

SCHEME 1

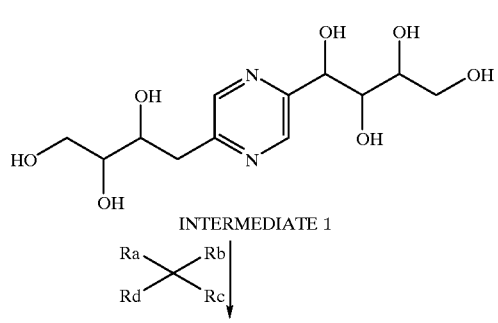

INTERMEDIATE 1

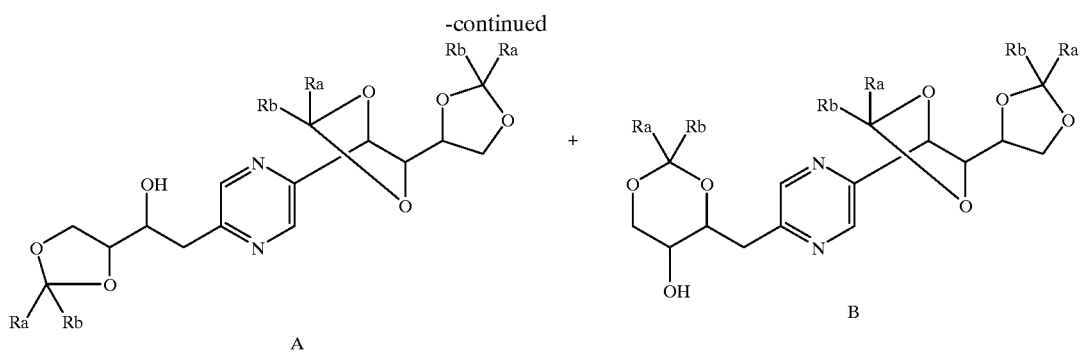
SCHEME 2
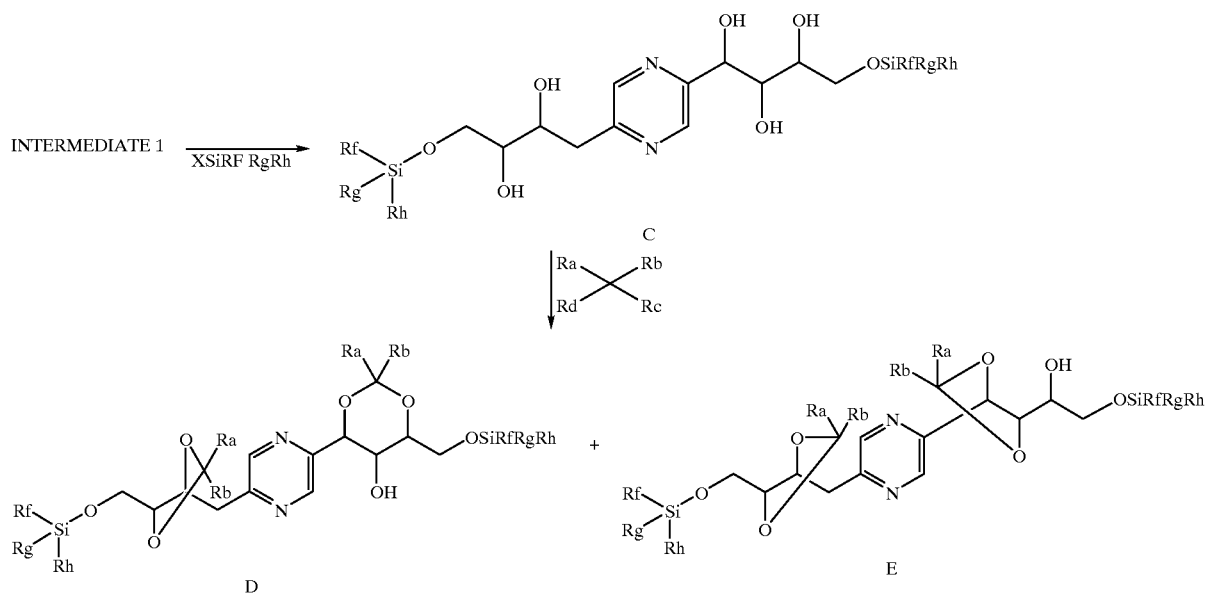
SCHEME 3
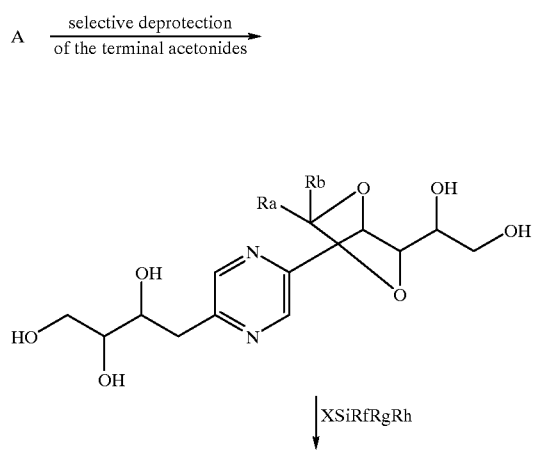
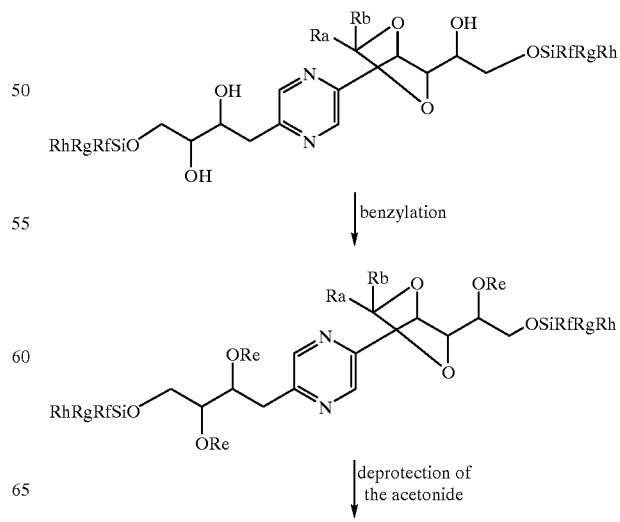

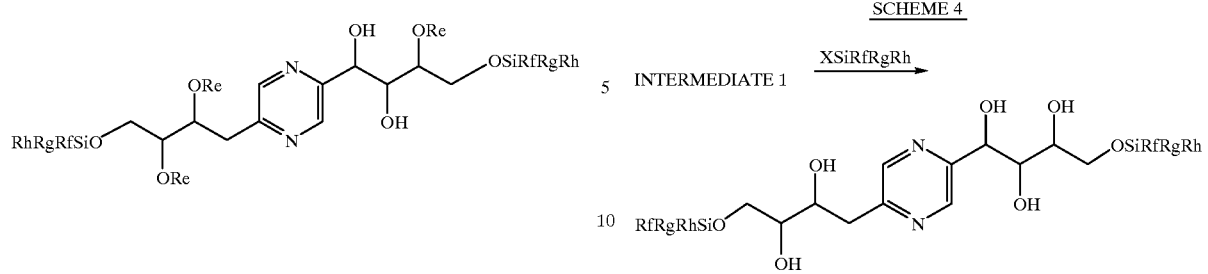
SCHEME 4
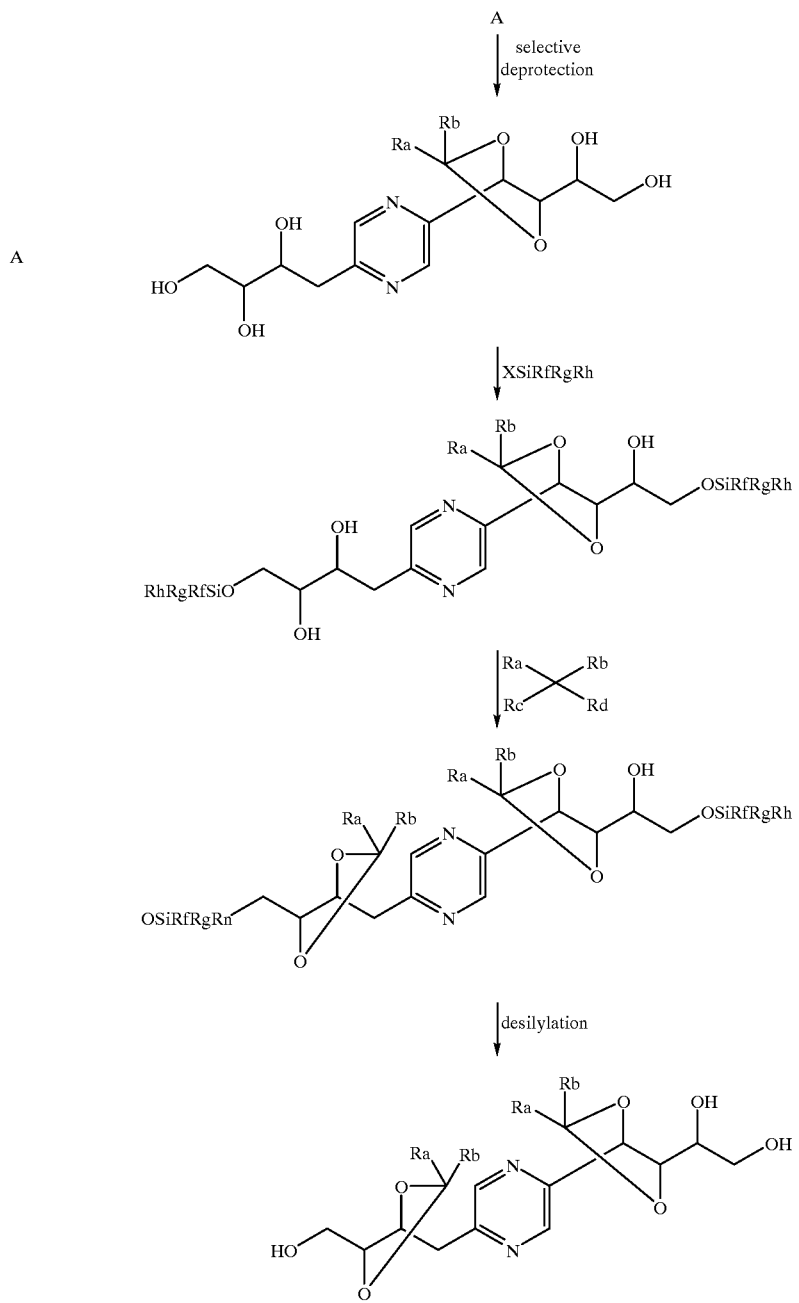
SCHEME 5

-continued
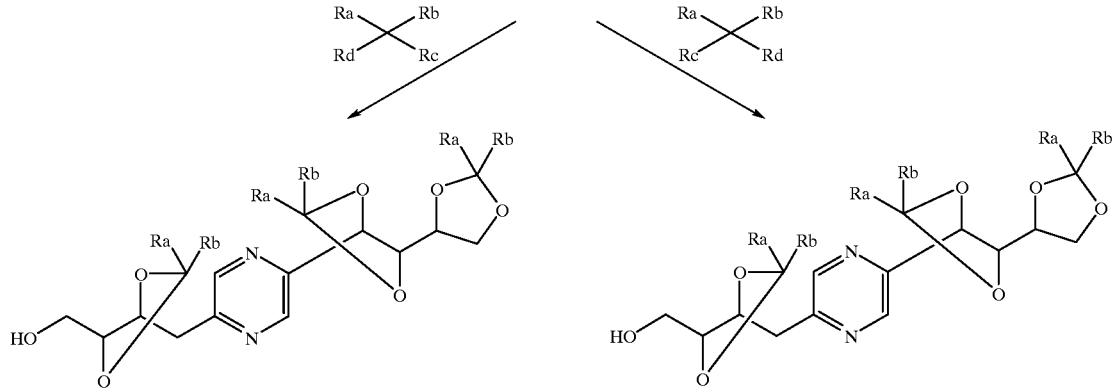
SCHEME 6
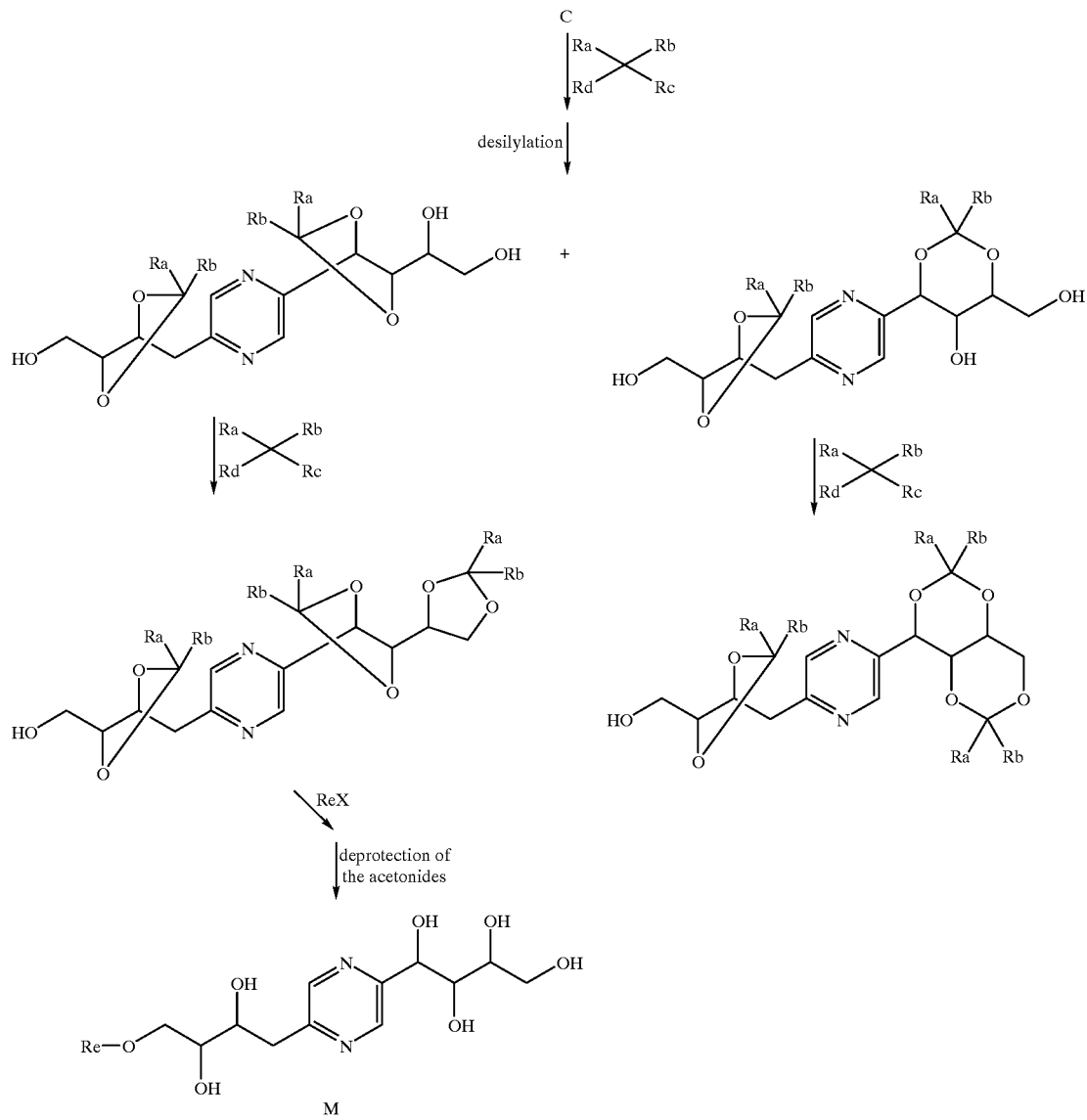

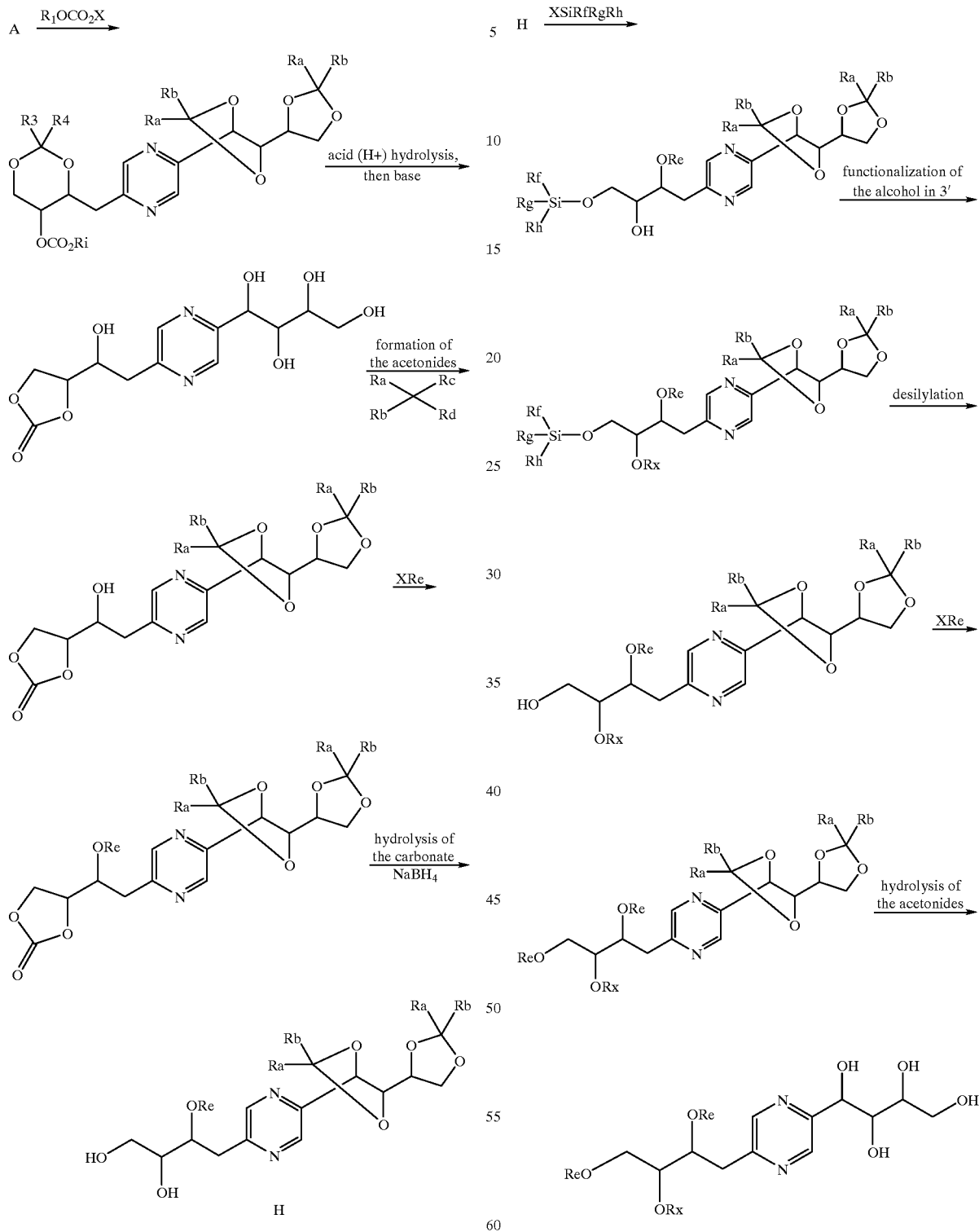

SCHEME 9
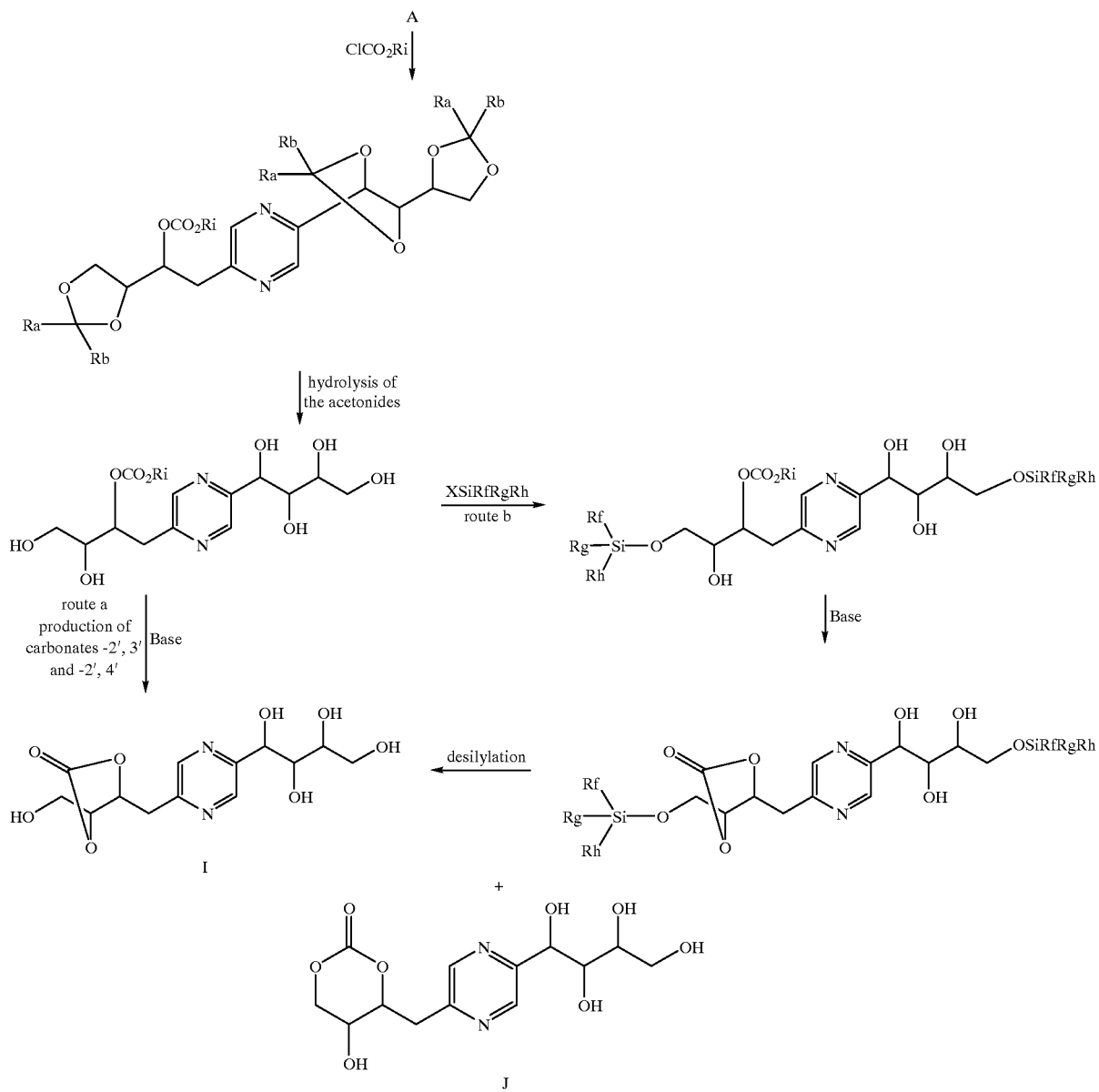
SCHEME 10
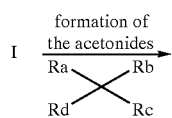
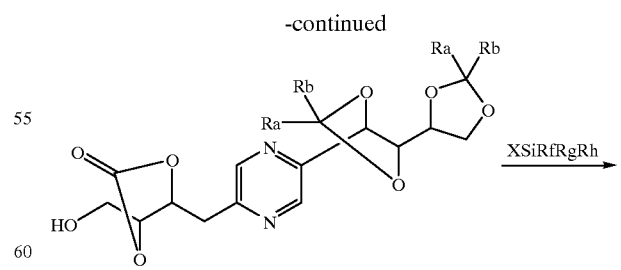

33
-continued
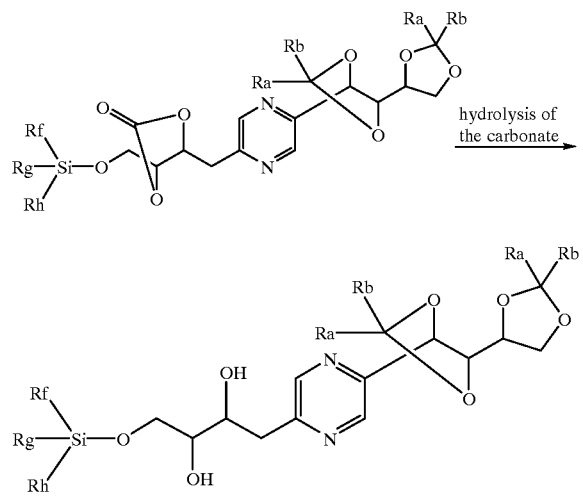
hydrolysis of the carbonate →
34
-continued
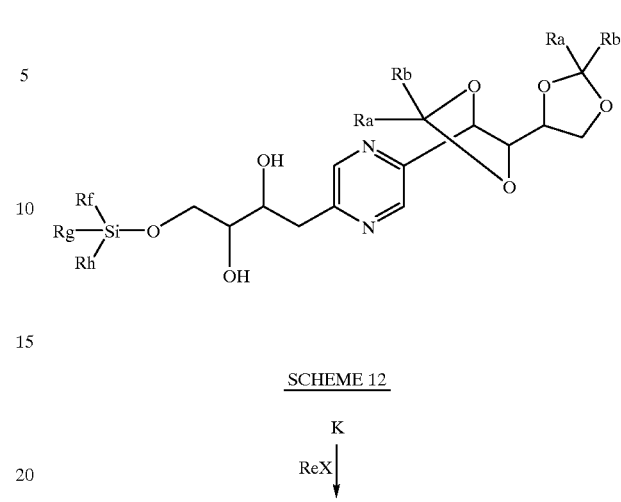
SCHEME 12
SCHEME 11
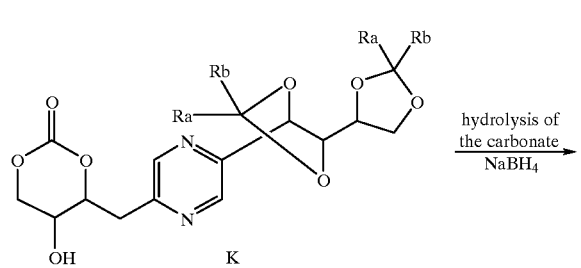
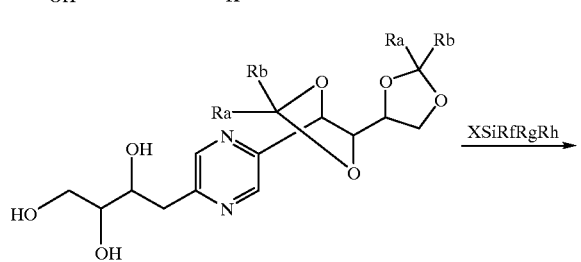
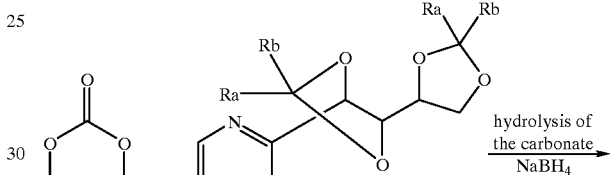
hydrolysis of the carbonate NaBH₄ →
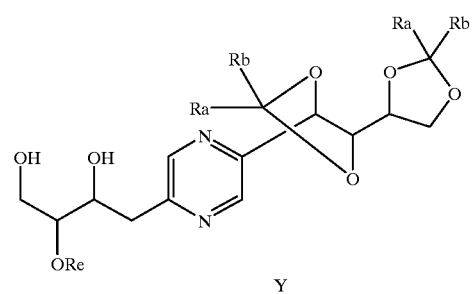
SCHEME 13
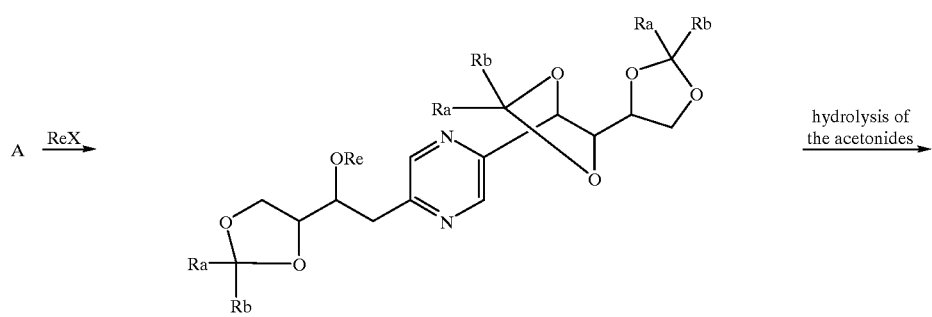
hydrolysis of the acetonides →

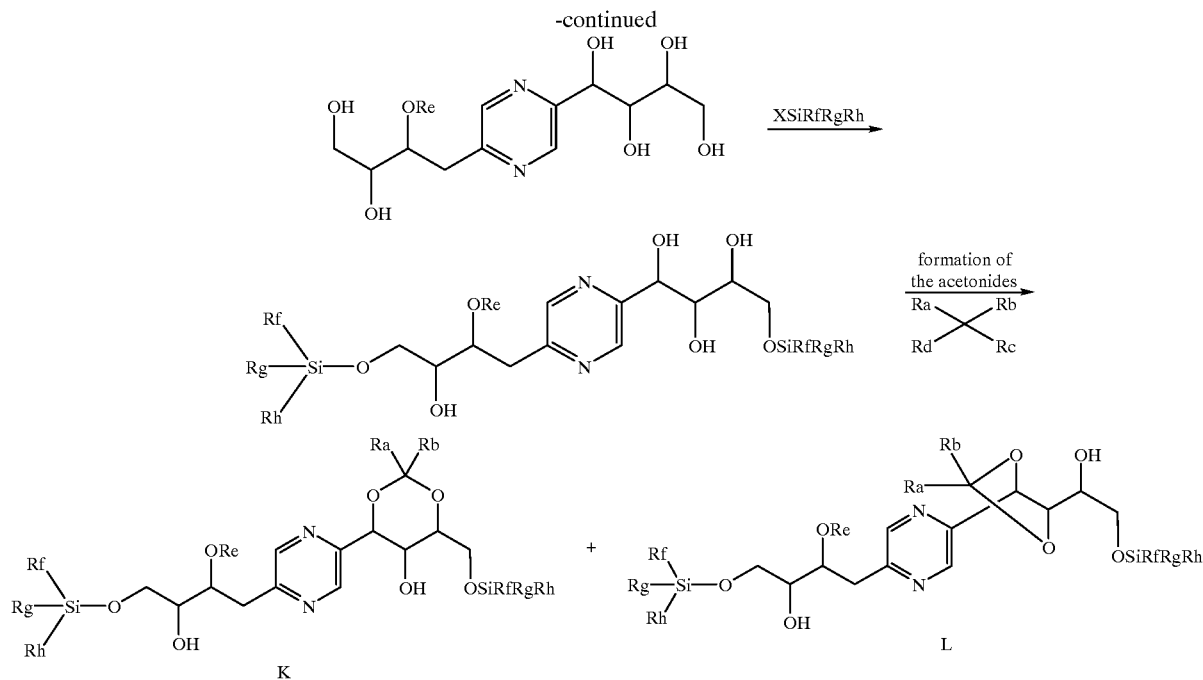
SCHEME 14
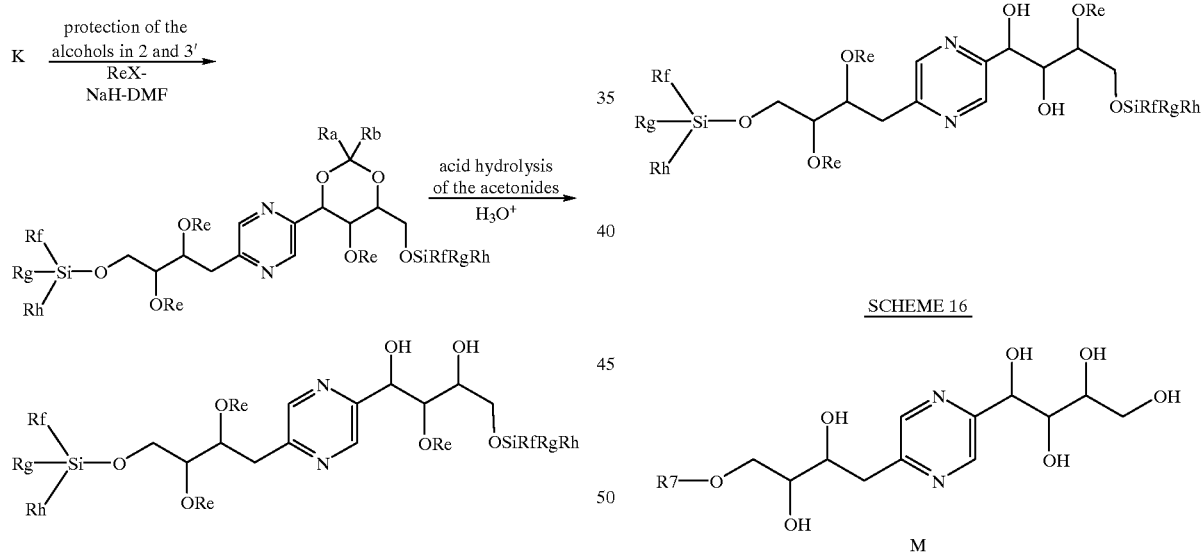
SCHEME 15
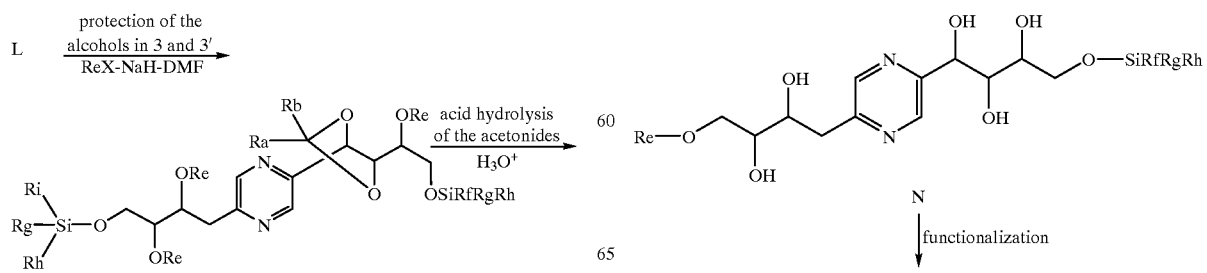
SCHEME 16

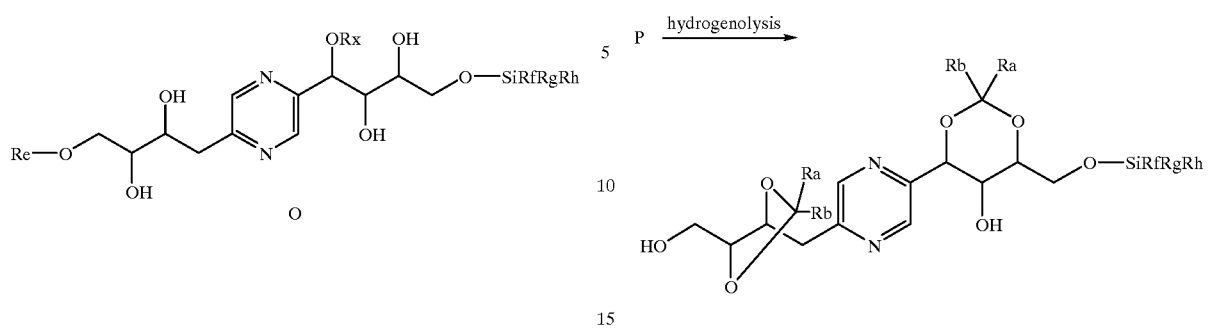
SCHEME 17
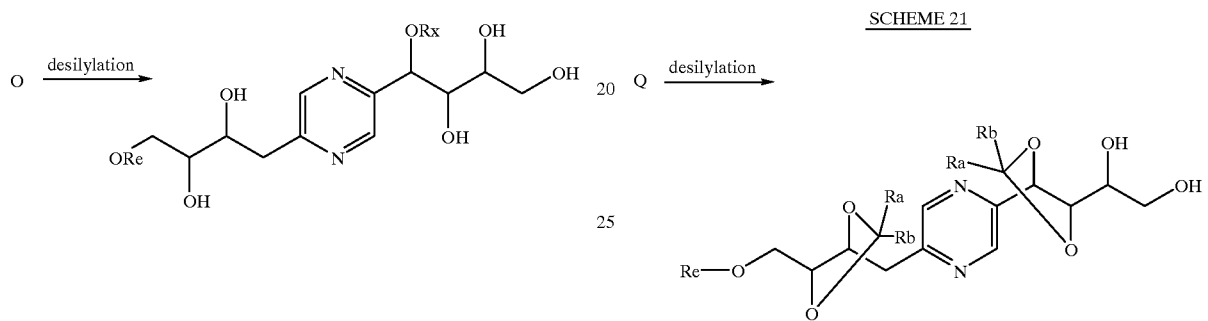
SCHEME 18
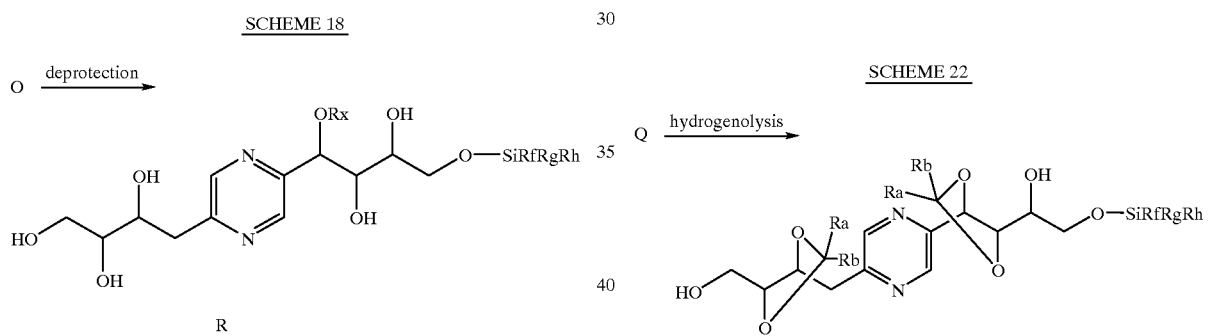
SCHEME 20
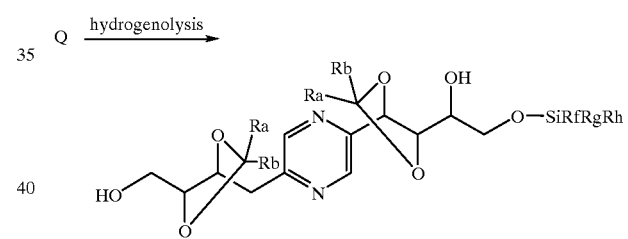
SCHEME 21
SCHEME 22
SCHEME 19
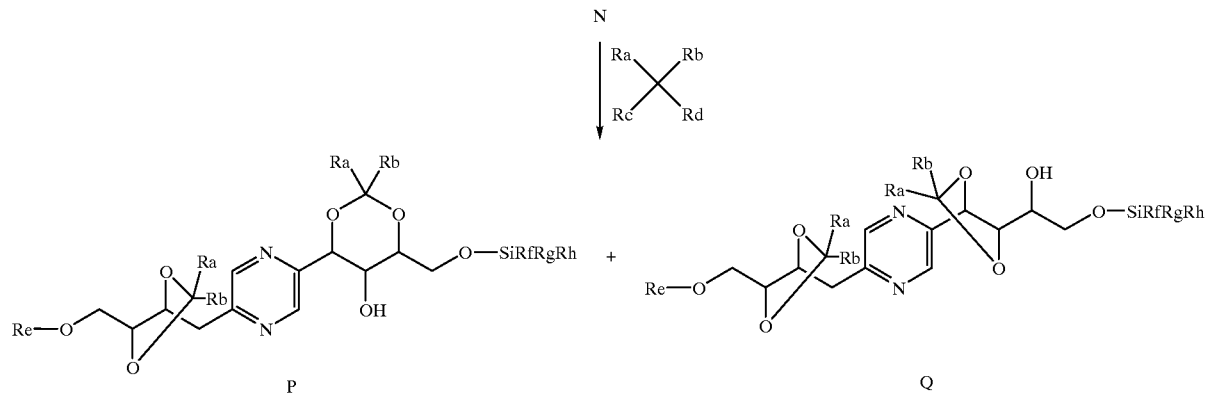

SCHEME 23
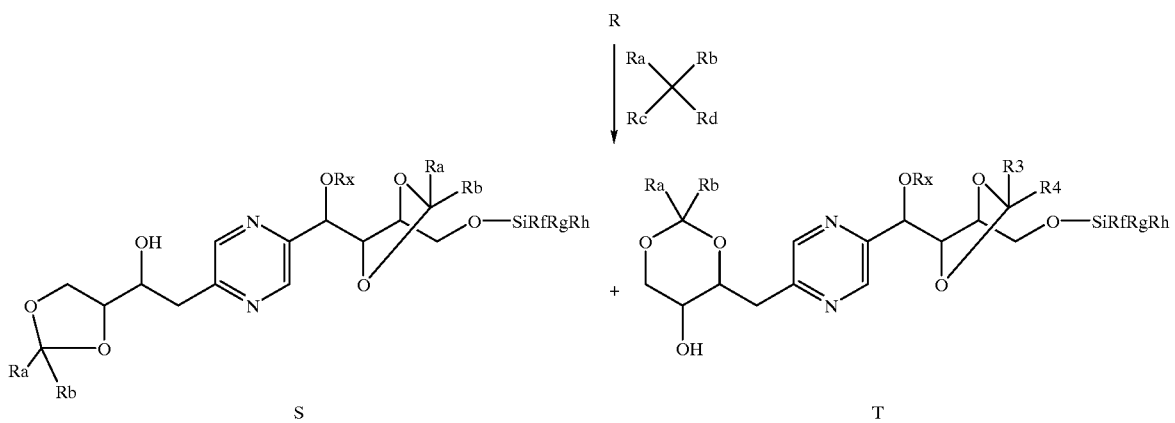
SCHEME 24
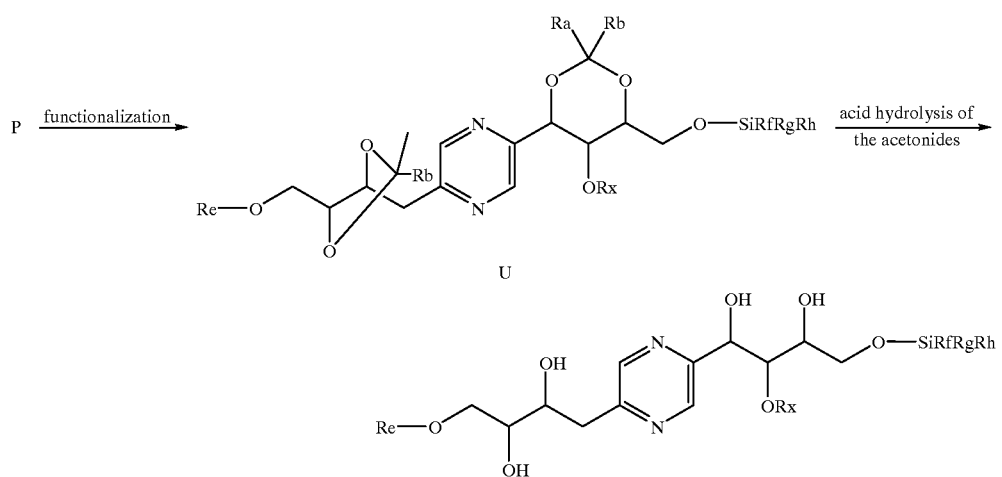
SCHEME 25
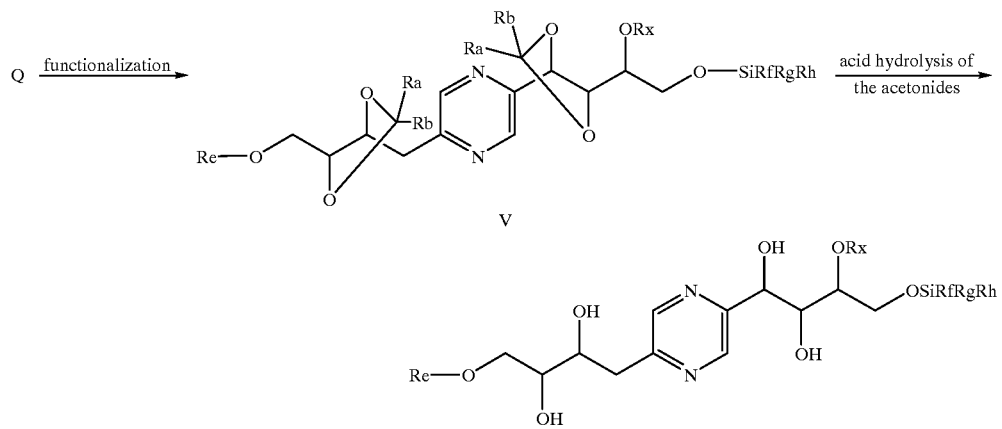

SCHEME 26
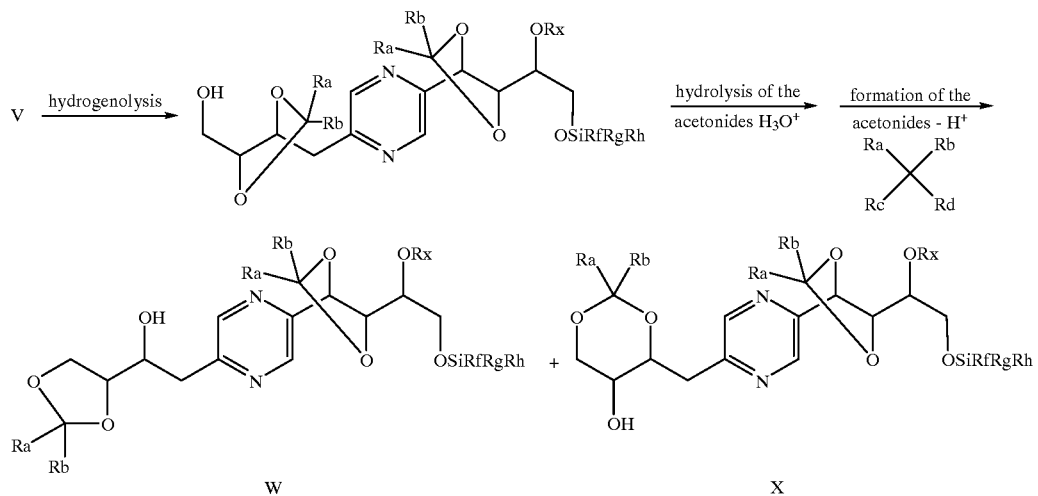
SCHEME 27
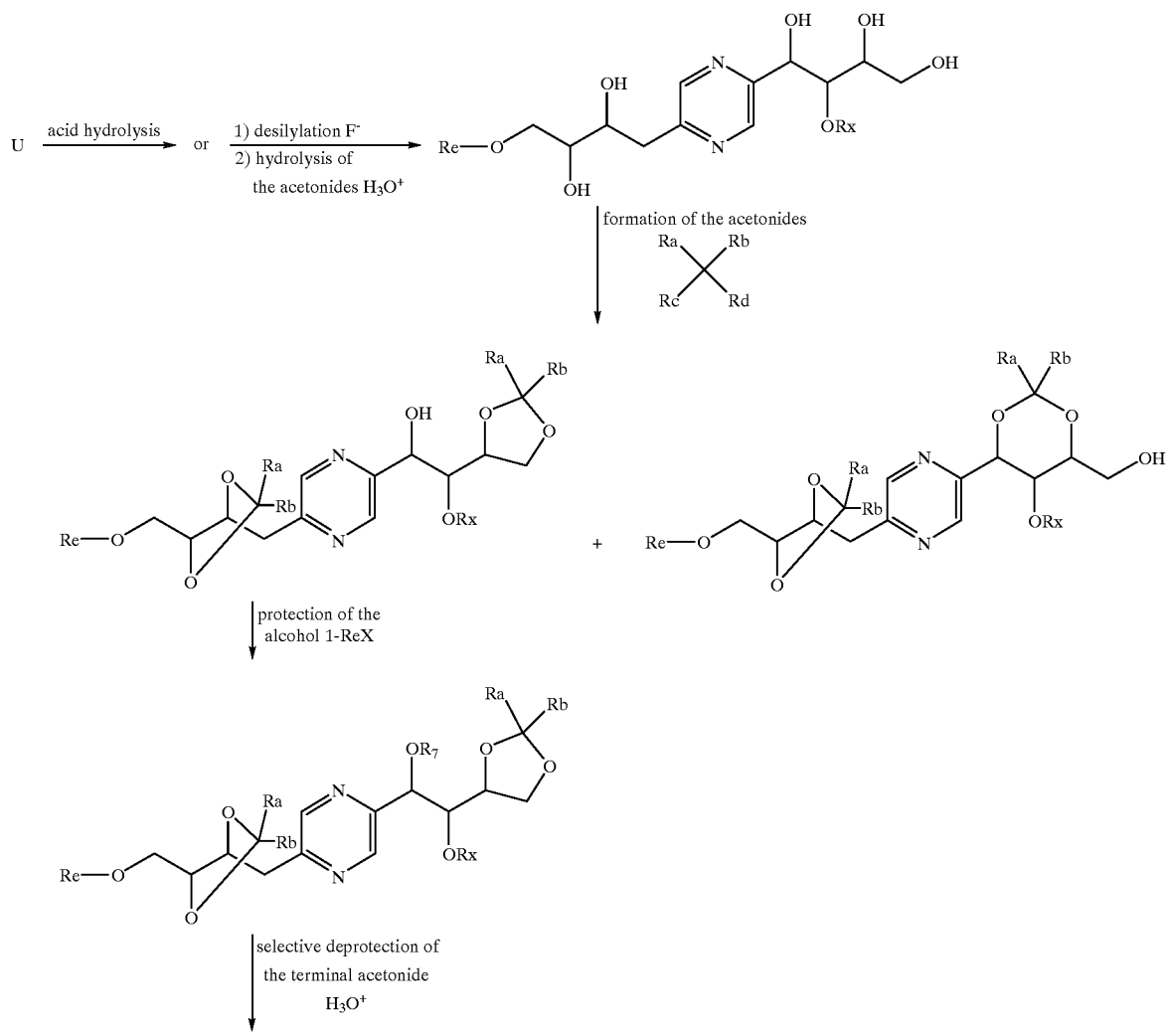

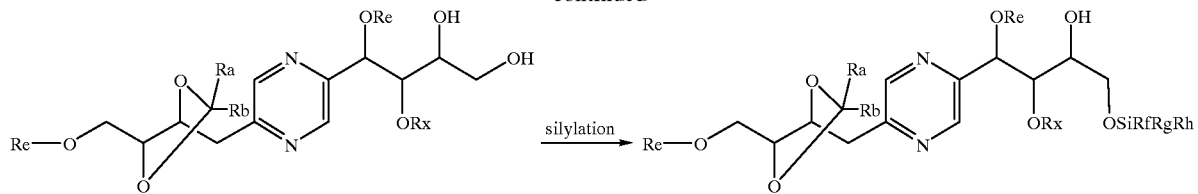
SCHEME 28
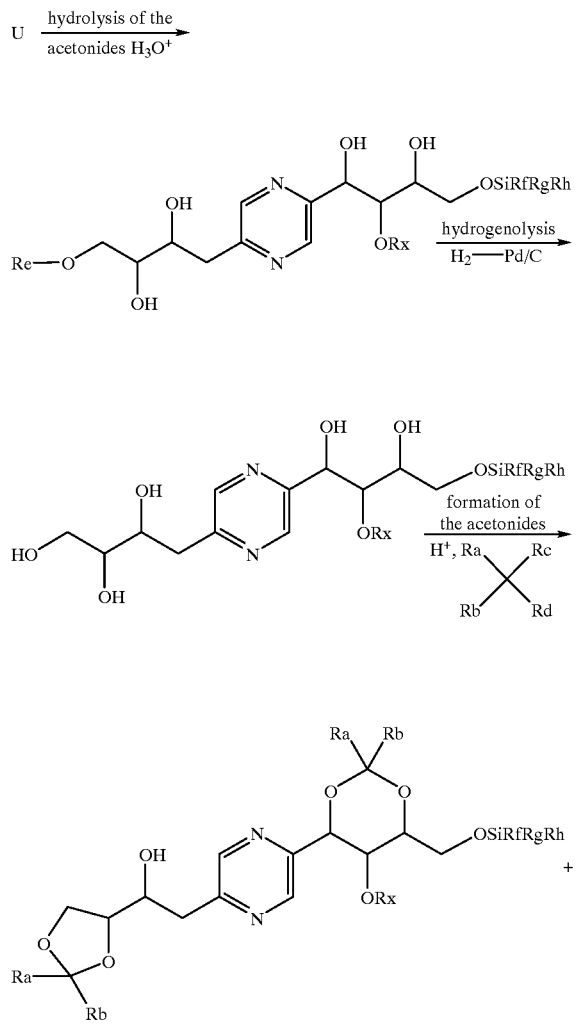
SCHEME 29
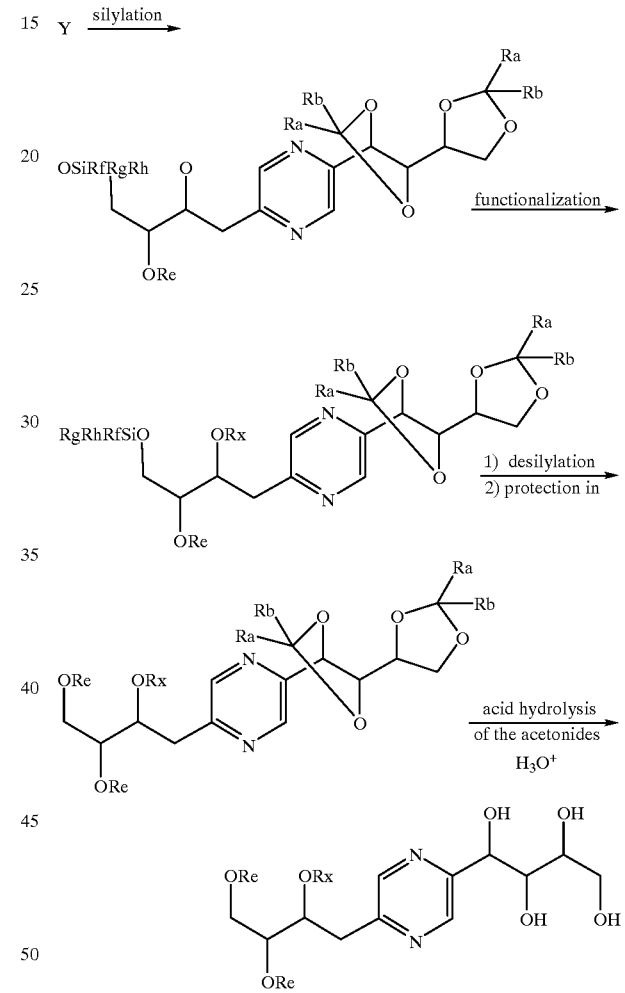
SCHEME 30
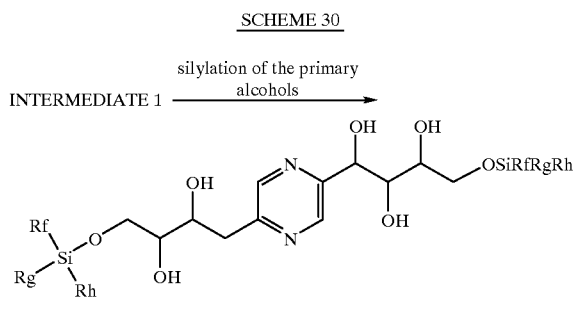

SCHEME 31
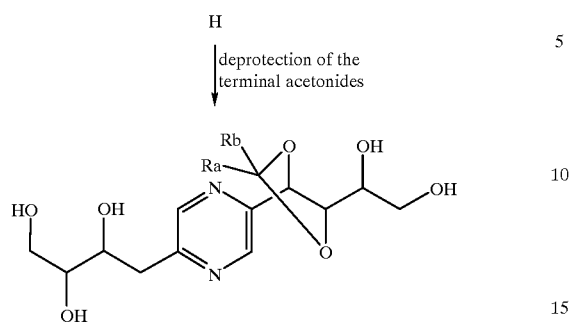
SCHEME 32
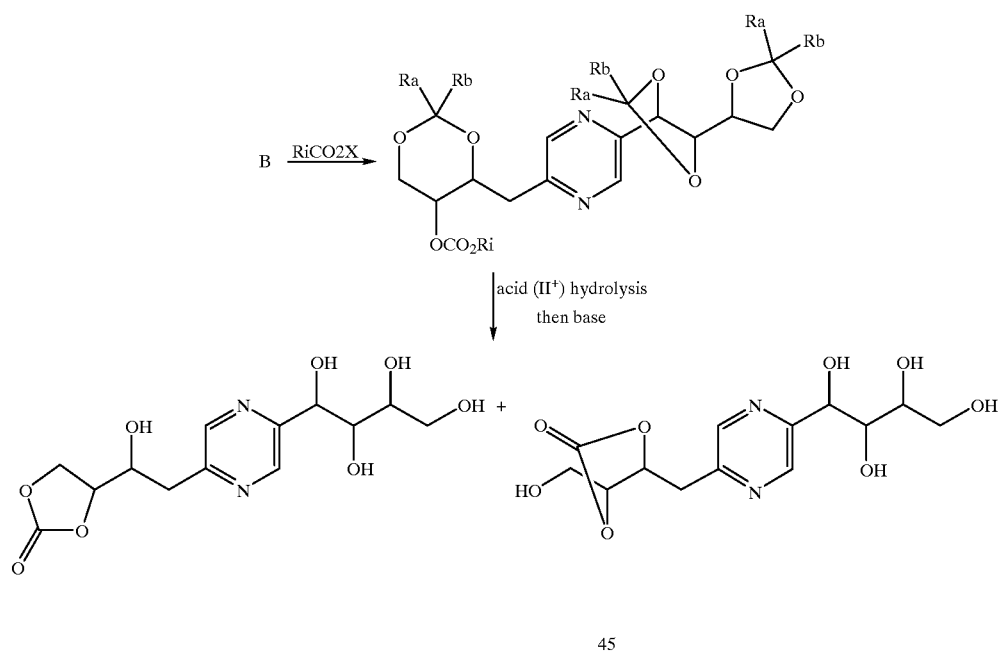
SCHEME 33
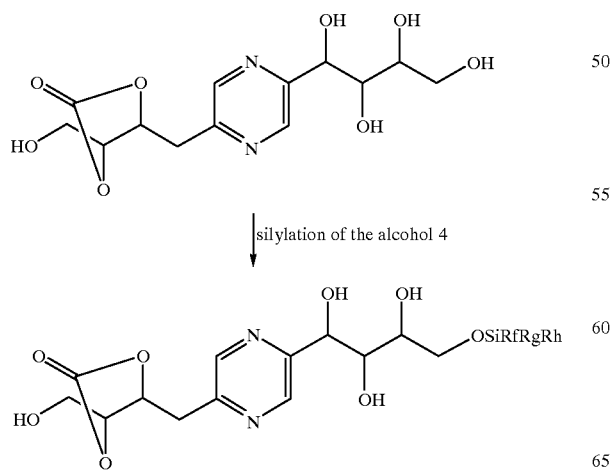
SCHEME 34
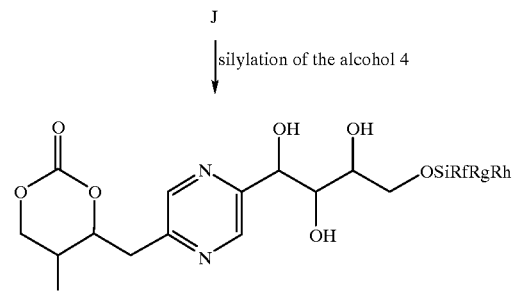

SCHEME 35
INTERMEDIATE 2
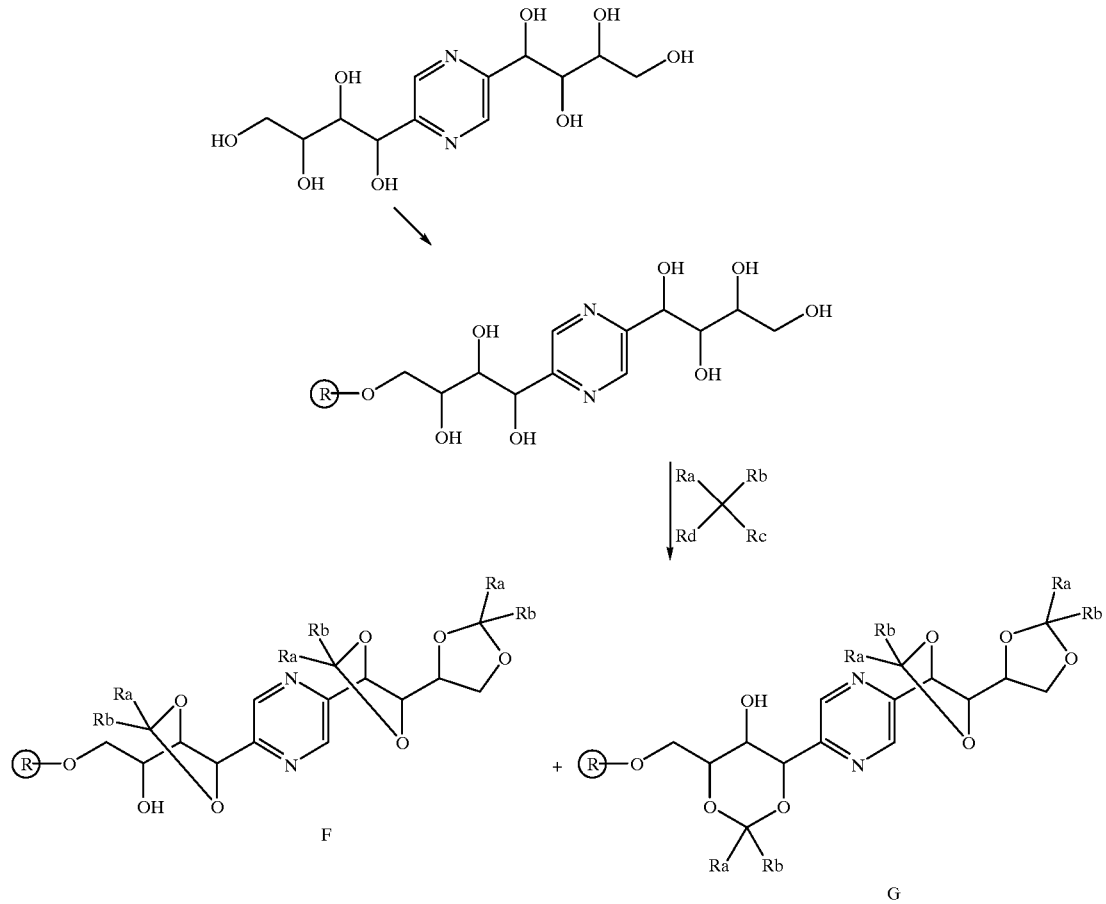
SCHEME 36
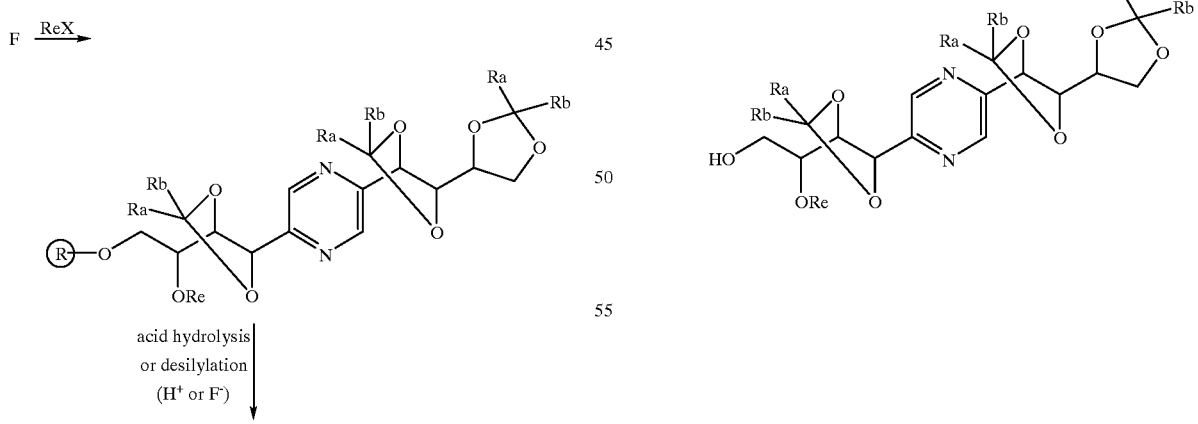

SCHEME 37
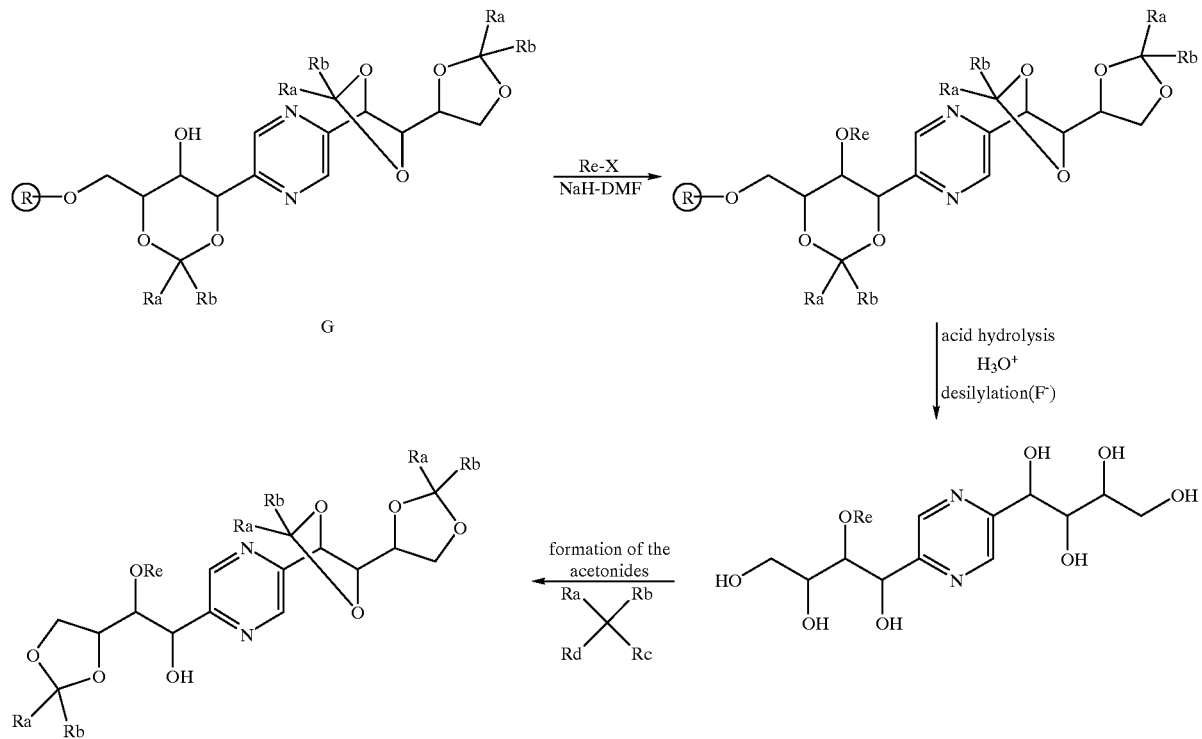
SCHEME 38
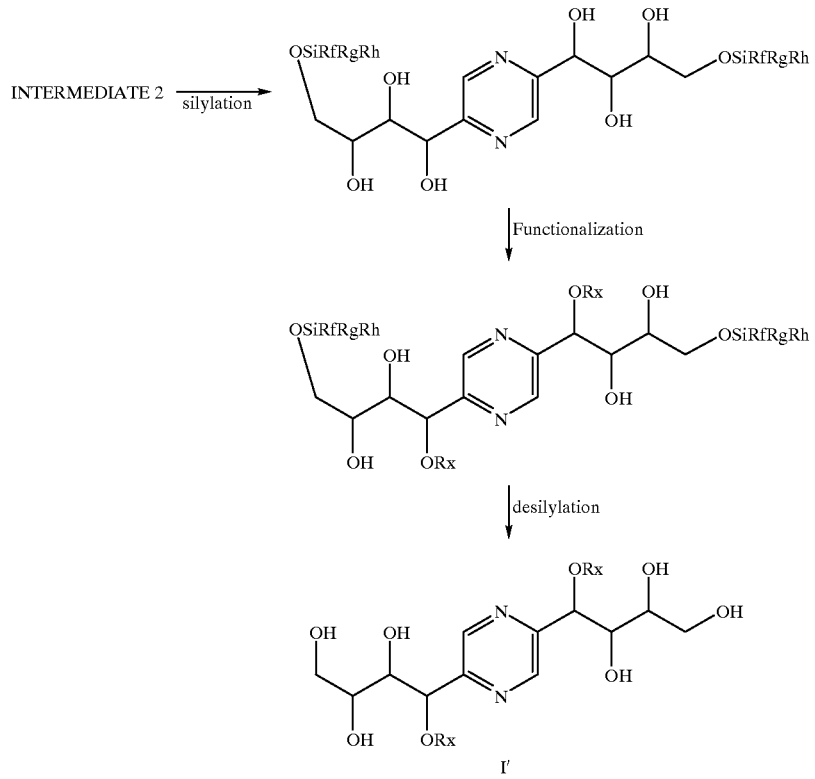

SCHEME 39
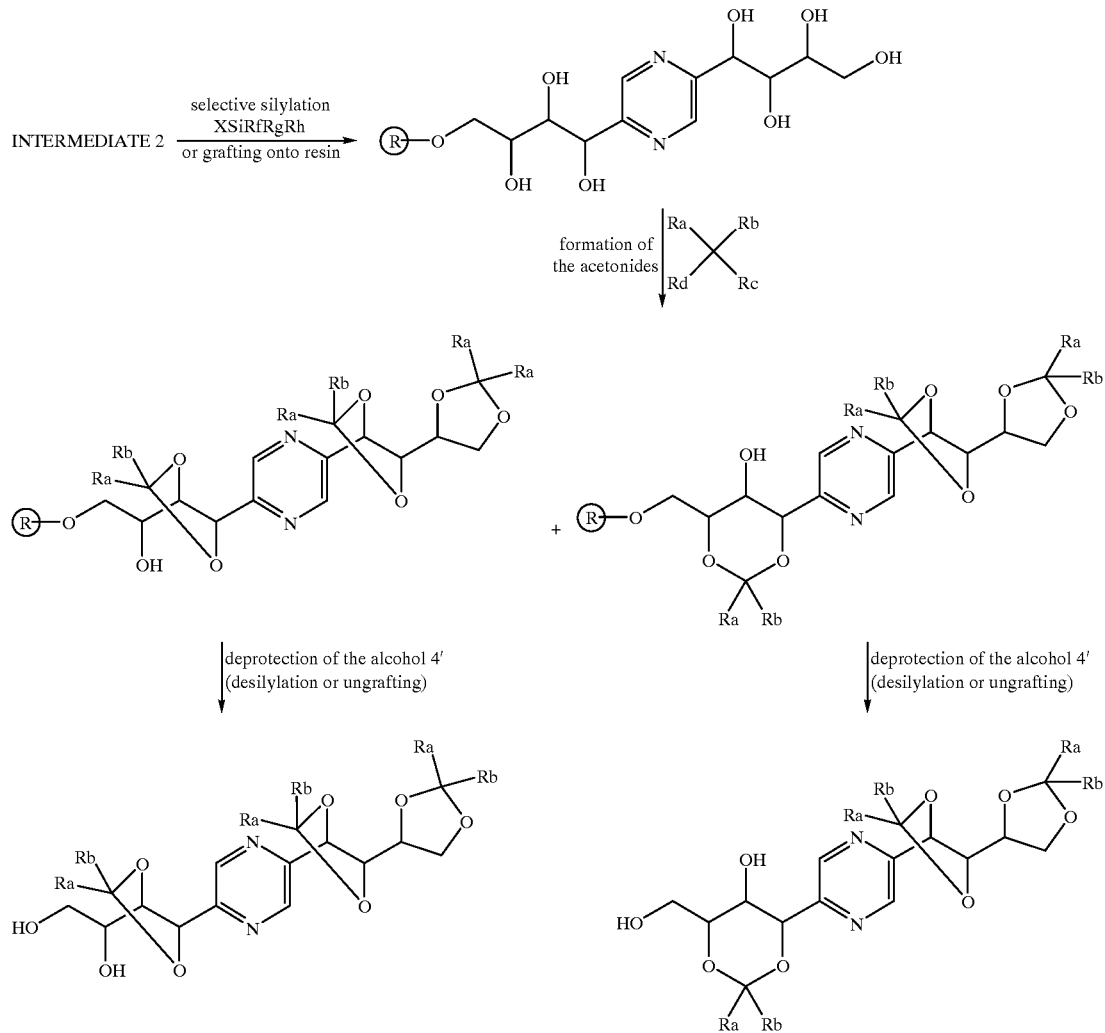
SCHEME 40
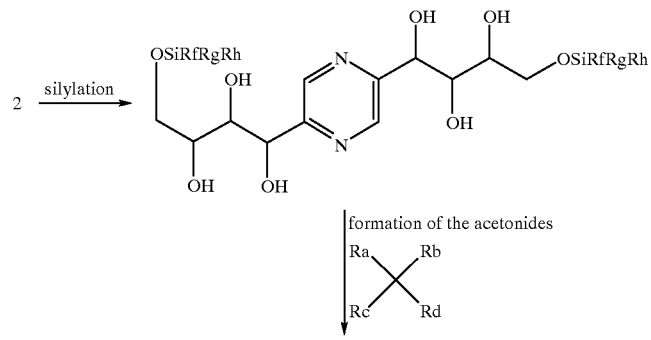

-continued
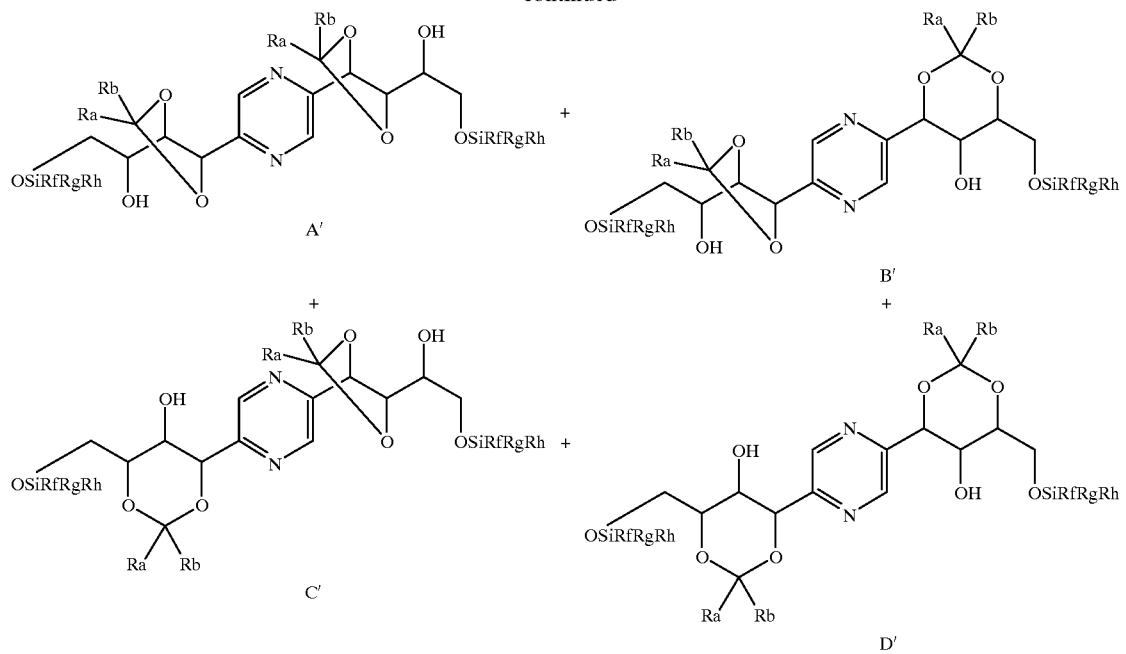
SCHEME 41
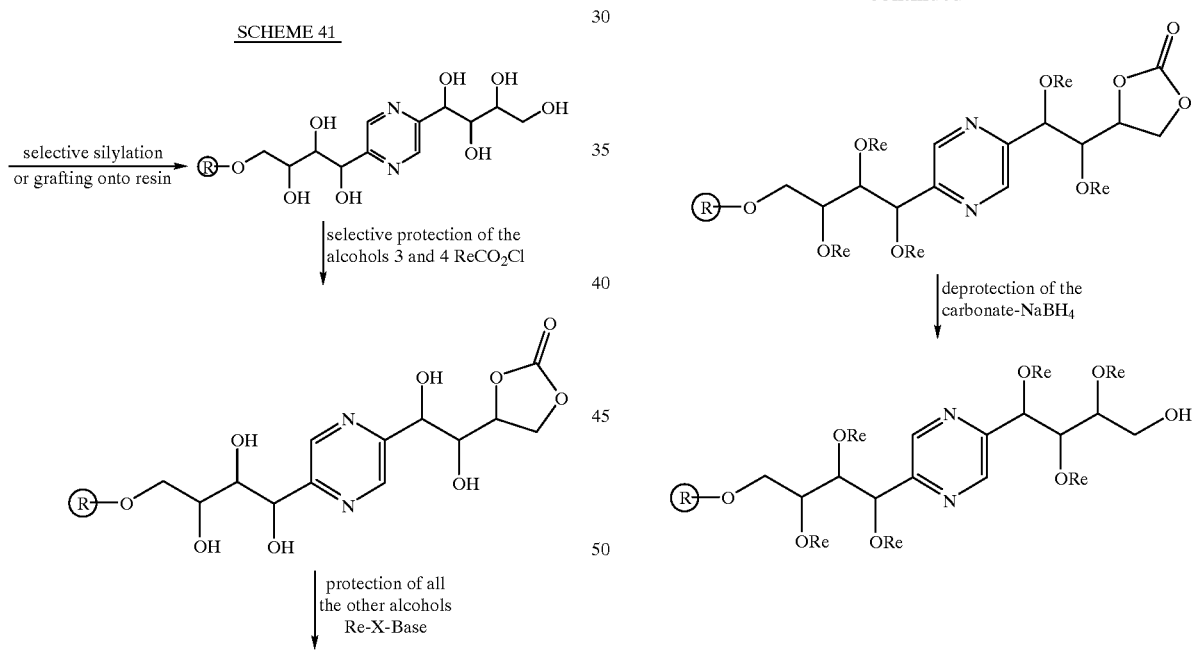

SCHEME 42
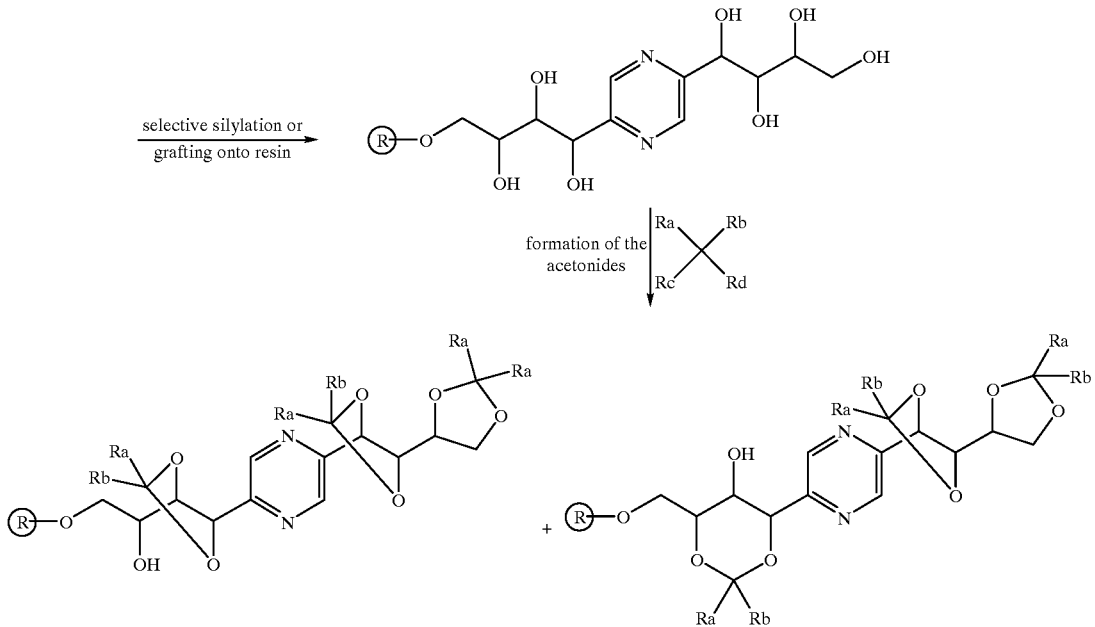
SCHEME 43
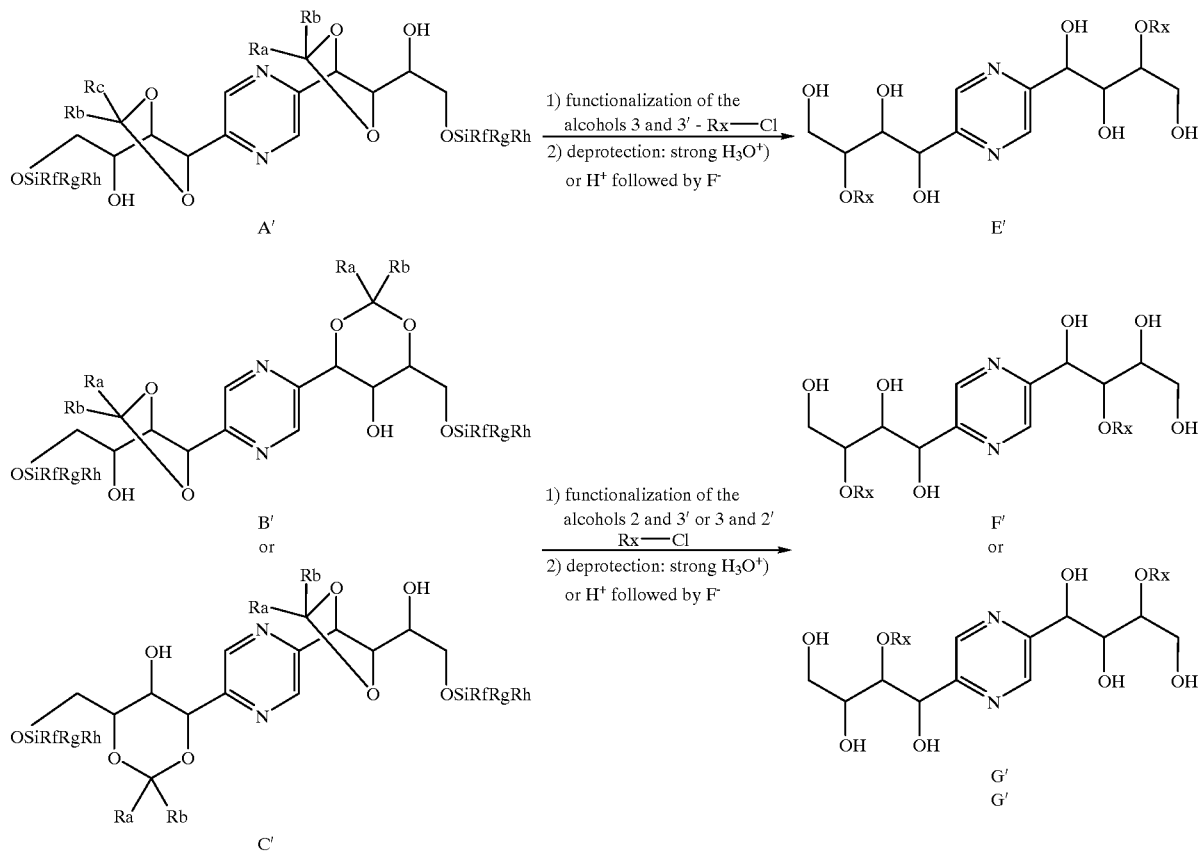

-continued
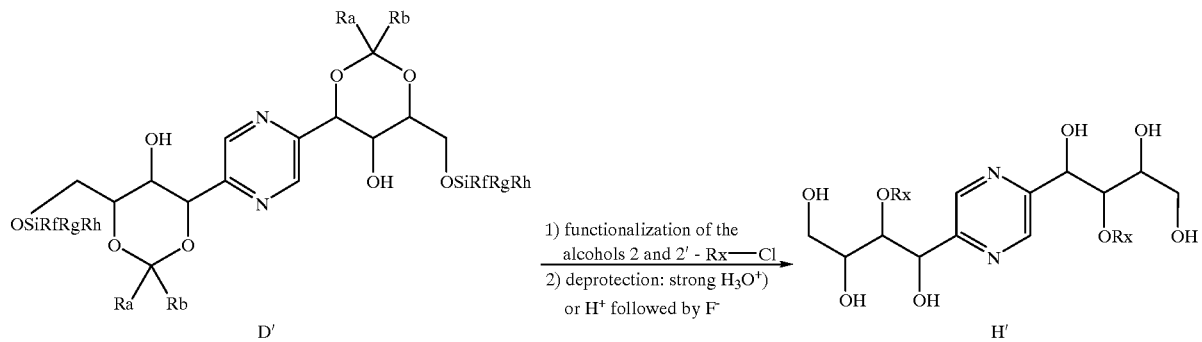
SCHEME 44
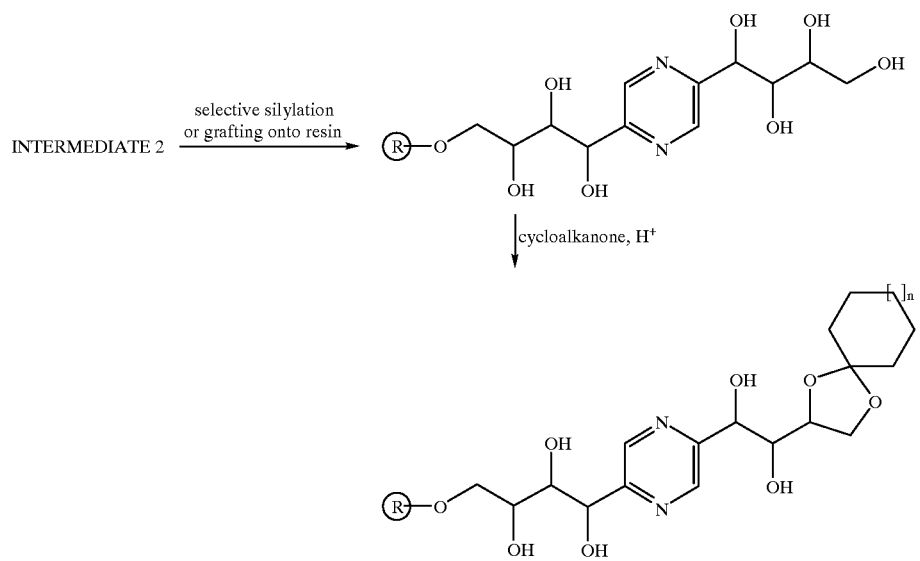
SCHEME 45
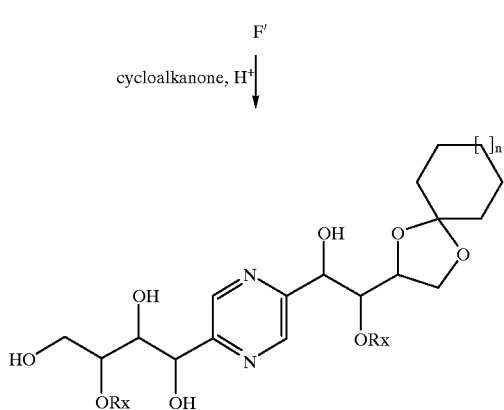
SCHEME 46
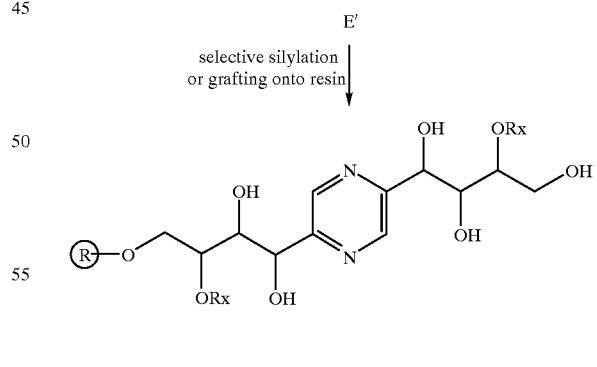
SCHEME 47

-continued
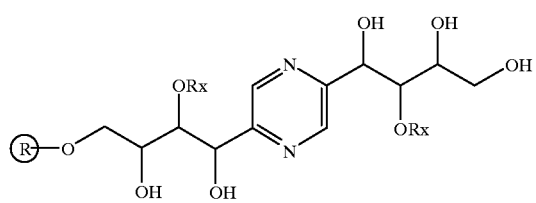
SCHEME 48
F'  
selective silylation  
or grafting onto resin ↓
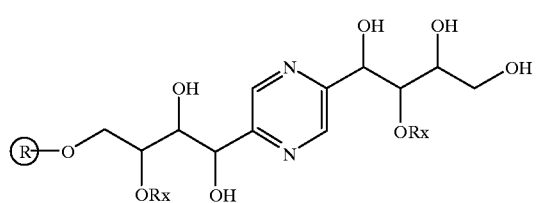
SCHEME 49
I' ↓
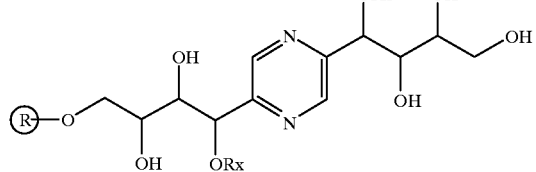
SCHEME 50
2 $\xrightarrow{\text{cycloalkanone, H}^+}$
-continued
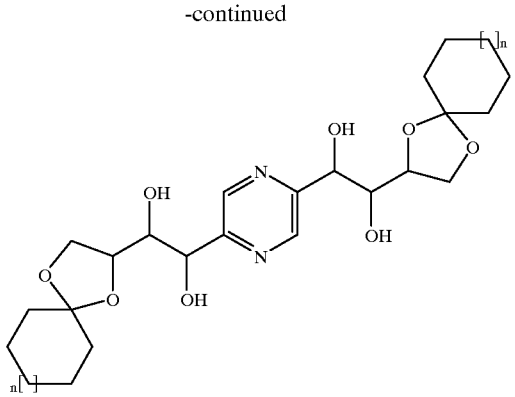
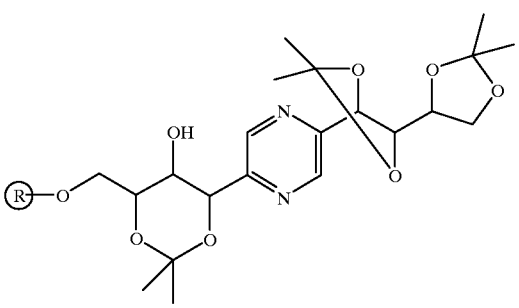
functionalization of  
the alcohols 2' or 3'  
R—Cl ↓
deprotection of the alcohol 4'  
(desilylation or ungrafting) ↓
acid hydrolysis of  
the acetonides ↓
functionalization of the  
alcohols in 4 and 4'  
R—Cl ↓
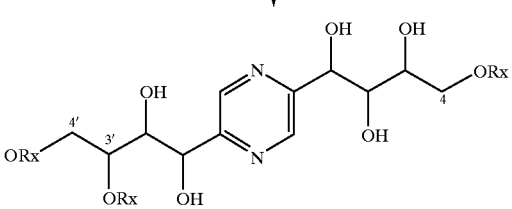
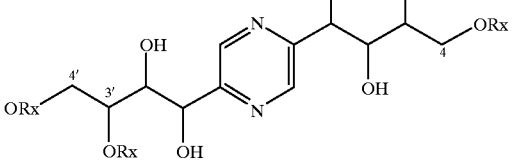
SCHEME 51
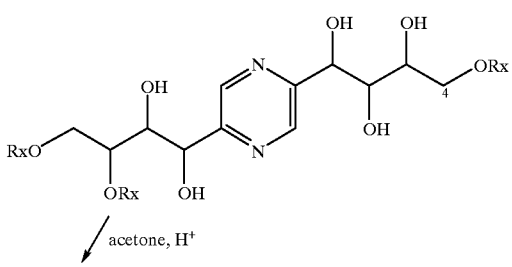
↙ acetone, H⁺

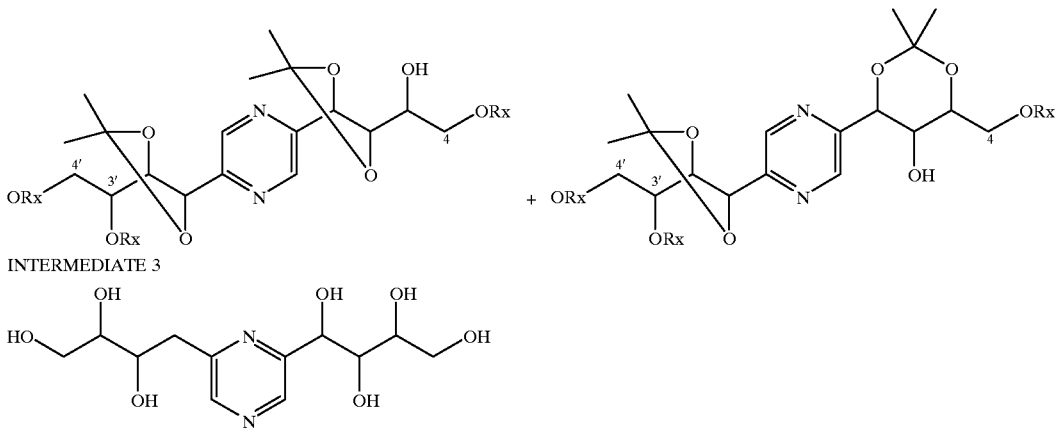

INTERMEDIATE 3

The reaction schemes using intermediate 3 may be established by applying the same schemes as those described above for intermediate 1.

The reaction mixtures obtained for the various processes described above are treated according to conventional physical methods (for example evaporation, extraction, distillation, chromatography or crystallization) or chemical methods (for example formation of salts).

The compounds of formula (I) may be optionally converted to addition salts with an inorganic or organic acid by the action of such an acid in a solvent such as an alcohol, a ketone, an ether or a chlorinated solvent. These salts also form part of the invention.

As an example of pharmaceutically acceptable salts, there may be mentioned the addition salts with inorganic or organic acids, such as acetates, propionate, succinate, benzoate, fumarate, maleate, oxalate, methanesulphonate, isethionate, theophyllineacetate, salicylate, methylene-bis-β-oxynaphthoate, hydrochloride, sulphate, nitrate and phosphate.

The compounds of formula (I) exhibit advantageous pharmacological properties. They are hypoglycaemic agents.

The hypoglycaemic activity of the comp6unds of formula (I) was determined on the hyperglycaemic response to the administration of glucose by the oral route in normoglycaemic mice, according to the following protocol:

Swiss albino mice weighing between 22 and 26 g are starved for 2 hours. At the end of this period, the glycaemia is measured and, immediately after, a dose of glucose (2 g/kg) is administered by the oral route. Thirty minutes later, the glycaemia is metasured once more. The mice which respond with a hyperglycaemia greater than 170 mg/dl are selected and used to detect the hypoglycaemic activity of the compounds according to the invention.

The mice thus chosen are divided into groups of at least 10 animals. Different groups receive doses of 3 to 50 mg/kg of product in a vehicle such as water or a mixture of methyl cellulose/Tweeh and water once per day by gastric feeding. The treatment lasts for 4 days. On the 4th day, after the last treatment, the animals receive a dose of glucose (2 g/kg) and the glycaemia is measured 20 to 40 minutes later. The percentage inhibition of the hyperglycaemic response to the administration of glucose is calculated relative to the response measured in the group treated with the vehicle.

In this test, the compounds according to the invention exhibit a percentage inhibition of glycaemia greater than or equal to 10%.

The compounds of general formula (I) according to the invention have a low toxicity. Their $LD_{50}$ is greater than 2000 mg/kg orally in mice.

In human therapy, these products are useful in the prevention and treatment of diabetes, and in particular of type II diabetes (NID diabetes), diabetes affecting obese individuals, diabetes affecting individuals in their fifties, metaplethoric diabetes, diabetes affecting the elderly and mild diabetes. They may be used as a supplement to insulin therapy in insulin-dependent diabetes where they make it possible to gradually reduce the dose of insulin, in unstable diabetes, in insulin-resistant diabetes, as a supplement to hypoglycaemic sulphamides when these do not produce a sufficient reduction in glycaemia. These products may also be used in the complications of diabetes such as hyperlipaemia, lipid metabolism disorders, dyslipaemias and obesity. They are also useful in the prevention and treatment of atherosclerosis lesions and their complications (coronopathies, myocardial infarction, cardiomyopathies, the development of these three complications into left ventricular insufficiency, various arteriopathies, arteritis of the lower limbs with claudication and development into ulcers and gangrene, cerebral vascular insufficiency and its complications, sexual impotence of vascular origin), diabetic retinopathy and all its manifestations (increase in capillary permeability, dilation and capillary thrombosis, microaneurism, arteriovenous shunt, venous dilation, punctiform and macular haemorrhages, exudates, macular oedemas, manifestations of proliferative retinopathy: neovessels, proliferative retinitis scars, haemorrhages of the vitreous body, detachment of the retina), diabetic cataract, diabetic neuropathy in its various forms (peripheral polyneuropathies and its manifestations such as patesthesias, hyperesthesias and pain, mononeuropathies, radiculopathies, autonomous neuropathies, diabetic amyotrophies), manifestations of diabetic foot (ulcers of the lower extremities and of the foot), diabetic nephropathy in its two diffuse and nodular forms, atherdmatosis (increase in the HDL lipoproteins promoting the removal of cholesterol from atheroma plaques, reduction in LDL lipoproteins, reduction in the LDL/HDL ratio, inhibition of the oxidation of LDLs, decrease in platelet adhesiveness), hyperlipaemias and dyslipaemias (hypercholesterolaemias, hypertriglyceridaemias, normalization of the fatty acid level, normalization of uricaemia, normalization of apoproteins A and B), cataract, high blood pressure and its consequences.

The medicaments according to the invention consist of a compound according to the invention or a combination of these products, in a pure state or in the form of a composition in which it is combined with any other pharmaceutically compatible product which may be inert or physiologically active. The medicaments according to the invention may be used orally, parenterally, rectally or topically.

As solid compositions for oral administration, there may be used tablets, pills, powders (gelatin capsules, cachets) or granules. In these compositions, the active ingredient according to the invention is mixed with one or more inert diluents, such as starch, cellulose, sucrose, lactose or silica, under an argon stream. These compositions may also comprise substances other than diluents, for example one or more lubricants such as magnesium stearate or talc, a colorant, a coating (sugar-coated tablets) or a glaze.

As liquid compositions for oral administration, there may be used pharmaceutically acceptable solutions, suspensions, emulsions, syrups and elixirs containing inert diluents such as water, ethanol, glycerol, vegetable oils or paraffin oil. These compositions may comprise substances other than diluents, for example wetting, sweetening, thickening, flavouring or stabilizing products.

Sterile compositions for parenteral administration may be preferably solutions which are aqueous or non-aqueous, suspensions or emulsions. Water, propylene glycol, polyethylene glycol, vegetable oils, in particular olive oil, injectable organic esters, for example ethyl oleate, or other suitable organic solvents may be used as solvent or vehicle. These compositions may also contain adjuvants, in particular wetting, isotonizing, emulsifying, dispersing and stabilizing agents. Sterilization may be performed in several ways, for example by aseptisizing filtration, by incorporating sterilizing agents into the composition, by irradiation or by heating. They may also be prepared in the form of sterile solid compositions which may be dissolved at the time of use in sterile water or in any other injectable sterile medium.

Compositions for rectal administration are suppositories or rectal capsules which contain, in addition to the active product, excipients such as butter, semisynthetic glycerides or polyethylene glycols.

The compositions for topical administration may be for example creams, lotions, collyria, collutoria, nasal drugs or aerosols.

The doses depend on the desired effect, the duration of treatment and the route of administration used; they are generally between 150 mg and 600 mg per day orally for an adult with unit doses ranging from 50 mg to 200 mg of active substance.

In general, the doctor will determine the appropriate dosage according to the age, weight and all other factors specific to the subject to be treated.

The following examples illustrate compositions according to the invention:

EXAMPLE A

Gelatin capsules containing a dose of 50 mg of active product and having the following composition are prepared according to the usual technique:

| | |
|---|---|
| Active product | 50 mg |
| Cellulose | 18 mg |
| Lactose | 55 mg |
| Colloidal silica | 1 mg |
| Sodium carboxymethylstarch | 10 mg |
| Talc | 10 mg |
| Magnesium stearate | 1 mg |

EXAMPLE B

Tablets containing a dose of 50 mg of active product and having the following composition are prepared according to the usual technique:

| | |
|---|---|
| Active product | 50 mg |
| Lactose | 104 mg |
| Cellulose | 40 mg |
| Polyvidone | 10 mg |
| Sodium carboxymethylstarch | 22 mg |
| Talc | 10 mg |
| Magnesium stearate | 2 mg |
| Colloidal silica | 2 mg |
| Mixture of hydroxymethylcellulose, glycerin, titanium oxide (72-3.5-24.5) qs 1 finished film-coated tablet of 245 mg | |

EXAMPLE C

An injectable solution containing 50 mg of active product and having the following composition is prepared:

| | |
|---|---|
| Active product | 50 mg |
| Benzoic acid | 80 mg |
| Benzyl alcohol | 0.06 ml |
| Sodium benzoate | 80 mg |
| Ethanol 95% | 0.4 ml |
| Sodium hydroxide | 24 mg |
| Propylene glycol | 1.6 ml |
| Water qs | 4 ml |

The invention also relates to the use of the compounds of general formula (I) for the preparation of pharmaceutical compositions useful for the treatment or the prevention of diabetes and the complications of diabetes.

The following examples illustrate more particularly and without limitation the method of preparation used according to the invention:

EXAMPLE 1

4,4'-O,O-dibenzoyl-2-[(1R,2S,3R)(1,2,3,4-tetrahydroxybutyl)]-5-[(2'S,3'R)(2',3',4'-trihydroxybutyl)]pyrazine 0.48 cm³ of benzoyl chloride is added, dropwise, at a temperature close to 20° C. under an argon atmosphere, to 500 mg of 2-[(1R,2S,3R)(1,2,3,4-tetrahydroxybutyl)]-5-[2'S,3'R)(2',3',4'-trihydroxybutyl)]pyrazine in suspension in 2.5 cm³ of pyridine dried over a 4 Å molecular sieve. The solution obtained after stirring for two minutes is again stirred for an additional 17 hours at a temperature close to 20° C. The pyridine is evaporated under an air stream at a temperature close to 20° C. The residue obtained is taken up in a minimum of a dichloromethane-methanol (98-2 by volume) mixture and is purified by chromatography under atmospheric pressure on 40 g of Merck silica gel 60 $F_{254}$ (0.063–0.200 mm) contained in a column 2.5 cm in diameter. An eluent gradient is used which consists of a dichloromethane-methanol mixture: 97.5-2.5 by volume (500 cm³), 95-5 by volume (500 cm³), 92.5-7.5 by volume (500 cm³) and then 90-10 by volume (500 cm³), collecting 10 cm³ fractions. The fractions containing only the desired product are combined and concentrated to dryness under reduced pressure (about 2.7 kPa) at a temperature close to 40° C. 1.02 g of a yellow solid containing the expected product are thus obtained. The latter is solubilized in a dichloromethane-methanol mixture. After a few minutes, a white solid is formed which is filtered on sintered glass, rinsing with dichloromethane, and then dried under reduced pressure (10 Pa) at a temperature close to 40° C.

133 mg of 4,4'-O,O-dibenzoyl-2-[(1R,2S,3R)(1,2,3,4-tetrahydroxybutyl)]-5-[(2'S, 3'R)(2',3',4'-trihydroxybutyl)]pyrazine are thus obtained in the form of a white solid.

The product obtained has the following characteristics:

$^1$H NMR spectrum (400 MHz, $(CD_3)_2SO$ d6, δ in ppm); 2.81 (dd, J=14 and 9 Hz, 1H: 1H of $CH_2$ 5α); 3.20 (dd, J=14 and 3 Hz, 1H: the other H of $CH_2$ 5α); from 3.65 to 3.75 (mt, 1H; CH 5β); 3.72 (broad d, J=9 Hz, 1H: CH 2β); 3.89 (mt, 1H CH 5γ); 4.01 (mt, 1H: CH 2γ); from 4.20 to 4.35 (mt, 2H; 1H of $CH_2$ 2δ and 1H of $CH_2$ 5δ); from 4.45 to 4.60 (mt, 2H; the other H of $CH_2$ 2δ and the other H of $CH_2$ 5δ); 5.02 (broad s, 1H: CH 2α); 7.56 (t, J=7.5 Hz, 4H: H at the meta position with respect to the 2 benzoyloxy); 7.67 (t, J=7.5 Hz, 2H: H at the para position with respect to the 2 benzoyloxy); 8.04 (d, J=7.5 Hz, 4H: H at the ortho position with respect to the 2 benzoyloxy); 8.47 (S, 1H; =CH at position 6); 8.70 (s, 1H; =CH at position 3).

2-[(1R,2S,3R)(1,2,3,4-tetrahydroxybutyl)]-5-[(2'S,3'R)(2',3',40-trihydroxybutyl)]pyrazine (deoxytructosazine) may be prepared according to the method described in patent JP 53-90401 of by Kuhn et al, J. L. Ann. Chem. 644, 122–7, 1961.

EXAMPLE 2

4,4'-O,O-diacetyl-2-[(1R,2S,3R)(1,2,3,4-tetrahydroxybutyl)]-5-[(2'S,3'R)(2',3',4'-trihydroxybutyl)]pyrazine 0.034 cm$^3$ of acetic anhydride is added, dropwise over 10 minutes, at a temperature close to 0° C., to 50 mg of 2-[(1R,2S,3R)( 1,2,3,4-tetrahydroxybutyl)]-5-[2'S,3'R)(2', 3',4'-trihydroxybutyl)]pyrazine in suspension in 0 5 cm$^2$ of pyridine dried over potassium hydroxide. The white suspension obtained is stirred for 2 hours at a temperature close to 0° C., and then the reaction medium is readjusted to a temperature close to 20° C. A few magnesium hydrogen carbonate granules are added, and the pyridine is evaporated at a temperature close to 20° C. under an air stream. The crude reaction medium is taken up in a dichloromethane-methanol mixture, and the soluble portion of the medium is purified by chromatography on Merck 60 $F_{254}$ silica gel plates (2 plates, thickness=0.5 mm, 20×20 cm), eluting with an ethyl acetate-water-acetic acid (30-10-12 by volume) mixture. The fraction containing only the desired product is extracted with a dichloromethane-methanol mixture, filtered on sintered glass and then concentrated to dryness under reduced pressure (2.7 kPa) at a temperature close to 40° C. 2 mg of 4,4'-O,O-diacetyl-2-[(1R,2S,3R)(1,2,3,4-tetrahydroxybutyl)]-5-[(2'S,3'R)(2',3',4'-trihydroxybutyl)]pyrazine are thus obtained in the form of a colourless lacquers.

The product obtained has the following characteristics:

$^1$H NMR spectrum (300 MHz, $(CD_3)_2SO$ d6 with addition of a few drops of CD3COOD d4, δ in ppm): 1.91 and 2.02 (2 s, 6H: the 2 $OCOCH_3$); 2.75 (dd, J=14 and 9 Hz, 1H: 1H of $CH_2$ 5α); 3.12 (dd, J=14 and 3 Hz, 1H: the other H of $CH_2$ 5α); 3.55 (mt, 1H: CH 5y); 3.60 (dd, J=9 and 1.5 Hz, 1H: CH 2β); 3.77 (mt, 1H: CH 5β); 3.84 (mt, 1H: CH 2γ); from 3.90 to 4.05 (mt, 2H: 1H of $CH_2$ 2δ and 1H of $CH_2$ 5δ); from 4.20 to 4.35 (mt, 2H: the other H of $CH_2$ 2δ and the other H of $CH_2$ 5δ); 4.95 (broad s, 1H: CH 2α); 8.43 (s, 1H: =CH at position 6); 8.66 (s, 1H: =CH at position 3).

EXAMPLE 3

4,4'-O,O-di-(2,2-dimethylpropanoyl)-2-[(1R,2S,3R)(1,2,3,4-tetrahydroxybutyl)]-5-[(2'S,3'R)(2',3',4'-trihydroxybutyl)]pyrazine 0.102 cm$^3$ of pivaloyl chloride is added, dropwise at a temperature close to 20° C. under an argon atmosphere, to 100 mg of 2-[(1R,2S,3R)(1,2,3,4-tetrahydroxybutyl)]-5-[2'S,3'R) (2',3',4'-trihydroxybutyl)]pyrazine in suspension in 2 cm$^3$ of pyridine dried over potassium hydroxide. The reaction suspension is stirred at a temperature close to 20° C. for 15 minutes. After homogenization of the medium, the solvent is evaporated under reduced pressure (2.7 kPa) at a temperature close to 30° C. A light yellow oil is obtained which is purified by chromatography on 2 Merck 60 $F_{254}$ silica gel plates (thickness=2 mm, 20×20 cm), eluting with a dichloromethane-methanol (90-10 by volume) mixture. The fraction containing only the desired product is extracted with a dichloromethanemethanol (90-10 by volume) mixture, filtered on sintered glass and then concentrated to dryness under reduced pressure (2.7 kPa) at a temperature close to 30° C.

67 mg of 4,4'-O,O-di-(2,2-dimethylpropanoyl)-2-[(1R,2S,3R)(1,2,3,4-tetrahydroxybutyl)]-5-[(2'S,3'R) (2',3',4'-trihydroxybutyl)]pyrazine are thus obtained in the form of a white powder.

The product obtained has the following characteristics:

$^1$H NMR spectrum (400 MHz, $(CD_3)_2SO$ d6, δ in ppm): 1.20 (s, 18H: the 2 $OCOC(CH_3)_3$); 2.78 (dd, J=14 and 9 Hz, 1H: 1H of $CH_2$ 5α); 3.14 (dd, J=14 and 2.5 Hz, 1H: the other H of $CH_2$ 5α); from 3.50 to 3.65 (mt, 1H: CH 5γ); 3.63 (broad t, J=9 Hz, 1H: CH 2β); 3.81 (mt, 1H: CH 5β); 3.88 (mt, 1H: CH 2γ); from 3.95 to 4.05 (mt, 2H: 1H of $CH_2$ 2δ and 1H of $CH_2$ 5δ); 4.24 (dd, J=12 and 3 Hz, 1H: the other H of $CH_2$ 5δ); 4.30 (dd, J=12 and 2 Hz, 1H: the other H of $CH_2$ 2δ); 4.63 (d, J=9 Hz, 1H: OH in 2β); 4.86 (d, J=6.5 Hz, 1H: OH in 5β); 4.99 (brqad d, J=6 Hz, 1H: CH 2α); 5.05 (d, J=6 Hz, 1H: OH at position 2γ); 5.10 (d, J=6 Hz, 1H: OH at position 5γ); 5.40 (d, J=6 Hz, 1H: OH at position 2α); 8.44 (s, 1H: =CH at position 6); 8.67 (s, 1H: =CH at position 3).

EXAMPLE 4

4,4'-O,O-dipentanoyl-2-[(1R,2S,3R)(1,2,3,4-tetrahydroxybutyl)]-5-[(2'S,3'R)(2',3',4'-trihydroxybutyl)]pyrazine 0.196 cm$^3$ of pentanoyl chloride is added, dropwise at a temperature close to 20° C. under an argon atmosphere, to 200 mg of 2-[(1R,2S,3R)(1,2,3,4-tetrahydroxybutyl)]-5-[2'S,3'R) (2',3',4'-trihydroxybutyl)]pyrazine in suspension in 4 cm$^3$ of pyridine dried over potassium hydroxide. The solution obtained is stirred at a temperature close to 20° C. for 21 hours. The solvent is evaporated under reduced pressure (2.7 kPa) at a temperature close to 30° C. The crude reaction product is purified by chromatography on 4 Merck 60 $F_{254}$ silica gel plates (thickness=2 and 1 mm, 20×20 cm), eluting with a dichloromethane-methanol (90-10 by volume) mixture. The fraction containing only the desired product is extracted with a dichloromethane-methanol (90-10 by volume) mixture, filtered on sintered glass and then concentrated to dryness under reduced pressure (2.7 kPa) at a temperature close to 30° C.

58 mg of 4,4'-O,O-dipentanoyl-2-[(1R,2S,3R)(1,2,3,4-tetrahydroxybutyl)]-5-[(2'S,3'R)(2',3',4'-trihydroxybutyl)]pyrazine are thus obtained in the form of a white powder.

The product obtained has the following characteristics:

$^1$H NMR spectrum (300 MHz, $(CD_3)_2SO$ d6, δ in ppm): 0.89 (t, J=7.5 Hz, 6H: the $CH_3$ of the two butyl chains); 1.32 and 1.52 (2 mts, 8H: the 2 central $CH_2$ of the two butyl chains); 2.32 (t, J=7.5 Hz, 4H: the $OCOCH_2$ of the two butyl chains); 2.75 (dd, J=14 and 9 Hz, 1H: 1H of $CH_2$ 5α); 3.12 (dd, J=14 and 3 Hz, 1H: the other H of $CH_2$ 5δ); from 3.50 to 3.65 (mt, 1H: CH 5γ); 3.61 (broad t, J=9 Hz, 1H: CH 2β); from 3.70 to 3.95 (mt, 2H: CH 2γ and CH 5β); from 3.95 to 4.10 .(mt, 2H: 1H of $CH_2$ 2δ and 1H of $CH_2$ 5δ); from 4.15 to 4.40 (mt, 2H: the other H of $CH_2$ 2δ and the other H of $CH_2$ 5δ); 4.64 (d, J=9 Hz, 1H: OH at position 2β); 4.88 (d, J=6 Hz, 1H: OH at position 5β); 4.96 (broad d, J=6 Hz, 1H: CH 2α); 5.06 (d, J=6 Hz, 1H: OH at position 2γ); 5.12 (d, J=6 Hz, 1H: OH at position 5γ); 5.42 (d, J=6 Hz, 1H: OH at position 2α); 8.42 (s, 1H: =CH at position 6); 8.66 (s, 1H: =CH at position 3).

EXAMPLE 5

4,4'-O,O-di-(acetoxybenzoyl)-2-[(1R,2S,3R)(1,2,3,4-tetrahydroxybutyl)]-5-[(2'S,3'R)(2',3',4'-trihydroxybutyl)]pyrazine 816 mg of 2-acetylsalicylic acid chloride are added, at a temperature close to 20° C. under an argon atmosphere, to 500 mg of 2-[(1R,2S,3R)(1,2,3,4-tetrahydroxybutyl)]-5-[(2'S,3'R)(2',3',4'-trihydroxybutyl)]pyrazine in suspension in 5 cm³ of pyridine dried over potassium hydroxide. The solution obtained is stirred at a temperature close to 20° C. for 15 minutes. The solvent is evaporated under reduced pressure (2.7 kPa) at a temperature close to 30° C. The crude reaction product is purified by chromatography under atmospheric pressure on 40 g of Merck silica gel 60 (0.040–0.063 mm) contained in a column 2 cm in diameter, eluting with an eluent gradient consisting of a mixture of dichloromethane-methanol: 100-0 then 95-5 by volume. The chromatography is followed by thin-layer chromatography. The fractions containing only the expected product are combined and concentrated to dryness under reduced pressure (2.7 kPa)at a temperature close to 30° C., to give 462 mg of impure expected product. The latter is purified by two chromatographies on Merck 60 $F_{254}$ silica gel plates (thickness=1 mm, 20×20 cm), eluting with an eluent gradient consisting of a dichloromethane-methanol mixture (once 100-0 by volume then twice 90-10 by volume). The fraction containing only the desired product is extracted with a dichloromethane-methanol (90-10 by volume) mixture, filtered on sintered.glass and then concentrated to dryness under reduced pressure (2.7 kPa) at a temperature close to 30° C.

108 mg of 4,4'-O,O-di-(acetoxybenzoyl)-2-[(1R,2S,3R)(1,2,3,4-tetrahydroxybutyl)]-5-[(2'S,3'R)(2',3',4'-trihydroxybutyl)]pyrazine are thus obtained in the form of a white powder.

The product obtained has the following characteristics:

¹H NMR spectrum (400 MHz, $(CD_3)_2SO$ d6, δ in ppm): 2.31 (s, 6H: the 2 $OCOCH_3$); 2.80 (dd, J=13.5 and 9 Hz, 1H: 1H of $CH_2$ 5α); 3.17 (dd, J=13.5 and 2.5 Hz, 1H: the other H of $CH_2$ 5δ); from 3.60 to 3.75 (mt, 1H: CH 5γ); 3.70 (broad t, J=9 Hz, 1H: CH 2β); 3.86 (mt, 1H: CH 5β); 3.97 (mt, 1H: CH 2γ); from 4.15 to 4.30 (mt, 2H: 1H of $CH_2$ 2δ and 1H of $CH_2$ 5δ); from 4.40 to 4.55 (mt, 2H: the other H of $CH_2$ 2δ and the other H of $CH_2$ 5δ); 4.74 (d, J=9 Hz, 1H: OH at position 2β); 4.96 (d, J=6 Hz, 1H: OH at position 5α); 5.01 (broad d, J=6 Hz, 1H: CH 2α); 5.23 (d, J=6 Hz, 1H: OH at position 2γ); 5.28 (d, J=6 Hz, 1H: OH at position 5γ); 5.46 (d, J=6 Hz, 1H: OH at position 2α); 7.24 (broad d, J=8 Hz, 2H: the 2 aromatic H at position 3); 7.43 (broad t, J=8 Hz, 2H: the 2 aromatic H at position 5); 7.69 (broad t, J=8 Hz, 2H: the 2 aromatic H at position 4); 8.04 (mt, 2H: the 2 aromatic H at position 6); 8.45 (s, 1H: =CH at position 6); 8.69 (s, 1H: =CH at position 3).

EXAMPLE 6

1,2,2',3,3',4,4'-O,O,O,O,O,O,O-heptabenzoyl-2-[(1R,2S,3R)(1,2,3,4-tetrahydroxybutyl)]-5-[(2'S,3'R)(2',3',4'-trihydroxybutyl)]pyrazine 0.63 cm³ of benzoyl chloride is added, dropwise, at a temperature close to 20° C. under an argon atmosphere, to 110 mg of 2-[(1R,2S,3R)(1,2,3,4-tetrahydroxybutyl)]-5-[(2'S,3'R) (2',3',4'-trihydroxybutyl)]-pyrazine in suspension in 2.5 cm³ of pyridine dried over a 4Å molecular sieve. The white reaction suspension is stirred for 16 hours at a temperature close to 20° C. The medium is diluted with 2 cm³ of a dichloromethane-methanol (94-5 by volume) mixture. The solvents are evaporated under an air stream at a temperature close to 20° C. The residue obtained is dissolved with 20 cm³ of dichloromethane. The organic phase is washed with 5 cm³ of water, dried over magnesium sulphate, filtered on sintered glass and then concentrated to dryness under reduced pressure (0.2 kPa) at a temperature close to 40° C. 490 mg of a white solid are obtained, which solid is purified by chromatography under atmospheric pressure on 40 g of Merck silica gel 60 $F_{254}$ (0.063–0.200 mm) contained in a column 2.5 cm in diameter. An eluent gradient is used which consists of a dichloromethane-methanol mixture: 100-0 by volume (500 cm³) and then 98-2 by volume (750 cm³), collecting 12 cm³ fractions. The fractions containing only the desired product are combined and concentrated to dryness under reduced pressure (about 2.7 kPa) ata temperature close to 40° C.

374 mg of 1,2,2',3,3',4,4'-O,O,O,O,O,O,O-heptabenzoyl-2-[(1R,2S,3R)(1,2,3,4-tetrahydroxybutyl)]-5-[(2'S,3'R)(2',3',4'-trihydroxybutyl)]pyrazine are thus obtained in the form of a white foam.

The product obtained has the following characteristics:

¹H NMR spectrum (400 MHz, $(CD_3)_2SO$ d6, δ in ppm): from 3.30 to 3.45 (mt, 2H: $CH_2$ 5δ); 4.60 (dd, J=12 and 5.5 Hz, 1H: 1H of $CH_2$ 2δ); 4.66 (dd, J=12 and 7 Hz, 1H: 1H of $CH_2$ 5δ); 4.83 (mt, 2H: the other H of $CH_2$ 2δ and the other H of $CH_2$ 5δ); 5.76 (mt, 1H: CH 5γ); from 5.80 to 5.95 (mt, 2H: CH 2γ and CH 5β); 6.20 (dd, J=7 and 4 Hz, 1H: CH 2β); 6.48 (d, J=4 Hz, 1H: CH 2α); from 7.30 to 8.05 (mt, 35H: the aromatic H of the 7 $OCOC_6H_5$); 8.63 (s, 1H: =CH at position 6); 8.70 (s, 1H: =CH at position 3).

EXAMPLE 7

1,2,2',3, 3',4,4'-O,O,O,O,O,O,O-heptaacetyl-2-[(1R,2S,3R)(1,2,3,4-tetrahydroxybutyl)]-5-[(2'S,3'R)(2',3',4'-trihydroxybutyl)]pyrazine 0.0945 cm³ of acetic anhydride is added, dropwise at a temperature close to 20° C. under an argon atmosphere, to 20 mg of 2-[(1R,2S,3R)(1,2,3,4-tetrahydroxybutyl)]-5-[(2'S,3'R) (2',3',4'-trihydroxybutyl)]pyrazine in suspension in 0.2 cm³ of pyridine dried over a 4 Å molecular sieve. The solution obtained after stirring for one hour is again stirred for an additional 17 hours at a temperature close to 20° C. The solvent is evaporated under reduced pressure (2.7 kPa) at a temperature close to 40° C. The residue thus obtained is purified by chromatography on 2 Merck 60 $F_{254}$ silica gel plates (thickness 0.5 mm, 20×20 cm), eluting with a dichloromethane-methanol (97-3 by volume) mixture. The fraction containing only the desired product is extracted with a dichloromethane-methanol (85-15 by volume) mixture, filtered on sintered glass and then concentrated to dryness under reduced pressure (2.7 kPa) at a temperature close to 40° C.

37.8 mg of 1,2,2',3,3',4,4'-O,O,O,O,O,O,O-heptaacetyl)-2-[(1R,2S,3R)(1,2,3,4-tetrahydroxybutyl)]-5-[(2'S,3'R)(2',3',4'-trihydroxybutyl)]pyrazine are thus obtained in the form of a pale yellow oil.

The product obtained has the following characteristics:

¹H NMR spectrum (300 MHz, $CDCl_3$, δ in ppm): 1.88–1.92–2.03–2.06–2.08 and 2.19 (6 s, respectively 3H–3H–3H–3H–6H and 3H: the 7 OCOCH$_3$); 3.09 (limiting AB, 2H: CH$_2$ 5α); from 4.05 to 4.40 (mt, 4H: CH$_2$ 2δ and CH$_2$ 5δ); from 5.20 to 5.35 and 5.50 (2 mts, respectively 2H and 1H: CH 2γ–CH 5β and CH 5γ); 5.62 (dd, J=9 and 2.5 Hz, 1H: CH 2β); 6.14 (d, J=2.5 Hz, 1H: CH 2α); 8.37 (s, 1H: =CH at position 6); 8.44 (s, 1H: =CH at position 3).

EXAMPLE 8

1,2,2',3,3',4,4'-O,O,O,O,O,O,O-heptaacetyl-2-[(1R,2S,3R)(1,2,3,4-tetrahydroxybutyl)]- 6-[(2'S,3'R)(2',3',4'-trihydroxybutyl)]pyrazine 0.285 cm$^3$ of acetic anhydride is added, dropwise at a temperature close to 20° C. under an argon atmosphere, to 60 mg of 2-[(1R,2S,3R)(1,2,3,4-tetrahydroxybutyl)]-6-[(2'S,3'R)(2',3',4'-trihydroxybutyl)]pyrazine in suspension in 0.6 cm$^3$ of pyridine dried over a 4 Å molecular sieve. The reaction suspension is stirred for 15 hours at a temperature close to 20° C. The solvent for the reaction medium thus obtained is evaporated under reduced pressure (2.7 kPa) at a temperature close to 40° C. The crude reaction product is purified by chromatography on 6 Merck 60 F$_{254}$ silica gel plates (thickness=0.5 mm, 20×20 cm), eluting with a dichloromethane-methanol (97-3 by volume) mixture. The fraction containing only the desired product is extracted with a dichloromethane-methanol (85-15 by volume) mixture, filtered on sintered glass and then concentrated to dryness under reduced pressure (2.7 kPa) at a temperature close to 40° C.

117 mg of 1,2,2',3,3',4,4'-O,O,O,O,O,O,O-heptaacetyl-2-[(1R,2S,3R)(1,2,3,4-tetrahydroxybutyl)]-6-[(2'S,3'R)(2',3',4'-trihydroxybutyl)]pyrazine are thus obtained in the form of a white foam.

The product obtained has the following characteristics:

$^1$H NMR spectrum (300 MHz, CDCl$_3$, δ in ppm): 1.90–1.99–2.05–2.10–2.12 and 2.20 (6 s, respectively 3H–3H–3H–3H–6H and 3H: the 7 OCOCH$_3$); 3.16 (limiting AB, 2H: CH$_2$ 6α); from 4.10 to 4.45 (mt, 4H: CH$_2$ 2δ and CH$_2$ 6δ); from 5.20 to 5.35 and 5.50 (2 mts, respectively 2H and 1H: CH 2γ–CH 6β and CH 6γ); 5.64 (dd, J=9 and 3 Hz, 1H: CH 2β); 6.10 (d, J=3 Hz, 1H: CH 2α); 8.38 and 8.41 (2s, 1H each: =CH at position 3 and =CH at position 5).

2-[(1R,2S,3R)(1,2,3,4-tetrahydroxybutyl)]-6-[(2'S,3'R)(2',3',4'-trihydroxybutyl)]pyrazine may be prepared according to the method described in patent JP 53-90401.

EXAMPLE 9

1,1',2,2',3,3',4,4'-O,O,O,O,O,O,O,O-octaacetyl-2-[(1R,2S,3R)(1,2,3,4-tetrahydroxybutyl)]-5-[(1'R,2'S,3'R)(1',2',3',4'-tetrahydroxybutyl)]pyrazine 0.104 cm$^3$ of acetic anhydride is added, dropwise at a temperature close to 20° C. under an argon atmosphere, to 20 mg of 2-[(1R,2S,3R)(1,2,3,4-tetrahydroxybutyl)]-6-[(1'R,2'S,3'R) (1',2',3',4'-tetrahydroxybutyl)]pyrazine in suspension in 0.2 cm$^3$ of pyridine dried over a 4 Å molecular sieve. The reaction suspension is stirred for 15 hours at a temperature close to 20° C. The solvent is evaporated under reduced pressure (2.7 kPa) at a temperature close to 40° C. 44.7 mg of a white solid are obtained, which solid is purified by chromatography on 2 Merck 60 F$_{254}$ silica gel plates (thickness=0.5 mm, 20×20 cm), eluting with a dichloromethane-methanol (97-3 by volume) mixture. The fraction containing only the desired product is extracted with a dichloromethane-methanol (85-15 by volume) mixture, filtered on sintered glass and then concentrated to dryness under reduced pressure (2.7 kPa) at a temperature close to 40° C.

36.1 mg of 1,1',2,2',3,3',4,4'-O,O,O,O,O,O,O,O-octaacetyl-2-[(1R,2S,3R)(1,2,3,4-tetrahydroxybutyl)]-5-[(1'R,2'S,3'R)(1',2',3',4'-tetrahydroxybutyl)]pyrazine are thus obtained in the form of a white solid.

The product obtained has the following characteristics:

$^1$H NMR spectrum (300 MHz, CDCl$_3$, δ in ppm): 1.90–2.03–2.10 and 2.22 (4 s, respectively 6H–6H–6H and 6H: the 8 OCOCH$_3$); 4.14 (dd, J=12.5 and 5.5 Hz, 2H: 1H of CH$_2$ 2δ and 1H of CH$_2$ 5δ); 4.29 (dd, J=12.5 and 3 Hz, 2H: the other H of CH$_2$ 2δ and the other H of CH$_2$ 5δ); 5.31 (mt, 2H: CH 2γ and CH 5γ); 5.67 (dd, J=9 and 2 Hz, 2H: CH 2β and CH 5β); 6.17 (d, J=2 Hz, 2H: CH 2α and CH 5α); 8.47 (s, 2H: =CH at position 3 and =CH at position 6).

2-[(1R,2S,3R)(1,2,3,4-tetrahydroxybutyl)]-6-[(1'R,2'S,3'R) (1',2',3',4'-tetrahydroxybutyl)]pyrazine may be prepared according to the method described in patent JP 53-90401 or by Kuhn et al, J. L. Ann. Chem. 644, 122–7, 1961.

EXAMPLE 10

1,2,2',3,3'-O,O,O,O,-pentabenzyl-2-[(1R,2S,3R)(1,2,3,4-tetrahydroxybutyl)]-5-[(2'S,3'R)(2',3',4'-trihydroxybutyl)]pyrazine Preparation of: 4,4'-O,O-di(diphenyl-tert-butylsilyl)-2-[(1R,2S,3S)(1,2,3,4-tetrahydroxybutyl)]-5-[(2'S,3'S)(2',3',4'-trihydroxybutyl)]pyrazine 2.30 cm$^3$ of tert-butyldiphenylsilyl chloride are added dropwise at a temperature close to 20° C. under an argon atmosphere to 1.19 g of 2-[(1R,2S,3S)(1,2,3,4-tetrahydroxybutyl)]-5-[(2'S, 3'R)(2',3',4'-trihydroxybutyl)]pyrazine in suspension in 30 cm$^3$ of pyridine dried over a 4 Å molecular sieve. The reaction suspension is stirred for two and a half days at a temperature close to 20° C., at the end of which the medium is solubilized. The solvent is evaporated under reduced pressure (0.2 kPa) at a temperature close to 40° C. The residual oil is coevaporated with twice 20 cm$^3$ of toluene under reduced pressure (0.2 kPa) at a temperature close to 40° C. A yellow oil is thus obtained which is purified by chromatography under atmospheric pressure on 200 g of Merck silica gel 60 F$_{254}$ (0.063–0.200 mm) contained in a column 4.5 cm in diameter. An eluent gradient is used which consists of a dichloromethane-methanol mixture: 98-2 by volume (1000 cm$^3$) and then 94-5 by volume (2000 cm$^3$), collecting 25 cm$^3$ fractions. The fractions containing only the desired product are combined and concentrated to dryness under reduced pressure (2.7 kPa) at a temperature close to 40° C.

2.568 g of 4,4'-O,O-di(diphenyl-tert-butylsilyl)-2-[(1R,2S,3S)(1,2,3,4-tetrahydroxybutyl)]-5-[(2'S,3'S)(2',3',4'-trihydroxybutyl)]pyrazine are thus obtained in the form of a white foam.

The product obtained has the following characteristics:

$^1$H NMR spectrum (250 MHz, (CD$_3$)$_2$SO d6, δ in ppm); 1.02 (s, 18H: the 2 C(CH$_3$)$_3$); 2.78 (dd, J=14 and 9 Hz, 1H: 1H of CH$_2$ 5α); 3.08 (dd, J=14 and 2.5 Hz, 1H: the other H of CH$_2$ 5α); from 3.55 to 4.00 (mt, 8H: CH 2β-CH 2γ-CH 5β-CH 5γ-CH$_2$O 2δ and CH$_2$O 5δ); 4.39 (d, J=9 Hz, 1H: OH at position 2β); 4.69 (d, J=7 Hz, 1H: OH at position 5β); from 4.85 to 5.00 (mt, 2H: OH at position 2γ and OH at position 5γ); 5.02 (broad d, J=6 Hz, 1H: CH 2α); 5.37 (d, J=6 Hz, 1H: OH at position 2α); from 7.30 to 7.60 and from 7.65 to 7.80 (2 mts, respectively 12H and 8H: the aromatic H of the 4 phenyls); 8.41 (d, J=1 Hz, 1H: =CH at position 6); 8.66 (d, J=1 Hz, 1H: =CH at position 3).

Preparation of: 1,2,2',3,3'-O,O,O,O',O-pentabenzyl-4,4'-O,O-di(diphenyl-tert-butylsilyl)-2-[(1R,2S,3S)(1,2,3,4-tetrahydroxybutyl)]-5-[(2'S,3'S)(2',3',4'-trihydroxybutyl)]pyrazine 1.15 cm³ of benzyl bromide, 5 mg of sodium iodide and 61.5 mg of sodium hydride (at 50% in oil) are successively added at a temperature close to 20° C. and under an argon atmosphere to 100 mg of 4, 4'-O,O-di(diphenyl-tert-butylsilyl)-2-[(1R,2S,3S)(1,2,3,4-tetrahydroxybutyl)]-5-[(2'S,3'S)(2',3',4'-trihydroxybutyl)]pyrazine in solution in 0.5 cm³ of dimethylformamide. The reaction medium is stirred for 3 hours 10 minutes at a temperature close to 20° C. under an argon atmosphere. The orange-coloured suspension thus obtained is diluted with 30 cm³ of ethyl ether, 5 cm³ of saturated aqueous ammonium chloride solution and 5 cm³ of distilled water. The organic phase is washed with 3 times 5 cm³ of a saturated aqueous sodium chloride solution, dried over magnesium sulphate; filtered on sintered glass and then concentrated to dryness under reduced pressure (0.4 kPa) at a temperature close to 40° C. 1.34 g of an orange-coloured oil are thus obtained, which oil is purified by chromatography under atmosphericpressure on 50 g of Merck silica gel 60 $F_{254}$ (0.063–0.200 nm) contained in a column 2.5 cm in diameter. An eluent gradient is used which consists of a dichloromethane-cyclohexane mixture from 0–100 to 100-0 by volume, collecting 10 cm³ fractions. The fractions containing only the desired product are combined and concentrated to dryness under reduced pressure (about 2.7 kPa) at a temperature close to 40° C.

39.8 mg of 1,2,2',3,3'-O,O,O,O,O-pentabenzyl-4, 4'-O,O-di(diphenyl-tert-butylsilyl)-2-[(1R,2S,3S)(1,2,3,4-tetrahydroxybutyl)]-5-[(2'S,3'S)(2',3',4'-trihydroxybutyl)]pyrazine are thus obtained in the form of a yellow oil.

The product obtained has the following characteristics:

¹H NMR spectrum (400 MHz, CDCl₃, δ in ppm): 1.08 (s, 18H: the 2 C(CH₃)₃); 3.12-(limiting AB, J=5Hz, 2H: CH₂ 5α); from 3.65 to 3.70 (mt, 2H: CH 5γ and 1H of an OCH₂Ar); from 3.75 to 3.95 (mt, 4H: CH 2γ-1H of CH₂O 2δ-1H of CH₂O 5δ and 1H of an OCH₂Ar); 4.04 (broad d, J=9 Hz, 1H: the other H of CH₂O 5δ); from 4.05 to 4.15 (mt, 3H: CH 2β- the other H of CH₂O 2δ and 1H of an OCH₂Ar); 4.19 (mt, 1H: CH 5O); from 4.25 to 4.35 (mt, 3H: 3H corresponding to OCH₂Ar); 4.43 (d, J=11 Hz, 1H: 1H of an OCH₂Ar); 4.50 (d, J=12 Hz, 1H: 1H of an OCH₂Ar); from 4.55 to 4.85 (mt, 3H: 1H of an OCH₂Ar and OCH₂Ar); 5.03 (d, J=3 Hz, 1H: CH 2α); from 6.65 to 7.80 (mt, 45H: aromatic H of the 9 phenyls); 8.45 (s, 1H: =CH at position 6); 8.80 (s, 1H: =CH at position 3).

Preparation of: 1,2,2',3,3'-O,O,O,O,O-pentabenzyl-2-[(1R,2S,3R)(1,2,3,4-tetrahydroxybutyl)]-5-[(2'S,3'R)(2',3',4'-trihydroxybutyl)]pyrazine 0.127 cm³ of a 1 M n-tetrabutylammonium fluoride solution in tetrahydrafuran is added at a temperature close to 24° C. to 39 mg of 1,2,2',3,3'-O,O,O,O,O-pentabenzyl-4,4'-O,O-di(diphenyl-tert-butylsilyl)-2-[(1R,2S,3S)(1,2,3,4-tetrahydroxybutyl)]-5-[(2'S,3'S)(2',3',4'-trihydroxybutyl)]pyrazine in solution in 0.5 cm³ of tetrahydrofuran dried over a 4 Å molecular sieve. The reaction medium immediately becomes red and is stirred at a temperature close to 24° C. for 40 min. The reaction mixture is directly purified by chromatography on 3 Merck 60 $F_{254}$ silica plates (thickness=0.5 mm, 20×20 cm:), eluting with a dichloromethane-methanol (97-3 by volume) mixture. The fraction containing only the desired product is extracted with a dichloromethane-methanol (85-15 by volume) mixture, filtered on sintered glass and then concentrated to dryness under reduced pressure (2.7 kPa) at a temperature close to 40° C.

2.9 mg of 1,2,2',3,3'-O,O,O,O,O-pentabenzyl-2-[(1R,2S,3R)(1,2,3,4-tetrahydroxybutyl)]-5-[(2'S,3'R)(2',3',4'-trihydroxybutyl)]pyrazine are thus obtained in the form of a colourless lacquer.

The product obtained has the following characteristics:

¹H NMR spectrum (400 MHz, (CD₃)₂SO d6, δ in ppm): 3.11 (limiting AB, 2H: CH₂ 5α); from 3.50 to 3.75 (mt, 6H: CH 2γ-CH 5γ-CH₂O-1H of the other CH₂O and 1H of an OCH₂Ar); 3.87 (broad d, J=10 Hz, 1H: the other H of OCH₂O); 3.93 (dd, J=8 and 3.5 Hz, 1H: CH 2β); 4.13 (mt, 2H: CH 5β and 1H of an OCH₂Ar); from 4.30 to 4.50 (mt, 5H: 5H corresponding to OCH₂Ar); from 4.60 to 4.75 (mt, 4H: 1H of an OCH₂Ar—OCH₂Ar and OH at position δ); 4.78 (t, J=5 Hz, 1H: OH at position δ); 4.89 (d, J=3.5 Hz, 1H: CH 2α); from 6.95 to 7.45 (mt, 25H: the aromatic H of the 5 phenyls); 8.56 (s, 1H: =CH at position 6); 8.64 (s, 1H: =CH at position 3).

EXAMPLE 11

4,4'-O,O-dimethoxyacetyl-2-[(1R,2S,3R)(1,2,3,4-tetrahydroxybutyl)]-5-[(2'S,3'R)(2',3',4'-trihydroxybutyl)]pyrazine 0.226 cm³ of methoxyacetyl chloride is added dropwise at a temperature close to 25° C. under an argon atmosphere to a suspension of 304 mg of 2-[(1R,2S,3R)(1,2,3,4-tetrahydroxybutyl)]-5-[(2'S,3'R)(2',3',4'-trihydroxybutyl)]pyrazine in 8 cm³ of anhydrous pyridine. After 48 hours at a temperature close to 25° C., the reaction mixture is concentrated to dryness under reduced pressure (0.5 kPa) at a temperature close to 40° C. The residue obtained is taken up in 2 cm³ of a dichloromethane-methanol (80-20 by volume) mixture and filtered on sintered glass. The filtrate is purified by preparative chromatography on 6 Merck 60 $F_{254}$ silica gel plates (thickness=1 mm, 20×20 cm), eluting with a dichloromethane-methanol (80-20 by volume) mixture. The fraction containing only the desired product is extracted with a dichloromethane-methanol (80-20 by volume) mixture, filtered on sintered glass and then concentrated to dryness under reduced pressure (0.5 kPa) at a temperature close to 35° C. 40 mg of 4,4'-O,O-dimethoxyacetyl-2-[(1R,2S,3R)(1,2,3,4-tetrahydroxybutyl)]-5-[(2'S,3'R)(2',3',4'-trihydroxybutyl)]pyrazine are thus obtained in the form of a viscous beige oil. This batch is grouped together with 4 other batches prepared in a similar manner (40, 70, 45 and 45 mg respectively), dissolved in a dichloromethane-methanol (80-20 by volume) mixture, filtered on sintered glass and then concentrated to dryness under reduced pressure (0.5 kPa) at a temperature close to 35° C. 225 mg. of 4,4'-O,O-dimethoxyacetyl-2-[(1R,2S,3R) (1,2,3,4-tetrahydroxybutyl)]-5-[(2'S,3'R) (2',3',4'-trihydroxybutyl)]pyrazine are thus obtained. This batch is purified by preparative chromatography on 7 Merck 60 $F_{254}$ silica gel plates (thickness=0.5 mm, 20×20 cm), eluting with dichloromethane-methanol (90-10 by volume) mixture. The fraction containing only the desired product is extracted with a dichloromethane-methanol (80-20 by volume) mixture, filtered on sintered glass and then concentrated to dryness under reduced pressure (0.5 kPa) at a temperature close to 20° C. 90 mg of 4,4'-O,O-dimethoxyacetyl-2-[(1R,2S,3R)(1,2,3,4-tetrahydroxybutyl)]-5-[(2'S,3'R)(2',3',4'-trihydroxybutyl)]pyrazine are thus obtained in the form of a thick beige oil. This batch is grouped together with another batch (105 mg) prepared in a similar manner, dissolved in 5 cm³ of methanol, filtered on cotton wool, and then concentrated to dryness under an argon stream at a temperature close to 20° C., and then under reduced pressure (1 kPa) at a temperature close to 30° C. 170 mg of 4,4'-O,O-dimethoxyacetyl-2-[(1R,2S,3R)(1,2,3,4-tetrahydroxybutyl)]-5-[(2'S,3'R) (2',3',4'-trihydroxybutyl)] pyrazine are thus obtained in the ford of a beige foam.

The product obtained has the following characteristics:

¹H NMR spectrum (400 MHz, (CD₃)₂SO d6, δ in ppm): 2.76 and 3.14 (2dd, respectively J=14 and 9 Hz and J=14 and 3 Hz, 1H each: CH₂ 5α); 3.35 (the 6H corresponding to OCH₃); from 3.50 to 3.65 (mt, 2H: CH 5γ and CH 2β); 3.78 (mt, 1H: CH 5β); 3.87 (mt, 1H: CH 2γ); from 4.05 to 4.15 (mt, 2H: 1H of CH₂O 2β and 1H of CH₂O 5δ); 4.08 (s, 4H: COCH₂O); 4.33 (dd, J=12 and 3 Hz, 1H: the other H of CH₂O 5δ); 4.37 (dd, J=11 and 2 Hz, 1H: the other H of CH₂O 2δ); 4.68 (d, J=9 Hz; 1H: OH at position 2β); 4.90 (d, J=6.5 Hz, 1H: OH at position 5β); 4.96 (broad d, J=6 Hz, 1H: CH 2α); 5.13 (d, J=5.5 Hz, 1H: OH at position 2γ); 5.18 (d, J=5.5 Hz, 1H: OH at position 5γ); 5.45 (d, J=6 Hz, 1H: OH at position 2α); 8.43 (broad s, 1H: =CH at position 6); 8.67 (broad s, 1H: =CH at position 3).

EXAMPLE 12

1,2,2',3,3',4,4'-O,O,O,O,O,O,O-heptaformyl-2-[(1R,2S,3R)(1,2,3,4-tetrahydroxybutyl)]-5-[(2'S,3'R)(2',3',4'-trihydroxybutyl)]pyrazine A mixture of 13 cm³ of formic acid and 6 cm³ of acetic anhydride is added, dropwise over 30 minutes, at a temperature close to 0° C. under an argon atmosphere, to 650 mg of 2-[(1R,2S,3R)(1,2,3,4-tetrahydroxybutyl)]-5-[(2'S,3'R)(2',3',4'-trihydroxybutyl)]pyrazine in suspension in 20 cm³ of pyridine dried over a 4 Å molecular sieve. The reaction mixture is then concentrated to dryness and then coevaporated with toluene, under reduced pressure (about 2.7 kPa), at a temperature close to 40° C. 1.1 g of a white solid are thus obtained. A sample of 500 mg of this white solid is taken up in 7.5 cm of dichloromethane and a few drops of methanol to form a suspension. The soluble portion of this suspension is purified by preparative chromatography on 5 Merck 60 F₂₅₄ silica gel plates (thickness=1 mm, 20×20 cm), eluting with a dichloromethane-ethyl acetate (7-3 by volume) mixture. The fraction containing only the desired product is extracted with a dichloromethane-methanol (90-10 by volume) mixture, filtered on sintered glass and then concentrated to dryness under reduced pressure (2.7 kPa) at a temperature close to 40° C. 116 mg of 1,2,2',3,3',4,4'-O,O,O,O,O,O,O-heptaformyl-2-[(1R,2S,3R)(1,2,3,4-tetrahydroxybutyl)]-5-[(2'S,3'R)(2',3',4'-trihydroxybutyl)]pyrazine are thus obtained in the form of a lacquer which partially crystallizes. The insoluble portion of the preceding suspension is taken up in dichloromethane and purified by preparative chromatography on 3 Merck 60 F₂₅₄ silica gel plates (thickness=1 mm, 20×20 cm), eluting with a dichloromethane-ethyl acetate (6-4 by volume) mixture. The fraction containing only the desired product is extracted with ethyl acetate, filtered on sintered glass and then concentrated to dryness under reduced pressure (2.7 kPa) at a temperature close to 40° C. 43 mg of a second fraction of 1,2,2',3,3',4,4'-O,O,O,O,O,O,O-heptaformyl-2-[(1R,2S,3R)(1,2,3,4-tetrahydroxybutyl)]-5-[(2'S,3'R) (2',3',4'-trihydroxybutyl)] pyrazine are thus obtained in the form of a colourless lacquer. The preceding two fractions of 1,2,2',3,3',4,4'-O,O,O,O,O,O,O-heptaformyl-2-[(1R,2S,3R)(1,2,3,4-tetrahydroxybutyl)]-5-[(2'S,3'R) (2',3',4'-trihydroxybutyl)] pyrazine are grouped together with another fraction of this same product prepared under identical conditions to form a single batch representing 232 mg.

The product obtained has the following characteristics:

¹H NMR spectrum (400 MHz, (CD₃)₂SO d6, δ in ppm): 3.22 (dd, J=15 and 9.5 Hz, 1H: 1H of CH₂ 5α); from 3.30 to 3.40 (mt: 1H corresponding to the other H of CH₂ 5α); 4.24 (dd, J=12 and 6 Hz, 1H: 1H of CH₂ 2δ); 4.32 (dd, J=12 and 7.5 Hz, 1H: 1H of CH₂ 5δ); 4.49 (dd, J=12 and 2.5 Hz, 1H: the other H of CH₂ 2δ); 4.53 (dd, J=12 and 3 Hz, 1H: the other H of CH₂ 5δ); 5.33 (mt, 1H: CH 2γ); 5.40 (mt, 1H: CH 5γ); 5.62 (mt, 1H: CH 5β); 5.74 (dd, J=7 and 4 Hz, 1H: CH 2β); 6.18 (d, J=4 Hz, 1H: CH 2α); 8.10–8.16–8.25–8.28–8.30–8.34 and 8.43 (7 s, 1H each: the 7 HC=O); 8.63 (broad s, 1H: =CH at position 6); 8.66 (broad s, 1H: =CH at position 3).

EXAMPLE 13

1,2,2',3,3',4,4'-O,O,O,O,O,O,O-(methyl heptamonosuccinate)-2-[(1R,2S,3R)(1,2,3,4-tetrahydroxybutyl)]-5-[(2'S,3'R)(2',3',4'-trihydroxybutyl)]pyrazine 368 mg of dicyclohexylcarbodiimide and 6 mg of 4-(N,N-dimethylamino)pyridine are successively added, at a temperature close to 24° C., under an argon atmosphere, to 50 mg of 2-[(1R,2S,3R)(1,2,3,4-tetrahydroxybutyl)]-5-[(2'S,3'R)(2',3',4'-trihydroxybutyl)]pyrazine, 50 mg of a 4 Å molecular sieve powder and 228 mg of methyl monosuccinate in suspension in 1 cm³ of anhydrous N,N-dimethylformamide. After 5 hours at a temperature close to 24° C., the reaction mixture is diluted with 30 cm³ of ethyl acetate, washed with 3 times 8 cm³ of water, 8 cm³ of a saturated aqueous sodium chloride solution, and then dried over magnesium sulphate, filtered on sintered glass, and concentrated to dryness under reduced pressure (0.5 kPa) at a temperature close to 42° C. 608 mg of a pink solid are thus obtained, which solid is purified by chromatography under atmospheric pressure on 40 g of Merck silica gel 60 F₂₅₄ (0.063–0.200 mm) contained in a column 2.5 cm in diameter. An elution gradient is used which consists of a dichloromethane-methanol mixture 99-1 by volume (0.25 l) and then 98-2 by volume (0.25 l), collecting 12 cm³ fractions. The fractions containing only the desired product are combined and concentrated to dryness under reduced pressure (about 2.7 kPa) at a temperature close to 40° C. 166.5 mg of 1,2,2',3,3',4,4'-O,O,O,O,O,O,O-(methyl heptamonosuccinate)-2-[(1R,2S,3R)(1,2,3,4-tetrahydroxybutyl)]-5-[(2'S,3'R)(2',3',4'-trihydroxybutyl)] pyrazine are thus obtained in the form of a colourless oil.

The product obtained has the following characteristics:

¹H NMR spectrum (400 MHz, (CD₃)₂SO d6, δ in ppm): from 2.25 to 2.85 (mt, 28H: the 7 COCH₂CH₂CO); 3.15 (dd, J=14 and 9 Hz, 1H: 1H of CH₂ 5α); from 3.20 to 3.35 (mt: 1H corresponding to the other H of CH₂ 5α); 3.62 and 3.65 (2 s, 21H in total: the 7 COOCH₃); 4.16 (dd, J=12 and 5.5 Hz, 1H: 1H of CH₂O 2δ); 4.25 (dd, J=12 and 7 Hz, 1H: 1H of CH₂O 5δ); 4.38 (mt, 2H: the other H of CH₂O 0 2δ and the other H of CH₂O 5δ); 5.25 (mt, 2H: CH 2γ and CH 5γ); 5.47 (mt, 1H: CH 5β); 5.59 (dd, J=8 and 4 Hz, 1H: CH 2β); 6.00 (d,J=4 Hz, 1H: CH 2α); 8.58 (s, 2H: =CH at position 6 and =CH at position 3).

EXAMPLE 14

1,2,2',3,3',4,4'-O,O,O,O,O,O,O-(ethyl heptamonoglutarate)-2-[(1R,2S,3R)(1,2,3,4-tetrahydroxybutyl)]-5-[(2'S,3'R)(2',3',4'-trihydroxybutyl)]pyrazine 3.68 g of dicyclohexylcarbodiimide and 60 mg of 4-(N,N-dimethylamino)pyridine are successively added, at a temperature close to 24° C., under an argon atmosphere, to 500 mg of 2-[(1R,2S,3R)(1,2,3,4-tetrahydroxybutyl)]-5-[(2'S,3'R) (2',3',4'-trihydroxybutyl)]pyrazine, 2 g of 4 Å molecular sieve powder and 2.76 g of ethyl monoglutarate in suspension in 10 cm$^3$ of anhydrous N,N-dimethylformamide. After 13 hours at a temperature close to 22° C., the reaction mixture is filtered on sintered glass. The sintered glass is rinsed with 60 cm$^3$ of ethyl acetate. The organic phase is washed with twice 30 cm$^3$ of a saturated aqueous sodium hydrogen carbonate solution, 6 times 30 cm$^3$ of water and 30 cm$^3$ of a saturated aqueous sodium chloride solution, and then dried over magnesium sulphate, filtered on sintered glass, and concentrated to dryness under reduced pressure (0.6 kPa) at a temperature close to 42° C. 2.16 g of a brown oil are thus obtained of which a sample of 200 mg is purified by preparative chromatography on 8 Merck 60 F$_{254}$ silica gel plates (thickness=0.5 mm, 20×20 cm), eluting with a dichloromethane-methanol (97-3 by volume) mixture. The fraction containing only the desired product is extracted with a dichloromethane-methanol (85-15 by volume) mixture, filtered on sintered glass and then concentrated to dryness under reduced pressure (2.7 kPa) at a temperature close to 40° C. 82.6 mg of 1,2,2',3,3',4,4'-O,O,O,O,O,O,O-(ethyl heptamonoglutarate)-2-[(1R,2S,3R)(1,2,3,4-tetrahydroxybutyl)]-5-[(2'S,3'R)(2',3',4'-trihydroxybutyl)]pyrazine are thus obtained in the form of a colourless oil.

The product obtained has the following characteristics:
$^1$H NMR spectrum (400 MHz, (CD$_3$)$_2$SO d6, δ in ppm): 1.17 (t, J=8 Hz, 21H: the 7 CH$_3$); from 1.50 to 1.85 (mt, 14H: the 7 central CH$_2$); from 2.10 to 2.60 (mt, 28H: the 14 COCH$_2$); 3.11 (dd, J=14 and 9 Hz, 1H: 1H of CH$_2$ 5α); 3.22 (dd, J=14 and 3.5 Hz, 1H: the other H of CH$_2$ 5α); 4.05 (mt, 14H: the 7 COOCH$_2$); from 4.10 to 4.25 (mt, 2H: 1H of CH$_2$ 2δ and 1H of CH$_2$ 5δ); 4.31 and 4.39 (broad d and dd, respectively J=12 Hz and J=12 and 3 Hz, 1H each: the other H of CH$_2$ 2α and the other H of CH$_2$ 5δ); 5.23 (mt, 2H: CH 2γ and CH 5γ); 5.44 (mt, 1H: CH 5β); 5.54 (dd, J=7 and 4 Hz, 1H: CH 2β); 5.98 (d, J=4 Hz, 1H: CH 2α); 8.53 (broad s, 2H: =CH at position 3 and =CH at position 6).

EXAMPLE 15

1,2-O,O-3,4-O,O-3',4'-O,O-tricarbonyl-2-[(1R,2S,3R)(1,2,3,4-tetrahydroxybutyl)]-5-[(2'S,3'R)(2',3',4'-trihydroxybutyl)]pyrazine 1.567 cm$^3$ of phenyl chloroformate are added to 1.52 g of 2-[(1R,2S,3R)(1,2,3,4-tetrahydroxybutyl)]-5-[(2'S,3'R) (2',3',4'-trihydroxybutyl)]pyrazine in suspension in 50 cm$^3$ of anhydrous pyridine, at a temperature close to 20° C., under an argon atmosphere. After 66 hours at a temperature close to 20° C., the reaction mixture is concentrated to dryness under reduced pressure at a temperature close to 40° C. The residue obtained is taken up and stirred in a mixture of 50 cm$^3$ of dichloromethane and 25 cm$^3$ of water. After decantation, the organic phase is dried over magnesium sulphate, filtered on sintered glass, and concentrated to dryness under reduced pressure at a temperature close to 40° C. 2 g of a thick beige oil are thus obtained. The aqueous phase is filtered on sintered glass and the solid residue, air-dried, gives 54 mg of 1,2-O,O-3,4-O,O-3',4'-O,O-tricarbonyl-2-[(1R,2S,3R)(1,2,3,4-tetrahydroxybutyl)]-5-[(2'S,3'R)(2',3',4'-trihydroxybutyl)]pyrazine. The filtrate is concentrated to dryness under reduced pressure at a temperature close to 40° C. 1.2 g of a light brown oil are thus obtained, which oil is purified by chromatography under atmospheric pressure on a 20 cm high Merck silica gel 60 F$_{254}$ (0.063–0.040 mm) contained in a column 1.5 cm in diameter, using an eluent consisting of a dichloromethane-methanol (94-5 by volume) mixture and collecting 15 cm$^3$ fractions. The fractions containing only the desired product are combined and concentrated to dryness under reduced pressure (about 2.7 kPa) at a temperature close to 40° C. 0.34 g of 1,2-O,O-3,4-O,O-3',4'-O,O-tricarbonyl-2-[(1R,2S,3R)(1,2,3,4-tetrahydroxybutyl)]-5-[(2'S,3'R)(2',3',4'-trihydroxybutyl)]pyrazine is thus obtained in the form of a yellow pasty solid. The preceding samples of 54 mg and 0.34 g of 1,2-O,O-3,4-O,O-3',4'-O,O,-tricarbonyl-2-[(1R,2S,3R)(1,2,3,4-tetrahydroxybutyl)]-5-[(2'S,3'R) (2',3',4'-trihydroxybutyl)]pyrazine are combined and dissolved in 10 cm$^3$ of dimethyl sulphoxide. The solution obtained is filtered on sintered glass and concentrated under reduced pressure (about 0.2 kPa) at a temperature close to 75° C. The light brown oil obtained is immediately dissolved in 4 cm$^3$ of methanol. The insoluble product formed is filtered on sintered glass, washed with 3 times 1 cm$^3$ of methanol, air-dried, and then dried under reduced pressure (1 kPa) at a temperature close to 40° C. 0.252 g of 1,2-O,O-3,4-O,O-3',4'-O,O-tricarbonyl-2-[(1R,2S,3R)(1,2,3,4-tetrahydroxybutyl)]-5-[(2'S,3'R)(2',3',4'-trihydroxybutyl)]pyrazine is thus obtained in the form of a beige powder.

The product obtained has the following characteristics:
$^1$H NMR spectrum (400 MHz, (CD$_3$)$_2$SO d6, δ in ppm): 2.91 and 3.00 (2dd, respectively J=14 and 9 Hz and J=14 and 4 Hz, 1H each: CH$_2$ 5α); 4.22 (mt, 1H: CH 5β); from 4.40 to 4.55 (mt, 2H: 1H of CH$_2$O 2δ and 1H of CH$_2$O 5δ); 4.56 (t, J=8.5 Hz, 1H: the other H of CH$_2$O 5δ); 4.70 (t, J=8.5 Hz, 1H: the other H of CH$_2$O 2δ); 4.82 (mt, 1H: CH 5γ); from 5.25 to 5.40 (mt, 2H: CH 2γ and CH 2β); 5.65 (d, J=5.5 Hz, 1H: OH at position 5β); 6.12 (d, J=5 Hz, 1H: CH 2α); 8.71 (d, J=1 Hz, 1H: =CH at position 6); 8.83 (d, J=1 Hz, 1H: =CH at position 3).

EXAMPLE 16

3,4-O,O-3',4'-O,O,-bis-carbonyl-2-[(1R,2S,3R)(1,2,3,4-tetrahydroxybutyl)]-5-[(2'S,3'R)(2',3',4'-trihydroxybutyl)]pyrazine 2.19 cm$^3$ of phenyl chloroformate are added to 1.52 g of 2-[(1R,2S,3R)(1,2,3,4-tetrahydroxybutyl)]-5-[(2'S,3'R) (2',3',4'-trihydroxybutyl)]pyrazine in suspension in 50 cm$^3$ of anhydrous pyridine, at a temperature close to 20° C., under an argon atmosphere. After 72 hours at a temperature close to 20° C., the reaction mixture is concentrated to dryness under reduced pressure (1 kPa) at a temperature close to 40° C. The light beige oil obtained is taken up and stirred in a mixture of 25 cm$^3$ of ethyl acetate and 25 cm$^3$ of water. After decantation, the organic phase is washed with twice 5 cm$^3$ of water, while the aqueous phase is washed with 5 cm$^3$ of ethyl acetate. The aqueous phases are pooled and concentrated to dryness under reduced pressure (0.5 kPa) at a temperature close to 50° C. 2.74 g of a light yellow pasty solid are thus obtained. The organic phases are pooled, dried over magnesium sulphate, filtered on sintered glass, and concentrated to dryness under reduced pressure (0.5 kPa) at a temperature close to 50° C. 2.86 g of a thick beige oil are thus obtained. The preceding light yellow pasty solid (2.74 g) is purified by chromatography under atmospheric pressure on a 20 cm high Merck silica gel 60 F$_{254}$ (0.063–0.040 mm) contained in a column 2.5 cm in diameter, using an eluent consisting of a dichloromethane-methanol mixture (94-5 and then 90-10 by volume) and collecting 15 cm$^3$ fractions. The fractions containing only the desired product are combined and concentrated to dryness under reduced pressure (about 2.7 kPa) at a temperature close to 40° C. The white pasty solid obtained (1.4 g) is taken up in 5 cm³ of methanol, stirred for a few minutes, filtered on sintered glass, washed with 3 times 2 cm³ of methanol, and air-dried. 0.183 g of a white powder is obtained, which powder is combined with another batch prepared in a similar manner (70 mg). The mixture obtained is dissolved in 4 cm³ of dimethyl sulphoxide, filtered on sintered glass, and concentrated under reduced pressure (0.5 kPa) at a temperature close to 70° C. 0.5 g of a beige oil is thus obtained, which oil is dissolved in 1 cm³ of methanol. After adding dropwise 5 cm³ of water, the mixture is placed at a temperature close to 4° C. for 48 hours and then filtered on sintered glass. The insoluble product formed is washed with 2 cm³ of water, air-dried, and then dried under reduced pressure (0.5 kPa) at a temperature close to 40° C. 188 mg of 3,4-O,O-3',4'-O,O-bis-carbonyl-2-[(1R,2S,3R)(1,2,3,4-tetrahydroxybutyl)]-5-[(2'S,3'R)(2',3',4'-trihydroxybutyl)]pyrazine are thus obtained in the form of a beige powder.

The product obtained has the following characteristics:
¹H NMR spectrum (400 MHz, (CD₃)₂SO d6, δ in ppm): 2.84 and 2.92 (2dd, respectively J=14 and 9 Hz and J=14 and 5 Hz, 1H each: CH₂ 5α); 4.11 (mt, 1H: CH 2β); 4.20 (mt, 1H: CH 5β); 4.48 (dd, J=9 and 6.5 Hz, 1H: 1H of CH₂O 5δ); from 4.50 to 4.60 (mt, 3H: CH₂O 2δ and the other H of CH₂O 5δ); 4.78 (broad s, 1H: CH 2α); 4.80 (mt, 1H: CH 5γ); 5.02 (mt, 1H: CH 2γ); from 5.40 to 6.00 (3 unresolved complexes, 1H each: OH at position 2α-OH at position 2β and OH at position 5β); 8.51 (s, 1H: =CH at position 6); 8.68 (s, 1H: =CH at position 3).

EXAMPLE 17

1,2,2',3,3',4,4'-O,O,O,O,O,O,O-(ethyl heptamonofumarate)-2-[(1R,2S,3R)(1,2,3,4-tetrahydroxybutyl)]-5-[(2'S,3'R) (2',3',4'-trihydroxybutyl)]pyrazine 6 cm³ of anhydrous N,N-dimethylformamide are added, at a temperature close to 20° C., under an argon atmosphere, to 304 mg of 2-[(1R,2S,3R)(1,2,3,4-tetrahydroxybutyl)]-5-[(2'S,3'R)(2',3',4'-trihydroxybutyl)]pyrazine, 1.51 g of ethyl monofumarate, 2.27 g of dicyclohexylcarbodiimide and 37 mg of 4-(N,N-dimethylamino)pyridine. After 24 hours at a temperature close to 22° C., the reaction mixture is diluted with 10 cm³ of water and 25 cm³ of ethyl acetate, stirred and filtered on sintered glass. The sintered glass is rinsed with 5 cm³ of ethyl acetate. After decantation of the filtrate, the organic phase is washed with 6 times 20 cm³ of water, dried over magnesium sulphate, filtered on sintered glass, and concentrated to dryness under reduced pressure at a temperature close to 40° C. 2.1 g of a brown oil are thus obtained, which oil is purified by chromatography under atmospheric pressure on a 20 cm high Merck silica gel 60 F₂₅₄ (0.063–0.040 mm) contained in a column 1 cm in diameter, using an eluent consisting of a dichloromethane-methanol (99-1 by volume) mixture and collecting 12 cm³ fractions. The fractions containing only the desired product are combined and concentrated to dryness under reduced pressure (about 2.7 kPa) at a temperature close to 40° C. 1.4 g of a virtually colourless thick oil are thus obtained, of which 1.3 g are purified by chromatography under atmospheric pressure on a 30 cm high Merck silica gel 60 F₂₅₄ (0.063–0.040 mm) contained in a column 1.5 cm in diameter, using an eluent consisting of a dichloromethane-methanol (99-1 by volume) mixture and collecting 12 cm³ fractions. The fractions containing only the desired product are combined and concentrated to dryness under reduced pressure (about 2.7 kPa) at a temperature close to 40° C. 305 mg of a pale beige paste are thus obtained, which paste is purified by preparative chromatography on 10 Merck 60 F₂₅₄ silica gel plates (thickness=0.5 mm, 20×20 cm), eluting with a dichloromethane-methanol (99-1 by volume) mixture. The fraction containing only the desired product is extracted with a dichloromethane-methanol (90-10 by volume) mixture, filtered on sintered glass and then concentrated to dryness under reduced pressure (2.7 kPa) at a temperature close to 40° C. 205 mg of a colourless oil are thus obtained, which oil is taken up in 5 cm³ of dichloromethane. The solution obtained is filtered on cotton wool, and concentrated to dryness under reduced pressure (about 2.7 kPa) at a temperature close to 30° C. 203 mg of 1,2,2',3,3',4,4'-O,O,O,O,O,O,O-(ethyl heptamonofumarate)-2-[(1R,2S,3R)(1,2,3,4-tetrahydroxybutyl)]-5-[(2'S,3'R) (2',3',4'-trihydroxybutyl)]pyrazine are thus obtained in the form of a colourless oil.

The product obtained has the following characteristics:
¹H NMR spectrum (400 MHz, (CD₃)₂SO d6, δ in ppm): 1.27 (mt, 21H: the CH₃ of the ethyls); from 3.20 to 3.40 (mt: the 2H corresponding to CH₂ 5β); 4.21 (mt, 14H: the OCH₂ of the ethyls); 4.41 (dd, J=13 and 5 Hz, 1H: 1H of CH₂O 2δ); 4.48 (dd, J=12 and 7 Hz, 1H: 1H of CH₂O 5δ); 4.57 (dd, J=13 and 2 Hz, 1H: the other H of CH₂O 2δ); 4.63 (dd, J=12 and 3 Hz, 1H: the other H of CH₂O 5δ); 5.46 (mt, 1H: CH 5γ); 5.53 (mt, 1H: CH 2γ); 5.66 (mt, 1H: CH 5β); 5.79 (dd, J=8 and 3.5 Hz, 1H: CH 2β); 6.23 (d, J=3.5 Hz, 1H: CH 2α); from 6.50 to 6.95 (mt, 14H: the CH=CH); 8.61 (broad s, 1H: =CH at position 6); 8.71 (broad s, 1H: =CH at position 3).

EXAMPLE 18

1,2,2'-O,O,O-tribenzoyl-2-[(1R,2S,3R)(1,2,3,4-tetrahydroxybutyl)]-5-[(2'S,3'R)(2',3',4'-trihydroxybutyl)]pyrazine First Route:

Preparation of: 3,4-O,O-3',4'-O,O-bis-pentylidene-2-[(1R,2S,3S)(1,2,3,4-tetrahydroxybutyl)]-5-[(2'S,3'S) (2',3',4'-trihydroxybutyl)]pyrazine 2.18 cm³ of cyclopentanone and 31 mg of para-toluenesulphonic acid monohydrate are successively added at a temperature close to 20° C. to 500 mg of 2-[(1R,2S,3R)(1,2,3,4-tetrahydroxybutyl)]-5-[(2'S,3'R)(2',3',4'-trihydroxybutyl)]pyrazine in suspension in 12 cm³ of dimethylformamide. The solution obtained after stirring for 30 minutes at a temperature close to 20° C. is again stirred for 2 hours 30 minutes at a temperature close to 20° C. Magnesium sulphate is then added and the reaction medium is stirred for an additional 16 hours at a temperature close to 20° C. The medium is then heated at a temperature close to 60° C. for 4 hours. The reaction medium is allowed to return to a temperature close to 20° C. and is diluted with a mixture of 10 cm³ of distilled water and 10 cm³ of ethyl acetate. The organic phase, after decantation, is washed with two times 10 cm³ of distilled water. The aqueous phases are combined and extracted with once 10 cm³ ethyl acetate. The combined organic phases are dried over magnesium sulphate, filtered on sintered glass and then concentrated to dryness under reduced pressure (0.27 kPa) at a temperature close to 30° C. 224 mg of a yellow lacquer are thus obtained, which lacquer is purified by chromatography on 4 Merck 60 F₂₅₄ silica gel plates (thickness=1 mm, 20×20 cm), eluting with ethyl acetate. The fraction containing only the desired product is extracted with a dichloromethane-methanol (90-10 by volume) mixture, filtered on sintered glass and then concentrated to dryness under reduced pressure (2.7 kPa) at a temperature close to 20° C.

77 mg of 3,4-O,O-3',4'-O,O-bis-cyclopentylidene-2-[(1R,2S,3S)(1,2,3,4-tetrahydroxybutyl)]-5-[(2'S,3'S) (2',3',4'-trihydroxybutyl)]pyrazine are thus obtained in the form of a pale yellow oil.

The product obtained has the following characteristics:

$^1$H NMR spectrum (400 MHz, $(CD_3)_2$SO d6, δ in ppm): from 1.50 to 1.80 (unresolved complex, 16H: the 4 $CH_2$ of the 2 cyclopentyls); 2.76 (dd, J=14 and 9 Hz, 1H: 1H of $CH_2$ 5α); 3.03 (dd, J=14 and 3.5 Hz, 1H: the other H of $CH_2$ 5α); 3.62 (broad t, J=7 Hz, 1H: CH 2β); 3.77 (mt, 1H: CH 5β); from 3.70 to 4.00 (2 mts) respectively 3H and 2H: CH 5γ-$CH_2$O 2δ and $CH_2$O 5δ); 4.15 (mt, 1H: CH 2γ); 4.78 (broad d, J=6 Hz, 1H.: CH 2α); 4.82 (d, J=8 Hz, 1H: OH at position 2β); 5.04 (d, J=6.5 Hz, 1H: OH at position 5β); 5.56 (d, J=6 Hz, 1H: OH at position 2α); 8.43 (s, 1H: =CH at position 6); 8.65 (s, 1H: =CH at position 3).

Preparation of: 1,2,2'-O,O,O-tribenzoyl-3,4-O,O-3', 4'-O,O-bis-cyclopentylidene-2-[(1R,2S,3R)(1,2,3,4-tetrahydroxybutyl)]-5-[(2'S,3'R)(2',3',4'-trihydroxybutyl)]pyrazine 0.97 cm$^3$ of benzoyl chloride is added dropwise to a solution of 730 mg of 3,4-O,O-3',4'-O,O-bis-cyclopentylidene-2-[(1R,2S,3R)(1,2,3,4-tetrahydroxybutyl)]-5-[(2'S,3'R)(2',3',4'-trihydroxybutyl)]pyrazine in 8 cm$^3$ of anhydrous pyridine, under an argon atmosphere, at a temperature close to 23° C. After 3 hours at a temperature close to 23° C., the reaction mixture is diluted with 10 cm$^3$ of dichloromethane and 5 cm$^3$ of water, stirred for 5 minutes and then decanted off. The organic phase is washed with 5 cm$^3$ of water, dried over magnesium sulphate, filtered on paper and then concentrated to dryness and coevaporated with toluene under reduced pressure (2 kPa) at a temperature close to 40° C. 1.9 g of a yellow oil areobtained, which oil is purified by chromatography under atmospheric pressure on 200 g of Merck silica gel 60 $F_{254}$ (0.063–0.200 mm) contained in a column 4 cm in diameter, using an elution gradient (dichloromethane-methanol 100-0 then 98-2 by volume) and collecting 30 cm$^3$ fractions. The fractions containing only the desired product are combined and concentrated to dryness under reduced pressure (about 2.7 kPa) at a temperature close to 40° C. The foam obtained is taken up in ethyl ether and concentrated to dryness under reduced pressure (about 2.7 kPa) at a temperature close to 40° C. 1.14 g of 1,2,2'-O,O,O-tribenzoyl-3,4-O,O-3',4'-O,O-bis-cyclopentylidene-2-[(1R,2S,3R)(1,2,3,4-tetrahydroxybutyl)]-5-[(2'S,3'R)(2',3',4'-trihydroxybutyl)]pyrazine are thus obtained in the form of an ivory-coloured amorphous solid.

The product obtained has the following characteristics:

$^1$H NMR spectrum (400 MHz, $(CD_3)_2$SO d6, δ in ppm): from 1.40 to 1.70 (unresolved complex., 16H: the $CH_2$ of the cyclopentyls); 3.14 and 3.23 (2 dd, respectively J=14 and 8 Hz and J=14 and 5 Hz, 1H each: $CH_2$ 5α); 3.89 (dd, J=9 and 6 Hz, 1H: 1H of CH 5δ); from 3.90 to 4.05 (mt, 3H: $CH_2$O 2δ and the other H of $CH_2$O 5δ); 4.25 (mt, 1H: CH 5γ); 4.39 (mt, 1H: CH 2γ); 5.48 (mt, 1H: CH 5β); 5.82 (t, J=5 Hz, 1H: CH 2β); 6.29 (d, J=5 Hz, 1H: CH 2α); from 7.35 to 8.05 (mt, 15H: aromatic H); 8.56 (d, J=1 Hz, 1H: =CH at position 6); 8.63 (d, J=1 Hz, 1H: =CH at position 3).

Preparation of: 1,2,2'-O,O,O-tribenzoyl-2-[(1R,2S,3R)(1,2,3,4-tetrahydroxybutyl)]-5-[(2'S,3'R)(2',3',4'-trihydroxybutyl)]pyrazine 0.614 cm$^3$ of trifluoroacetic acid (80% trifluoroacetic acid in aqueous solution) is slowly added to a solution of 500 mg of 1,2,2'-O,O,O-tribenzoyl-3,4-O,O-3',4'-O,O-bis-cyclopentylidene-2-[(1R,2S,3R)(1,2,3,4-tetrahydroxybutyl)]-5-[(2'S,3'R)(2',3',4'-trihydroxybutyl)]pyrazine in 4 cm$^3$ of dichloromethane, at a temperature close to 20° C. After 80 minutes at a temperature close to 20° C., 6 cm$^3$ of a saturated aqueous sodium bicarbonate solution are added to the reaction mixture while limiting the gaseous emission. After decantation, the aqueous phase is reextracted with 3 cm$^3$ of dichloromethane. The organic phases are pooled, dried over magnesium sulphate, filtered and then concentrated to dryness under reduced pressure (2 kPa) at a temperature close to 40° C. 400 mg of an ivory-coloured foam are obtained. Half of this ivory-coloured foam is purified by preparative chromatography on 8 Merck 60 $F_{254}$ silica gel plates (thickness=0.5 mm, 20×20), eluting with a dichloromethane-methanol (94-5 by volume) mixture. The fraction containing only the desired product is extracted with a dichloromethane-methanol (90-10 by volume) mixture, filtered on sintered glass and then concentrated to dryness under reduced pressure (2.7 kPa) at a temperature close to 40° C. 116 mg of 1,2,2'-O,O,O-tribenzoyl-2-[(1R,2S,3R)(1,2,3,4-tetrahydroxybutyl)]-5-[(2'S,3'R) (2',3',4'-trihydroxybutyl)]pyrazine are thus obtained in the form of a white foam. The remainder of the preceding ivory-coloured foam is purified according to the same method and gives 124 mg of 1,2,2'-O,O,O-tribenzoyl-2-[(1R,2S,3R)(1,2,3,4-tetrahydroxybutyl)]-5-[(2'S,3'R)(2',3',4'-trihydroxybutyl)]pyrazine in the form of a white foam.

The product obtained has the following characteristics:

$^1$H NMR spectrum (400 MHz, $(CD_3)_2$SO d6, δ in ppm): 3.21 (limiting AB, 2H: $CH_2$ 5α); from 3.30 to 3.55 (mt: 4H corresponding to $CH_2$ 2δ and $CH_2$ 5δ); 3.74 (mt, 1H: CH 5γ); 3.84 (mt, 1H: CH 2γ); 4.71 (mt, 2H: OH at position 2δ and OH at position 5δ); 5.16 (d, J=5.5 Hz, 1H: OH at position 5γ); 5.39 (mt, 2H: CH 5β and OH at position 2γ); 5.67 (dd, J=7 and 4 Hz, 1H: CH 2β); 6.43 (d, J=4 Hz, 1H: CH 2α); from 7.30 to 8.05 (mt, 15H: aromatic H); 8.45 (d, J=1 Hz, 1H: =CH at position 6); 8.53 (d, J=1 Hz, 1H: =CH at position 3).

Second Route:

1,2, 2'-O,0,0-tribenzoyl-2-[(1R,2S,3R)(1,2,3,4-tetrahydroxybutyl)]-5-[(2'S,3'R)(2',3',4'-trihydroxybutyl)]pyrazine may also be obtained, under the same conditions as above (deprotection in a dichloromethane-trifluoroacetic acid medium, at a temperature of between 0° C. and 40° C.), from 1,2,2'-O,O,O-tribenzoyl-3,4-O,O-3',4'-O,O,-bis-cyclohexylidene-2-[(1R,2S,3R)(1,2,3,4-tetrahydroxybutyl)]-5-[(2'S,3'R)(2',3',4'-trihydroxybutyl)]pyrazine, which may be prepared in the following manner:

Preparation of: 3,4-O,O-3',4'-O,O-bis-cyclohexylidene-2-[(1R,2S,3S)(1,2,3,4-tetrahydroxybutyl)]-5-[(2'S,3'S)(2',3',4'-trihydroxybutyl)]pyrazine First Method 2.54 cm$^3$ of cyclohexanone and 31 mg of para-toluenesulphonic acid monohydrate are successively added at a temperature close to 20° C. to 500 mg of 2-[(1R,2S,3R)(1,2,3,4-tetrahydroxybutyl)]-5-[(2'S,3'R)(2',3',4'-trihydroxybutyl)]pyrazine in suspension in 12 cm$^3$ of dimethylformamide. The solution obtained after stirring for 15 min at a temperature close to 20° C. is again stirred for 2 hours 30 minutes at a temperature close to 20° C. Magnesium sulphate is then added and the reaction medium is stirred for an additional 16 hours at a temperature close to 20° C. The medium is then heated at a temperature close to 60° C. for a few minutes and becomes milky white. The reaction medium is allowed to return to a temperature close to 20° C. and is diluted with a mixture of 10 cm³ of distilled water and 10 cm³ of ethyl acetate. The organic phase, after decantation, is washed with twice 10 cm³ of distilled water. The aqueous phases are combined and extracted with once 10 cm³ of ethyl acetate. The combined organic phases are dried over magnesium sulphate, filtered on sintered glass anid concentrated to dryness under reduced pressure (0.27 kPa) at a temperature close to 30° C. 910 mg of a pale yellow foam are thus obtained, which foam is taken up in 10 cm³ of ethyl ether. After stirring for 10 minutes at a temperature close to 20° C., the insoluble matter is filtered on sintered glass, rinsed with 5 cm³ of ethyl ether to give a flocculent white product which is dried at a temperature close to 40° C. under reduced pressure (0.27 kPa).

417 mg of 3,4-O,0–3',4'-O,O-bis-cyclohexylidene-2-[(1R,2S,3S)(1,2,3,4-tetrahydroxybutyl)]-5-[(2'S,3'S)(2',3',4'-trihydroxybutyl)]pyrazine are thus obtained in the form of a white solid.

Second Method:

0.153 cm³ of cyclohexanone, 0.244 cm³ of triethyl orthoformate and 0.05 cm³ of tetrahydrofuran saturated with hydrochloric acid (titre ≧10 M). The solution obtained after stirring for 5 minutes at a temperature close to 20° C. is stirred for an additional five days at a temperature close to 20° C. The reaction medium is taken up in a mixture of 10 cm³ of distilled water and 10 cm³ of ethyl acetate. The organic phase, after decantation, is washed with twice 10 cm³ of distilled water. The aqueous phases are combined and extracted with once 12 cm³ of ethyl acetate. The combined organic phases are dried over magnesium sulphate, filtered on sintered glass and then concentrated to dryness under reduced pressure (1.33 kPa) at a temperature close to 30° C. 324 mg of a colourless lacquer are thus obtained, which lacquer is purified, after dissolution in a minimum of dichloromethane with a trace of methanol, by chromatography on 6 Merck 60 $F_{254}$ silica gel plates (thickness=1 mm, 20×20 cm), eluting with ethyl acetate. The fraction containing only the desired product is extracted with a dichloromethane-methanol (90-10 by volume) mixture, filtered on sintered glass and then concentrated to dryness under reduced pressure (2.7 kPa) at a temperature close to 40° C. The white solid thus obtained is taken up in ethyl ether and then filtered on sintered glass to give 116 mg of 3,4-O,O-3',4'-O,O,-bis-cyclohexylidene-2-[(1R,2S,3S)(1,2,3,4-tetrahydroxybutyl)]-5-[(2'S,3'S)(2',3',4'-trihydroxybutyl)]pyrazine.

The product obtained has the following characteristics:

¹H NMR spectrum (400 MHz, (CD₃)₂SO d6, δ in ppm): from 1.25 to 1.65 (unresolved complex, 20H: the 10 CH₂ of the 2 cyclohexyls); 2.76 (dd, J=14 and 9 Hz, 1H: 1H of CH₂ 5α); 3.04 (dd, J=14 and 3.5 Hz, 1H: the other H of CH₂ 5α); 3.61 (dt, J=7 and 1.5 Hz, 1H: CH 2β); 3.77 (mt, 1H: CH 5β); from 3.80 to 3.95 and from 3.95 to 4.10 (2 mts, respectively 3H and 2H: CH 5γ-CH₂O 2δ and CH₂O 5δ); 4.18 (mt, IH: CH 2γ); 4.80 (mt, 2H: CH 2α and OH at position 2β); 5.02 (d, J=7 Hz, 1H: OH at position 5β); 5.54 (d, J=6.5 Hz, 1H: OH at position 2α); 8.43 (s, 1H: =CH at position 6); 8.65 (s, 1H: =CH at position 3).

Preparation of: 1,2,2'-O,O,O-tribenzoyl-3,4-O,O-3',4'-O,O-bis-cyclohexylidene-2-[(1R,2S,3R)(1,2,3,4-tetrahydroxybutyl)]-5-[(2'S,3'R)(2',3',4'-trihydroxybutyl)]pyrazine 0.175 cm³ of benzoyl chloride is added dropwise to a solution of 200 mg of 3,4-O,O-3',4'-O,O-bis-cyclohexylidene-2-[(1R,2S,3R)(1,2,3,4-tetrahydroxybutyl)]-5-[(2'S,3'R)(2',3',4'-trihydroxybutyl)]pyrazine in 5 cm³ of anhydrous pyridine, under an argon atmosphere, at a temperature close to 23° C. After 1.25 hours at a temperature close to 23° C., the reaction mixture is concentrated to dryness under reduced pressure (about 2.7 kPa) at a temperature close to 40° C. The off-white solid obtained is taken up in dichloromethane. The suspension obtained is filtered on sintered glass, and the filtrate is purified by preparative chromatography deposition (4 Merck 60 $F_{254}$ silica gel plates, thickness=1 mm, 20×20 cm), eluting with a cyclohexane-ethyl acetate (50-50 by volume) mixture. The fractions containing only the desired products are extracted with ethyl acetate, filtered on sintered glass and then concentrated to dryness under reduced pressure (2.7 kPa) at a temperature close to 40° C. There are thus obtained:

64 mg of 1,2'-O,O-dibenzoyl-3,4-O,O-3',4'-O,O-bis-cyclohexylidene-2-[(1R,2S,3R)(1,2,3,4-tetrahydroxybutyl)]-5-[(2'S,3'R)(2',3',4'-trihydroxybutyl)]pyrazine in the form of a white foam, and 210 mg of 1,2,2'-O,O,O-tribenzoyl-3,4-O,O-3',4'-O,O-bis-cyclohexylidene- 2-[(1R,2S,3R)(1,2,3,4-tetrahydroxybutyl)]-5-[(2'S,3'R)(2',3',4'-trihydroxybutyl)]pyrazine in the form of a white foam.

The products obtained have the following characteristics:

1,2'-O,O-dibenzoyl-3,4-O,O-3',4'-O,O,-bis-cyclohexylidene-2-[(1R,2S,3R)(1,2,3,4-tetrahydroxybutyl)]-5-[(2'S,3'R)(2',3',4'-trihydroxybutyl)]pyrazine:

¹H NMR spectrum (400 MHz, (CD₃)₂SO d6, δ in ppm): from 1.20 to 1.60 (unresolved complex, 20H: the CH₂ of the cyclohexyls); 3.18 and 3.25 (2dd, respectively J=14 and 8 Hz and J=14 and 5 Hz, 1H each: CH₂ 5α); 3.84 (split t, J=8 and 3 Hz, 1H: CH 2β); 3.91 and 4.01 (2 dd, respectively J=8.5 and 5 Hz and J=8.5 and 7 Hz, 1H each: CH₂O 2δ); 3.96 (dd, J=8 and 5.5 Hz, 1H: 1H of CH₂O 5δ); from 4.05 to 4.15 (mt, 2H: CH 2γ and the other H of CH₂O 5δ); 4.35 (mt, 1H: CH 5γ); 5.54 (d, J=8 Hz, 1H: OH at position 2β); 5.58 (mt, 1H: CH 5β); 6.03 (d, J=3 Hz, 1H: CH 2α); 7.47 and 7.58 (2 t, J 7.5 Hz, 2H each: aromatic H at the meta position with respect to the C=O); 7.62 and 7.72 (2 t, J=7.5 Hz, 1H each: aromatic H at the para position with respect to the C=O); 7.87 and 8.13 (2 d, J=7.5 Hz, 2H each: aromatic H at the ortho position with respect to the C=O); 8.50 (broad s, 1H: =CH at position 6); 8.59 (broad s, 1H: =CH at position 3).

1,2,2'-O,O,O-tribenzoyl-3,4-O,O-3',4'-O,O-bis-cyclohexylidene-2-[(1R,2S,3R)(1,2,3,4-tetrahydroxybutyl)]-5-[(2'S,3'R)(2',3',4'-trihydroxybutyl)]pyrazine:

¹H NMR spectrum (400 MHz, (CD₃)₂SO d6, δ in ppm): from 1.20 to 1.60 (unresolved complex, 20H: the CH₂ of the cyclohexyls); 3.14 and 3.23 (2dd, respectively J=14 and 8 Hz and J=14 and 5 Hz, 1H each: CH₂ 5α); 3.88 (dd, J=9 and 6 Hz, 1H: 1H of CH₂O 5δ); from 3.95 to 4.10 (mt, 3H: CH₂O 2δ and the other H of CH₂O 5δ); 4.29 (mt, 1H: CH 5γ); 4.43 (mt, 1H: CH 2γ); 5.49 (mt, 1H: CH 5D); 5.83 (t, J=5 Hz, 1H: CH 2γ); 6.31 (d, J=5 Hz, 1H: CH 2α); from 7.35 to 8.10 (mts, 15H: aromatic H); 8.56 (s, 1H: =CH at position 6); 8.64 (s, 1H: =CH at position 3).

EXAMPLE 19

1,2'-O,O-dibenzoyl-2-[(1R,2S,3R)(1,2,3,4-tetrahydroxybutyl)]-5-[(2'S,3'R)(2',3',4'-trihydroxybutyl)]pyrazine 1,2'-O,O-dibenzoyl-2-[(1R,2S,3R)(1,2,3,4-tetrahydroxybutyl)]-5-[(2'S,3'R)(2',3',4'-trihydroxybutyl)]

pyrazine may be obtained under the same conditions as those used for the preparation of 1,2,2'-O,O,O-tribenzoyl-2-[(1R,2S,3R)(1,2,3,4-tetrahydroxybutyl)]-5-[(2'S,3'R)(2',3',4'-trihydroxybutyl)]pyrazine but starting with the 1,2'-O,O-dibenzoyl-3,4-O,O-3',4'-O,O-bis-cyclohexylidene-2-[(1R,2S,3R)(1,2,3,4-tetrahydroxybutyl)]-5-[(2'S, 3'R)(2',3',4'-trihydroxybutyl)]pyrazine derivative, prepared as described in the preceding example.

EXAMPLE 20

20a) 1,2,2',4,4'-O,O,O,O,O-pentabenzoyl-2-[(1R,2S,3R)(1,2,3,4-tetrahydroxybutyl)]-5-(2'S,3'R)(2',3',4'-trihydroxybutyl)]pyrazine 20b) 1,2,2',3,4'-O,O,O,O,O-pentabenzoyl-2-[(1R,2S,3R)(1,2,3,4-tetrahydroxybutyl)]-5-[(2'S,3'R)(2',3',4'-trihydroxybutyl)]pyrazine 20c) 1,2,2',3',4-O,O,O,O,O-pentabenzoyl-2-[(1R,2S,3R)(1,2,3,4-tetrahydroxybutyl)]-5-[(2'S,3'R)(2',3',4'-trihydroxybutyl)]pyrazine 20d) 1,2,2',3,3'-O,O,O,O,O-pentabenzoyl-2-[(1R,2S,3R)(1,2,3,4-tetrahydroxybutyl)]-5-[(2'S,3'R)(2',3',4'-trihydroxybutyl)]pyrazine Preparation of: 1,2,2',3,3'-O,O,O,O,O,-pentabenzoyl-4,4'-O,O-di(diphenyl-tert-butylsilyl)-2-[(1R,2S,3R)(1,2,3,4-tetrahydroxybutyl)]-5-[(2'S,3'R)(2',3',4'-trihydroxybutyl)]pyrazine 0.892 cm$^3$ of benzoyl chloride is added dropwise to a solution of 600 mg of 4,4'-O,O-di(diphenyl-tert-butylsilyl)-2-[(1R,2S,3R)(1,2,3,4-tetrahydroxybutyl)]-5-[(2'S,3'R)(2',3',4'-trihydroxybutyl)]pyrazine in 6 cm$^3$ of anhydrous pyridine, under an argon atmosphere, at a temperature close to 25° C. After 20 hours at a temperature close to 25° C., the reaction mixture is diluted with 50 cm$^3$ of ethyl acetate, washed with twice 10 cm$^3$ of water, and then 10 cm$^3$ of a saturated aqueous sodium chloride solution. After decantation, the organic phase is dried over magnesium sulphate, filtered on sintered glass and then concentrated to dryness under reduced pressure (2 kPa) at a temperature close to 40° C. 1.81 g of a yellow oil are obtained, which oil is purified by chromatography under atmospheric pressure on 100 g of Merck silica gel 60 F$_{254}$ (0.063–0.200 mm) contained in a columnn3 cm in diameter, eluting with dichloromethane and collecting 25 cm$^3$ fractions. The fractions containing only the desired product are combined and concentrated to dryness under reduced pressure (about 2.7 kPa) at a temperature close to 40° C. 838 mg of 1,2,2',3,3'-O,O,O,O,O-pentabenzoyl-4,4'-O,O-di(diphenyltert-butylsilyl)-2-[(1R,2S,3R)(1,2,3,4-tetrahydroxybutyl)]-5-[(2'S,3'R)(2',3',4'-trihydroxybutyl)]pyrazine are thus obtained in the form of a white foam.

The 4,4'-O,O-di(diphenyl-tert-butylsilyl)-2-[(1R,2S,3R)(1,2,3,4-tetrahydroxybutyl)]-5-[(2'S,3'R)(2',3',4'-trihydroxybutyl)]pyrazine may be prepared as described in Example 10.

Preparation of 20a) 1,2,2',4,4'-O,O,O,O,O-pentabenzoyl-2-[(1R,2S,3R)(1,2,3,4-tetrahydroxybutyl)]-5-[(2'S,3'R)(2',3',4'-trihydroxybutyl)]pyrazine 20b) 1,2,2',3,4'-O,O,O,O,O-pentabenzoyl-2-[(1R,2S,3R)(1,2,3,4-tetrahydroxybutyl)]-5-[(2'S,3'R)(2',3',4'-trihydroxybutyl)]pyrazine 20c) 1,2,2',3',4-O,O,O,O,O-pentabenzoyl-2-[(1R,2S,3R)(1,2,3,4-tetrahydroxybutyl)]-5-[(2'S,3'R)(2',3',4'-trihydroxybutyl)]pyrazine 20d) 1,2,2',3,3'-O,O,O,O,O-pentabenzoyl-2-[(1R,2S,3R)(1,2,3,4-tetrahydroxybutyl)]-5-[(2'S,3'R)(2',3',4'-trihydroxybutyl)]pyrazine 0.0375 cm$^3$ of hydrofluoric acid-triethylamine (3HF.Et$_3$N) complex is slowly added to a solution of 30 mg of 1,2,2',3,3'-O,O,O,O,O-pentabenzoyl-4,4'-O,O-di(diphenyl-tert-butylsilyl)-2-[(1R,2S,3R)(1,2,3,4-tetrahydroxybutyl)]-5-[(2'S,3'R)(2',3',4'-trihydroxybutyl)]pyrazine in 0.5 cm$^3$ of dichloromethane, under an argon atmosphere, at a temperature close to 29° C. After 5 hours at a temperature close to 29° C., an additional 0.075 cm$^3$ of hydrofluoric acid-triethylamine complex is slowly added. After 15 hours at a temperature close to 29° C., the crude reaction mixture is directly purified by preparative chromatography deposition (2 Merck 60 F$_{254}$ silica gel plates, thickness=0.5 mm, 20×20 cm), eluting with a dichloromethane-methanol (97-3 by volume) mixture. The fractions containing only the desired products are extracted with a dichloromethane-methanol (85-15 by volume) mixture, filtered on sintered glass and then concentrated to dryness under reduced pressure (2.7 kPa) at a temperature close to 40° C.

There are thus obtained:

2.3 mg of 1,2,2',4,4'-O,O,O,O,O-pentabenzoyl-2-[(1R,2S,3R)(1,2,3,4-tetrahydroxybutyl)]-5-[(2'S,3'R)(2',3',4'-trihydroxybutyl)]pyrazine in the form of a white solid, 1.5 mg of 1,2,2',3,4'-O,O,O,O,O-pentabenzoyl-2-[(1R,2S,3R)(1,2,3,4-tetrahydroxybutyl)]-5-[(2'S,3'R)(2',3',4'-trihydroxybutyl)]pyrazine in the form of a white solid, 1.8 mg of 1,2,2',3',4-O,O,O,O,O-pentabenzoyl-2-[(1R,2S,3R)(1,2,3,4-tetrahydroxybutyl)]- 5-[(2'S,3'R)(2',3',4'-trihydroxybutyl)]pyrazine in the form of a white solid, and 3.0 mg of 1,2,2',3,3'-O,O,O,O,O-pentabenzoyl-2-[(1R,2S,3R)(1,2,3,4-tetrahydroxybutyl)]-5-[(2'S,3'R)(2',3',4'-trihydroxybutyl)]pyrazine in the form of a white solid.

The products obtained have the following characteristics:

20a) 1,2,2',4,4'-O,O,O,O,O-pentabenzoyl-2-[(1R,2S,3R)(1,2,3,4-tetrahydroxybutyl)]-5-[(2'S,3'R)(2',3',4'-trihydroxybutyl)]pyrazine $^1$H NMR spectrum (400 MHz, (CD$_3$)$_2$SO d6, δ in ppm): 3.26 (dd, J=14 and 8.5 Hz, 1H: 1H of CH$_2$ 5α); from 3.30 to 3.40 (mt: 1H corresponding to the other H of CH$_2$ 5α); 4.07 (mt, 1H: CH 5γ); from 4.20 to 4.45 (mt, 5H: CH$_2$ 2δ-CH$_2$ 5δ and CH 2γ); 5.46 (mt, 1H: CH 5β); 5.73 (d, J=6 Hz, 1H: OH at position 5γ); 5.76 (dd, J=8 and 3.5 Hz, 1H: CH 2β); 5.99 (d, J=6.5 Hz, 1H: OH at position 2γ); 6.48 (d, J=3.5 Hz, 1H: CH 2α); from 7.30 to 8.15 (mt, 25H: aromatic H); 8.51 (broad s, 1H: =CH at position 6); 8.57 (broad s, 1H: =CH at position 3).

20b) 1,2,2',3,4'-O,O,O,O,O-pentabenzoyl-2-[(1R,2S,3R)(1,2,3,4-tetrahydroxybutyl)]-5-[(2'S,3'R)(2',3',4'-trihydroxybutyl)]pyrazine $^1$H NMR spectrum (400 MHz, (CD$_3$)$_2$SO d6, δ in ppm): from 3.20 to 3.40 (mt: 2H corresponding to CH$_2$ 5α); 3.70 (mt, 1H: 1H of CH$_2$ 2δ); 3.86 (mt, 1H: the other H of CH$_2$ 2δ); 4.11 (mt, 1H: CH 5γ); 4.31 (dd, J=11.5 and 5.5 Hz, 1H: 1H of CH$_2$ 5δ); 4.39 (dd, J=11.5 and 4.5 Hz, 1H: the other H of CH$_2$ 5δ); 5.06 (t, J=6 Hz, 1H: OH at position 2δ); 5.40 (mt, 1H: CH 2γ); 5.48 (mt, 1H: CH 5β); 5.74 (d, J=6 Hz, 1H: OH at position 5γ); 6.13 (t, J=5.5 Hz, 1H: CH 2β); 6.47 (d, J=5.5 Hz, 1H: CH 2α); from 7.30 to 8.00 (mt, 25H: aromatic H); 8.60 (broad s, 1H: =CH at position 6); 8.64 (broad s, 1H: =CH at position 3).

20c) 1,2,2',3',4-O,O,O,O,O-pentabenzoyl-2-[(1R,2S,3R)(1,2,3,4-tetrahydroxybutyl)]-5-[(2'S,3'R)(2',3',4'-trihydroxybutyl)]pyrazine $^1$H NMR spectrum (400 MHz, (CD$_3$)$_2$SO d6, δ in ppm): from 3.25 to 3.45 (mt: 2H corresponding to CH$_2$ 5α); 3.75

(mt, 1H: 1H of CH₂ 5δ); 3.86 (mt, 1H: the other H of CH₂ 5δ); 4.26 (dd, J=12 and 4 Hz, 1H: 1H of CH₂ 2δ); 4.32 (mt, 1H: CH 2γ); 4.40 (dd, J=12 and 3 Hz, 1H: the other H of CH₂ 2δ); 5.14 (t, J=6 Hz, 1H: OH 5δ); 5.43 (mt, 1H: CH 5γ); from 5.70 to 5.80 (mt, 2H: CH 2β and CH 5β); 5.98 (d, J=6.5 Hz, 1H: OH at position 2γ); 6.48 (d, J=3 Hz, 1H: CH 2α); from 7.30 to 8.15 (mt, 25H: aromatic H); 8.51 (broad s, 1H: =CH at position 6); 8.61 (broad s, 1H: =CH at position 3).

20d) 1,2,2',3,3'-O,O,O,O,O-pentabenzoyl-2-[(1R,2S,3R)(1,2,3,4-tetrahydroxybutyl)]-5-[(2'S,3'R)(2',3',4'-trihydroxybutyl)]pyrazine ¹H NMR spectrum (400 MHz, (CD₃)₂SO d6, δ in ppm): from 3.25 to 3.45 (mt: 2H corresponding to CH₂ 5α); from 3.65 to 3.80 and from 3.80 to 3.90 (mt, 2H each: CH₂ 2δ and CH₂ 5δ); 5.16 (t, J=6 Hz, 2H: OH at position 2δ and OH at position 5δ); 5.40 (mt, 1H: CH 2γ); 5.44 (mt, 1H: CH 5δ); 5.77 (mt, 1H: CH 5β); 6.10 (dd, J=6.5 and 5 Hz, 1H: CH 2β); 6.46 (d, J=5 Hz, 1H: CH 2α); from 7.30 to 8.00 (mt, 25H: aromatic H); 8.64 (s, 2H: =CH at position 6 and =CH at position 3).

EXAMPLE 21

1,2-O,O-carbonyl-2',3',3'-O,O,O,-tribenzoyl-2-[(1R,2S,3R)(1,2,3,4-tetrahydroxybutyl)]-5-[(2'S,3'R)(2',3',4'-trihydroxybutyl)]pyrazine Preparation of: 1,2-O,O-carbonyl-4,4'-O,O-di(diphenyl-tert-butylsilyl)-2-[(1R,2S,3R)-(1,2,3,4-tetrahydroxybutyl)]-5-[(2'S,3'R)(2',3',4'-trihydroxybutyl)]pyrazine 5.5 cm³ of benzyl chloroformate are added dropwise to a clear solution of 2 g of 4,4'-O,O-di(diphenyl-tert-butylsilyl)-2-[(1R,2S,3R)-(1,2,3,4-tetrahydroxybutyl)]-5-[(2'S,3'R)(2',3',4'-trihydroxybutyl)]pyrazine in 40 cm³ of dichloromethane and 6.7 cm³ of diisopropylethylamine, under an argon atmosphere, at a temperature close to 20° C. After 3 hours at a temperature close to 20° C., 10 cm³ of water are added to the reaction medium. After stirring for 5 minutes, and decantation, the aqueous phase is reextracted with 5 cm³ of dichloromethane. The organic phases are pooled, dried over magnesium sulphate, filtered on paper and then concentrated to dryness under reduced pressure (2 kPa) at a temperature close to 40° C. 6.2 g of a yellowish oil are obtained, which oil is purified by chromatography under atmospheric pressure on 600 g of Merck silica gel 60 F₂₅₄ (0.063–0.200 mm) contained in a column 6 cm in diameter. An elution gradient is used which consists of a dichloromethane-methanol mixture (from 100-0 to 98-2 by volume), collecting 120 cm³ fractions. The fractions containing only the desired product are combined and concentrated to dryness under reduced pressure (about 2.7 kPa) at a temperature close to 40° C. 619 mg of 1,2-O,O-carbonyl-4,4'-O,O-di(diphenyl-tert-butylsilyl)-2-[(1R,2S,3R)(1,2,3,4-tetrahydroxybutyl)]-5-[(2'S,3'R)(2',3',4'-trihydroxybutyl)]pyrazine are thus obtained in the form of a beige foam.

The product obtained has the following characteristics:
¹H NMR spectrum (400 MHz, (CD₃)₂SO d6, δ in ppm): 0.83 and 1.02 (2 s, 9H each: the 2 SiC(CH₃)₃); 2.88 and 3.01 (2 dd, respectively J=14 and 9 Hz and J=14 and 2.5 Hz, 1H each: CH₂ 5α); from 3.55 to 3.75 and 3.81 (respectively mt and dd, J=9 and 4 Hz, 4H and 1H: CH₂O 2δ-CH₂O 5δ and CH 5γ); 3.94 (mt, 1H: CH at position 5β); 4.12 (mt, 1H: CH at position 2γ); 4.75 (d, J=7 Hz, 1H: OH at position 5β); 4.96 (d, J=5 Hz, 1H: OH at position 5γ); 5.22 (dd, J=5 and 3.5 Hz, 1H: CH 2β); 5.95 (broad s, 1H: OH at position 2γ); 6.01 (d, J=5 Hz, 1H: CH 2α); from 7.30 to 7.75 (mt, 20H: aromatic H); 8.65 (broad s, 1H: =CH at position 6); 8.82 (broad s, 1H: =CH at position 3).

The 4,4'-O,O-di(diphenyl-tert-butylsilyl)-2-[(1R,2S,3R)(1,2,3,4-tetrahydroxybutyl)]-5-[(2'S,3'R)(2',3',4'-trihydroxybutyl)]pyrazine derivative may be prepared as described in Example 10.

Preparation of: 1,2-O,O-carbonyl-2',3,3'-O,O,O,-tribenzoyl-4,4'-O,O-di(diphenyl-tert-butylsilyl)-2-[(1R,2S,3R)(1,2,3,4-tetrahydroxybutyl)]-5-[(2'S,3'R)(2',3',4'-trihydroxybutyl)]pyrazine 0.403 cm³ of benzoyl chloride is slowly added to a clear solution of 560 mg of 1,2-O,O-carbonyl-4,4'-O,O-di(diphenyl-tert-butylsilyl)-2-[(1R,2S,3R)(1,2,3,4-tetrahydroxybutyl)]-5-[(2'S,3'R)-(2',3',4'-trihydroxybutyl)]pyrazine in 6 cm³ of pyridine, under an argon atmosphere, at a temperature close to 20° C. After 3 hours and 45 minutes at a temperature close to 20° C., 0.161 cm³ of benzoyl chloride is slowly added. After 2.5 hours at a temperature close to 20° C., 10 cm³ of dichloromethane and 7 cm³ of water are added to the reaction medium. After decantation, the organic phase is washed with 4 cm³ of water, dried over magnesium sulphate, filtered and then concentrated to dryness under reduced pressure (2 kPa) at a temperature close to 40° C. 1.12 g of a caramel-coloured oil are obtained, which oil is purified by chromatography under atmospheric pressure on 100 g of Merck silica gel 60 F₂₅₄ (0.063–0.200 mm) contained in a column 3.5 cm in diameter. An elution gradient is used which consists of a dichloromethane-methanol mixture, collecting 25 cm³ fractions. The fractions containing only the desired product are combined and concentrated to dryness under reduced pressure (about 2.7 kPa) at a temperature close to 40° C. 0.6 g of 1,2-O,O-carbonyl-2',3,3'-O,O,O,-tribenzoyl-4,4'-O,O-di(diphenyl-tert-butylsilyl)-2-[(1R,2S,3R)(1,2,3,4-tetrahydroxybutyl)]-5-[(2'S,3'R)(2',3',4'-trihydroxybutyl)]pyrazine is thus obtained in the form of a cream-coloured foam.

The product obtained has the following characteristics:
¹H NMR spectrum (400 MHz, (CD₃)₂SO d6, δ in ppm): 0.81 and 0.93 (2 s, 9H each: the 2 SiC(CH₃)₃); 3.50 (d, J=6.5 Hz, 2H: CH₂ 5α); 3.97–4.02 and 4.09 (respectively 2 dd, J=12 and 4.5 Hz and limiting AB, 1H–1H and 2H: CH₂O 2δ and CH₂O 5δ); 5.51 (t, J=4.5 Hz, 1H: CH at position 2β); from 5.60 to 5.70 (mt, 2H: CH 2γ and CH 5γ); 6.01 (mt, 1H: CH 5β); 6.30 (d, J=4.5 Hz, 1H: CH 2α); from 7.15 to 8.05 (mt, 35H: aromatic H); 8.74 (broad s, 1H: =CH at position 6); 8.76 (broad s, 1H: =CH at position 3).

Preparation of: 1,2-O,O-carbonyl-2',3,3'-O,O,O,-tribenzoyl-2-[(1R,2S,3R)(1,2,3,4-tetrahydroxybutyl)]-5-[(2'S,3'R)(2',3',4'-trihydroxybutyl)]pyrazine 6.55 cm³ of hydrofluoric acid-triethylamine (3HF.Et₃N) complex are slowly added to a solution of 600 mg of 1,2-O,O-carbonyl-2',3,3'-O,O,O,-tribenzoyl-4,4'-O,O-di(diphenyl-tert-butylsilyl)-2-[(1R,2S,3R)(1,2,3,4-tetrahydroxybutyl)]-5-[(2'S,3'R)(2',3',4'-trihydroxybutyl)]pyrazine in 5 cm³ of dichloromethane, under an argon atmosphere, at a temperature close to 22° C. After 4 hours at a temperature close to 22° C., 25 cm³ of a saturated aqueous sodium hydrogen carbonate solution are slowly added. After decantation, the organic phase is washed with 7 cm³ of water. The aqueous phases are combined and reextracted with a few cm³ of dichloromethane. The organic phases are pooled, dried over magnesium sulphate and filtered on paper then concentrated to dryness under reduced pressure (2 kPa) at a temperature close to 40° C. 600 mg of a pale yellow foam are obtained, which foam is purified by preparative chromatography on 10 Merck 60 $F_{254}$ silica gel plates (thickness=1 mm, 20×20 cm), eluting with a dichloromethane-methanol (94-5 by volume) mixture. The fraction containing only the desired product is extracted with a dichloromethane-methanol (90-10 by volume) mixture, filtered on sintered glass and then concentrated to dryness under reduced pressure (2.7 kPa) at a temperature close to 40° C. 161 mg of 1,2-O,O-carbonyl-2',3,3'-O,O,O,-tribenzoyl-2-[(1R,2S,3R)(1,2,3,4-tetrahydroxybutyl)]-5-[(2'S,3'R)(2',3',4'-trihydroxybutyl)]pyrazine are thus obtained in total in the form of a white foam.

The product obtained has the following characteristics:

$^1$H NMR spectrum (400 MHz, $(CD_3)_2SO$ d6, δ in ppm): 3.51 (d, J=6.5 Hz, 2H: $CH_2$ 5α); from 3.70 to 3.85 and from 3.85 to 4.00 (2 mts, respectively 3H and 1H: $CH_2O$ 2δ and $CH_2O$ 5δ); 5.20 and 5.26 (2 unresolved complexes, 1H each: OH 2δ and OH 5δ); 5.30 (dd, J=5 and 3 Hz, 1H: CH at position 2β); 5.44 (mt, 1H: CH 2γ); 5.50 (mt, 1H: CH 5γ); 5.90 (mt, 1H: CH 5β); 6.30 (d, J=5 Hz, 1H: CH 2α); from 7.40 to 8.05 (mt, 15H: aromatic H); 8.76 (broad s, 1H: =CH at position 6); 8.79 (broad s, 1H: =CH at position 3).

EXAMPLE 22

1,2,2',3, 3',4,4'-O,O,O,O,O,O,O-heptamonosuccinoyl-2-[(1R,2S,3R)(1,2,3,4-tetrahydroxybutyl)]-5-[(2'S, 3'R)(2',3',4'-trihydroxybutyl)]pyrazine Preparation of: 1,2,2',3,3',4,4'-O,O,O,O,O,O,O-(benzyl heptamonosuccinate)-2-[(1R,2S,3R)-(1,2,3,4-tetrahydroxybutyl)]-5-[(2'S,3'R)(2',3',4'-trihydroxybutyl)]pyrazine 3.59 g of benzyl monosuccinate, 3.68 g of dicyclohexylcarbodiimide and 60 mg of 4-(N,N-dimethylamino) pyridine are successively added, at a temperature close to 26° C., under an argon atmosphere, to 500 mg of 2-[(1R,2S,3R)(1,2,3,4-tetrahydroxybutyl)]-5-[(2'S,3'R)(2',3',4'-trihydroxybutyl)]pyrazine and 500 mg of a 4 Å molecular sieve powder in suspension in 10 cm$^3$ of anhydrous N,N-dimethylformamide. After 16 hours at a temperature close to 26° C., the reaction mixture is diluted with 60 cm$^3$ of ethyl acetate and filtered on sintered glass. The filtrate is washed with twice 10 cm$^3$ of water, 10 cm$^3$ of a saturated aqueous sodium hydrogen carbonate solution, 3 times 10 cm$^3$ of water, 10 cm$^3$ of a saturated aqueous sodium chloride solution, and then dried over magnesium sulpnate, filtered on sintered glass and concentrated to dryness under reduced pressure (0.7 kPa) at a temperature close to 42° C. 4.4 g of a chestnut-coloured oil are thus. obtained, purified by chromatography under atmospheric pressure on 250 g of Merck silica gel 60 $F_{254}$ (0.063–0.200 mm) contained in a column 4 cm in diameter. An elution gradient is used which consists of a cyclohexane-ethyl acetate mixture 80-20 by volume (1 l) and then 60-40 by volume (2 l), collecting 50 cm$^3$ fractions. The fractions containing only the desired product are combined and concentrated to dryness under reduced pressure (about 2.7 kPa) at a temperature close to 40° C. 2.6 g of 1,2,2',3,3',4,4'-O,O,O,O,O,O,O-(benzyl heptamonosuccinate)-2-[(1R,2S,3R)(1,2,3,4-tetrahydroxybutyl)]-5-[(2'S, 3'R)(2',3',4'- trihydroxybutyl)] pyrazine are thus obtained in the form of a pale yellow oil.

The product obtained has the following characteristics:

$^1$H NMR spectrum (400 MHz, $(CD_3)_2SO$. d6, δ in ppm): from 2.25 to 2.80 (mt, 28H: the 7 $COCH_2CH_2CO$); 3.05 and 3.15 (2dd, respectively J=14 and 9 Hz, and J=14 and 4 Hz, 1H each: $CH_2$ 5α); 4.09 (dd, J=12 and 5.5 Hz, 1H: 1H of $CH_2O$ 2δ); 4.17 (dd, J=12 and 8 Hz, 1H: 1H of $CH_2O$ 5δ); 4.30 (mt, 2H: the other H of $CH_2O$ 2δ and the other H of $CH_2O$ 5δ); 4.53 and 5.07 (2 s, 14H in total: the 7 $OCH_{2\alpha}r$); 5.20 (mt, 2H: CH 2γ and CH 5γ); 5.44 (mt, 1H: CH 5β); 5.58 (dd, J=8 and 4 Hz,. 1H: CH 2β); 5.99 (d, J=4 Hz, 1H: CH 2α); 7.33 (mt, 35H: aromatic H); 8.48 (broad s, 1H: =CH at position 6); 8.55 (broad s, 1H: =CH at position 3).

Benzyl monosuccinate may be prepared in the following manner:

4.65 cm$^3$ of benzyl alcohol and 0.1 g of 4-(N,N-dimethylamino)pyridine are successively added, at a temperature close to 20° C., under an argon atmosphere, to 5 g of succinic anhydride in 10 cm$^3$ of ethyl acetate. The reaction mixture is heated at a temperature close to 60° C. for 15 hours, and then readjusted to a temperature close to 20° C., diluted with 50 cm$^3$ of ethyl acetate and washed with twice 30 cm$^3$ of a saturated aqueous sodium hydrogen carbonate solution. The aqueous phases are pooled, washed with twice 20 cm$^3$ of ethyl acetate, cooled to a temperature close to 0° C., and then acidified to a pH close to 2 by addition of a concentrated hydrochloric acid solution (37% minimum). The white insoluble matter formed is filtered on sintered glass, dried under an air stream, and then in an oven under reduced pressure (0.1 kPa) at a temperature close to 40° C. 5.9 g of benzyl monosuccinate are thus obtained in the form of a white powder.

Preparation of: 1,2,2',3,3',4,4'-O,O,O,O,O,O,O-heptamonosuccinoyl-2-[(1R,2S,3R)(1,2,3,4-tetrahydroxybutyl)]-5-[(2'S,3'R)(2',3',4'-trihydroxybutyl)]pyrazine 520 mg of Pd(OH)$_2$ on carbon (20% of Pd by weight) are added to a solution of 2.6 g of 1,2,2',3,3',4,4'-O,O,O,O,O,O,O-(benzyl heptamonosuccinate)-2-[(1R,2S,3R)(1,2,3,4-tetrahydroxybutyl)]-5-[(2'S,3'R)(2',3',4'-trihydroxybutyl)]pyrazine in 52 cm$^3$ of dioxane and 20 cm$^3$ of distilled water. The suspension obtained is vigorously stirred under a hydrogen atmosphere (about 1 atm) for 2 hours, at a temperature close to 22° C., and then filtered on sintered glass coated with Celite. After rinsing the sintered glass with twice 20 cm$^3$ of distilled water, and then concentrating the filtrate to dryness under reduced pressure (about 2.7 kPa) at a temperature close to 42° C., the residue obtained is taken up in 20 cm$^3$ of distilled water. After filtration, and concentration of the filtrate to dryness under reduced pressure (about 2.7 kPa) at a temperature close to 42° C., 1.278 g of 1,2,2',3,3',4,4'-O,O,O,O,O,O,O-heptamonosuccinoyl-2-[(1R,2S,3R)(1,2,3,4-tetrahydroxybutyl)]-5-[(2'S,3'R)(2',3',4'-trihydroxybutyl)]pyrazine are obtained in the form of a white foam.

The product obtained has the following characteristics:

$^1$H NMR spectrum (400 MHz, $(CD_3)_2SO$ d6, δ in ppm): from 2.25 to 2.80 (mt, 28H: the 7 $COCH_2CH_2CO$); 3.13 and 3.25 (2dd, respectively J=14 and 9 Hz, and J=14 and 4 Hz, 1H each: $CH_2$ 5α); 4.16 (dd, J=12 and 5.5 Hz, 1H: 1H of $CH_2O$ 2δ); 4.24 (dd, J=12 and 7 Hz, 1H: 1H of CH2O 5δ); 4.37 (mt, 2H: the other H of $CH_2O$ 2δ and the other H of $CH_2O$ 5δ); 5.23 (mt, 2H: CH 2γ and CH 5γ); 5.46 (mt, 1H: CH 5β); 5.61 (dd, J=8 and 4 Hz, 1H: CH 2β); 5.99 (d, J=4 Hz, 1H: CH 2α); 8.57 and 8.59 (2 s, 1H each: =CH at position 3 and =CH at position 6).

EXAMPLE 23

1,2,2',3,3',4,4'-O,O,O,O,O,O,O-heptamonoglutaroyl-2-[(1R,2S,3R)(1,2,3,4-tetrahydroxybutyl)]-5-[(2'S, 3'R)(2',3',4'-trihydroxybutyl)]pyrazine 1,2,2',3, 3',4, 4'-O,O,O,O,O,O,O-heptamonoglutaroyl-2-[(1R,2S,3R)(1,2,3,4-tetrahydroxybutyl)]-5-[(2'S,3'R)(2',3', 4'-trtihydroxybutyl)]pyrazine may be prepared according to the procedure as described in Example 22 for the preparation of 1,2,2',3,3',4,4'-O,O,O,O,O,O,O-heptamonosuccinoyl-2-[(1R,2S,3R)(1,2,3,4-tetrahydroxybutyl)]-5-[(2'S, 3'R)(2',3',4'-trihydroxybutyl)]pyrazine, from 2-[(1R,2S,3R)(1,2,3,4-tetrahydroxybutyl)]-5-[(2'S, 3'R)(2',3',4'-trihydroxybutyl)]pyrazine, but using glutaric anhydride, and preparing successively benzyl monoglutarate, and then 1,2,2',3,3',4,4'-O,O,O,O,O,O,O-(benzyl heptamonoglutarate)-2-[(1R,2S,3R)(1,2,3,4-tetrahydroxybutyl)]-5-[(2'S,3'R)(2',3',4'-trihydroxybutyl)]pyrazine and finally 1,2,2',3,3',4,4'-O,O,O,O,O,O,O-heptamonoglutaroyl-2-[(1R,2S,3R)(1,2,3,4-tetrahydroxybutyl)]-5-[(2'S,3'R)(2',3',4'-trihydroxybutyl)]pyrazine.

EXAMPLE 24

4,4'-O,O-di(ethoxycarbonyl)-2-[(1R,2S,3R)(1,2,3,4-tetrahydroxybutyl)-5-[(2'S,3'R)(2',3',4'-trihydroxybutyl)]pyrazine 0.472 cm³ of ethyl chloroformate is added dropwise to a suspension of 500 mg of 2-[(1R,2S,3R)(1,2,3,4-tetrahydroxybutyl)]-5-[(2'S,3'R)(2',3',4'-trihydroxybutyl) 3pyrazine in 10 cm³ of anhydrous pyridine, at a temperature close to 20° C. After 45 hours at a temperature close to 20° C., the reaction mixture is concentrated to dryness under reduced pressure (about 0.5 kPa) at a temperature close to 40° C. The residue obtained is purified by preparative chromatography on Merck 60 $F_{254}$ silica gel plates (thickness=2 mm, 20×20 cm), eluting with a dichloromethane-methanol (90-10 by volume) mixture. The fraction containing only the desired product is extracted with a dichloromethane-methanol (80-20 by volume) mixture, filtered on sintered glass and then concentrated to dryness under reduced pressure (0.5 kPa) at a temperature close to 40° C. 71 mg of 4,4'-O,O-di(ethoxycarbonyl)-2-[(1R,2S,3R)(1,2,3,4-tetrahydroxybutyl)]-5-[(2'S,3'R)(2',3',4'-trihydroxybutyl)]pyrazine are thus obtained in the form of a white powder.

The product obtained has the following characteristics:

¹H NMR spectrum (400 MHz, $(CD_3)_2SO$ d6, δ in ppm): 1.24 (t, J=7.5 Hz, 6H: $CH_3$ ethyl); 2.75 and 3.14 (2dd, respectively J=14 and 9 Hz and J=14 and 3 Hz, 1H each: $CH_2$ 5α); 3.56 (mt, 1H: CH 5γ); 3.60 (broad t, J=9 Hz, 1H: CH 20); 3.78 (mt, 1H: CH 5β); 3.85 (mt, 1H: CH 2γ; from 4.00 to 4.25 (mt, 6H: 1H of $CH_2O$ 2δ-1H of $CH_2O$ 5δ and $OCH_2$ ethyl); 4.32 (mt, 2H: the other H of $CH_2O$ 2δ and the other H of $CH_2O$ 5δ); 4.67 (d, J=8.5 Hz, 1H: OH at position 2β); 4.90 (d, J=6.5 Hz, 1H: OH at position 5β); 4.95 (broad d, J=6 Hz, 1H: CH 2α); 5.18 (d, J=6 Hz, 1H: OH at position 2γ); 5.22 (d, J'=6 Hz, 1H: OH at position 5γ); 5.43 (d, J=6 Hz, 1H: OH at position 2α); 8.42 (s, 1H: =CH at position 6); 8.66 (s, 1H: =CH at position 3).

EXAMPLE 25

1,2,2',3,3',4,4'-O,O,O,O,O,O,O-heptapentanoyl-2-[(1R,2S,3R)(1,2,3,4-tetrahydroxybutyl)]-5-[(2'S,3'R)(2',3',4'-trihydroxybutyl)]pyrazine 2.97 cm³ of n-pentanoyl chloride are added, dropwise, at a temperature close to 0° C., to a suspension of 500 mg of 2-[(1R,2S,3R)(1,2,3,4-tetrahydroxybutyl)]-5-[(2'S,3'R)(2',3',4'-trihydroxybutyl)]pyrazine in 6 cm³ of anhydrous pyridine. After 17 hours at a temperature close to 20° C., the reaction mixture is concentrated to dryness under reduced pressure at a temperature close to 35° C. The crude residue obtained is purified by chromatography under pressure (1.4 bar) on a volume of 100 cm³ of Merck silica gel 60 $F_{254}$ (0.063–0.040 mm) contained in a column 2 cm in diameter, using dichloromethane as eluent. The fractions containing only the desired product are combined and concentrated to dryness under reduced pressure (about 2.7 kPa) at a temperature close to 35° C. 1.832 g of an orange-coloured oil are thus obtained, which oil is purified by chromatography under pressure (1.4 bar) on a volume of 200 cm³ of Merck silica gel 60 $F_{254}$ (0.063–0.040 mm) contained in a column 3 cm in diameter, using an ethyl acetate-cyclohexane (20-80 by volume) eluent mixture. The fractions containing only the desired product are combined and concentrated to dryness under reduced pressure (about 2.7 kPa) at a temperature close to 35° C. 538 mg of 1,2,2',3,3',4,4'-O,O,O,O,O,O,O-heptapentanoyl-2-[(1R, 2S, 3R)(1,2,3,4-tetrahydroxybutyl)]-5-[2'S,3'R)(2',3',4'-trihydroxybutyl)]pyrazine are thus obtained in the form of a transparent oil.

The product obtained has the following characteristics:

¹H NMR spectrum (400 MHz, $(CD_3)_2SO$ d6, δ in ppm): from 0.75 to 0.95 (mt, 21H: the $CH_3$ of the pentanoyls); from 1.05 to 1.60 (mt, 28H in total : the central $CH_2$ of the pentanoyls) from 2.00 to 2.50 (mt, 14H in total: the $COCH_2$ of the pentanoyls); 3.11 and 3.21 (2dd, respectively J=14 and 10 Hz and J=14 and 4 Hz, IH each: $CH_2$ 5α); 4.10 (dd, J=12 and 5 Hz, 1H: 1H of $CH_2O$ 2δ); 4.20 (dd, J=12 and 8 Hz, 1H: 1H of $CH_2O$ 5δ); 4.30 (dd, J=12 and 2.5 Hz, 1H: the other 1H of $CH_2O$ 2δ); 4.39 (dd, J=12 and 3 Hz, 1H: the other H of $CH_2O$ 5δ); 5.23 (mt, 2H: CH 2γ and CH 5γ); 5.45 (mt, 1H: CH 5β); 5.55 (dd, J=8 and 3 Hz, 1H: CH 2β); 5.97 (d, J=3 Hz, 1H: CH 2α); 8.53 (s, 1H: =CH at position 6); 8.54 (s, 1H: =CH at position 3).

EXAMPLE 26 a) 4-O-benzoyl-2-[(1R,2S,3R)(1,2,3,4-tetrahydroxybutyl)]-5-[(2'S, 3'R)(2',3',4'-trihydroxybutyl)]pyrazine b) 3-O-benzoyl-2-[(1R,2S,3R)(1,2,3,4-tetrahydroxybutyl)]-5-[(2'S, 3'R)(2',3',4'-trihydroxybutyl)]pyrazine c) 3,4,4'-O,O,O-tribenzoyl-2-[(1R,2S,3R)(1,2,3,4-tetrahydroxybutyl)]-5-[(2'S, 3'R)(2',3',4'-trihydroxybutyl)]pyrazine d) 3,4,2',3',4'-O,O,O,O,O-pentabenzoyl-2-[(1R,2S,3R)(1,2,3,4-tetrahydroxybutyl)]-5-[(2'S,3'R)(2',3',4'-trihydroxybutyl)]pyrazine Preparation of 1,2-O,O-2',3'-O,O-di(dimethylacetonide)-4,4'-O,O-di(diphenyl-tert-butylsilyl)-2-[(1R,2S,3R)(1,2,3,4-tetrahydroxybutyl)]-5-[(2'S, 3'R)(2',3',4'-trihydroxybutyl)]pyrazine 2,3-O,O-2',3'-O,O-di(dimethylacetonide)-4,4'-O,O-di(diphenyl-tert-butylsilyl)-2-[(1R,2S,3R)( 1,2,3,4-tetrahydroxybutyl)]-5-[(2'S, 3'R)(2',3',4'-trihydroxybutyl)]pyrazine 1,3-O,O-2',3'-O,O-di(dimethylacetonide)-4,4'-O,O-di(diphenyl-tert-butylsilyl)-2-[(1R,2S,3R)(1,2,3,4-tetrahydroxybutyl)]-5-[(2'S,3'R)(2',3',4'-trihydroxybutyl)]pyrazine 47.5 mg of para-toluenesulphonic acid (monohydrate) and 18.4 cm³ of 2,2-dimethoxypropane are added to 3.9 g of 4,4'-O,O-di(diphenyl)-tert-butylsilyl)-2-[(1R,2S,3R)(1,2,3,4-tetrahydroxybutyl)]-5-[(2'S, 3'R)(2',3',4'-trihydroxybutyl)]pyrazine in solution in 190 cm³ of anhydrous N,N-dimethylformamide, under an inert argon atmosphere, at a temperature close to 20° C. The reaction mixture is heated at a temperature close to 60° C. for 40 hours, concentrated to dryness under reduced pressure (0.5 kPa) at a temperature close to 50° C., and then taken up in 100 cm³ of dichloromethane. The organic phase obtained is washed with twice 25 cm³ of a saturated aqueous sodium hydrogen carbonate solution, twice 50 cm³ of water, and then dried over magnesium sulphate, filtered on paper and concentrated to dryness under reduced pressure (0.5 kPa) at a temperature close to 30° C. 4.5 g of a thick chestnut-coloured oil are obtained, which oil is dissolved in 50 cm³ of a cyclohexane-ethyl acetate (90-10 by volume) mixture and purified by chromatography under pressure (about 130 bar) on 500 g of Merck silica gel 60 (0.015–0.040 mm), using an elution gradient (cyclohexane-ethyl acetate 90-10 and then 50-50 by volume) and collecting 70 cm³ fractions. The fractions containing only the desired products are combined and concentrated to dryness under reduced pressure (about 1 kPa) at a temperature close to 40° C. There are thus obtained 1.05 g of 1,2-O,O-2',3'-O,O-di(dimethylacetonide)-4,4'-O,O-di(diphenyl-tert-butylsilyl)-2-[(1R,2S,3R)(1,2,3,4-tetrahydroxybutyl)]-5-[(2'S,3'R)(2',3',4'-trihydroxybutyl)]pyrazine in the form of a light yellow oil and 1.53 g of a mixture containing 2,3-O,O-2',3'-O,O-di(dimethylacetonide)-4,4'-O,O-di(diphenyl-tert-butylsilyl)-2-[(1R,2S,3R)(1,2,3,4-tetrahydroxybutyl)]-5-[(2'S, 3'R)(2',3',4'-trihydroxybutyl)]pyrazine and 1,3-O,O-2',3'-O,O-di(dimethylacetonide)-4,4'-O,O-di(diphenyl-tert-butylsilyl)-2-[(1R,2S,3R)(1,2,3,4-tetrahydroxybutyl)]-5-[(2'S,3'R)(2',3',4'-trihydroxybutyl)]pyrazine. The latter mixture of 1.53 g is repurified by chromatography under pressure (about 130 bar) on 500 g of Merck silica gel 60 (0.015–0.040 mm), using a cyclohexane-ethyl acetate (90-10 by volume) eluent mixture and collecting 70 cm³ fractions. The fractions containing only the desired products are combined and concentrated to dryness under reduced pressure (about 1 kPa) at a temperature close to 40° C. 187 mg of 2,3-O,O-2',3'-O,O-di(dimethylacetonide)-4,4'-O,O-di(diphenyl-tert-butylsilyl)-2-[(1R,2S,3R)(1,2,3,4-tetrahydroxybutyl)]-5-[2'S, 3'R)(2',3',4'-trihydroxybutyl)]pyrazine in the form of a thick colourless oil and 300 mg of 1,3-O,O-2',3'-O,O-di(dimethylacetonide)-4,4'-O,O-di(diphenyl-tert-butylsilyl)-2-[(1R,2S,3R)(1,2,3,4-tetrahydroxybutyl)]-5-[(2'S,3'R)(2',3',4'-trihydroxybutyl)]pyrazine are thus obtained in the form of a thick colourless oil.

The products obtained have the following characteristics:

1,2-O,O-2',3'-O,O-di(dimethylacetonide)-4,4'-O,O-di(diphenyl-tert-butylsilyl)-2-[(1R,2S,3R)(1,2,3,4-tetrahydroxybutyl)]-5-[(2'S,3'R)(2',3',4'-trihydroxybutyl)]pyrazine: ¹H NMR spectrum (400 MHz, (CD₃)₂SO d6, δ in ppm): 0.90 and 1.01 (2 s, 9H each; the 2 C(CH₃)₃); 1.22–1.35–1.44 and 1.46 (4 s, 3H each: the 4 CH₃); 3.08 (dd, J=14 and 9 Hz, 1H: 1H of CH₂5α); 3.15 (dd, J=14 and 3.5 Hz, 1H: the other H of CH₂5α); 3.60 (limiting AB, CH₂O 2δ); 3.71 (dd, J=11 and 5 Hz, 1H: 1H of CH₂O 5δ); from 3.80 to 3.95 (mt,2H: the other H of CH₂5δ and CH 2γ); 4.32 (q, J=5 Hz, 1H: CH 5γ); 4.48 (dd, J=7 and 5 Hz, 1H; CH 2β); 4.70 (mt, 1H: CH 5β); 5.14 (d, J=7 Hz, 1H: CH 2α); 5.19 (d, J=5 Hz, 1H: OH at position 2γ); from 7.35 to 7.80 (mt, 20H: aromatic H of the 4 phenyls.); 8.53 (s, 1H: =CH at position 6); 8.68 (s, 1H: =CH at position 3).

2,3-O,O-2',3'-O,O-di(dimethylacetonide)-4,4'-O,O-di(diphenyl-tert-butylsilyl)-2-[(1R,2S,3R)(1,2,3,4-tetrahydroxybutyl)]-5-[(2'S,3'R)(2',3',4'-trihydroxybutyl)]pyrazine: ¹H NMR spectrum (400 MHz, (CD₃)₂SO d6 δ in ppm) from 0.90 to 1.00 (mt, 18H: SiC(CH₃)₃); from 1.10 to 1.60 (mt, 12H: C(CH₃)₂); 3.09 (mt, 2H: CH₂ 5α); 3.73 (dd, J=11 and 5.5 Hz, 1H: 1H of CH₂O 5δ); 3.82 (dd, J=10 and 5.5 Hz, 1H: 1H of CH₂O 2δ); 3.88 (dd, J=11 and 5.5 Hz, 1H: the other H of CH₂O 5δ); 3.99 (dd, J=10 and 5.5 Hz, 1H: the other H of CH₂O 2δ); from 4.25 to 4.40 (mt, 2H: CH 2γ and CH 5γ); 4.58 (dd, J=7 and 4 Hz, 1H: CH 2β); 4.70 (mt, 1H: CH 5β); 4.88 (unresolved complex, 1H: CH 2α); 5.53 (unresolved complex, 1H: OH at position 2α); from 7.30 to 7.75 (mt, 20H: aromaticH); 8.43 (s, 1H: =CH at position 6); 8.64 (s, 1H: =CH at position 3).

1,3-O,O-2',3'-O,O-di(dimethylacetonide)-4,4'-O,O-di(diphenyl-tert-butylsilyl)-2-[(1R,2S,3R)(1,2,3,4-tetrahydroxybutyl)]-5-[(2'S,3'R)(2',3',4'-trihydroxybutyl)]pyrazine ¹H NMR spectrum (400 MHz, (CD₃)₂SO d6, δ in ppm): 1.01 and 1.05 (2s, 9H each: the 2 C(CH₃)₃); 1.24–1.36 and 1.50 (3 s, respectively 3H–6H and 3H: the 4 CH₃); 3.03 (dd, J=14 and 9 Hz, 1H: 1H of CH₂ 5α); 3.12 (dd, J=14 and 3.5 Hz, 1H: the other H of CH₂ 5α); 3.70 (dd, J=11 and 5.5 Hz, 1H: 1H of CH₂O 5δ); from 3.75 to 3.95 (mt, 4H: CH 2δ-CH₂O 2γ and the other H of CH₂O 5δ); 4.03 (mt, 1H: CH 2β); 4.32 (mt, 1H: CH 5γ); 4.70 (mt, 1H: CH 5β); from 4.95 to 5.05 (mt, 2H: CH 2α and OH 2β); from 7.35 to 7.55 and from 7.60 to 7.80 (2 mts, respectively 12H and 8H: aromatic H of the 4 phenyls); 8.46 (s, 1H: =CH at position 6); 8.53 (s, 1H: =CH at position 3).

The preparation of the 4,4'-O,O-di(diphenyl-tert-butylsilyl)-2-[(1R,2S,3R)(1,2,3,4-tetrahydroxybutyl)]-5-[(2'S, 3'R)(2',3',4'-trihydroxybutyl)]pyrazine derivative may be prepared as described in Example 10.

Preparation of 1,2-O,O-2',3'-O,O-di(dimethylacetonide)-3-O-benzoyl-4, 4'-O,-O-di(diphenyl-tert-butylsilyl)-2-[(1R,2S,3R)(1,2,3,4-tetrahydroxybutyl)]-5-[(2'S,3'R)(2',3',4'-trihydroxybutyl)]pyrazine 0.0175 cm³ of benzoyl chloride is added to 0.086 g of 1,2-O,O-2',3'-O,O-di(dimethylacetonide)-4,4'-O,O-di(diphenyl-tert-butylsilyl)-2-[(1R,2S,3R)(1,2,3,4-tetrahydroxybutyl)]-5-[(2'S, 3'R)(2',3',4'-trihydroxybutyl)]pyrazine in solution in 0.5 cm³ of armydrous pyridine, under an inert argon atmosphere, at a temperature close to 20° C. After 20 hours at a temperature close to 20° C., the reaction mixture is concentrated to dryness under an argon stream, at a temperature close to 20° C., and then purified by preparative chromatography on 4 Merck 60 F₂₅₄ silica gel plates (thickness=0.5 mm, 20×20 cm), eluting with a cyclohexane-ethyl acetate (75-25 by volume) mixture. The fractions containing only the desired products are extracted with a dichloromethane-methanol (80-20 by volume) mixture, filtered on sinter glass and then concentrated to dryness under reduced pressure (0.5 kPa) at a temperature close to 30° C. 62 mg of 1,2-O,O-2',3'-O,O-di(dimethylacetonide)-3-O-benzoyl-4,4'-O,-O-di(diphenyl-tert-butylsilyl)2-[(1R,2S,3R)(1,2,3,4-tetrahydroxybutyl)]-5-(2'S,3'R)(2',3 ,4'-trihydroxybutyl)]pyrazine are thus obtained in the form of a white foam.

The product obtained has the following characteristics:
¹H NMR spectrum (400 MHz, (CD₃)₂SO d6, δ in ppm): 0.88 and 1.02 (2 s, 9H each: the SiC(CH₃)₃); 1.22–1.35–1.39 and 1.47 (4 s, 3H each: the C(CH₃)₂); 3.07 (d, J=7 Hz, 2H: CH₂ 5α); 3.69 and 3.86 (2dd, respectively J=10 and 5 Hz and J=11 and 6.5 Hz, 1H each: CH₂O 5δ); 3.90 (limiting AB, 2H: CH$_2$O 2δ); 4.30 (mt, 1H: CH 5γ); 4.64 (mt, 1H: CH 5β); 4.82 (dd, J=8 and 7 Hz, 1H: CH 2β); 5.18 (d, J=8 Hz, 1H: CH 2α); 5.49 (mt, 1H: CH 2γ); from 7.25 to 7.75 (mt, 25H: aromatic H); 8.43 (d, J=1 Hz, 1H: =CH at position 6); 8.62 (d, J=1 Hz, 1H: =CH at position 3).

Preparation of 1,2-O,O-2',3'-O,O-di(dimethylacetonide)-3-O-benzoyl-2-[(1R,2S,3R)(1,2,3,4-tetrahydroxybutyl)]-5-[(2'S, 3'R)(2',3',4'-trihydroxybutyl)]pyrazine 0.632 cm$^3$ of hydrofluoric acid-triethylamine (3HF.Et$_3$N) complex is added to 0.05 g of 1,2-O,O-2',3'-O,O-di(dimethylacetonide)-3-O-benzoyl-4,4'-O,O-di(diphenyl-tert-butylsilyl)-2-[(1R,2S,3R)(1,2,3,4-tetrahydroxybutyl)]-5-[(2'S,3'R)(2',3',4'-trihydroxybutyl)]pyrazine in solution in 0.25 cm$^3$ of dichloromethane at a temperature close to 20° C. After 20 hours at a temperature close to 20° C., the reaction mixture is supplemented with 2 cm$^3$ of dichloromethane and 5 cm$^3$ of phosphate buffer. After decantation, the organic phase is washed with 5 times 2 cm$^3$ of water, dried over magnesium sulphate and concentrated to dryness under reduced pressure (about 1 kPa) at a temperature close to 30° C. 41 mg of a thick yellow-beige oil are obtained, which oil is purified by preparative chromatography on 2 Merck 60 F$_{254}$ silica gel plates (thickness=0.5 mm, 20×20 cm) eluting with a dichloromethane-methanol (80-20 by volume) mixture. The fractions containing only the desired products are extracted with a dichloromethane-methanol (80-20 by volume) mixture, filtered on sintered glass and then concentrated to dryness under reduced pressure (0.5 kPa) at a temperature close to 25° C. 16mg of 1,2-O,O-2',3'-O,O-di(dimethylacetonide)-3-O-benzoyl-2-[(1R,2S,3R)(1,2,3,4-tetrahydroxybutyl)]-5-[(2'S, 3'R)(2',3',4'-trihydroxybutyl)]pyrazine are thus obtained in the form of a white foam.

The product obtained has the following characteristics:

$^1$H NMR spectrum (400 MHz, (CD$_3$)$_2$SO d6, δ in 4 ppm): 1.24–1.39 and 1.47 (3 s, respectively 3H–6H and 3H; the 2 C(CH$_3$)$_3$); 2.97 (limiting AB, 2H: CH$_2$ 5α); 3.57 (limiting AB, 2H: CH$_2$O 5δ); 3.61 and 3.71 (respectively mt and broad d, J=12 Hz, 1H each: CH$_2$O 2δ); 4.19 (mt, 1H: CH 5γ); 4.56 (mt, 1H: CH 5β); 4.69 (dd, J=8 and 6.5 Hz, 1H: CH 2β); 4.87 (broad t, J=5 Hz, 1H: OH at position 5δ); 4.94 (broad t, J=5 Hz, 1H: OH at position 2δ); 5.18 (d, J=8 Hz, 1H: CH 2α); 5.32 (mt, 1H: CH 2γ); 7.48 (t, J=7.5 Hz, 2H: aromatic H at the meta position with respect to the CO); 7.65 (t, J=7.5 Hz, 1H: H at the para position with respect to the CO); 7.75 (t, J=7.5 Hz, 2H: aromatic H at the ortho position with respect to the CO; 8.49 (s, 1H: =CH at position 6); 8.65 (s, 1H: =CH at position 3).

Preparation of 1,2-O,O-(dimethylacetonide)-4-O-benzoyl-2-[(1R, 2S,3R)(1,2,3,4-tetrahydroxybutyl)]-5-[(2'S,3'R)(2',3', 4'-trihydroxybutyl)]pyrazine 1,2-O,O-(dimethylacetonide)-3-O-benzoyl-2-[(1R, 2S, 3R)(1,2,3,4-tetrahydroxybutyl)]-5-(2'S,3'R)(2',3', 4'-trihydroxybutyl)]pyrazine 0.03 cm$^3$ of a trifluoroacetic acid-water (80-20 by volume) mixture is added to 0.015 g of 1,2-O,O-2',3'-O,O-di(dimethylacetonide)-3-O-benzoyl-2-[(1R,2S,3R)(1,2,3,4-tetrahydroxybutyl)]-5-[(2'S,3'R)(2',3',4'-trihydroxybutyl)]pyrazine in solution in 0.2 cm$^3$ of dichloromethane, at a temperature close to 20° C. After 1 hour at a temperature close to 20° C., the reaction mixture is neutralized by addition of 0.45 cm$^3$ of a saturated aqueous sodium hydrogen carbonate solution. After decantation, the organic phase is purified by preparative chromatography on 1 Merck 60 F$_{254}$ silica gel plate (thickness=0.25 mm, 20×20 cm), eluting with a dichloromethane-methanol (90-10 by volume) mixture. The fractions containing only the desired products are extracted with a dichloromethane-methanol (80-20 by volume) mixture, filtered on sintered glass and then concentrated to dryness under reduced pressure (2.7 kPa) at a temperature close to 40° C. 3.5 mg of 1,2-O,O-(dimethylacetonide)-4-O-benzoyl-2-[(1R,2S,3R)(1,2,3,4-tetrahydroxybutyl)]-5-[(2'S,3'R)(2',3',4'-trihydroxybutyl)]pyrazine and 5 mg of 1,2-O,O-(dimethylacetonide)-3-O-benzoyl-2-[(1R,2S,3R)(1,2,3,4-tetrahydroxybutyl)]-5-[(2'S, 3'R)(2',3',4'-trihydroxybutyl)]pyrazine are thus obtained.

The products obtained have the following characteristics:

1,2-O,O,-(dimethylacetonide)-4-O-benzoyl-2-[(1R,2S, 3R)(1,2,3,4-tetrahydroxybutyl)]-5-[(2'S,3'R)-(2',3',4'-trihydroxybutyl)]pyrazine; $^1$H NMR spectrum (400 MHz, (CD$_3$)$_2$SO d6 with addition of a few drops of CF$_3$COOD, δ in ppm): 1.44 and 1.47 (2 s, 3H each: C(CH$_3$)$_2$); 2.77 and 3.10 (2dd, respectively J=14 and 10 Hz and J=14 and 3 Hz, 1H each: CH$_2$ 5α); from 3.35 to 3.45 (mt, 2H: 1H of CH$_2$O 5δ and CH 5γ); 3.58 (dd, J=9 and 2.5 Hz, 1H: the other H of CH$_2$O 5δ); 3.78 (mt, 1H: CH 5β); 4.09 (mt, 1H: CH 2γ); 4.23 (dd, J=11 and 7 Hz, 1H: 1H of CH$_2$O 2δ); from 4.35 to 4.45 (mt, 2H; the other H of CH$_2$O 2δ and CH 2β); 5.16 (d, J=7 Hz, 1H: CH 2α); 7.53 (t, J=8 Hz, 2H: aromatic H at the meta position with respect to the CO); 7.67 (t, J=8 Hz, 1H: aromatic H at the para position with respect to the CO); 7.97 (d, J=8 Hz, 2H: aromatic H at the ortho position with respect to the CO); 8.53 (d, J=1 Hz, 1H: =CH at position 6); 8.67 (d, J=1 Hz, 1H: =CH at position 3).

1,2-O,O-(dimethylacetonide)-3-O-benzoyl-2-[(1R,2S, 3R)(1,2,3,4-tetrahydroxybutyl)]-5-[(2'S,3'R)(2',3',4'-trihydroxybutyl)]pyrazine; $^1$H NMR spectrum (400 MHz, (CD$_3$)$_2$SO d6, δ in ppm): 1.39 and 1.47 (2 s, 3H each: C(CH$_3$)$_2$); 2.77 and 3.06 (2dd, respectively J=14 and 9 Hz and J=14 and 3 Hz, 1H each: CH$_2$ 5α); from 3.30 to 3.40 (mt: the 2H corresponding to CH 5γ and 1H of CH$_2$O 5δ); from 3.50 to 3.65 (mt, 2H: 1H of CH$_2$O 2δ and the other H of CH$_2$O 5δ); 3.70 (broad d, J=13 Hz, 1H: the other H of CH$_2$O 2δ); 3.77 (mt, 1H: CH 5β); from 4.30 to 4.95 (3 s, 4H corresponding to 4 OH); 4.69 (dd, J=8 and 6.5 Hz, 1H: CH 2β); 5.19 (d, J=8 Hz, 1H: CH 2α); 5.33 (mt, 1H: CH 2γ); 7.48 (t, J=7.5 Hz, 2H: aromatic H at the meta position with respect to the CO); 7.64 (t, J=7.5 Hz, 1H: aromatic H at the para position with respect to the CO); 7.76 (d, J=7.5 Hz, 2H: aromatic H at the ortho position with respect to the CO); 8.46 (broad s, 1H: =CH at position 6); 8.62 (broad s, 1H: =CH at position 3).

Preparation of

4-O-benzoyl-2-[(1R,2S,3R)( 1,2,3,4-tetrahydroxybutyl)]-5-[(2'S,3'R)(2',3',4'-trihydroxybutyl)]pyrazine Starting with 1,2-O,O-(dimethylacetonide)-4-O-benzoyl-2-[(1R,2S,3R)(1,2,3,4-tetrahydroxybutyl)]-5-[(2'S,3'R)(2',3',4'-trihydroxybutyl)]pyrazine, following the procedure for the preparation of 1,2-O,O-(dimethylacetonide)-4-O-benzoyl-2-[(1R,2S,3R)(1,2,3,4-tetrahydroxybutyl)]-5-[(2'S,3'R)(2',3',4'-trihydroxybutyl)]pyrazine (dissolution of 1,2-O,O-(dimethylacetonide)-4-O-benzoyl-2-[(1R,2S,3R)(1,2,3,4- tetrahydroxybutyl)-5-(2'S, 3'R)(2',3',4'-trihydroxybutyl)] pyrazine in a dichloromethane-trifluoroacetic acid-water mixture at a temperature close to 20° C.), 4-O-benzoyl-2-[(1R,2S,3R)(1,2,3,4-tetrahydroxybutyl)]-5-[(2'S,3'R)(2',3',4'-trihydroxybutyl)]pyrazine is obtained.

Preparation of

3-O-benzoyl-2-[(1R,2S,3R)(1,2,3,4-tetrahydroxybutyl)]-5-[(2'S, 3'R)(2',3',4'-trihydroxybutyl)]pyrazine Starting with 1,2-O,O-(dimethylacetonide)-3-O-benzoyl-2-[(1R,2S,3R)(1,2,3,4-tetrahydroxybutyl)]-5-[(2'S,3'R)(2',3',4'-trihydroxybutyl)]pyrazine, following the procedure for the preparation of 1,2-O,O-(dimethylacetonide)-3-O-benzoyl-2-[(1R,2S,3R)(1,2,3,4-tetrahydroxybutyl)]-5-[(2'S, 3'R)( 2',3',4'-trihydroxybutyl)]pyrazine (dissolution of 1,2-O,O-(dimethylacetonide)-3-O-benzoyl-2-[(1R,2S,3R)(1,2,3,4-tetrahydroxybutyl)]-5-[(2'S, 3'R)(2',3',4'-trihydroxybutyl)3pyrazine in a dichloromethane-trifluoroacetic acid-water mixture at a temperature close to 20° C.), 3-O-benzoyl-2-[(1R,2S,3R)(1,2,3,4-tetrahydroxybutyl)]-5-[(2'S, 3'R)(2',3',4'-trihydroxybutyl)3pyrazine is obtained.

Preparation of 3,4,4',0,0,0-tribenzoyl-2-(1R,2S,3R)(1,2,3,4-tetrahydroxybutyl]-5-[(2'S,3'R)(2',3',4'-trihydroxybutyl)]pyrazine By reacting 1,2-O,O-(dimethylacetonide)-3-O-benzoyl-2-[(1R,2S,3R)(1,2,3,4-tetrahydroxybutyl)]-5-(2'S,3'R)(2',3',4'-trihydroxybutyl)]pyrazine, in solution in anhydrous pyridine, under an inert atmosphere, at a temperature close to 20° C., with benzoyl chloride (2.5 eq.), 1,2-O,O-(dimethylacetonide)-3,4,4'-O,O,O-tribenzoyl-2-[(1R,2S,3R)(1,2,3,4-tetrahydroxybutyl)]-5-[(2'S,3'R)(2',3',4'-trihydroxybutyl)]pyrazine is obtained. Starting with 1,2-O,O-(dimethylacetonide)-3,4,4'-O,O,O-tribenzoyl-2-[(1R,2S,3R)(1,2,3,4-tetrahydroxybutyl)]-5-[(2'S,3'R)(2',3',4'-trihydroxybutyl)]pyrazine, following the procedure for the preparation of 1,2-O,O-(dimethylacetonide)- 3-O-enzoyl-2-[(1R,2S,3R)(1,2,3,4-tetrahydroxybutyl)]-5-[(2'S,3'R)(2',3',4'-trihydroxybutyl)]pyrazine (dissolution of 1,2-O,O-(dimethylacetonide)-3,4,4'-O,O,O-tribenzoyl-2-[(1R, 2S, 3R)(1,2,3,4-tetrahydroxybutyl)]-5-[(2'S, 3'R)(2',3',4'-trihydroxybutyl)]pyrazine in a dichloromethane-trifluoroacetic acid-water mixture at a temperature close to 20° C.), 3,4,4'-O,O-O-tribenzoyl-2-[(1R,2S,3R)(1,2,3,4-tetrahydroxybutyl)]-5-[(2'S, 3'R)(2',3',4'-trihydroxybutyl)]pyrazine is obtained.

Preparation of 3,4,2',3',4'-O,O,O,O,O-pentabenzoyl-2-[(1R,2S,3R)(1,2,3,4-tetrahydroxybutyl)]-5-[(2'S, 3'R)(2',3',4'-trihydroxybutyl)]pyrazine By reacting 1,2-O,O-(dimethylacetonide)-3-O-benzoyl-2-[(1R,2S,3R)(1,2,3,4-tetrahydroxybutyl)]-5-[(2'S, 3'R)(2',3', 4'-trihydroxybutyl)]pyrazine in solution in anhydrous pyridine under an inert atmosphere, at a temperature close to 20° C., with benzoyl chloride (8.6 eq.), 1,2-O,O-(dimethylacetonide)-3,4,2',3',4'-O,O,O,O,O-pentabenzoyl-2-[(1R, 2S, 3R)(1,2,3,4-tetrahydroxybutyl)]-5-[(2'S, 3'R)(2', 3',4'-trihydroxybutyl)]pyrazine is obtained. Starting with 1,2-O,O-(dimethylacetonide)- 3,4, 2',3',4'-O,O,O,O,O-pentabenzoyl-2-[(1R,2S,3R)-(1,2,3,4-tetrahydroxybutyl)]-5-[(2'S,3'R)(2',3',4'-trihydroxybutyl)]pyrazine, following the procedure for the preparation of 1,2-O,O-(dimethylacetonide)-3-O-benzoyl-2-[(1R,2S,3R)(1,2,3,4-tetrahydroxybutyl)]-5-[(2'S,3'R)(2',3',4'-trihydroxybutyl)] pyrazine (dissolution of 1,2-O,O-(dimethylacetonide)-3,4, 2',3',4'-O,O,O,O,O-pentabenzoyl-2-[(1R,2S,3R)-(1,2,3,4-tetrahydroxybutyl)]-5-[(2'S, 3'R)(2',3',4'-trihydroxybutyl)] pyrazine in a dichloromethane-trifluoroacetic acid-water mixture at a temperature close to 20° C.), 3,4,2',3',4'-O,O,O,O,O-pentabenzoyl-2-[(1R,2S,3R)(1,2,3,4-tetrahydroxybutyl)]-5-[(2'S,3'R)(2',3',4'-trihydroxybutyl)] pyrazine is obtained.

3,4,2',3',4'-O,O,O,O,O-pentabenzoyl-2-[(1R,2S,3R)(1,2,3,4-tetrahydroxybutyl)]-5-[(2'S,3'R)(2',3',4'-trihydroxybutyl)]pyrazine may also be obtained according to the same procedure as described above from 1,2-O,O-(dimethylacetonide)-4-O-benzoyl-2-[(1R,2S,3R)(1,2,3,4-tetrahydroxybutyl)]-5-[(2'S,3'R)(2',3',4'-trihydroxybutyl)] pyrazine.

EXAMPLE 27

2'-O-benzoyl-2-[(1R,2S,3R)(1,2,3,4-tetrahydroxybutyl)]-5-[(2'S,3'R)( 2',3',4'-trihydroxybutyl)]pyrazine Preparation of 1,2-O,O-3,4-O,O-3',4'-O,O,-tri(dimethylacetonide)-2'-O-benzoyl-2-[(1R,2S,3R)(1,2,3,4-tetrahydroxybutyl)]-5-[(2'S,3'R)(2',3',4'-trihydroxybutyl)]pyrazine 0.492 cm$^3$ of benzoyl chloride is added dropwise to a solution of 1 g of 1,2-O,O-3,4-O,O-3',4'-O,O-tri(dimethylacetonide)-2-[(1R,2S,3R)(1,2,3,4-tetrahydroxybutyl)]-5-[(2'S,3'R)(2',3',4'-trihydroxybutyl)] pyrazine in 15 cm$^3$ of anhydrous pyridine, at a temperature close to 20° C. After 18 hours at a temperature close to 20° C., an additional 0.272 cm$^3$ of benzoyl chloride is added. After 2 hours at a temperature close to 20° C., the reaction mixture is filtered, concentrated to dryness under reduced pressure at a temperature close to 35° C. 1.3 g of a crude residue are thus obtained, which residue is purified by chromatography under pressure (1.4 bar) on a volume of 150 cm$^3$ of Merck silica gel 60 F$_{254}$ (0.063–0.040 mm) contained in a column 3 cm in diameter, using an ethyl acetate-cyclohexane (20-80 by volume) eluent mixture. The fractions containing only the desired product are combined and concentrated to dryness under reduced pressure (about 2.7 kPa) at a temperature close to 35° C. 884 mg of 1,2-O,O-3,4-O,O-3',4'-O,O-tri(dimethylacetonide)-2'-O-benzoyl-2-[(1R,2S,3R)(1,2,3,4-tetrahydroxybutyl)]-5-[(2'S,3'R)(2',3', 4'-trihydroxybutyl)]pyrazine are thus obtained.

The product obtained has the following characteristics:

$^1$H NMR spectrum (400 MHz, (CD$_3$)$_2$SO d6, δ in ppm): 0.86–1.10–1.26–1.29–1.37 and 1.40 (6 s, 3H each: the 3 C(CH$_3$)$_2$); 3.18 (dd, J=14 and 9 Hz, 1H: 1H of CH$_2$ 5α); from 3.20 to 3.40 (mt: 1H corresponding to the other H of CH$_2$ 5α); 3.78-from 3.95 to 4.05 and 4.11 (respectively dd, J=9 and 4 Hz-mt and dd, J=7.5 Hz, 1H–2H and 1H: CH$_2$O 5δ and CH$_2$O 2δ); 4.20 and 4.37 (2 mts, respectively 2H and 1H: CH 2β-CH 5γ and CH 2γ); 4.95 (d, J=6.5 Hz, 1'H: CH 2α); 5.57 (mt, 1H: CH 5β); 7.50 (t, J=7 Hz, 2H: aromatic H at the meta position with respect to the CO); 7.64 (t, J=7.5 Hz, 1H: aromatic H at the para position with respect to the CO); 7.87 (d, J=7.5 Hz, 2H: aromatic H at the ortho position with respect to the CO); 8.60 (s, 1H: =CH at position 6); 8.63 (s, 1H: =CH at position 3).

1,2-O,O-3,4-O,O-3',4'-O,O-tri(dimethylacetonide)-2-[(1R,2S,3R)(1,2,3,4-tetrahydroxybutyl)]-5-[(2'S,3'R)(2',3',4'-trihydroxybutyl)]pyrazine may be prepared in the following manner: 81 cm³ of 2,2-dimethoxypropane and then 0.3 g of para-toluenesulphonic acid are added to a solution of 10 g of deoxyfructosazine in 250 cm³ of dimethylformamide, with stirring. The reaction mixture is stirred at a temperature of about 25° C. for 20 hours, then 10 cm³ of 2,2-dimethoxypropane are added and the stirring is continued for 3 hours. The mixture is then heated at a temperature of 50° C. for 21 hours. After concentration under reduced pressure (2.7 kPa) at a temperature of 60° C., the residual oil is dissolved in 300 cm³ of dichloromethane and washed twice with 100 cm³ of a 5% aqueous sodium bicarbonate solution and then twice with 200 cm³ of water. The organic phase is dried over magnesium sulphate and then concentrated under reduced pressure (2.7 kPa) at a temperature of 40° C. The oil obtained is chromatographed on a silica column (0.020–0.045 mm) eluted with an ethyl acetate/cyclohexane (1:1 by volume) mixture at a pressure of about $1.5 \times 10^5$ Pa. The fractions containing the expected products are combined and concentrated under reduced pressure (2.7 kPa) at a temperature of 40° C. 5.2 g of 1,2-O,O-3,4-O,O-3',4'-O,O-tri(dimethylacetonide)-2-[(1R,2S,3R)(1,2,3,4-tetrahydroxybutyl)]-5-[(2'S,3'R)(2',3',4'-trihydroxybutyl)]pyrazine are thus obtained in the form of a white solid as well as 2.4 g of the same impure product. The latter is recrystallized from a water/absolute ethanol (5:1 by volume) mixture. 0.6 g of 1,2-O,O-3,4-O,O,3',4'-O,O-tri(dimethylacetonide)-2-[(1R,2S,3R)(1,2,3,4-tetrahydroxybutyl)]-5-[(2'S,3'R)(2',3',4'-trihydroxybutyl)]pyrazine is thus isolated in the form of white crystals melting at 74° C. [¹H NMR spectrum (400 MHz, $(CD_3)_2SO$ d6, δ in ppm): 1.04–1.20–1.28–1.33 and 1.44 (5 s, respectively 3H–3H–3H–3H and 6H: the 6 $CH_3$); 2.79 (dd, J=13 and 9 Hz, 1H: 1H of $CH_2$ 5α); 3.06 (dd, J=13 and 2.5 Hz, 1H: the other H of $CH_2$ 5α); 3,79 (unresolved complex, 1H: CH 5β); from 3.80 to 3.90 (mt, 2H: 1H of $CH_2$ 2δ and 1H of $CH_2$ 5δ); 3.91 (mt, 1H: CH 5γ); 4.00 (t, J=7 Hz, 1H: the other H of $CH_2$ 5δ); 4.06 (t, J=7.5 Hz: 1H; the other H of $CH_2$ 2δ); 4.28 (mt, 1H: CH 2γ); 4.33 (t, J=7 Hz, 1H: CH 2β); 4.99 (d, J=7.5 Hz, 1H: CH 2α); 5.07 (broad d, J=5 Hz, 1H: OH at position 5β); 8.54 (s, 1H: =CH at position 6); 8.66 (s, 1H: =CH at position 3); $[α]°=+6.7°±1.1$ (c=0.5/dichloromethane); (Rf= 0.36; thin-layer chromatography on silica gel; eluent ethyl acetate/cyclohexane 1:1 by volume mixture)].

Deoxyfructosazine may be prepared according to the method described by K. Sumoto et al. in Chem. Pharm. Bull., 39, 792 (1991).

2'-O-benzoyl-2-(1R,2S,3R)(1,2,3,4-tetrahydroxybutyl)]-5-[(2'S,3'R)(2',3',4'-trihydroxybutyl)]pyrazine 0.67 cm³ of trifluoroacetic acid and 0.018 cm³ of water, and then 1 cm³ of dichloromethane are successively added to 50 mg of 1,2-O,O-3,4-O,O-3',4'-O,O-tri(dimethylacetonide)-2'-O-benzoyl-2-[(1R,2S,3R)(1,2,3,4-tetrahydroxybutyl)]-5-[(2'S,3'R)(2',3',4'-trihydroxybutyl)]pyrazine, at a temperature close to 20° C. After 23 hours at a temperature close to 20° C., an additional 0.033 cm³ of trifluoroacetic acid is added. After 3 hours at a temperature close to 20° C., the reaction mixture is concentrated to dryness under reduced pressure at a temperature close to 35° C. The crude residue obtained is purified by preparative chromatography on 1 Merck 60 $F_{254}$ silica gel plate (thickness=1 mm, 20×20 cm), eluting with a dichloromethane-methanol (90-10 by volume) mixture. The fractions containing only the desired products are extracted with a dichloromethane-methanol (80-20 by volume) mixture, filtered on sintered glass and then concentrated to dryness under reduced pressure at a temperature close to 35° C. 13 mg of 2'-O-benzoyl-2-[(1R, 2S, 3R)(1,2,3,4-tetrahydroxybutyl)]-5-[(2'S, 3'R)(2',3',4'-trihydroxybutyl)]pyrazine are thus obtained.

The product obtained has the following characteristics:

¹H NMR spectrum (400 MHz, $(CD_3)_2SO$ d6, δ in ppm): 3.25 (limiting AB, 2H: $CH_2$ 5α); from 3.35 to 3.65 (mt, 6H: CH 2β-CH 2γ-$CH_2O$ 2δ and $CH_2O$ 5δ); 3.80 (mt, 1H: CH 5γ); 4.36 (t, J=5.5 Hz, 1H: OH at position 2δ); 4.39 (d, J=8 Hz, 1H: OH at position 2γ); 4.63 (d, J=5 Hz, 1H: OH at position 2β); 4.74 (t, J=5.5 Hz, 1H: OH at position 5δ); 4.91 (broad d, J=6.5 Hz, 1H: CH 2α); 5.21 (d, J=7 Hz, 1H: OH at position 5γ); 5.30 (d, J=7 Hz, 1H: OH at position 2α); 5.48 (mt, 1H: CH 5β); 7.51 (t, J=8 Hz, 2H: aromatic H at the meta position with respect to the CO); 7.64 (t, J=8 Hz, 1H: aromatic H at the para position with respect to the CO); 7.89 (d, J=8 Hz, 2H: aromatic H at the ortho position with respect to the CO); 8.47 (d, J=1 Hz, 1H: =CH at position 6); 8.60 (d, J=1 Hz, 1H: =CH at position 3).

EXAMPLE 28

4'-O-pentanoyl-2-[(1R,2S,3R)(1,2,3,4-tetrahydroxybutyl)]-5-[(2'S, 3'R)(2',3',4'-trihydroxybutyl)]pyrazine Preparation of 1,2-O,O-3,4-O,O-3',4'-O,O-tri(dimethylacetonide)-2'-O-pentanoyl-2-[(1R,2S,3R)(1,2,3,4-tetrahydroxybutyl)]-5-[(2'S,3'R)(2',3',4'-trihydroxybutyl)]pyrazine 0.672 cm³ of pentanoyl chloride is added dropwise to a solution of 2 g of 1,2-O,O-3,4-O,O-3',4'-O,O-tri(dimethylacetonide)-2-[(1R,2S,3R)(1,2,3,4-tetrahydroxybutyl)]-5-[(2'S,3'R)(2',3',4'-trihydroxybutyl)]pyrazine in 30 cm³ of anhydrous pyridine, at a temperature close to 20° C. After 17 hours at a temperature close to 20° C., an additional 0.28 cm³ of pentanoyl chloride is added. After 23 hours at a temperature close to 20° C., the reaction mixture is concentrated to dryness under reduced pressure at a temperature close to 35° C. 3.8 g of an orange-coloured oil are thus obtained, which oil is purified by chromatography under pressure (1.4 bar) on a volume of 300 cm³ of Merck silica gel 60 $F_{254}$ (0.063–0.040 mm) contained in a column 4 cm in diameter, using an ethyl acetate-cyclohexane (40-60 by volume) eluent mixture. The fractions containing only the desired product are combined and concentrated to dryness under reduced pressure at a temperature close to 35° C. 2.107 g of 1,2-O,O-3,4-O,O-3',4'-O,O-tri(dimethylacetonide)-2'-O-pentanoyl-2-[(1R,2S,3R)(1,2,3,4-tetrahydroxybutyl)]-5-[(2'S,3'R)(2',3',4'-trihydroxybutyl)]pyrazine are thus obtained in the form of a yellow oil.

The product obtained has the following characteristics:

¹H NMR spectrum (400 MHz, $(CD_3)_2SO$ d6, δ in ppm): 0.80 (t, J=7.5 Hz, 3H: $CH_3$ of pentanoyl); 1.03–1.20–1.30–1.35–1.42 and 1.45 (6 s, 3H each: the 3 $C(CH_3)_2$); 1.13 and 1.35 (2 mts, 2H each: central $CH_2$ of pentanoyl); 2.18 (limiting AB, 2H: $CH_2CO$ of pentanoyl); 3.01 and 3.16 (2dd, respectively J=14 and 9 Hz and J=14 and 4 Hz, 1H each: $CH_2$ 5α); 3.80 (mt, 2H: 1H of $CH_2O$ 5δ and 1H of CH$_2$O 2δ); 4.05 (mt, 2H: the other H of CH$_2$O 2δ and the other H of CH$_2$O 5δ); from 4.15 to 4.35 (mt, 3H: CH 2β-CH 2γ and CH 5γ); 5.00 (d, J=8 Hz, 1H: CH 2α); 5.29 (mt, 1H: CH 5β); 8.57 (d, J=1 Hz, 1H: =CH at position 6); 8.67 (d, J=1 Hz, 1H: =CH at position 3).

The preparation of 1,2-O,O-3,4-O,O-3',4'-O,O-tri (dimethylacetonide)-2-[(1R,2S,3R)(1,2,3,4-tetrahydroxybutyl)]-5-[(2'S,3'R)( 2',3',4'-trihydroxybutyl)]pyrazine is described in Example 27.

Preparation of
4'-O-pentanoyl-2-[(1R,2S,3R)(1,2,3,4-tetrahydroxybutyl)]-5-[(2'S,3'R)(2',3',4'-trihydroxybutyl)]pyrazine 0.775 cm$^3$ of trifluoroacetic acid and 0.194 cm$^3$ of water are successively added to a solution of 500 mg of 1,2-O,O-3,4-O,O-3',4'-O,O-tri(dimethylacetonide)-2'-O-pentanoyl-2-[(1R,2S,3R)(1,2,3,4-tetrahydroxybutyl)]-5-[(2'S,3'R)(2', 3',4'-trihydroxybutyl)]pyrazine, at a temperature close to 20° C. in 5 cm$^3$ of dichloromethane. After about 23 hours at a temperature close to 20° C., the reaction mixture is concentrated to dryness under reduced pressure at a temperature close to 35° C. The crude residue obtained (865 mg) is purified by preparative chromatography on Merck 60 F$_{254}$ silica gel plates (thickness=1 mm, 20×20 cm), eluting with a dichloromethane-methanol (85-15 by volume) mixture. The fraction containing only the desired product is extracted with a dichloromethane-methanol (80-20 by volume) mixture, filtered on sintered glass and then concentrated to dryness under reduced pressure at a temperature close to 35° C. The impure product thus obtained is pooled with 3 other samples prepared in an identical manner (24, 78 and 57 mg), and this mixture is purified by preparative chromatography on 2 Merck 60 F$_{254}$ silica gel plates (thickness=1 mm, 20×20 cm), eluting with a dichloromethane-methanol (85-15 by volume) mixture. The fraction containing only the desired product is extracted with a dichloromethane-methanol (80-20 by volume) mixture, filtered on sintered glass and then concentrated to dryness under reduced pressure at a temperature close to 35° C. 45 mg of 4'-O-pentanoyl-2-[(1R, 2S,3R)(1,2,3,4-tetrahydroxybutyl)]-5-[(2'S, 3'R)(2',3',4'-trihydroxybutyl)]pyrazine are thus obtained.

The product obtained has the following characteristics:
$^1$H NMR spectrum (400 MHz, (CD$_3$)$_2$SO d6, δ in ppm): 0.90 (t, J=7 Hz, 3H: CH$_3$ of pentanoyl); 1.32 and 1.55 (2 mts, 2H each: central CH$_2$ of pentanoyl); 2.34 (t, J=7.5 Hz, 2H: COCH$_2$ of pentanoyl); 2.77 and 3.13 (2dd, respectively J=14 and 10 Hz and J=14 and 3 Hz, 1H each: CH$_2$ 5α); from 3.20 to 3.70 (mt: the 5H corresponding to CH 2β-CH 2γ-CH$_2$O 2δ and CH 5γ); 3.78 (mt, 1H: CH at position 5β); 4.00 and 4.26 (2dd, J=11 and 7 Hz and J=11 and 3 Hz, 1H each: CH$_2$O 5δ); 4.38 (t, J=6 Hz, 1H: OH at position 2δ); 4.42 (d, J=8 Hz, 1H: OH at position 2γ); 4.65 (d, J=5 Hz, 1H: OH at position 2β); 4.86 (d, J=7 Hz, 1H: OH at position 5β); 4.97 (d, J=6.5 Hz, 1H: CH 2α); 5.10 (d, J=6 Hz, 1H: OH at position 5γ); 5.31 (d, J=.6.5 Hz, 1H: OH at position 2α); 8.42 (broad s, 1H: =CH at position 6); 8.66 (broad s, 1H: =CH at position 3).

EXAMPLE 29

4'-O-acetyl-2-[(1R,2S,3R)(1,2,3,4-tetrahydroxybutyl)]-5-[(2'S,3'R)(2',3',4'-trihydroxybutyl)]pyrazine Preparation of
1,2-O,O-3,4-O,O-3',4'-O,O,-tri(dimethylacetonide)-2'-O-acetyl-2-[(1R,2S,3R)(1,2,3,4-tetrahydroxybutyl)]-5-[(2'S,3'R)(2',3',4'-trihydroxybutyl)]pyrazine 0.133 cm$^3$ of acetic anhydride is added dropwise to a solution of 0.5 g of 1,2-O,O-3,4-O,O-3',4'-O,O-tri (dimethylacetonide)-2-[(1R,2S,3R)(1,2,3,4-tetrahydroxybutyl)]-5-[(2'S,3'R)(2',3',4'-trihydroxybutyl)] pyrazine in 10 cm$^3$ of anhydrous pyridine at a temperature close to 20° C. After 42 hours at a temperature close to 20° C., the reaction mixture is concentrated to dryness under reduced pressure at a temperature close to 35° C. The crude residue obtained is purified by chromatography under pressure (1.4 bar) on 30 g of Merck silica gel 60 F$_{254}$ (0.063–0.040 mm) contained in a column 2 cm in diameter, using an ethyl acetate-cyclohexane (50-50 by volume) eluent mixture. The fractions containing only the desired product are combined and concentrated to dryness under reduced pressure at a temperature close to 35° C. 0.408 g of 1,2-O, O-3,4-O,O-3',4'-O,O-tri(dimethylacetonide)-2'-O-acetyl-2-[(1R,2S,3R)(1,2,3,4-tetrahydroxybutyl)]-5-[(2'S,3'R)(2',3', 4'-trihydroxybutyl)]pyrazine is thus obtained in the form of a light yellow oil.

The product obtained has the following characteristics:
$^1$H NMR spectrum (400 MHz, (CD$_3$)$_2$SO d6, δ in ppm): 1.00–1.20–1.28 1.35–1.42 and 1.45 (6 s, 3H each: the 6 CH$_3$); 1.90 (s, 3H: CH$_3$CO at position 5β); 3.00 and 3.15 (2dd, respectively J=14 and 9 Hz and J=14 and 4 Hz, 1H each: CH$_2$ 5α); 3.80 (mt, 2H: 1H of CH$_2$O 2δ and 1H of CH$_2$O 5δ); 4.04 (mt, 2H: the other H of CH$_2$O 2δ and the other H of CH$_2$O 5δ); from 4.15 to 4.35 (mt, 3H: CH 2γ-CH 2β and CH 5γ); 4.99 (d, J=7 Hz, 1H: CH 2α); 5.25 (mt, 1H: CH 5β); 8.57 (d, J=1 Hz, 1H: =CH at position 6); 8.67 (d, J=1 Hz, 1H: =CH at position 3).

The preparation of 1,2-O,O-3,4-O,O- 3',4'-O,O-tri (dimethylacetonide)-2-[(1R,2S,3R)(1,2,3,4-tetrahydroxybutyl)]-5-[(2'S,3'R)(2',3',4'-trihydroxybutyl)] pyrazine is described in Example 27.

Preparation of

4'-O-acetyl-2-[(1R,2S,3R)(1,2,3,4-tetrahydroxybutyl)]-5-[(2'S,3'R)(2',3',4-trihydroxybutyl)]pyrazine A mixture of 19.68 cm$^3$ of trifluoroacetic acid and 4.9 cm$^3$ of water is added to 100 mg of 1,2-O,O-3,4-O,O-3',4'-O,O,-tri(dimethylacetonide)-2'-O-acetyl-2-[(1R,2S,3R)(1,2,3,4-tetrahydroxybutyl)]-5-[(2'S,3'R)(2',3',4'-trihydroxybutyl)] pyrazine, at a temperature close to 20° C. After about 3.5 hours at a temperature close to 20° C., the reaction mixture is concentrated to dryness under reduced pressure at a temperature close to 35° C. 199 mg of an orange-coloured oil are thus obtained, which oil is purified by preparative chromatography on 4 Merck 60 F$_{254}$ silica gel plates (thickness=1 mm, 20×20 cm), eluting with a dichloromethane-methanol (90-10 by volume) mixture. The fraction containing only the desired product is extracted with a dichloromethane-methanol (80-20 by volume) mixture, filtered on sintered glass and then concentrated to dryness under reduced pressure at a temperature close to 35° C. 18 mg of 4'-O-acetyl-2-[(1R,2S,3R)(1,2,3,4-tetrahydroxybutyl)]-5-[(2'S,3'R)(2',3',4-trihydroxybutyl)] pyrazine are thus obtained.

The product obtained has the following characteristics:
$^1$H NMR spectrum (400 MHz, (CD$_3$)$_2$SO d6, δ in ppm): 2.04 (s, 3H: CH$_3$CO); 2.76 and 3.13 (2dd, respectively J=14 and 9 Hz and J=14 and 3 Hz, 1H each: CH$_2$ 5α); 3.45 (mt, 1H: 1H of CH$_2$O 2δ); from 3.50 to 3.75 (mt, 4H: CH 2β-CH 2γ-the other H of CH$_2$O 2δ and CH 5γ); 3.78 (mt, 1H: CH 5β); 3.99 and 4.25 (2dd, respectively J=11 and 7 Hz and J=11 and 3 Hz, 1H each: CH$_2$O 5δ); 4.40 (t, J=5.5 Hz, 1H: OH and 2δ); 4.45 (d, J=7.5 Hz, 1H: OH at position 2); 4.68

(d, J=5 Hz, 1H: OH at position 2); 4.89 (d, J=6.5 Hz, 1H: OH at position 5β); 4.96 (broad d, J=6.5 Hz, 1H: CH 2α); 5.15 (d, J=6.5 Hz, 1H: OH at position 5γ); 5.34 (d, J=6.5 Hz, 1H: OH at position 2α); 8.42 (broad s, 1H: =CH at position 6); 8.66 (s, 1H: =CH at position 3).

EXAMPLE 30

4,4'-O,O-di(4-methylbenzoyl)-2-[(1R,2S,3R)-(1,2,3,4-tetrahydroxybutyl)]-5-[(2'S,3'R)( 2',3',4'-trihydroxybutyl)]pyrazine 0.326 cm$^3$ of 4-methylbenzoyl chloride is added, dropwise, at a temperature close to 20° C. under an argon atmosphere, to 300 mg of 2-[(1R,2S,3R)-(1,2,3,4-tetrahydroxybutyl)]-5-[(2'S,3'R)(2',3',4'-trihydroxybutyl)] pyrazine in suspension in 7.5 cm$^3$ of anhydrous pyridine. After stirring for 15 hours at a temperature close to 20° C., the reaction mixture is concentrated to dryness under reduced pressure (0.4 kPa) at a temperature close to 40° C. The crude residue thus obtained is purified by chromatography under atmospheric pressure on 40 g of Merck silica gel 60 F$_{254}$ (0.063–0.200 mm) contained in a column 3.5 cm in diameter, eluting with an elution gradient consisting of a dichloromethane-methanol mixture (from 100-10 to 90-10 by volume), collecting 10 cm fractions. The fractions containing only the desired product are combined and concentrated to dryness under reduced pressure (about 0.5 kPa) at a temperature close to 40° C. 139 mg of 4,4'-O,O-di(4-methylbenzoyl)-2-[(1R,2S,3R)(1,2,3,4-tetrahydroxybutyl)]-5-[(2'S,3'R)(2',3',4'-trihydroxybutyl)pyrazine are thus obtained in the form of a white solid.

The product obtained has the following characteristics:

$^1$H NMR spectrum (400 MHz, (CD$_3$)$_2$SO d6, δ in ppm): 2.41 (s, 6H: ArCH$_3$); 2.82 and 3.21 (2dd, espectively J=14 and 9.5 Hz and J=14 and 3 Hz, 1H each: CH$_2$ 5α); from 3.65 to 3.75 (mt, 1H: CH 5γ); 3.72 (broad t, J=8 Hz, 1H: CH 2β); (mt, 1H: CH 5β); 4.01 (mt, 1H: CH 2γ); 4.25 and 4.49 (2 dd, respectively J=12 and 6.5 Hz and J=12 and 3 Hz, 1H each: H$_2$O 5δ); 4.28 and 4.52 (2 dd, respectively J=12 and 6.5 Hz and J=12 and 3 Hz, 1H each: CH$_2$O 2δ); 4.74 (d, J=8 Hz, 1H: OH at position 2β); 4.97 (d, J=7 Hz, 1H: OH at position 5β); 5.04 (broad d, J=6 Hz, 1H: CH 2α); 5.25 (d, J=6 Hz, 1H: OH at position 2γ); 5.29 (d, J=6 Hz, 1H: OH at position 5γ); 5.46 (d, J=6 Hz, 1H: OH at position 2α); 7.36 (d, J=8 Hz, 4H: aromatic H at the meta position with respect to the CO); 7.94 (mt, 4H: aromatic H at the ortho position with respect to the CO); 8.47 (d, J=1 Hz, 1H: =CH at position 6) 8.70 (broad s, 1H: =CH at position 3).

By carrying out the operation according to the above procedure, the following compounds may be obtained in a similar manner:

EXAMPLE 31

4,4'-O,O-di(4-methoxybenzoyl)-2-[(1R,2S,3R)(1,2,3,4-tetrahydroxybutyl)]-5-(2'S,3'R)(2',3',4'-trihydroxybutyl)]pyrazine $^1$H NMR spectrum (400 MHz, (CD$_3$)$_2$SO d6, δ in ppm): 2.82 and 3.20 (respectively dd and broad d, J=14 and 9 Hz and J=14 Hz, 1H each: CH$_2$ 5α); from 3.65 to 3.75 (mt, 1H: CH 5α); 3.72 (broad t, J=8 Hz, 1H: CH 2β); 3.87 (s, 6H: ArOCH$_3$); from 3.80 to 3.95 (mt, 1H: CH 5β); 4.00 (mt, 1H: CH 2γ); from 4.15 to 4.30 (mt, 2H: 1H of CH$_2$O 5δ and 1H of CH$_2$O 2δ); 4.47 and 4.50 (respectively dd and broad d, J=12 and 3 Hz and J=12 Hz, 1H each: the other H of CH$_2$O 5δ and the other of CH$_2$O 2δ); 4.72 (d, J=8 Hz, 1H: OH at position 2β); 4.94 (d, J=6.5 Hz, 1H: OH at position 5β); 5.03 (broad d, J=5.5 Hz, 1H: CH 2α); 5.22 (d, J=6 Hz, 1H: OH at position 2γ); 5.25 (d, J=6 Hz, 1H: OH at position 5γ); 5.44 (d, J=5.5 Hz, 1H: OH at position 2α); 7.08 (d, J=8.5 Hz, 4H: aromatic H at the meta position with respect to the CO); 8.00 (broad d, J=8.5 Hz, 4H: aromatic H at the ortho position with respect to the CO); 8.47 (broad s, 1H: =CH at position 6); 8.70 (broad s, 1H: =CH at position 3).

EXAMPLE 32

4,4'-O,O-di(3-methylbenzoyl)-2-[(1R,2S,3R)(1,2,3,4-tetrahydroxybutyl)]-5-[(2'S,3'R)(2',3',4'-trihydroxybutyl)]pyrazine $^1$H NMR spectrum (400 MHz, (CD$_3$)$_2$SO d6, δ in ppm): 2.40 (s, 6H: ArCH$_3$); 2.83 and 3.20 (2 dd, respectively J=14 and 9 Hz and J=14 and 3 Hz, 1H each: CH$_2$ 5α); from 3.65 to 3.80 (mt, 2H: CH 5γ and CH 2β); 3.89 (mt, 1H: CH 5β); 4.01 (mt, 1H: CH 2γ); from 4.20 to 4.30 (mt, 2H: 1H of CH$_2$O 5δ and 1H of CH$_2$O 2δ); 4.50 and 4.54 (2 dd, J=12 and 3 Hz, 1H each: respectively the other H of CH$_2$O 5δ and the other of CH$_2$O 2δ); 4.74 (d, J=8 Hz, 1H: OH at position 2β); 4.96 (d, J=7 Hz, 1H: OH at position 5β); 5.02 (broad s, 1H: CH 2α); 5.27 (mt, 2H: OH at position 2γ and OH at position 5γ); 5.47 (unresolved complex, 1H: OH at position 2α); 7.43 (t, J=7.5 Hz, 2H: aromatic H at position 5); 7.48 (broad d, J=7.5 Hz, 2H: aromatic H at position 4); 7.83 (broad d, J=7.5 Hz, 2H: aromatic H at position 6); 7,96 (broad s, 2H: aromatic H at position 2); 8.47 (d, J=1 Hz, 1H: =CH at position 6); 8.70 (broad s, 1H: =CH at position 3).

EXAMPLE 33

4,4'-O,O-di(4-fluorobenzoyl)-2-[(1R,2S,3R)(1,2,3,4-tetrahydroxybutyl)]-5-[(2'S,3'R)(2',3',4'-trihydroxybutyl)]pyrazine $^1$H NMR spectrum (400 MHz, (CD$_3$)$_2$SO d6, δ in ppm): 2.82 and 3.21 (2 dd, respectively J=14 and 9.5 Hz and J=14 and 3.5 Hz, 1H each: CH$_5$ 5α); from 3.65 to 3 75 (mt, 1H: CH 5γ); 3.72 (broad t, J=8 Hz, 1H; CH 2β) 3.90 (mt, 1H: CH 5β) 4.01 (mt, 1H: CH 2γ); 4.26 and 4.50 (2 dd, respectively J=12 and 6.5 Hz and J=12 and 3 Hz, 1H each: CH$_2$O 5δ); 4.28 and 4.53 (2 dd, respectively J=12 and 6.5 Hz and J=12 and 3 Hz, 1H each: CH$_2$O 2δ); 4.74 (d, J=8 Hz, 1H: OH at position 2β); 4.97 (d, J=6.5 Hz, 1H: OH at position 5δ); 5.01 (broad d, J=6 Hz, 1H: CH 2α); 5.26 (d, J=6 Hz, 1H: OH at position 2γ); 5.30 (d, J=6 Hz, 1H OH at position 5γ); 5.45 (d, J=6 Hz, 1H: OH at position 2α); 7.38 (t, J , 8.5 Hz, 4H: aromatic H at the ortho position with respect to F); 8.10 (mt, 4H: aromatic H at the ortho position with respect to the CO); 8.47 (broad s, 1H: =CH at position 6); 8.70 (broad s, 1H =CH at position 3).

EXAMPLE 34

4,4'-O,O-dithienoyl-2-[(1R,2S,3R)(1,2,3,4-tetrahydroxybutyl)]-5-[(2'S,3'R)(2',3',4'-trihydroxybutyl)]pyrazine $^1$H NMR spectrum (400 MHz, (CD$_3$)$_2$SO d6, δ in ppm); 2.81 and 3.19 (2 dd, respectively J=14 and 9.5 Hz and J=14 and 3 Hz, 1H each: CH$_2$ 5α); from 3.65 to 3.75 (mt, 1H: CH 5γ); 3.71 (broad t, J=8 Hz, 1H: CH 2β); 3.87 (mt, 1H: CH 5β); 3.98 (mt, 1H: CH 2γ); 4.25 and 4.49 (2 dd, respectively J=12 and 7 Hz and J=12 and 3 Hz, 1H each: CH$_2$O 5δ); 4.29 and 4.52 (2 dd, respectively J=12 and 7 Hz and J=12 and 3 Hz, 1H each: CH$_2$O 2δ); 4.75 (d, J=8 Hz, 1H: OH at position 2β); 4.97 (d, J=7 Hz, 1H: OH at position 5β); 5.01 (broad d, J=6 Hz, 1H: CH 2α); 5.25 (d, J=6 Hz, 1H: OH at position 2γ); 5.28 (d, J=6 Hz, 1H: OH at position 5γ); 5.47 (d, J=6 Hz, 1H: OH at position 2α); 7.25 (mt, 2H: H4 of thienyl); 7.87 and 7.97 (2 mts, 2H each: H3 and H5 of thienyl); 8.47 (s, 1H: =CH at position 6); 8.71 (s, 1H: =CH at position 3).

EXAMPLE 35

4,4'-O,O-di(4-nitrobenzoyl)-2-[(1R,2S,3R)(1,2,3,4-tetrahydroxybutyl)]-5-[(2'S,3'R)(2',3',4'-trihydroxybutyl)]pyrazine $^1$H NMR spectrum (400 MHz, (CD$_3$)$_2$SO d6, δ in ppm): 2.82 and 3.22 (2 dd, respectively J=14 and 9 Hz and J=14 and 3 Hz, 1H each: CH$_2$ 5α); from 3.70 to 3.80 (mt, 1H: CH 5γ); 3.74 (broad t, J=8 Hz, 1H: CH 2β); 3.90 (mt, 1H: CH 5β); 4.03 (mt, 1H: CH 2γ); 4.35 and 4.56 (2 dd, respectively J=12 and 7 Hz and J=12 and 3 Hz, 1H each: CH$_2$O 5δ); 4.37 and 4.59 (2 dd, respectively J=12 and 7 Hz and J=12 and 3H, 1H each: CH$_2$O 2δ); 4.80 (d, J=8 Hz, 1H: OH at position 2β); from 5.00 to 5.10 (mt, 2H: OH at position 5β and CH 2α); 5.34 (d, J=6 Hz, 1H: OH at position 2γ); 5.38 (d, J=6 Hz, 1H: OH at position 5γ); 5.50 (1, J=6 Hz, 1H: OH at position 2α); 8.28 (mt, 4H: aromatic H at the ortho position with respect to the CO); 8.40 (d, J=8 Hz, 4H: aromatic H at the ortho position with respect to the NO$_2$); 8.47 (s, 1H: =CH at position 6); 8.71 (s, 1H: =CH at position 3).

EXAMPLE 36

4,4'-O,O-di(4-chlorobenzoyl)-2-[(1R,2S,3R)(1,2,3,4-tetrahydroxybutyl)]-5-[(2'S,3'R)(2',3',4'-trihydroxybutyl)]pyrazine $^1$H NMR spectrum (400 MHz, (CD$_3$)$_2$SO d6, δ in ppm): 2.80 and 3.20 (2 dd, respectively J=14 and 9.5 Hz and J=14 and 3.5 Hz, 1H each: CH$_2$ 5α); from 3.65 to 3.75 (mt, 1H: CH 5γ); 3.72 (broad t, J=8 Hz, 1H: CH 2β); 3.89 (mt, 1H: CH 5β); 4.00 (mt, 1H: CH 2γ); 4.28 and 4.50 (2 dd, respectively J=12 and 6 Hz and J=12 and 3 Hz, 1H each: CH$_2$O 5δ); 4.31 and 4.53 (2 dd, respectively J=12 and 6 Hz and J=12 and 3 Hz, 1H each: CH$_2$O 2δ); 4.76 (d, J=8 Hz, 1H: OH at position 2β; 4.99 (d, J=7 Hz, 1H: OH at position 5β); 5.02 (broad d, J=6 Hz, 1H: CH 2α); 5.30 (d, J=6 Hz, 1H: OH at position 2γ); 5.32 (d, J=6 Hz, 1H: OH at position 5γ); 5.48 (d, J=6 Hz, 1H: OH at position 2α); 7.63 (d, J=8 Hz, 4H: aromatic H at the ortho position with respect to Cl); 8.05 (mt, 4H: aromatic H at the ortho position with respect to the CO); 8,47 (d, J=1 Hz, 1H: =CH at position 6); 8.70 (broad s, 1H: =CH at position 3).

EXAMPLE 37

4,4'-O,O-di(4-N,N-dimethylaminobenzoyl)-2-[(1R,2S,3R)(1,2,3,4-tetrahydroxybutyl)]-5-[(2'S,3'R)(2',3',4'-trihydroxybutyl)]pyrazine $^1$H NMR spectrum (400 MHz, (CD$_3$)$_2$SO d6, δ in ppm): 2.82 and 3.19 (2 dd, respectively J=14 and 9 Hz and J=14 and 3 Hz, 1H each: CH$_2$ 5α); 3.03 (s, 12H: ArN(CH$_3$)$_2$); from 3.65 to 3.80 (mt, 1H: CH 5γ); 3.71 (broad t, J=8 Hz, 1H: CH 2β); 3.89 (mt, 1H: CH 5β); 3.98 (mt, 1H: CH 2γ); from 4.15 to 4.25 (mt, 2H: 1H of CH$_2$O 5δ and 1H of CH$_2$O 2δ); from 4.40 to 4.55 (mt, 2H: the other H of CH$_2$O 5δ and the other of CH$_2$O 2δ); 4.69 (d, J=8 Hz, 1H: OH at position 2β); 4.92 (d, J=6.5 Hz, 1H: OH at position 5β); 5.03 (broad d, J=6 Hz, 1H: CH 2α); 5.17 and 5.21 (2 d, J=6 Hz, 1H each: OH at position 2γ and OH at position 5γ); 5.43 (d, J=6 Hz, 1H: OH at position 2α); 6.76 (d, J=8.5 Hz, 4H: aromatic H at the meta position with respect to the CO); 7.85 (mt, 4H: aromatic H at the ortho position with respect to the CO); 8.47 (broad s, 1H: =CH at position 6); 8.70 (broad s, 1H: =CH at position 3).

The 4,4'-O,O-di(4-aminobenzoyl)-2-[(1R,2S,3R)(1,2,3,4-tetrahydroxybutyl)]-5-[(2'S,3'R)(2',3',4'-trihydroxybutyl)]pyrazine derivative may be prepared by using a similar procedure.

EXAMPLE 38

4,4'-O,O-di(4-benzyloxybenzoyl)-2-[(1R,2S,3R)(1,2,3,4-tetrahydroxybutyl)]-5-[(2'S,3'R)(2',3',4'-trihydroxybutyl)]pyrazine $^1$H NMR spectrum (400 MHz, (CD$_3$)$_2$SO d6, δ in ppm): 2.81 and 3.21 (2 dd, respectively J=14 and 9 Hz and J=14 and 3 Hz, 1H each: CH$_2$ 5α); from 3.65 to 3.80 (mt, 1H: CH 5γ); 3.71 (broad t, J=8 Hz, 1H: CH 2β); 3.89 (mt, 1H; CH 5β); 4.00 (mt, 1H: CH 2γ); 4.22 and 4.51 (2 dd, respectively J=12 and 7 Hz and J=12 and 3 Hz, 1H each: CH$_2$O 5δ); 4.25 and 4.51 (2 dd, respectively J=12 and 7 Hz and J=12 and 2.5 Hz, 1H each: CH$_2$O 2δ); 4.75 (d, J=8 Hz, 1H: OH at position 2β); 4.97 (d, J=6.5 Hz, 1H: OH at position 5β); 5.03 (mt, 1H: CH 2α); from 5.20 to 5.35 (mt, 2H: OH at position 2γ and OH at position 5γ); 5.22 (s, 4H: ArCH$_2$O); 5.47 (broad d, J=5.5 Hz, 1H: OH at position 2α); 7.17 (d, J=8.5 Hz, 4H: aromatic H at the meta position with respect to the CO); 7.38 (t, J=7.5 Hz, 2H: aromatic H at the para position for the benzyls); 7.44 (t, J=7.5 Hz, 4H: aromatic H at the meta position for the benzyls); 7.50 (d, J=7.5 Hz, 4H: aromatic H at the ortho position for the benzyls; 8.00 (mt, 4H: aromatic H at the ortho position with respect to the CO); 8.47 (d, J=1 Hz, 1H: =CH at position 6); 8.70 (broad s, 1H: =CH at position 3).

EXAMPLE 39

4,4'-O,O-di(3,5-dichlorobenzoyl)-2-[(1R,2S,3R)(1,2,3,4-tetrahydroxybutyl)]-5-[(2'S,3'R)(2',3',4'-trihydroxybutyl)]pyrazine $^1$H NMR spectrum (400 MHz, (CD$_3$)$_2$SO d6, δ in ppm): 2.81 and 3.22 (2 dd, respectively J=14 and 9 Hz and J=14 and 3 Hz, 1H each: CH$_2$ 5α); from 3.65 to 3.75 (mt, 1H: CH 5γ); 3.72 (broad t, J=9 Hz, 1H: CH 2β); 3.88 (mt, 1H: CH 5β); 4.02 (mt 1H: CH 2γ); from 4.20 to 4.35 (mt, 2H: 1H of CH$_2$O 5δ and 1H of CH$_2$O 2δ); 4.51 (dd, J=12 and 3 Hz, 1H: the other H of CH$_2$O 5δ); 4.53 (dd, J=12 and 3 Hz, 1H: the other of CH$_2$O 2δ); 4.79 (d, J=9 Hz, 1H: OH at position 2β); from 5.00 to 5.10 (mt, 2H: OH at position 5β and CH 2α); 5.38 (d, J=6 Hz, 1H: OH at position 2γ); 5.41 (d, J=6 Hz, 1H: OH at position 5γ); 5.50 (d, J=5.5 Hz, 1H: OH at position 2α); from 8.00 to 8.10 (mt, 6H: aromatic H); 8.47 (d, J=1 Hz, 1H: =CH at position 6); 8.71 (d, J=1 Hz, 1H: =CH at position 3).

EXAMPLE 40

4,4'-O,O-di-phenylacetyl-2-[(1R,2S,3R)(1,2,3,4-tetrahydroxybutyl)]-5-[(2'S,3'R)(2',3',4'-trihydroxybutyl)]pyrazine $^1$H NMR spectrum (400 MHz, (CD$_3$)$_2$SO d6, δ in ppm): 2.77 and 3.14 (2 dd, respectively J=14 and 9 Hz and J=14 and 3 Hz, 1H each: CH$_2$ 5α); from 3.55 to 3.65 (mt, 1H: CH 5γ); 3.64 (broad t, J=9 Hz, 1H: CH 2β); 3.71 (s, 4H: OCOCH$_{2α}$r); 3.80 (mt, 1H: CH 5β); 3.88 (mt, 1H: CH 2γ);

from 4.00 to 4.15 (mt, 2H: 1H of CH₂O 5δ and 1H of CH₂O 2δ); 4.30 (dd, J=12 and 3 Hz, 1H: the other H of CH₂O 5δ); 4.34 (dd, J=12 and 2.5 Hz, 1H: the other H of CH₂O 2δ); 4.65 (d, J=9 Hz, 1H: OH at position 2β); 4.88 (d, J=7 Hz, 1H: OH at position 5β); 4.99 (broad s, 1H: CH 2α); 5.13 (d, J=6 Hz, 1H: OH at position 2γ); 5.16 (d, J=6 Hz, 1H: OH at position 5γ); 5.45 (unresolved complex, 1H: OH at position 2α); from 7.20 to 7.45 (mt, 10H: aromatic H); 8.44 (broad s, 1H: =CH at position 6); 8.68 (broad s, 1H: =CH at position 3).

EXAMPLE 41

4,4'-O,O-di(4-hydroxybenzoyl)-2-[(1R,2S,3R)(1,2,3,4-tetrahydroxybutyl)]-5-[(2'S,3'R)(2',3',4'-trihydroxybutyl)]pyrazine 80 mg of palladium on carbon (10% by weight of palladium) are added, at a temperature close to 20° C., to a solution of 158 mg of 4,4'-O,O-di(4-benzyloxy-benzoyl)-2-[(1R,2S,3R)(1,2,3,4-tetrahydroxybutyl)]-5-[(2'S,3'R)(2',3',4'-trihydroxybutyl)]pyrazine in 5 cm³ of methanol. The suspension obtained is stirred under a hydrogen atmosphere (300 kPa), at a temperature close to 26° C., for 3 hours. The reaction medium is then filtered on 20 Celite. The Celite is rinsed with methanol and then with a methanol-dichloromethane (10-90 by volume) mixture. The filtrate is concentrated to dryness under reduced pressure at a temperature close to 40° C. 89 mg of 4,4'-O,O-di(4-hydroxybenzoyl)-2-[(1R,2S,3R)(1,2,3,4-tetrahydroxybutyl)-5-[(2'S,3'R)( 2',3',4'-trihydroxybutyl)]pyrazine are thus obtained in the form of a yellow lacquer.

The product obtained has the following characteristics:

¹H NMR spectrum (400 MHz, (CD₃)₂SO d6, δ in ppm): 2.82 and 3.20 (respectively dd and broad d, J=14 and 9 Hz and J=14 Hz, 1H each: CH₂ 5α); from 3.65 to 3.75 (mt, 1H: CH 5γ); 3.71 (broad t, J=9 Hz, 1H: CH 2β); 3.90 (mt, 1H: CH 5β); .3.98 (mt, 1H: CH 2γ); from 4.15 to 4.25 (mt, 2H: 1H of CH₂O 5δ and 1H of CH₂O 2δ); 4.45 (dd, J=12 and 3 Hz, 1H: the other H of CH₂O 5δ); 4.49 (broad d, J=12 Hz, 1H: the other of CH₂O 2δ); 4.73 (d, J=9 Hz, 1H: OH at position 2β); 4.95 (d, J=6.5 Hz, 1H: OH at position 5β); 5.03 (broad d, J=5.5 Hz, 1H: CH 2α); 5.22 (d, J=6 Hz, 1H: OH at position 2γ); 5.26 (d, J=6 Hz, 1H: OH at position 5γ); 5.46 (d, J=5.5 Hz, 1H: OH at position 2α); 6.88 (d, J=8.5 Hz, 4H: aromatic H at the meta position with respect to the CO); 7.90 (broad d, J=8.5 Hz, 4H: aromatic H at the ortho position with respect to the CO); 8.47 (broad s, 1H: =CH at position 6); 8.71 (broad s, 1H: =CH at position 3); 10.30 (broad unresolved complex, 2H: ArOH).

The products below may also be prepared by carrying out the operation according to the same procedure starting with deoxyfructosazine, and using the suitably chosen corresponding starting materials (acids or acyl chlorides):

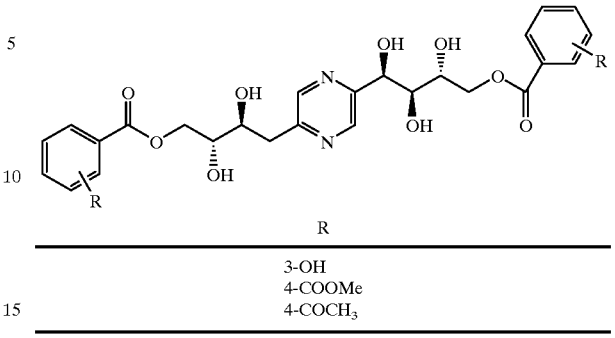

| R |
|---|
| 3-OH |
| 4-COOMe |
| 4-COCH₃ |

EXAMPLE 42

4,4'-O,O-di(4-(N,N-di-n-propyl-aminomethylene)benzoyl)-2-[(1R,2S,3R)(1,2,3,4-tetrahydroxybutyl)]-5-[(2'S,3'R)(2',3',4'-trihydroxybutyl)]pyrazine Methyl 4-(N,N-di-n-propylaminomethylene) benzoate 1.37 cm³ of N,N-di-n-propylamine are added to a suspension of 2.29 g of methyl 4-(bromomethyl)benzoate and 1.52 g of potassium carbonate in 40 cm³ of acetonitrile, at a temperature close to 20° C. The reaction mixture is heated under reflux for about 16 hours, and then after cooling to a temperature close to 20° C., it is filtered on sintered glass. The sintered glass is rinsed with 3 times 30 cm³ of ethyl acetate. The filtrate is concentrated to dryness under reduced pressure at a temperature close to 40° C. After dissolution of the residue in 100 cm³ of ethyl acetate, the organic phase is successively washed with 3 times 100 cm³ of distilled water, 100 cm³ of a saturated aqueous sodium chloride solution, dried over magnesium sulphate and concentrated to dryness under reduced pressure (about 1 kPa) at a temperature close to 40° C. 2.5 g of methyl 4-(N,N-di-n-propylaminomethylene)benzoate are thus obtained in the form of a yellow oil.

4-(N,N-di-n-propylaminomethylene)benzoic Acid (monohydrochloride)

9 cm³ of distilled water are added to an oily suspension of 2.4 g of methyl 4-(N,N-di-n-propylaminomethylene) benzoate in 9 cm³ of concentrated hydrochloric acid (36% minimum), at a temperature close to 20° C. The reaction mixture is heated under reflux for 24 hours and then supplemented with 3S charcoal, and filtered while hot on a sintered glass. The filtrate is concentrated to dryness under reduced pressure (about 1 kPa) at a temperature close to 40° C. The white solid thus obtained is filtered on sintered glass, rinsed with 3 times 10 cm³ of acetonitrile, 10 cm³ of diisopropyl ether, air-dried and then dried under reduced pressure (about 0.2 kPa) at a temperature close to 50° C. 1.8 g of 4-(N,N-di-n-propylaminomethylene)benzoic acid (monohydrochloride) are thus obtained in the form of white crystals.

4-(N,N-di-n-propylaminomethylene)benzoyl Chloride (monohydrochloride)

0.283 cm³ of oxalyl chloride and then a drop of dimethylformamide are successively added, at a temperature close to 20° C., to a suspension of 0.748 g of 4-(N,N-di-n- propylaminomethylene)benzoic acid monohydrochloride in 20 cm$^3$ of dichloromethane. The reaction medium is kept stirred at a temperature close to 20° C. until the gaseous emission ceases, and then concentrated to dryness under reduced pressure (about 0.5 kPa) at a temperature close to 35° C. The white solid thus obtained is used as a base for the preparation of 4,4'-O,O-di(4-(N,N-di-n-propylaminomethylene)benzoyl)-2-[(1R,2S,3R)(1,2,3,4-tetrahydroxybutyl)]-5-[(2'S, 3'R)(2',3',4'-trihydroxybutyl)]pyrazine.

4,4'-O, O-di(4-(N,N-di-n-propylaminomethylene) benzoyl)-2-[(1R,2S,3R)(1,2,3,4-tetrahydroxybutyl)]-5-[(2'S, 3'R)(2',3',4'-trihydroxybutyl)]pyrazine 0.00275 mol of 4-(N,N-di-n-propylamindmethylene) benzoyl chloride (in monohydrochioride form) is added, in small portions, at a temperature close to 20° C. under an argon atmosphere, to 304 mg of 2-[(1R,2S,3R)(1,2,3,4-tetrahydroxybutyl)]-5-[(2'S,3'R)(2',3',4'-trihydroxybutyl)] pyrazine in suspension in 10 cm$^3$ of anhydrous pyridine. After stirring for about 17 hours at a temperature close to 20° C., the reaction medium is concentrated to dryness under reduced pressure (about 0.5 kPa at a temperature close to 35° C. The yellow paste obtained is redissolved in 30 cm$^3$ of water, washed with 3 times 20 cm$^3$ of ethyl acetate. The aqueous phase is concentrated to dryness under reduced pressure (about 0.5 kPa) at a temperature close to 40° C. 1.3 g of a pale yellow foam are obtained, which foam is purified by chromatography under pressure (180 kPa) on a volume of 120 cm$^3$ of Merck silica gel 60 $F_{254}$ (0.063–0.040 mm) contained in a column 3 cm in diameter, eluting with an elution gradient which consists of a chloroform-methanol-ammonium hydroxide mixture (12-3-0 and then 12-3-0.2 by volume), collecting 20 cm$^3$ fractions. The fractions containing only the desired product are combined and concentrated to dryness under reduced pressure (about 0.5 kPa) at a temperature close to 40° C. 280 mg of a solid are thus obtained, which solid is repurified by chromatography under pressure (180 kPa) on a volume of 90 cm$^3$ of Merck silica gel 60 $F_{254}$ (0.063–0.040 mm) contained in a column 3 cm in diameter, eluting with an elution gradient consisting of a chloroform-methanol-ammonium hydroxide mixture (80-20-0 and then 80-20-1 by volume). The fractions containing only the desired product are combined and concentrated to dryness under reduced pressure (about 0.5 kPa) at a temperature close to 40° C. 170 mg of 4,4'-O,O-di(4-(N,N-di-n-propylaminomethylene)benzoyl)-2-[(1R,2S,3R)(1,2,3,4-tetrahydroxybutyl)]-5-[(2'S,3'R)(2',3',4'-trihydroxybutyl)] pyrazine are thus obtained in the form of a white crystalline powder.

The product obtained has the following characteristics:

$^1$H NMR spectrum (400 MHz, $(CD_3)_2SO$ d6, δ in ppm): 0.83 (t, J=7.5 Hz, 12H: $CH_3$ of the propyls); 1.44 (mt, 8H: central $CH_2$ of the propyls); 2.34 (mt, 8H: $NCH_2$ of the propyls); 2.82 and 3.20 (2 dd, respectively J=14 and 9.5 Hz and J=14 and 3 Hz, 1H each: $CH_2$ 5α); 3.60 (s, 4H: $ArCH_2N$); from 3.65 to 3.75 (mt, 1H: CH 5γ); 3.71 (t, J=9 Hz, 1H: CH 2β); 3.89 (mt, 1H: CH 5β); 3.99 (mt, 1H: CH 2γ); from 4.20 to 4.30 (mt, 2H: 1H of $CH_2O$ 5δ and 1H of $CH_2O$ 2δ); 4.48 (dd, J=12 and 3 Hz, 1H: the other H of $CH_2O$ 5δ); 4.51 (dd, J=12 and 3 Hz, 1H: the other H of $CH_2O$ 2δ); 4.74 (d, J=9 Hz, 1H: OH at position 2β); 4.96 (d, J=7 Hz, 1H: OH at position 5β); 5.01 (broad d, J=6 Hz, 1H: CH 2α); 5.23 (d, J=7 Hz, 1H: OH at position 2γ); 5.27 (d, J=7 Hz, 1H: OH at position 5γ); 5.46 (d, J=6 Hz, 1H: OH at position 2α); 7.48 (d, J=8 Hz, 4H: aromatic H at the meta position with respect to the CO); 7.98 (d, J=8 Hz, 4H: aromatic H at the ortho position with respect to the CO); 8.47 (broad s, 1H: =CH at position 6); 8.70 (broad s, 1H: =CH at position 3).

EXAMPLE 43

(4,4'-O,O-di(4-(N,N-di-n-propylaminomethylene) benzoyl)-2-[(1R,2S,3R)(1,2,3,4-tetrahydroxybutyl)]-5-[(2'S,3'R)(2',3',4'-trihydroxybutyl)]pyrazine) trihydrochloride 7.3 cm$^3$ of aqueous hydrochloric acid solution of concentration 0.1 N are added, at a temperature close to 20° C., to a solution of 170 mg of 4,4'-O,O-di(4-(N,N-di-n-propylaminomethylene)benzoyl)-2-[(1R,2S,3R)(1,2,3,4-tetrahydroxybutyl)]-5-[(2'S,3'R)(2',3',4'-trihydroxybutyl)] pyrazine in 10 cm$^3$ of water. After stirring for 30 minutes at a temperature close to 20° C., the reaction medium is freeze-dried under reduced pressure. 182 mg of (4,4'-O,O-di(4-(N,N-di-n-propylaminomethylene)benzoyl)- 2-[(1R, 2S,3R)(1,2,3,4-tetrahydroxybutyl)]-5-[(2'S,3'R)(2',3',4'-trihydroxybutyl)]pyrazine) trihydrochloride are thus obtained in the form of a white powder.

The product obtained has the following characteristics:

$^1$H NMR spectrum (400 MHz, $(CD_3)_2SO$ d6, δ in ppm): 0.88 (t,J=7.5 Hz, 12H: $CH_3$ of the propyls); 1.72 (mt, 8H: central $CH_2$ of the propyls); 2.81 (dd, J=14 and 9.5 Hz, 1H: 1H of $CH_2$ 5α); 2.96 (mt, 8H: $NCH_2$ of the propyls); 3.21 (dd, J=14 and 3 Hz, 1H: the other H of $CH_2$ 5α); from 3.65 to 3.80 (mt, 2H: CH 5γ and CH 2β); 3.89 (mt, 1H: CH 5β); 4.02 (mt, 1H: CH 2γ); from 4.25 to 4.35 (mt, 2H: 1H of $CH_2O$ 5δ and 1H of $CH_2O$ 2δ); 4.42 (d, J=5.5 Hz, 4H: $ArCH_2N$); 4.51 (dd, J=12 and 3 Hz, 1H: the other H of $CH_2O$ 5δ); 4.55 (dd, J=12 and 3 Hz, 1H: the other H of $CH_2O$ 2δ), 5.03 (broad s, 1H: CH 2α); 7.78 (d, J=8 Hz, 4H: aromatic H at the meta position with respect to the CO); 7.97 (d, J=8 Hz, 4H: aromatic H at the ortho position with respect to the CO); 8.47 (broad s, 1H: =CH at position 6); 8.70 (broad s, 1H: =CH at position 3); 11.28 (unresolved complex, 2H: $NH^+Cl^-$).

By carrying out the operation according to the procedure of Examples 42 and 43, the following compounds may be obtained in a similar manner:

EXAMPLE 44

4,4'-O,O-di(4-(N,N-diethylaminomethylene) benzoyl)-2-[(1R,2S,3R)(1,2,3,4-tetrahydroxybutyl)]-5-[(2'S, 3'R)(2'S, 3'R)(2',3',4'-trihydroxybutyl)]-pyrazine $^1$H NMR spectrum (400 MHz, $(CD_3)_2SO$ d6, δ in ppm): 1.01 (t, J=7.5 Hz, 12H: $CH_3$ of the ethyls); 2.48 (q, J=7.5 Hz, 8H: $NCH_2$ of the ethyls); 2.82 and 3.20 (2 dd, respectively J=14 and 9.5 Hz and J=14 and 3 Hz, 1H each: $CH_2$ 5α); 3.62 (s, 4H: $ArCH_2N$); from 3.65 to 3.80 (mt, 1H: CH 5γ); 3.72 (t, J=8.5 Hz, 1H: CH 2β); 3.88 (mt, 1H: CH 5β); 3.99 (mt, 1H: CH 2γ); from 4.20 to 4.35 (mt, 2H: 1H of $CH_2O$ 5δ and 1H of $CH_2O$ 2δ); 4.49 (dd, J=12 and 3 Hz, 1H: the other H of $CH_2O$ 5δ); 4.53 (dd, J=12 and 3 Hz, 1H: the other H of $CH_2O$ 2δ); 4.75 (d, J=8.5 Hz, 1H: OH at position 2β); 4.97 (d, J=7 Hz, 1H: OH at position 5β); 5.02 (broad d, J=6 Hz, 1H: CH 2α); 5.25 (d, J=7 Hz, 1H: OH at position 2γ); 5.28 (d, J=7 Hz, 1H: OH at position 5γ); 5.47 (d, J=6 Hz, 1H: OH at position 2α); 7.48 (d, J=8 Hz, 4H: aromatic H at the meta position with respect to the CO); 7.99 (d, J=8 Hz, 4H: aromatic H at the ortho position with respect to the CO); 8.48 (d, J=1 Hz, 1H: =CH at position 6); 8.72 (broad s, 1H: =CH at position 3).

EXAMPLE 45

(4, 4'-O,O-di(4-(N,N-diethylaminomethylene)-benzoyl)-2-[(1R,2S,3R)(1,2,3,4-tetrahydroxybutyl)]-5-[(2'S,3'R)(2',3',4'-trihydroxybutyl)]-pyrazine) Trihydrochloride $^1$H NMR spectrum (500 MHz, $(CD_3)_2SO$ d6, δ in ppm): 1.30 (t, J=7.5 Hz, 12H: $CH_3$ of the ethyls); 2.92 and 3.22 (2 dd, respectively J=14 and 9.5 Hz and J=14 and 3 Hz, 1H each: $CH_2$ 5α); 3.11 (mt, 8H: $NCH_2$ of the ethyls): 3.79 (mt, 1H: CH 5γ); 3.83 (broad d, J=8.5 Hz, 1H: CH 2β); 3.99 (mt, 1H: CH 5β); 4.04 (mt, 1H: CH 2γ); from 4.30 to 4.45 (mt, 2H: 1H of $CH_2O$ 5δ and 1H of $CH_2O$ 2δ); 4.38 (s, 4H: $ArCH_2N$); 4.55 (dd, J=12 and 3 Hz, 1H: the other H of $CH_2O$ 5δ); 4.60 (dd, J=12 and 3 Hz, 1H: the other H of $CH_2O$ 2δ); 5.04 (broad s, 1H: CH 2α); 7.82 (d, J=8 Hz, 4H: aromatic H at the meta position with respect to the CO); 8.09 (broad d, J=8 Hz, 4H: aromatic H at the ortho position with respect to the CO); 8.49 (broad s, 1H: =CH at position 6); 8.72 (broad s, 1H: =CH at position 3); 10.70 (broad unresolved complex, 2H: $NH^+Cl^-$).

EXAMPLE 46

4,4'-O,O-di(4-(piperidinomethylene)benzoyl)-2-[1R,2S,3R)( 1,2,3,4-tetrahydroxybutyl)]-5-[(2'S,3'R)(2',3',4'-trihydroxybutyl)]pyrazine $^1$H NMR spectrum (400 MHz, $(CD_3)_2SO$ d6, δ in ppm): from 1.30 to 1.60 (mt, 12H: $CH_2CH_2CH_2$ of the piperidyls); 2.34 (unresolved complex, 8H: $CH_2NCH_2$ of the piperidyls); 2.80 and 3.19 (2 dd, respectively J=14 and 9.5 Hz and J=14 and 3.5 Hz, 1H each: $CH_2$ 5α); 3.52 (unresolved complex, 4H; $ArCH_2N$); from 3.65 to 3.75 (mt, 2H: CH 5γ and CH 2β); 3.86 (mt, 1H: CH 5β); 3.98 (mt, 1H: CH 2γ); from 4.15 to 4.30 (mt, 2H: 1H of $CH_2O$ 5δ and 1H of $CH_2O$ 2δ); 4.46 (dd, J=12 and 3 Hz, 1H: the other H of $CH_2O$ 5δ); 4.49 (dd, J=12 and 2.5 Hz, 1H: the other H of $CH_2O$ 2δ); 4.72 (d, J=8.5 Hz, 1H: OH at position 2β); 4.96 (d, J=6.5 Hz, 1H: OH at position 5β); 5.00 (broad d, J=6 Hz, 1H: CH 2α); 5.23 (d, J=6.5 Hz, 1H: OH at position 2γ); 5.26 (d, J=6.5 Hz, 1H: OH at position 5γ); 5.44 (d, J=6 Hz, 1H: OH at position 2α); 7.45 (broad d, J=8 Hz, 4H: aromatic H at the meta position with respect to the CO); 7.97 (d, J=8 Hz, 4H: aromatic H at the ortho position with respect to the CO); 8.45 (s, 1H: =CH at position 6); 8.69 (s, 1H: =CH at position 3).

EXAMPLE 47

4,4'-O,O-di(4-(morpholinomethylene)benzoyl)-2-[1R,2S,3R)(1,2,3,4-tetrahydroxybutyl)]- 5-[(2'S,3'R)(2',3',4'-trihydroxybutyl)]pyrazine $^1$H NMR spectrum (500 MHz, $(CD_3)_2SO$ d6, δ in ppm): 2.38 (mt, 8H: $CH_2NCH_2$ of the morpholines); 2.82 and 3.20 (2 dd, respectively J=14 and 9.5 Hz and J=14 and 3.5 Hz, 1H each: $CH_2$ 5α); 3.56 (s, 4H: $ArCH_2N$); 3.60 (mt, 8H: $CH_2OCH_2$ of the morpholines); from 3.65 to 3.75 (mt, 1H: CH 5γ); 3.73 (broad t, J=8.5 Hz, 1H: CH 2β); 3.89 (mt, 1H: CH 5β); 4.01 (mt, 1H: CH 2γ); 4.27 (mt, 2H: 1H of $CH_2O$ 5δ and 1H of $CH_2O$ 2δ); 4.49 (dd, J=12 and 3 Hz, 1H: the other H of $CH_2O$ 5δ); 4.52 (dd, J=12 and 2.5 Hz, 1H: the other H of $CH_2O$ 2δ); 4.70 (d, J=8.5 Hz, 1H: OH at position 2β); 4.93 (d, J=6.5 Hz, 1H: OH at position 5β); 5.02 (broad d, J=6 Hz, 1H: CH 2α); 5.21 (d, J=6.5 Hz, 1H: OH at position 2γ); 5.24 (d, J=6.5 Hz, 1H: OH at position 5γ); 5.44 (d, J=6 Hz, 1H: OH at position 2α); 7.49 (broad d, J=8 Hz, 4H: aromatic H at the meta position with respect to the CO); 8.00 (broad d, J=8 Hz, 4H: aromatic H at the ortho position with respect to the CO); 8.46 (broad s, 1H: =CH at position 6); 8.70 (s, 1H: =CH at position 3).

EXAMPLE 48

4,4'-O,O-di(4-(N,N-dimethylaminomethylene)-bezoyl)-2-[1R,2S,3R)(1,2,3,4-tetrahydroxybutyl)]-5-[(2'S,3'R)(2',3',4'-trihydroxybutyl)]pyrazine $^1$H NMR spectrum (500 MHz, $(CD_3)_2SO$ d6, δ in ppm): 2.15 (s, 12H: $NCH_3$); 2.81 and 3.20 (2 dd, respectively J=14 and 9.5 Hz and J=14 and 3 Hz, 1H each: $CH_2$ 5α); 3.48 (s, 4H: $ArCH_2N$); from 3.65 to 3.80 (mt, 1H: CH 5γ); 3.71 (t, J=8.5 Hz, 1H: CH 2β); 3.89 (mt, 1H: CH 5β); 4.00 (mt, 1H: CH 2γ); 4.27 (mt, 2H: 1H of $CH_2O$ 5δ and 1H of $CH_2O$ 2δ); 4.49 (dd, J=12 and 3 Hz, 1H: the other H of $CH_2O$ 5δ); 4.52 (dd, J=12 and 3 Hz, 1H: the other H of $CH_2O$ 2δ); 4.72 (d, J=8.5 Hz, 1H: OH at position 2β); 4.95 (d, J=7 Hz, 1H: OH at position 5β); 5.02 (broad d, J=6 Hz, 1H: CH 2α); 5.23 (d, J=7 Hz, 1H: OH at position 2γ); 5.26 (d, J=7 Hz, 1H: OH at position 5γ); 5.43 (d, J=6 Hz, 1H: OH at position 2α); 7.45 (d, J=8 Hz, 4H: aromatic H at the meta position with respect to the CO); 7.99 (broad d, J=8 Hz, 4H: aromatic H at the ortho position with respect to the CO); 8.47 (d, J=1 Hz, 1H: =CH at position 6); 8.70 (broad s, 1H: =CH at position 3).

EXAMPLE 49

4,4'-O,O-di(N-phenylcarbamoyl)-2-[1R,2S,3R)(1,2,3,4-tetrahydroxybutyl)]-5-[(2'S, 3'R)(2',3',4'-trihydroxybutyl)]pyrazine 0.36 cm of phenyl isocyanate is added, at a temperature close to 20° C. under an argon atmosphere, to a suspension of 400 mg of 2-[(1R,2S,3R)(1,2,3,4-tetrahydroxybutyl)]-5-[(2'S,3'R)(2',3',4'-trihydroxybutyl)]pyrazine in 10 cm$^3$ of anhydrous pyridine. After stirring for about 22 hours at a temperature close to 20° C., the reaction medium is supplemented with 10 cm$^3$ of a mixture consisting of methanol-dichloromethane (5-95 by volume), and then purified by chromatography under pressure (180 kPa) on a volume of 100 cm$^3$ of Merck silica gel 60 $F_{254}$ (0.063–0.040 mm) contained in a column 2.5 cm in diameter, eluting with an elution gradient which consists of a ciichloromethane-methanol (90-10 by volume) mixture, collecting 20 cm$^3$ fractions. The fractions containing only the desired product are combined and concentrated to dryness under reduced pressure (about 0.5 kPa) at a temperature close to 40° C. 280 mg of a solid are thus obtained, which solid is repurified by chromatography under pressure (180 kPa) on a volume of 90 cm$^3$ of Merck silica gel 60 $F_{254}$ (0.063–0.040 mm) contained in a column 3 cm in diameter, eluting with an elution gradient consisting of a chloroform-methanol-ammonium hydroxide mixture (80-20-0 and then 80-20-1 by volume). The fractions containing only the desired product are combined and concentrated to dryness under reduced pressure (about 0.5 kPa) at a temperature close to 40° C. Two (solid) fractions are thus obtained which contain 4,4'-O,O-di(N-phenylcarbamoyl)-2-[(1R,2S,3R)(1,2,3,4-tetrahydroxybutyl)]-5-[(2'S,3'R)(2',3',4'-trihydroxybutyl)]pyrazine. These two solids are washed with distilled water and then with ethyl acetate, and finally dried under reduced pressure (about 1 kPa) at a temperature close to 40° C. 47.4 mg and 65.2 mg of 4,4'-O,O-di(N-phenylcarbamoyl)-2-[(1R,2S,3R)(1,2,3,4-tetrahydroxybutyl)]-5-[(2'S,3'R)(2',3',4'-trihydroxybutyl)]pyrazine are thus obtained in the form of a white powder.

The product obtained has the following characteristics:

$^1$H NMR spectrum (400 MHz, (CD$_3$)$_2$SO d6, δ in ppm): 2.79 and 3.16 (respectively dd and broad d, J=14 and 9 Hz and J=14 Hz, 1H each: CH$_2$ 5α); 3.62 (mt, 1H: CH 5γ); 3.70 (broad t, J=8 Hz, 1H: CH 2β); from 3.80 to 4.00 (mt, 2H: CH 5β and CH 2γ); from 4.05 to 4.20 (mt, 2H: 1H of CH$_2$O 5δ and 1H of CH$_2$O 2δ); from 4.30 to 4.45 (mt, 2H each: the other H of CH$_2$O 5δ and the other of CH$_2$O 2δ); 4.66 (d, J=8 Hz, 1H: OH at position 2β); 4.89 (d, J=6.5 Hz, 1H: OH at position 5β); 5.00 (broad d, J=5.5 Hz, 1H: CH 2α); 5.08 (d, J=6 Hz, 1H: OH at position 2γ); 5.13 (d, J=6 Hz, 1H: OH at position 5γ); 5.44 (d, J=5.5 Hz, 1H: OH at position 2α); 6.98 (broad t, J=7.5 Hz, 2H: aromatic H at the para position with respect to the NHCO); 7.27 (broad t, 4H: aromatic H at the meta position with respect to the NHCO); 7.49 (broad d, J=7.5 Hz, 4H: aromatic H at the ortho position with respect to the NHCO); 8.46 (broad s, 1H: =CH at position 6); 8.68 (broad s, 1H: =CH at position 3); 9.63 and 9.66 (broad 2s, 1H each: NHCO).

EXAMPLE 50

4,4'-O,O-di(N-benzylcarbamoyl)-2-[(1R,2S,3R)(1,2,3,4-tetrahydroxybutyl)]-5-[(2'S,3'R)-(2',3',4'-trihydroxybutyl)]pyrazine 0.207 cm$^3$ of benzyl isocyanate is added, at a temperature close to 20° C. under an argon atmosphere, to a suspension of 200 mg of 2-[(1R,2S,3R)(1,2,3,4-tetrahydroxybutyl)]-5-[(2'S,3'R)(2',3',4'-trihydroxybutyl)]pyrazine in 5 cm$^3$ of anhydrous pyridine. The reaction medium is stirred for about 1 hour at a temperature close to 50° C. After cooling the reaction medium to a temperature close to 20° C., 5 cm$^3$ of a mixture consisting of methanol-dichloromethane (5-95 by volume) are added. The insoluble matter formed is filtered on sintered glass, washed with water, with ethyl acetate and then dried under reduced pressure (about 0.5 kPa) at a temperature close to 40° C. 39 mg of 4,4'-O,O-di(N-benzylcarbamoyl)-2-[(1R,2S,3R)(1,2,3,4-tetrahydroxybutyl)]-5-[(2'S,3'R)(2',3',4'-trihydroxybutyl)]pyrazine are thus obtained.

The product obtained has the following characteristics:

$^1$H NMR spectrum (400 MHz, (CD$_3$)$_2$SO d6, δ in ppm): 2.80 and 3.13 (2dd, respectively J=14 and 9.5 Hz and J=14 Hz and 3 Hz, 1H each: CH$_2$ 5α); 3.58 (mt, 1H: CH 5γ); 3.67 (broad t, J=8 Hz, 1H: CH 2β); from 3.80 to 3.90 (mt, 2H: CH 5β and CH 2γ); 4.00 and 4.24 (2 dd, respectively J=12 and 7.5 Hz and J=12 and 3 Hz, 1H each: CH$_2$O 5δ); 4.03 and 4.30 (2 dd, respectively J=12 and 7.5 Hz and J=12 and 2.5 Hz, 1H each: CH$_2$O 2δ); 4.22 (d, J=6 Hz, 4H: NCH$_2$Ar); 4.47 (d, J=8 Hz, 1H: OH at position 2β); 4.71 (d, J=6.5 Hz, 1H: OH at position 5β); 4.86 (d, J=6 Hz, 1H: OH at position 2γ); 4.90 (d, J=6 Hz, 1H: OH at position 5γ); 4.99 (broad s, 1H: CH 2α); 5.25 (unresolved complex, 1H: OH at position 2α); from 7.20 to 7.40 (mt, 10H: aromatic H); from 7.50 to 7.65 (mt, 2H: the 2 NHCO); 8.44 (d, J=1 Hz, 1H: =CH at position 6); 8.68 (broad s, 1H: =CH at position 3).

EXAMPLE 51

1,1',2,2',3,3',4,4'-O,O,O,O,O,O,O,O-octabenzoyl-2-[(1R,2S,3R)(1,2,3,4-tetrahydroxybutyl)]-5-[(1'R,2'S, 3'R)(1',2',3',4'-tetrahydroxybutyl)]-pyrazine 0.124 cm$^3$ of benzoyl chloride is added, dropwise at a temperature close to 20° C. under an argon atmosphere, to 20 mg of 2-[(1R,2S,3R)(1,2,3,4-tetrahydroxybutyl)]-6-[(1'R,2'S,3'R)(1',2',3',4'-tetrahydroxybutyl)]pyrazine in suspension in 0.5 cm$^3$ of anhydrous pyridine. The reaction mixture is stirred for 6 hours at a temperature close to 20° C. The solvent is evaporated under an air stream at a temperature close to 20° C. for about 16 hours. The residue obtained is purified by preparative chromatography on 2 Merck 60 F$_{254}$ silica gel plates (thickness=0.5 mm, 20×20 cm), eluting with a dichloromethane-methanol (98-2 by volume) mixture. The fraction containing only the desired product is extracted with a dichloromethane-methanol (85-15 by volume) mixture, filtered on sintered glass and then concentrated to dryness under reduced pressure (0.5 kPa) at a temperature close to 40° C. 63.5 mg of 1,1',2,2',3,3',4,4'-O,O,O,O,O,O,O,O-octabenzoyl-2-[(1R,2S,3R)(1,2,3,4-tetrahydroxybutyl)]-5-[(1'R,2'S,3'R)(1',2',3',4'-tetrahydroxybutyl)]-pyrazine are thus obtained in the form of a white foam.

The product obtained has the following characteristics:

$^1$H NMR spectrum (400 MHz, (CD$_3$)$_2$SO d6, δ in ppm): 4.60 and 4.82 (2 dd, respectively J=12.5 and 5.5 Hz and J=12.5 and 2 Hz, 2H each: CH$_2$O δ); 5.86 (mt, 2H: CH γ); 6.18 (dd, J=7.5 and 4 Hz, 2H: CH β); 6.50 (d, J=4 Hz, 2H: CH α); from 7.30 to 8.00 (mt, 40H: aromatic H); 8.78 (s, 2H: =CHN).

EXAMPLE 52

1,2,2',3,3',4,4'-O,O,O,O,O,O,O-heptabenzoyl-2-[(1R,2S,3R)(1,2,3,4-tetrahydroxybutyl)]-6-[(2'S,3'R)(2',3',4'-trihydroxybutyl)]pyrazine 0.115 cm$^3$ of benzoyl chloride is added, dropwise at a temperature close to 20° C. under an argon atmosphere, to 20 mg of 2-[(1R,2S,3R)(1,2,3,4-tetrahydroxybutyl)]-6-[(2'S,3'R)(2',3',4'-trihydroxybutyl)]pyrazine in suspension in 0.5 cm$^3$ of anhydrous pyridine. The reaction mixture is stirred for 6 hours at a temperature close to 20° C. The solvent is evaporated under an air stream at a temperature close to 20° C. for about 16 hours. The residue obtained is purified by preparative chromatography on 2 Merck 60 F$_{254}$ silica gel plates (thickness=0.5 mm, 20×20 cm), eluting with a dichloromethane-methanol (98-2 by volume) mixture. The fraction containing only the desired product is extracted with a dichloromethane-methanol (85-15 by volume) mixture, filtered on sintered glass and then concentrated to dryness under reduced pressure (0.5 kPa) at a temperature close to 40° C. 56.3 mg of 1,2,2',3,3',4,4'-O,O,O,O,O,O,O,-heptabenzoyl-2-[(1R,2S,3R)(1,2,3,4-tetrahydroxybutyl)]-6-[(2'S,3'R)(2',3',4'-trihydroxybutyl)]pyrazine are thus obtained in the form of a white foam.

The product obtained has the following characteristics:

$^1$H NMR spectrum (400 MHz, (CD$_3$)$_2$SO d6, δ in ppm): 3.41 and 3.51 (2 dd, respectively J=14 and 7.5 Hz and J=14 and 4.5 Hz, 1H each: CH$_2$ 6α); 4.63 and 4.86 (2 mts, 2H each: CH$_2$O 2δ and CH$_2$O 6δ); 5.94 (mt, 2H: CH 6γ and CH 2γ); 6.02 (mt, 1H: CH 6β; 6.40 (dd, J=7.5 and 4 Hz, 1H: CH 2β); 6.47 (d, J=4 Hz, 1H: CH 2α); from 7.35 to 8.10 (mt, 35H: aromatic H); 8.52 (s, 1H: =CH at position 5); 8.60 (s, 1H: =CH at position 3).

EXAMPLE 53

4,4'-O,O-dibenzoyl-2-[(1R,2S,3R)( 1,2,3,4-tetrahydroxybutyl)]-6-[(2'S,3'R)(2',3',4'-trihydroxybutyl)]pyrazine 0.0191 cm$^3$ of benzoyl chloride is added, dropwise at a temperature close to 20° C. under an argon atmosphere, to 20 mg of 2-[(1R,2S,3R)(1,2,3,4-tetrahydroxybutyl)]-6-[(2'S, 3'R)(2',3',4'-trihydroxybutyl)]-pyrazine in suspension in 0.5 cm³ of anhydrous pyridine. The reaction mixture is stirred for 22 hours at a temperature close to 20° C. The solvent is evaporated under an air stream at a temperature close to 20° C. for about 72 hours. The residue obtained is purified by preparative chromatography on 2 Merck 60 $F_{254}$ silica gel plates (thickness=0.5 mm, 20×20 cm), eluting with a dichloromethane-methanol (90-10 by volume) mixture. The fraction containing only the desired product is extracted with a dichloromethane-methanol (85-15 by volume) mixture, filtered on sintered glass and then concentrated to dryness under reduced pressure (0.5 kPa) at a temperature close to 40° C. 12 mg of 1,2,2',3,3',4,4'-O,O,O,O,O,O,O-heptabenzoyl-2-[(1R,2S,3R)(1,2,3,4-tetrahydroxybutyl)]-6-[(2'S,3'R)(2',3',4'-trihydroxybutyl)]pyrazine are thus obtained in the form of a colourless lacquer.

The product obtained has the following characteristics:
$^1$H NMR spectrum (400 MHz, $(CD_3)_2SO$ d6, δ in ppm): 2.81 and 3.21 (2 dd, respectively J=14 and 9.5 Hz and J=14 and 3 Hz, 1H each: $CH_2$ 6α); 3.72 (mt, 1H: CH 6γ); 3.75 (broad t, J=8 Hz, 1H: CH 2β); 3.89 (mt, 1H: CH 6β); 4.03 (mt, 1H: CH 2γ); 4.28 and 4.52 (2 dd, respectively J=12 and 2.5 Hz and J=12 and 3 Hz, 1H each: $CH_2O$ 6δ); 4.30 and 4.56 (2 dd, respectively J=12 and 2.5 Hz and J=12 and 3 Hz, 1H each: $CH_2O$ 2δ); 4.74 (d, J=8 Hz, 1H: OH at position 2β); 4.96 (d, J=7 Hz, 1H: OH at position 6β); 5.04 (broad d, J=6 Hz, 1H: CH 2α); 5.31 (mt, 2H: OH at position 2γ and OH at position 6γ); 5.48 (d, J=6 Hz, 1H: OH at position 2α); 7.54 (mt, 4H: aromatic H at the meta position with respect to the CO); 7.67 (mt, 2H: aromatic H at the para position with respect to the CO); 8.05 (d, J=8 Hz, 4H: aromatic H at the ortho position with respect to the CO); 8.41 (s, 1H: =CH at position 5); 8.61 (s, 1H: =CH at position 3).

What is claimed is:
1. A compound of formula:

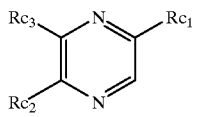

(I)

or a stereoisomer thereof or a salt thereof with an organic or inorganic acid wherein $Rc_1$ is the chain

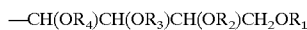

(II)

and
either (A) $Rc_2$ is a hydrogen atom and $Rc_3$ is the chain

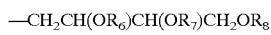

(III)

or (B) $Rc_2$ is the chain

(III)

and $Rc_3$ is a hydrogen atom,
and at least one of the substituents $R_1$, $R_2$, $R_3$, $R_4$, $R_6$, $R_7$, $R_8$, which may be identical to or different from each other, is a radical independently selected from ithe radicals
a) —$COR_9$,
b) —$COOR_{10}$,
c) —$CR_{11}R_{12}OCOR_{13}$,
d) —$CR_{11}R_{12}OR_{13}$,
e) —$CONR_{14}OR_{15}$, and f) one or more pairs of the substituents $R_1$, $R_2$, $R_3$, $R_4$, $R_6$, $R_7$, $R_8$, consecutive or separated by one of the other said substituents, may form a group: —C(O)—;

the other substituents $R_1$, $R_2$, $R_4$, $R_6$, $R_7$, $R_8$ are hydrogen atoms and $R_9$ is a hydrogen atom, an alkenyl radical, an alkyl radical, an amino radical, a heterocyclyl radical, a heteroaryl radical, or an aryl radical;

$R_{10}$ is an alkyl radical, an aralkyl radical or an aryl radical;

$R_{11}$, $R_{12}$, and $R_{13}$ independently are a hydrogen atomn or an alkyl, aryl or aralkyl radical;

$R_{14}$ and $R_{15}$ independently are a hydrogen atom, an alkyl radical, an aryl radical, an aralkl radical, or a heterocyclyl radical or, alternatively, $R_{14}$ and $R_{15}$ together form, with the nitrogen atom to which they are attached, a 4- to 7-membered heterocycle which may be substituted with 1 to 3 alkyl radicals or with an aryl radical, it being understood that the term "alkenyl radical" represents the hydrocarbon portions containing from 1 to 6 straight- or branched-chain carbon atoms and possessing one or more double bonds, optionally substituted with one or more identical or different substituents selected from the following radicals: alkyloxy, carboxyl, alikylcarbonyl, alkyloxycarbonyl, carbamoyl, amino, alkylamino, dialkylamino and halogen;

the terra "alkyl radical" defines saturated straight- or branched-chain hydrocarbon portions containing 1 to 6 carbon atoms optionally substituted with one or more identical or different substituents selected frorn the following radicals: hydroxyl, alkyloxy, carboxyl, alkylcarbonyl, alkyloxycarbonyl, aralkyloxycarbonyl, aryl, aryloxy, carbamoyl, amino, alkylamino, dialkylamino, carboxycarbonyl, heterocyclyl, and halogen;

the term "aryl radical" refers to mono- or bi-cyclic hydrocarbons optionally substituted with one or more identical or different substituents selected from the following radicals: alkyl, alkyloxy; aralkyloxy, alkycarbonyl, alkyloxyalkyl, alkyloxycarbonyl, alkylcarbonyloxy, nitro, hydroxyl, a halogen atom, an amino, alkylamino, dialkylamino, aminoalkyl, alkylaminoalkyl, dialkylaminoalkyl, carbamoylalkylaminoalkyl, hydroxyalkylaminoalkyl, (hydroxyalkyl)(alkyl) aminoallyl, dihydroxyalkyla oalkyl, and a hetercyclylalkyl, the hetercyclyl portion of which comprises 5 or 6 atoms, is optionally substituted with am alkyl radical on any one of its constituent atoms, and contains at least one nitrogen atom and optionally another heteroatom such as oxygen, nitrogen or sulphur, the term "heterocyclyl radical" represents a mono- or poly-cyclic carbon system optionally substituted with one or more identical or different substituents selected from the following radicals: alkyl, alkyloxy, and halogen, each ring of which heterocyclyl radical may contain up to 7 carbon atoms, saturated or otherwise, and which contains from 1 to 4 heteroatoms selected fom N, O and S, capable of being condensed with an aromatic nucleus, wherein the heterocyclyl radical optionally is linked to the alkyl radical by a nitrogen, to form a piperidinyl, piperazinyl, or moxpholinyl linkage, and the term "aralkyl radical" denotes an aliphatic hydrocarbon of 1 to 4 carbon atoms in a straight or branched otbain, linked to a mono- or bi-cyclic ring system optionally substituted with one or more identical or different substitents selected from the following radicals: alkyl, alkyloxy, alkylcarbonyl, alkylcarbonyloxy and aryl, each ring of said system containing up to 7 members, at least one of said rings being aromatic, provided, however, that said compound is not a compound selected fom the group consisting of 1,2,2',3,3',4,4'-O,O,O,O,O,O-heptaacetyl-2-[(1R,2S,3R)(1,2,3,4-tetrahydroxybutyl)]-5-[(2'S,3'R)(2',3',4'-trihydrocybutyl)]pyrazine, 1,1',2,2',33 ',4,4'-O,O,O,O,O,O,O,O-octaacetyl-2-[(1R2S,3R)(1,2,3,4-tetrahydroxybutyl)]-5-[(1'R,2'S,3'R)(1',2',3',4'-tetrehydroxyutyl)]pyrazine, 1,1',2,2',3,3 ',4,4'-O,O,O,O,O,O,O,O-octabenzoyl-2-[(1,R2S,3R)(1,2,3,4-tetrahydroxybutyl)]-5-[(1'R,2'S,3'R)(1',2',3',4'-tetrahydroxybutyl)]-pyrazine 1,2,2',3,3',4,4'-O,O,O,O,O,O,O-heptaacetrl-2-[(1,R2S,3R)(1,2,3,4-tetrahydroxybutyl)]-6-[(2S,3'R)(2',3 ',4'-trihydroxybutyl)]pyrazine 1,2,2',3,3 ',4,4'-O,O,O,O,O,O-heptaacetyl-2-[(R2S,3S)(1,2,3,4tetrahydroxybutl)]-6-[(2'S,3'S)(2',3',4'-trihydroxybutyl)]pyrazine, and their stereoisomers or the salts of such compounds with an orgamc or inorgamic acid.

2. A compound according to claim 1, wherein said compound is selected from stretures (V) and (VII):

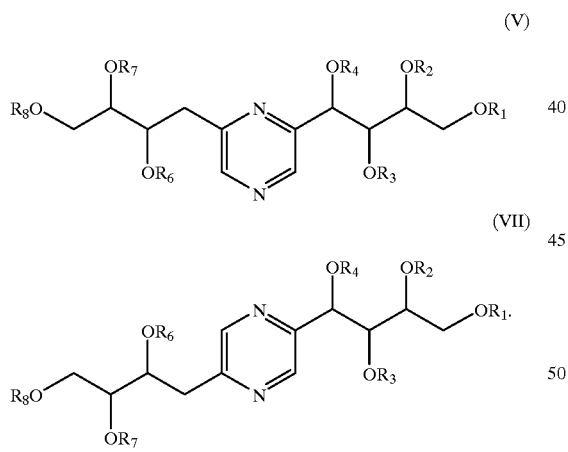

3. A compound according to claim 1 wherein the compound is selected from the steroisomers (VIII) and (X):

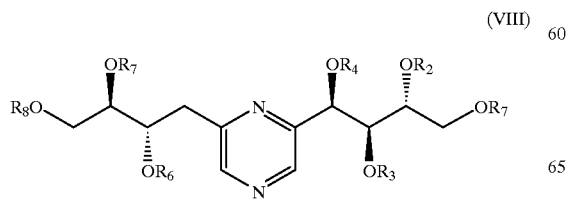

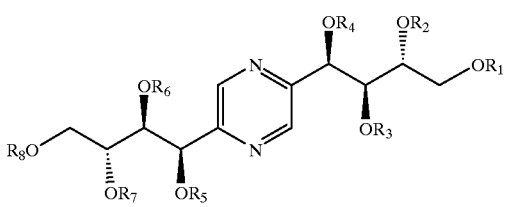

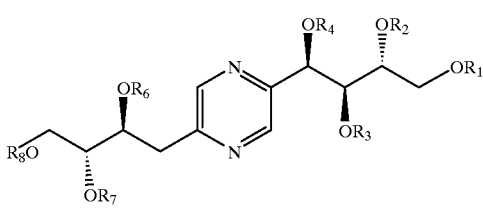

4. A process for preparing a compound accordig to claim 1, said process comprising reacting a compound of formula (XI) or (XIII):

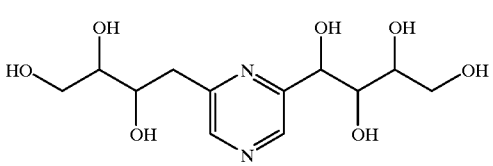

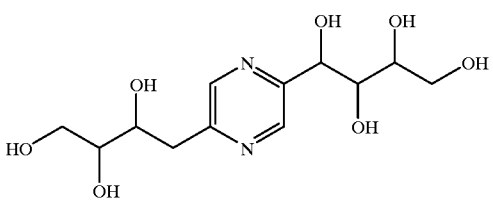

wherein the hydroxyl functional groups are optionally protected with protecting groups, either with a compound of formula R—X (XIV) in which R is a group selected from —$COR_9$, —$COOR_{10}$, —$CR_{11}R_{12}OCOR_{13}$, —$CR_{11}R_{12}OR_{13}$, —$CONR_{14}R_{15}$ and X is a halogen atom, or with a compound of formula $(R_9CO)_2O$ (XV) or with a compound of formula $R_{14}N=C=O$ (XVI) or with a compound of formula $CR_{11}R_{12}(OR_{13})_2$ (XVII), wherein $R_9$ is a hydrogen atom, an alkenyl radical, an alkyl radical, an amino radical, a heterocyclyl radical, a heteroaryl radical, or an aryl radical;

$R_{10}$ is an alkyl radical, an aralkyl radical, or an aryl radical;

$R_{11}$, $R_{12}$, and $R_{13}$ independently are a hydrogen atom or an alkyl, aryl or aralky radical;

$R_{14}$ and $R_{15}$ independently are a hydrogen atom, an alkyl radical, an aryl radical, an aralkyl radical, or a heterocyclyl radical or, alternatively, $R_{14}$ and $R_{15}$ together form, with the nitrogen atom to which they are attached, a 4- to 7-membered heterocycle which may be substituted with 1 to 3 alkyl radicals or with an aryl radical, optionally followed by complete deprotection, or optionally followed by selective deprotection and by one or more other functionalizations with the aid of one of the reagents of formulas (XIV), (XV), (XVI), and (XVII) which are identical to or different from the first, it being possible to repeat the funtionalization and deprotection steps several times, it beling understood that the reagents of formula (XIV), (XV), (XVI) and (XVII) may be identical or different on each functionalization, and isolating the product and optionally converting it to a salt with an inorganic or organic acid, it being understood that the term "alkenyl radical" represents the hydrocarbon portions containing from 1 to 6 straight- or branched-chain carbon atoms and possessing one or more double bonds, optionally substituted with one or more identical or different substituents selected from thae following radicals: alkyloxy, carboxyl, alkylcarbonyl, alkyloxycarbonyl, carbamoyl, amino, alkylamino, dialkyl amio and halogen;

the term "alkyl radical" defines saturated straight or branched-chain hydrocarbon portions containing 1 to 6 carbon atoms optionally substituted with one or more identical or different substituents selected fromn the following radicals: hydroxyl, alkyloxy, carboxyl, alkylcarbonyl, alkyloxycarbonyl, aralkyloxycarbonyl, aryl, aryloxy, carbamoyl, amino, alkylamino, dialkylamino, carboxycarbonyl, heterocyclyl, and halogen;

the term "aryl radical" refers to mono- or bi-cyclic hydrocarbons optionally substitute with one or more identical or different substituents selected from the following radicals: alkyl, alkyloxy, aralkyloxy, alkcarbonyl, alkyloxyalkyl, allkyloxycarbonyl, alkylcarbonyloxy, nitro, hydroxyl, halogen, amino, alkylamino, dialkylamino, aminoalkyl, alklaminoalkyl, dialkylaminoalkyl, carbamoylalkylaminoalkyl, hydroxyalkylaminoalkyl, (hydroxyalkyl)(alkyl) aminoalkyl, dihydroxyalkylaminoalkl, and heterocyclyclalkyl, the hetercyclyl portion of which comprises 5 or 6 atoms and is optionally substituted with an alkyl radical on any one of its constituent atoms, and contains at least one nitrogen atom and optionally another hetero atom selected from oxygen, nitrogen and sulphur, the term "heterocyclyl radical" represents a mono- or poly-cyclic; carbon ring system optionally substituted with one or more identical or different substituents selected from alkyl, alkyloxy, and halogen, in which each ring may contain up to 7 carbon atoms, saturated or otherwise, and containing from 1 to 4 heteroatoms selected from N, O and S, capable of being optionally condensed with an aromatic nucleus, wherein said heterocyclyl radical optionally is linked to the alkyl radical by a nitrogen, to form a piperidinyl, piperazinyl, or morpholinyl linkage, and the term "aralkyl radical" denotes an aliphatic hydrocarbon of 1 to 4 carbon atoms in a straight or branched chain, linked to a mono- or bi-cyclic ring system optionally substituted with one or more identical or different substituents selected from alkyl, alkyloxy, alkylcarbonyl, alkylcarbonyloxy and aryl, each ring containing up to 7 members and in which at least one of the rings is aromatic.

5. The process of claim wherein 4 is chlorine or bromine.

6. The compound according to claim 1 wherein $Rc_1$ is structure (II) in which each of $R_2$, $R_3$ and $R_4$ is H, and $R_1$ is $COR_9$, $R_9$ being phenyl; $Rc_2$ is structure (III) in which each of $R_6$ and $R_7$ is H, and $R_8$ is $COR_9$, $R_9$ being phenyl; and $Rc_3$ is H.

7. A pharmaceutical composition comprising at least one compound of formula:

(I)

or a stereoisomer thereof or a salt of such compoumd with an organic or inorganic acid, in which:

$Rc_1$ is the chain $$—CH(OR_4)CH(OR_3)CH(OR_2)CH_2OR_1 \quad (II)$$

and either (A) $Rc_2$ is a hydrogen atom and $Rc_3$ is the chain $$—CH_2CH(OR_6)CH(OR_7)CH_2OR_8 \quad (III)$$

or (B) $Rc_2$ is the chain $$—CH_2CH(OR_6)CH(OR_7)CH_2OR_8 \quad (III)$$

and $Rc_3$ is a hydrogen atom, and at least one of the substituents $R_1$, $R_2$, $R_3$, $R_4$, $R_6$, $R_7$, $R_8$, which may be identical to or different from each other, is a radical independently selected from the radicals a) —$COR_9$,
b) —$COOR_{10}$,
c) —$CR_{11}R_{12}OCOR_{13}$,
d) —$CR_{11}R_{12}OR_{13}$,
e) —$CON_{14}R_{15}$, and
f) one or more pairs of the substituents $R_1$, $R_2$, $R_3$, $R_4$, $R_6$, $R_7$, $P_8$, consecutive or separated by one of the other said substituents, may form a group: —C(O)—;

the other substituents $R_1$, $R_2$, $R_3$, $R_4$, $R_6$, $R_7$, $R_8$ are hydrogen atoms and $R_9$ is a hydrogen atom, an alkenyl radical, an alkyl radical, an amino radical, a heterocyclyl radical, a heteroaryl radical, or an aryl radical;

$R_{10}$ is an alkyl radical, an aralkyl radical or an aryl radical;

$R_{11}$, $R_{12}$, and $R_{13}$ independently are a hydrogen atom or an alkyl, aryl or arkyl radical;

$R_{14}$ and $R_{15}$ independently are a hydrogen atom, an alkyl radical, an aryl radical, an aralkyl radical, or a heterocyclyl radical or, alternatively, $R_{14}$ and $R_{15}$ together form, with the nitrogen atom to whih they are attached, a 4 to 7-membered heterocycle which may be substituted with 1 to 3 alkyl radicals or with an aryl radical, it being understood that the term "alkenyl radical" represents the hydrocarbon portions containing from 1 to 6 straight- or branched-chain carbon atoms and possessing one or more double bonds, optionally substituted with one or more identical or different substituents selected from the following radicals: alkyloxy, carboxyl, alkylcarbonyl, alkyl oxycarbonyl, carbamoyl, amino, alkylamino, dialkylamino and halogen;

the term "alkyl radical" defines saturated straight- or branched-chain hydrocarbon portions containing 1 to 6 carbon atoms optionally substituted with one or more identical or different substituents selected from the following radicals: hydroxyl, alkyloxy, carboxyl, alkylcarbonyl, alkyloxycarbonyl, aralkyloxycarbonyl, aryl, aryloxy, carbamoyl, amino, alkylamino, dialkylamino, carboxycarbonyl, heterocyclyl, and halogen;

the term "aryl radical" refers to mono- or bi-cyclic hydrocarbons optionally substituted with one or more identical or different substituents selected from the following radicals: alkyl, alkyloxy, aralkyloxy, alkycarbonyl, alkyloxyalkyl, alkyloxycarbonyl, alkyloarbonyloxy, nitro, hydroxyl, a halogen atom, an amino, alkylamino, dialkylamino, aminoalkyl, alkylaminoalkyl, dialkylanioalkyl, carbamoylalkylaminoalkyl, hydroxyalkyla cinoalkyl, (hydroxyalkyl)(alkyl) aminoalkyl, dibydroxyalkylaminoalkyl, and a heterocyclylalkyl, the hetercyclyl portion of which compnses 5 or 6 atoms, is optionally substituted with an alkyl radical on any one of its constituent atoms, and contains at least one nitrogen atom and optionally another heteroatom sucb as oxygen, nitrogen or sulphur;

the term "heterocyclyl radical" represents a mono- or poly-cyclic carbon system optionally substituted with one or more identical or different substituents selected from the following radicals: alkyl, alkyloxy, and halogen, each ring of which heterocyclyl radical may contain up to 7 carbon atoms, saturated or otherwise, and which contains from 1 to 4 heteroatoms selected from N, O and S, capable of being condensed with an aromatic nucleus, wherein the heterocyclyl radical optionally is linced to the alykl radical by a nitrogen, to form a pip eridinyl, piperazinyl, or morpholinyl linkage; and the term "aralkyl radical" denotes an aliphatc hydrocarbon of 1 to 4 carbon atoms in a straight or branched chain, linked to a mono- or bi-cyclic ring system optionally substituted with one or more identical or different substituents selected from the following radicals: alkyl, alkyloxy, alkylcarbonyl, alkylcarbonyloxy and aryl, each ring of said system containing up to 7 members, at least one of said rings being aromatic, and a pharmaceutically acceptable camer compatible therewith.

8. A pharmaceutical composition according to claim 7, wherein $R_9$ is selected from hydrogen alkyl, aralkyl, alkyloxyalkyl, aryloxyalkyl, alkyloxycarbonylalkyl, alkyloxycarbonylalkenyl, carboxyalkyl, aralkyloxycarbonylalkyl, heteroaryl and aryl radicals, said aryl radical being optionally substituted with one or more identical or different substituents selected from aryl, alkyl, alkyloxy, aralkyloxy, alkylcarbonyl, alkyloxyalkyl, alkyloxycarbonyl, alkylcarbonyloxy, nitro, hydroxyl, halogen, amino, alkylamino, dialkylamino, aminoalkyl, alkylaminoalkyl, dialkylaoalkyl, carbamoylalkylaminoalkyl, hydroxyalkylaminoalkyl, (hydroxyalkyl)(alkyl)aminoalkyl, dihydroxyalkylaminoalkyl and heterocyclylalkyl radicals, the heterocyclyl portion of which heterocyclylalkyl radical comprises 5 or 6 atoms and is optionally substituted with an alkyl radical on any one of its constituent atoms and contains at least one nitrogen atom and optionally another heteroatom selected from oxygen, nitrogen and sulphur, said heterocyclyl radical being linked to the alkyl radical by a nitrogen to form a piperidinyl, piperazinyl, or morpholinyl linkage.

9. A pharmaceutical composition according to claim 7, wherein $R_{10}$ is an alkyl radical.

10. A pharmaceutical composition according to claim 8, wherein $R_{10}$ is an alkyl radical.

11. A pharmaceutical composition according to claim 7 wherein $R_{14}$ and $R_{15}$ are independently selected from hydrogen, aryland aralkyl radicals.

12. A pharmaceutical composition according to claim 9 wherein $R_{14}$ and $R_{15}$ are independently selected fom hydrogen, aryland aralkyl radicals.

13. A pharmaceutical cornposition according to claim 10 wherein $R_{14}$ and $R_{15}$ is are independently selected from hydrogen, aryl and aralkyl radicals.

14. A pharmaceutical composition according to claim 7 wherein said compouid is selected from the group consisting of:

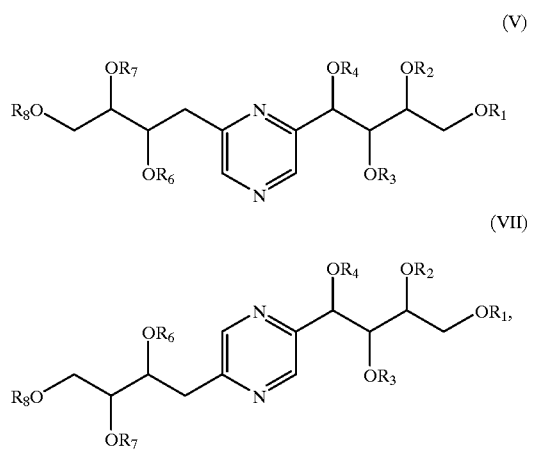

a stereoisomer of compouind (V), a stereoisomer of compound (VII), a salt of compound (V) with an organic or inorganic acids a salt of compound (VII) with an organic or inorganic acid, a salt of the stereoisomer of compound (V) with an organic or wnorganic acid, and a salt of the stereoisomer of compound (VII) with an organic or inorganic acid.

15. A pharmaceutical composition according to claim 1, wherein said compound is selected from the group consisting of:

A-compounds of general formula:

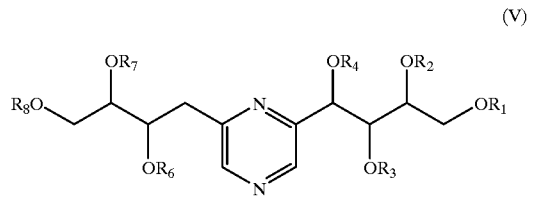

wherein
(1) at least one of the substituents $R_1$, $R_2$, $R_3$, $R_4$, $R_7$ and $R_8$ is a radical selected from the radicals of list (L), the remaining substituents $R_1$, $R_2$, $R_3$, $R_4$, $R_6$, $R_7$, $R_8$ are hydrogen atomrs, the radicals of list (L) consisting of foamyl, alkylearbonyl, aralkylcarbonyl, alkyloxyalkylcarbonyl, alkyloxycarbonylalkyrcabonyl, alkyloxycarbonylalkenylcarbonyl, carboxyalkylcarbonyl, aralkyloxycarbonylalkylcarbonyl, heteroarylcarbonyl, alkyloxycarbonyl, aryloxyalkylcarbonyl, N-arylcarbamoyl N-aralkylcarbamoyl, arylcarbonyl, wherein the aryl portion of said radical is optionally substituted with one or more identical or different substituents selected from aryl, alkyl, alkyloxy, alkylcarbonyl, alkyloxyalkyl, alkyloxycarbonyl, aralkyloxy, alkylcarbonyloxy, nitro, hydroxyl, halogen, amino, alkylamino, dialkylamino, aminoalkyl, alkylamioalkyl, dialkylaminoalkyl, and heterocyclylalkyl radicals wherein the heterocyclyl radical contains 5 or 6 atoms and is optionally substituted with an alkyl radical on any one of its constituent atoms, said heterocyclyl radical containing at least one nitrogen atom and optionally another heteroatom such as oxygen or nitrogen, said heterocyclyl radical being linked to the alkyl radical by a nitrogen atom, and either (1i) one of the substituents $R_1$ and $R_8$ is a radical selected from list (L), and each of the other substituents $R_1$, $R_2$, $R_3$, $R_4$, $R_6$, $R_7$ and $R_8$ is a hydrogen atom;

or (1ii) each of substituents $R_1$ and $R_8$ is an identical radical selected from the list (L), and each of the other substituents $R_2$, $R_3$, $R_4$, $R_6$ and $R_7$ is hydrogen;

or (1iii) each of $R_1$, $R_2$, $R_3$, $R_4$, $R_6$, $R_7$, and $R_8$ is an identical radical selected from the list (L);

or (2) $R_1$ and $R_2$ together form the group —CO—, and each of $R_3$, $R_4$, $R_6$, $R_7$, and $R_8$ is a hydrogen atom;

or (3) $R_7$ and $R_8$ together form the group —CO—, and each of $R_1$, $R_2$, $R_3$, $R_4$, and $R_6$ is a hydrogen atom;

or (4) $R_1$ and $R_2$, on the one hand, and $R_7$ and $R_8$, on the other hand, form in pairs the group —CO— and each of $R_3$, $R_4$ and $R_6$ is a hydrogen atom;

or (5) $R_1$ and $R_2$, $R_3$ and $R_4$, $R_7$ and $R_8$ form in pairs the group —CO— and $R_6$ is a hydrogen atom;

and B—compounds of general formula

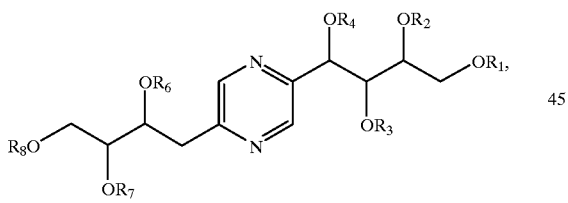

(VII)

wherein
(1) at least one of the substituents $R_1$, $R_2$, $R_3$, $R_4$, $R_7$ and $R_8$ is a radical selected from list (L), and each of the other of substituents $R_1$, $R_2$, $R_3$, $R_6$, $R_7$, and $R_8$ is a hydrogen atom; and either (1i): one of the substituents $R_1$ and $R_8$ is a radical selected from list (L), and each of the other substituents $R_1$, $R_2$, $R_3$, $R_6$, $R_7$, $R_8$ is hydrogen;

or (1ii): each of the two substituents $R_1$ and $R_8$ is an identical radical selected from list (L), and each of the other substituents $R_2$, $R_3$, $R_4$, $R_6$, $R_7$ is a hydrogen atom;

or (1iii): each of $R_1$, $R_2$, $R_3$, $R_4$, $R_7$ and $R_8$ is an identical radical selected from list (L);

or (2) $R_1$ and $R_2$ together form the group —CO—, and each of $R_3$, $R_4$, $R_6$, $R_7$, and $R_8$ is a hydrogen atom;

or (3) $R_7$ and $R_8$ together form the group —CO—, and each of $R_1$, $R_2$, $R_3$, $R_4$ and $R_6$ is a hydrogen atom;

or (4) the pairs $R_1$ and $R_2$, on the one hand, and $R_7$ and $R_8$, on the other hand, form in pairs the group —CO— and each of $R_3$, $R_4$ and $R_6$ is a hydrogen atom;

or (5) each of pairs $R_1$ and $R_2$, $R_3$ and $R_4$ and $R_7$ and $R_8$ form in pairs the group —CO— and $R_8$ is a hydrogen atom.

16. A pharmaceutical compositions according to claim 15, wherein the radicals of the list (L) are selected from the group consisting of the radicals listed in the following list (L'):

formyl, acetyl, propanoyl, 2-methylpropanoyl, 2,2-dimethylpropanoyl, butanoyl, 2-methylbutanoyl, 3-methylbutanoyl, 2,2-dimethylbutanoyl, 2,3-dimethylbutanoyl, 3,3-dimethylbutanoyl, 2-ethylbutanoyl, 2-ethyl-3-methylbutanoyl, 2-propylbutanoyl, pentanoyl, 2-methylpentanoyl, 3-methylpentanoyl, 4-methylpentanoyl, 2,2-dimethylpentanoyl, 2,3-dimethylpentanoyl, 2,4-dimethylpentanoyl, 3,4-dimethylpentanoyl, 3,3-dimethylpentanoyl, 4,4-dimethylpentanoyl, 2-ethylpentanoyl, 3-ethylpentanoyl, hexanoyl, 2-methylhexanoyl, 3-methylhexanoyl, 4-methylhexanoyl, 5-methylhexanoyl, heptanoyl, phenylacetyl, biphenylacetyl, 1-naphthylacetyl, 2-naphthylacetyl, 2-phenylpropanoyl, 3-phenylpropanoyl, 2-biphenylpropanoyl, 3-biphenylpropanoyl, 2-(1-naphthyl)propanoyl, 3-(1-naphthyl)propanoyl, 2-(2-naphthyl)propanoyl, 3-(2-naphthyl)propanoyl, 2-phenylbutanoyl, 3-phenylbutanoyl, 4-phenylbutanoyl, 2-biphenylbutanoyl, 3-biphenylbutanoyl, 4-biphenylbutanoyl, 2-(1-naphthyl)butanoyl, 3-(1-naphthyl)butanoyl, 4-(1-naphthyl)butanoyl, 2-(2-naphthyl)butanoyl, 3-(2-naphthyl)butanoyl, 4-(2-naphthyl)butanoyl, methoxyacetyl, ethoxyacetyl, n-propyloxyacetyl, isopropyloxyacetyl, n-butyloxyacetyl, isobutyloxyacetyl, tert-butyloxyacetyl, 2-methoxypropanoyl, 2-ethoxypropanoyl, 2-n-propyloxypropanoyl, 2-isopropyloxypropanoyl, 2-n-butyloxypropanoyl, 2-isobutyloxypropanoyl, 2-tert-butyloxypropanoyl, 2-methoxybutanoyl, 2-ethoxybutanoyl, 2-n-propyloxyrbutanoyl, 2-isopropyloxybutanoyl, 2-n-butyloxybutanoyl, 2-isobutyloxybutanoyl, 2-tert-butyloxybutanoyl, aminoacetyl, 2-aminopropanoyl, 3-aminopropanoyl, 2-aminobutanoyl, 3-aminobutanoyl, 4-aminobutanoyl, 2-aminopentanoyl, 3-aminopentanoyl, 4-aminopentanoyl, 5-aminopentanoyl, methylaminoacetyl, ethylaminoacetyl, n-propylaminoacetyl, isopropylaminoacetyl, n-butylaminoacetyl, isobutylaminoacetyl, tert-butylaminoacetyl, 2-methylaminopropanoyl, 2-ethylaminopropanoyl, 2-n-propylaminopropanoyl, 2-isopropylaminopropanoyl, 2-n-butylaminopropanoyl, 2-isobutylaminopropanoyl, 2-tert-butylaminopropanoyl, 3-methylaminopropanoyl, 3-ethylaminopropanoyl, 3-n-propylaminopropanoyl, 3-isopropylaminopropanoyl, 3-n-butylaminopropanoyl, 3-isobutylaminopropanoyl, 3-tert-butylaminopropanoyl, 2-methylaminobutanoyl, 2-ethylaminobutanoyl, 2-n-propylaminobutanoyl, 2-isopropylaminobutanoyl, 2-n-butylaminobutanoyl, 2-isobutylaminobutanoyl, 2-tert-butylaminobutanoyl, 3-methylaminobutanoyl, 3-ethylaminobutanoyl, 3-n-propylaminobutanoyl, 3-isopropylaminobutanoyl, 3-n- butylaminobutanoyl, 3-isobutylaminobutanoyl, 3-tert-butylaminobutanoyl, 4-methylaminobutanoyl, 4-ethylaminobutanoyl, 4-n-propylaminobutanoyl, 4-isopropylaminobutanoyl, 4-n-butylaminobutanoyl, 4-isobutylaminobutanoyl, 4-tert-butylaminobutanoyl, 2-methylaminopentanoyl, 2-ethylaminopentanoyl, 2-n-propylaminopentanoyl, 2-isopropylaminopentanoyl, 2-n-butylaminopentanoyl, 2-isobutylaminopentanoyl, 2-tert-butylaminopentanoyl, 3-methylaminopentanoyl, 3-ethylaminopentanoyl, 3-n-propylaminopentanoyl, 3-isopropylaminopentanoyl, 3-n-butylaminopentanoyl, 3-isobutylaminopentanoyl, 3-tert-butylaminopentanoyl, 4-methylaminopentanoyl, 4-ethylaminopentanoyl, 4-n-propylaminopentanoyl, 4-isopropylaminopentanoyl, 4-n-butylaminopentanoyl, 4-isobutylaminopentanoyl, 4-tert-butylaminopentanoyl, 5-methylaminopentanoyl, 5-ethylaminopentanoyl, 5-n-propylaminopentanoyl, 5-isopropylaminopentanoyl, 5-n-butylaminopentanoyl, 5-isobutylaminopentanoyl, 5-tert-butylaminopentanoyl, dimethylaminoacetyl, diethylaminoacetyl, di-n-propylaminoacetyl, diisopropylaminoacetyl, di-n-butylaminoacetyl, diisobutylaminoacetyl, di-tert-butylaminoacetyl, 2-dimethylaminopropanoyl, 2-diethylaminopropanoyl, 2-di-n-propylaminopropanoyl, 2-diisopropylaminopropanoyl, 2-di-n-butylaminopropanoyl, 2-diisobutylaminopropanoyl, 2-di-tert-butylaminopropanoyl, 3-dimethylaminopropanoyl, 3-diethylaminopropanoyl, 3-di-n-propylaminopropanoyl, 3-diisopropylaminopropanoyl, 3-di-n-butylaminopropanoyl, 3-diisobutylaminopropanoyl, 3-di-tert-butylaminopropanoyl, 2-dimethylaminobutanoyl, 2-diethylaminobutanoyl, 2-di-n-propylaminobutanoyl, 2-diisopropylaminobutanoyl, 2-di-n-butylaminobutanoyl, 2-diisobutylaminobutanoyl, 2-di-tert-butylaminobutanoyl, 3-dimethylaminobutanoyl, 3-diethylaminobutanoyl, 3-di-n-propylaminobutanoyl, 3-diisopropylaminobutanoyl, 3-di-n-butylaminobutanoyl, 3-diisobutylaminobutanoyl, 3-di-tert-butylaminobutanoyl, 4-dimethylaminobutanoyl, 4-diethylaminobutanoyl, 4-di-n-propylaminobutanoyl, 4-diisopropylaminobutanoyl, 4-di-n-butylaminobutanoyl, 4-diisobutylaminobutanoyl, 4-di-tert-butylaminobutanoyl, 2-dimethylaminopentanoyl, 2-diethylaminopentanoyl, 2-di-n-propylaminopentanoyl, 2-diisopropylaminopentanoyl, 2-di-n-butylaminopentanoyl, 2-diisobutylaminopentanoyl, 2-di-tert-butylaminopentanoyl, 3-dimethylaminopentanoyl, 3-diethylaminopentanoyl, 3-di-n-propylaminopentanoyl, 3-diisopropylaminopentanoyl, 3-di-n-butylaminopentanoyl, 3-diisobutylaminopentanoyl, 3-di-tert-butylaminopentanoyl, 4-dimethylaminopentanoyl, 4-diethylaminopentanoyl, 4-di-n-propylaminopentanoyl, 4-diisopropylaminopentanoyl, 4-di-n-butylaminopentanoyl, 4-diisobutylaminopentanoyl, 4-di-tert-butylaminopentanoyl, 5-dimethylaminopentanoyl, 5-diethylaminopentanoyl, 5-di-n-propylaminopentanoyl, 5-diisopropylaminopentanoyl, 5-di-n-butylaminopentanoyl, 5-diisobutylaminopentanoyl, 5-di-tert-butylaminopentanoyl, benzoyl, 1-naphthoyl, 2-naphthoyl, 1-indanoyl, 2-indanoyl, 2-fluorobenzoyl, 2-chlorobenzoyl, 2-bromobenzoyl, 2-nitrobenzoyl, 2-aminobenzoyl, 2-methylaminobenzoyl, 2-ethylaminobenzoyl, 2-dimethylaminobenzoyl, 2-diethylaminobenzoyl, 2-dimethylaminomethylbenzoyl, 2-hydroxybenzoyl, 2-methoxybenzoyl, 2-ethoxybenzoyl, 2-methoxymethylbenzoyl, 2-ethoxymethylbenzoyl, 2-methylbenzoyl, 2-ethylbenzoyl, 2-isopropylbenzoyl, (2-acetyl)benzoyl, (2-propanoyl)benzoyl, (2-acetyloxy)benzoyl, (2-propanoyloxy)benzoyl, 3-fluorobenzoyl, 3-chlorobenzoyl, 3-bromobenzoyl, 3-nitrobenzoyl, 3-aminobenzoyl, 3-methylaminobenzoyl, 3-ethylaminobenzoyl, 3-dimethylaminobenzoyl, 3-diethylaminobenzoyl, 3-dimethylaminomethylbenzoyl, 3-hydroxybenzoyl, 3-methoxybenzoyl, 3-ethoxybenzoyl, 3-methoxymethylbenzoyl, 3-ethoxymethylbenzoyl, 3-methylbenzoyl, 3-ethylbenzoyl, 3-isopropylbenzoyl, (3-acetyl)benzoyl, (3-propanoyl)benzoyl, (3-acetyloxy)benzoyl, (3-propanoyloxy)benzoyl, 4-fluorobenzoyl, 4-chlorobenzoyl, 4-bromobenzoyl, 4-nitrobenzoyl, 4-aminobenzoyl, 4-methylaminobenzoyl, 4-ethylaminobenzoyl, 4-dimethylaminobenzoyl, 4-diethylaminobenzoyl, 4-dimethylaminomethylbenzoyl, 4-hydroxybenzoyl, 4-methoxybenzoyl, 4-ethoxybenzoyl, 4-methoxymethylbenzoyl, 4-ethoxymethylbenzoyl, 4-methylbenzoyl, 4-ethylbenzoyl, 4-isopropylbenzoyl, (4-acetyl)benzoyl, (4-propanoyl)benzoyl, (4-acetyloxy)benzoyl, (4-propanoyloxy)benzoyl, 2,4-difluorobenzoyl, 2,4-dichlorobenzoyl, 2,4-dibromobenzoyl, 2,4-dinitrobenzoyl, 2,4-diaminobenzoyl, 2,4-dimethylaminobenzoyl, 2,4-diethylaminobenzoyl, 2,4-didimethylaminobenzoyl, 2,4-didiethylaminobenzoyl, 2,4-di(dimethylaminomethyl)benzoyl, 2,4-dihydroxybenzoyl, 2,4-dimethoxybenzoyl, 2,4-diethoxybenzoyl, 2,4-dimethoxymethylbenzoyl, 2,4-diethoxymethylbenzoyl, 2,4-dimethylbenzoyl, 2,4-diethylbenzoyl, 2,4-diisopropylbenzoyl, (2,4-diacetyl)benzoyl, (2,4-dipropanoyl)benzoyl, (2,4-diacetyloxy)benzoyl, (2,4-dipropanoyloxy)benzoyl, 4-benzyloxybenzoyl, 3-benzyloxybenzoyl, 3,5-dichlorobenzoyl, 4-methoxycarbonylbenzoyl, 3-methoxycarbonylbenzoyl, 1-piperidinylmethylenebenzoyl, N-4-methylpiperazinylmethylenebenzoyl, N-morpholinylmethylenebenzoyl, N-(2-hydroxyethyl)aminomethylenebenzoyl, N,N-diisopropylaminomethylenebenzoyl, N-carbamoylmethylaminomethylenebenzoyl, N,N-dimethylaminomethylenebenzoyl, N,N-diethylaminomethylenebenzoyl, N-ethylaminomethylenebenzoyl, aminomethylenebenzoyl, N-(2-hydroxyethyl)-N-(methyl)aminomethylenebenzoyl, methoxycarbonyl, ethoxycarbonyl, n-propoxycarbonyl, isopropoxycarbonyl, n-butoxycarbonyl, isobutoxycarbonyl, tert-butoxycarbonyl, phenoxycarbonyl, 4-nitrophenoxycarbonyl, 4-fluorophenoxycarbonyl, 4-chlorophenoxycarbonyl, 4-bromophenoxycarbonyl, 4-methylphenoxycarbonyl, 4-methoxyphenoxycarbonyl,. 4-methoxycarbonylphenoxycarbonyl, 1-naphthoxycarbonyl, 2-naphthoxycarbonyl, 1-indanoxycarbonyl, 2-indanoxycarbonyl, benzyloxycarbonyl, 4-nitrobenzyloxycarbonyl, formyloxymethylene, acetyloxymethylene, propanoyloxymethylene, 2-methylpropanoyloxymethylene, 2,2-dimethylpropanoyloxymethylene, butanoyloxymethylene, 2-methylbutanoyloxymethylene, 3-methylbutanoyloxymethylene, 2,2-dimethylbutanoyloxymethylene, 2,3-dimethylbutanoyloxymethylene, 3,3-dimethylbutanoyloxymethylene, 2-ethylbutanoyloxymethylene, 2-ethyl-3-methylbutanoylmethylbutanoyloxymethylene, 2-propylbutanoyloxymethylene, pentanoyloxymethylene, 2-methylpentanoyloxymethylene, 3-methylpentanoyloxymethylene, 4-methylpentanoyloxymethylene, 2,2-dimethylpentanoyloxymethylene, 2,3-dimethylpentanoyloxymethylene, 2,4-dimethylpentanoyloxymethylene, 3,4-dimethylpentanoyloxymethylene, 3,3-dimethylpentanoyloxymethylene, 4,4-dimethylpentanoyloxymethylene, 2-ethylpentanoyloxymethylene, 3-ethylpentanoyloxymethylene, hexanoyloxymethylene, 2-methylhexanoyloxymethylene, 3-methylhexanoyloxymethylene, 4-methylhexanoyloxymethylene, 5-methylhexanoyloxymethylene, heptanoyloxymethylene, methoxymethylene, ethoxymethylene, propanoxymethylene, 2-methylpropanoxymethylene, 2,2-dimethylpropanoxymethylene, butanoxymethylene, 2-methylbutanoxymethylene, 3-methylbutanoxymethylene, 2,2-dimethylbutanoxymethylene, 2,3-dimethylbutanoxymethylene, 3,3-dimethylbutanoxymethylene, 2-ethylbutanoxymethylene, pentanoxymethylene, 2-methylpentanoxymethylene, 3-methylpentanoxymethylene, 4-methylpentanoxymethylene, hexanoxymethylene, aminocarbonyl, methylaminocarbonyl, dimethylaminocarbonyl, ethylaminocarbonyl, diethylaminocarbonyl, n-propylaminocarbonyl, di-n-propylaminocarbonyl, isopropylaminocarbonyl, diisopropylaminocarbonyl, n-butylaminocarbonyl, di-n-butylaminocarbonyl, isobutylaminocarbonyl, diisobutylaminocarbonyl, tert-butylaminocarbonyl, di-tert-butylaminocarbonyl, phenylaminocarbonyl, diphenylaminocarbonyl, 4-nitrophenylaminocarbonyl, 4-fluorophenylaminocarbonyl, 4-chlorophenylaminocarbonyl, 4-bromophenylaminocarbonyl, 4-methylphenylaminocarbonyl, 4-methoxyphenylaminocarbonyl, (4-methylaminocarbonyl)phenylaminocarbonyl, 1-naphthylaminocarbonyl, 2-naphthylaminocarbonyl, 1-indanylaminocarbonyl, 2-indanylaminocarbonyl, benzylylaminocarbonyl, dibenzylylaminocarbonyl, (4-nitrobenzylyl)aminocarbonyl, methoxycarbonylpropanoyl, carboxypropanoyl, carboxybutanoyl, ethoxycarbonylpropenoyl, ethoxycarbonylbutanoyl, benzyloxycarbonylpropanoyl, carboxybutanoyl, benzyloxycarbonylbutanoyl, 2-furanylcarbonyl, 2-thienylcarbonyl, phenoxyacetyl, ethoxycarbonyl, N-phenylcarbamoyl, and N-benzylcarbamoyl.

17. A pharmaceutical composition according to claim 16, wherein the substituents of list (L') are selected from the following list (L"):

acetyl, 2,2-dimethylpropanoyl, benzoyl, 4-dimethylaminobenzoyl, 4-aminobenzoyl, 4-benzyloxyloxybenzoyl, 4-hydroxybenzoyl, 4-methoxybenzoyl, 4-methylbenzoyl, 3-methylbenzoyl, 4-fluorobenzoyl, 3-hydroxybenzoyl, 4-chlorobenzoyl, 4-methoxycarbonylbenzoyl, (4-acetyl)benzoyl, 4-nitrobenzoyl, 3,5-dichlorobenzoyl, N,N-diisopropylaminomethylenebenzoyl, N,N-diethylaminomethylenebenzoyl, pentanoyl, (2-acetyloxy)benzoyl, phenylacetyl, formyl, butanoyl, methoxyacetyl, methoxycarbonylpropanoyl, carboxypropanoyl, carboxybutanoyl, ethoxycarbonylpropenoyl, ethoxycarbonylbutanoyl, benzyloxycarbonylpropanoyl, benzyloxycarbonylbutanoyl, N-(phenyl)aminocarbonyl, N-(benzyl)aminocarbonyl, 2-thienylcarbonyl, 1-piperidinylmethylenebenzoyl, N-morpholinylmethylenebenzoyl, N,N-dimethylaminomethylenebenzoyl, N-4-methylpiperazinylmethylenebenzoyl, N-(2-hydroxyethyl)aminomethylenebenzoyl, N-carbamoylmethylaminomethylenebenzoyl, N-ethylaminomethylenebenzoyl, aminomethylenebenzoyl, N-(2-hydroxyethyl)-N-(methyl)aminomethylenebenzoyl, 2-furanylcarbonyl, phenoxyacetyl, ethoxycarbonyl, N-phenylcarbamoyl, N-benzylcarbamoyl, and 4-dimethylaminobutanoyl.

18. A pharmaceutical composition according to claim 17, wherein the substituents of list (L") are selected from the following list (L'''):

acetyl, 2,2-dimethylpropanoyl, benzoyl, 4-dimethylaminobenzoyl, 4-benzyloxyloxybenzoyl, 4-hydroxybenzoyl, 4-methoxybenzoyl, 4-methylbenzoyl, 3-methylbenzoyl, 4-fluorobenzoyl, 4-chlorobenzoyl, 4-nitrobenzoyl, 3,5-dichlorobenzoyl, 4-(N,N-diisopropylaminomethylene)benzoyl, 4-(N,N-diethylaminomethylene)benzoyl, 4-(1-piperidinylmethylene)benzoyl, 4-(N-morpholinylmethylene)benzoyl, 4-(N,N-dimethylaminomethylene)benzoyl, pentanoyl, (2-acetyloxy)benzoyl, phenylacetyl, formyl, butanoyl, methoxyacetyl, methoxycarbonylpropanoyl, carboxypropanoyl, carboxybutanoyl, ethoxycarbonylpropenoyl, ethoxycarbonylbutanoyl, benzyloxycarbonylpropanoyl, benzyloxycarbonylbutanoyl, N-(phenyl)aminocarbonyl, N-(benzyl)aminocarbonyl, and 2-thienylcarbonyl.

19. A pharmaceutical composition according to claim 14, wherein the stereoisomer of compound (V) has the general formula of compound (VIII) and the stereoisomer of compound (VIII) has the general formula of compound (X):

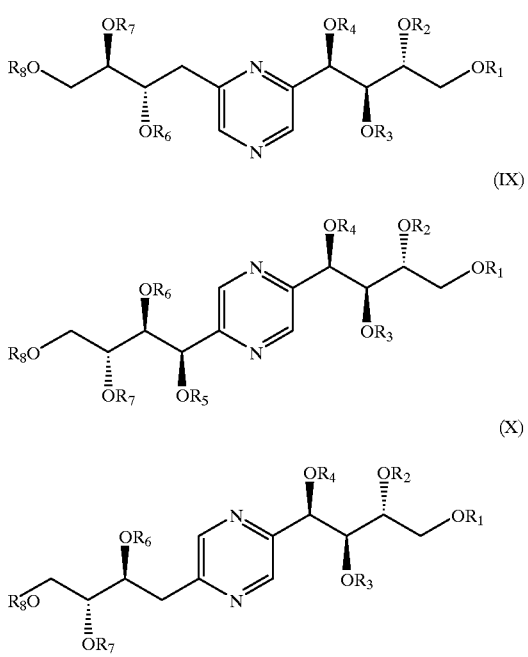

(VIII)

(IX)

(X)

or the salts of such compounds with an organic or inorganic acid.

20. A pharmaceutical composition according to claim 19 wherein either (i) each of the pairs $R_1$ and $R_2$, $R_3$ and $R_4$ and $R_7$ and $R_8$ forms the group —CO— and $R_6$ is hydrogenl; or (ii) each of the pairs $R_1$ and $R_2$, $R_7$ and $R_8$ forms the group —CO— and each of $R_3$, $R_4$, and $R_6$ is hydrogen; or (iii) one of the groups $R_1$, $R_2$, $R_6$; $R_4$, $R_6$; $R_1$, $R_3$, $R_4$, $R_6$, $R_8$; $R_2$, $R_3$, $R_4$, $R_6$; $R_1$, $R_3$, $R_4$, $R_6$, $R_7$; $R_2$; $R_1$, $R_2$, $R_8$; $R_1$, $R_2$, $R_6$, $R_7$, $R_8$ and $R_6$ forms a bhenzoyl radical and each of the remainig substituents $R_1$, $R_2$, $R_3$, $R_4$, $R_6$, $R_7$, and $R_8$ is hydrogen or (iv) the group $R_2$, $R_6$ and $R_7$ together forms a benzoyl radical and the group $R_3$, $R_4$ together forms the radical —CO— and each of $R_1$ and $R_8$ is hydrogen; or (v) $R_8$ is a pentanoyl or acetyl radical and each of the other substituents $R_1$, $R_2$, $R_3$, $R_4$, $R_6$, and $R_7$ is hydrogen; or (vi) each of the two substituents $R_1$ and $R_8$ is an identical radical selected from acetyl, 2,2-dimethylpropanoyl, benzoyl, 4-dimethiylaminobcnzoyl, 4-benzyloxyloxybenzoyl, 4-hydroxybenzoyl, 4-methoxybenzoyl, 4-methylbenzoyl, 3-meothylbenzoyl, 4fluorobenzoy, 4-chlorobenzoyl, 4-nitrobenzoyl, 3,5-dichlorobenzoyl, 4-(N,N-diisopropylaminomhethylone)benzoyl, 4-(N,N-diethylwnomethylene)benzoyl, 4-(1-piperidinylrnethylene) benzoyl, 4-(N-morpholinylmethylene)benzoyl, 4-(N,N-diinethylanminametiylcnebenzoyl, pentanoyl, (2-acetyloxy) benzoyl, phenylacetyl, formyl, butanloyl, mothoxyacetyl, methoxycarbonylpropaaoyl, carboxypropauoyl, tarboxybutanoyl, ethoxyarbonylpropenoy), ethoxycarbonylbutanloyl, benzloxycarbonylpropanoyl, benzyloxycarbonylbutanoyl, N-(phenyl)aminocarlonyl, N-(benzyl)aminorcarbonyl, anld 2-thienylcarbonyl and each of the othxer substitutents $R_2$, $R_3$, $R_4$, $R_6$, and $R_7$ is hydrogen; or (vii)each of $R_1$, $R_2$, $R_3$, $R_4$, $R_6$, $R_7$, and $R_9$ is an identical radical selected from benzoyl, acetyl, 2,2-dimlethylpropanoyl, (2-aretyloxy)benzoyl, methoxyacetyl, pentanoyl, formyl, methoxycarbonylpropanoyl, carboxypropanoyl, ethoxycabonylbutanoyel, carboxybutanoyl, etboxycarbonylpropenoyl, benzyloxycarbonylpropanoyl, and benzyloxybutanoyl.

21. A method for the treatment of diabetes or complications thereof, this method comprising administering to a patient in need of such treatment an effective amount of a compound of general formula (I)

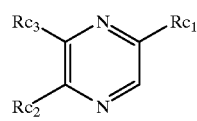

(I)

wherein $Rc_1$, $Rc_2$, $Rc_3$ are as defined in claim 1, or a stereoisomer thereof or a salt thereof with an organic or inorganic acid, in a pharmaceutically acceptable vehicle.

* * * * *